United States Patent
Ding et al.

(10) Patent No.: US 11,078,467 B2
(45) Date of Patent: Aug. 3, 2021

(54) HIGHLY ACTIVE SELF-SUFFICIENT NITRATION BIOCATALYSTS

(71) Applicant: University of Florida Research Foundation, Incorporated, Gainesville, FL (US)

(72) Inventors: Yousong Ding, Gainesville, FL (US); Ran Zuo, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/345,224

(22) PCT Filed: Oct. 26, 2017

(86) PCT No.: PCT/US2017/058579
§ 371 (c)(1),
(2) Date: Apr. 25, 2019

(87) PCT Pub. No.: WO2018/081456
PCT Pub. Date: May 3, 2018

(65) Prior Publication Data
US 2019/0292527 A1     Sep. 26, 2019

Related U.S. Application Data

(60) Provisional application No. 62/413,228, filed on Oct. 26, 2016.

(51) Int. Cl.
| | |
|---|---|
| *C12N 9/02* | (2006.01) |
| *C12N 15/00* | (2006.01) |
| *C12N 9/04* | (2006.01) |
| *C12P 7/40* | (2006.01) |
| *C12P 17/10* | (2006.01) |
| *C12P 17/16* | (2006.01) |
| *C12P 17/18* | (2006.01) |
| *C07K 14/80* | (2006.01) |

(52) U.S. Cl.
CPC ............ *C12N 9/0071* (2013.01); *C07K 14/80* (2013.01); *C12N 9/0042* (2013.01); *C12P 17/10* (2013.01); *C12P 17/16* (2013.01); *C12P 17/165* (2013.01); *C12P 17/182* (2013.01); *C12Y 106/02004* (2013.01); *C12Y 114/14001* (2013.01); *C07K 2319/00* (2013.01)

(58) Field of Classification Search
CPC .... C12N 9/0071; C12N 15/00; C12N 9/0004; C12N 9/0073; C12N 9/14; C12Y 114/14001; C12Y 114/13008; C12P 7/22; C12P 7/26; C12P 17/165

USPC ........ 435/69.7, 189, 123, 132, 252.3, 320.1, 435/440
See application file for complete search history.

(56) References Cited

FOREIGN PATENT DOCUMENTS

WO     WO 2016/134145 A2     8/2016

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report and Written Opinion dated Mar. 9, 2018, corresponding to International Application No. PCT/US2017/058579, 19 pages.
Dodani et al., Discovery of a regioselectivity switch in nitrating P450s guided by molecular dynamics simulations and Markov models. Nat Chem. May 2016;8(5):419-25. doi: 10.1038/nchem.2474. Epub Mar. 21, 2016.
Dodani et al., Structural, functional, and spectroscopic characterization of the substrate scope of the novel nitrating cytochrome P450 TxtE. Chembiochem. Oct. 13, 2014;15(15):2259-67. doi: 10.1002/cbic.201402241. Epub Sep. 2, 2014.
Robin et al., Engineering and improvement of the efficiency of a chimeric [P450cam-RhFRed reductase domain] enzyme. Chem Commun (Camb). May 14, 2009;(18):2478-80. doi: 10.1039/b901716j. Epub Mar. 24, 2009.

(Continued)

*Primary Examiner* — Robert B Mondesi
*Assistant Examiner* — Mohammad Y Meah
(74) *Attorney, Agent, or Firm* — Wolf, Greenfield & Sacks, P.C.

(57) ABSTRACT

The disclosure relates to the field of fusion proteins. In some aspects, the disclosure relates to artificial fusion proteins comprising cytochrome P450 enzymes linked to reductase enzymes and uses thereof. In some aspects, the disclosure relates to corn-pounds produced by artificial cytochrome P450 enzymes.

10 Claims, 19 Drawing Sheets
Specification includes a Sequence Listing.

(56) References Cited

OTHER PUBLICATIONS

Zuo et al., An artificial self-sufficient cytochrome P450 directly nitrates fluorinated tryptophan analogs with a different regioselectivity. Biotechnol J. May 2016; 11(5):624-32. doi: 10.1002/biot.201500416. Epub Feb. 4, 2016.
Zuo et al., Engineered P450 biocatalysts show improved activity and regio-promiscuity in aromatic nitration. Sci Rep. Apr. 12, 2017;7(1):842. doi: 10.1038/s41598-017-00897-z.
EP17865713.6, May 28, 2020, Partial Supplementary European Search Report.
EP17865713.6, Sep. 11, 2020, Extended European Search Report.
PCT/US2017/058579, Jan. 19, 2018, Invitation to Pay Additional Fees.
Partial Supplementary European Search Report dated May 28, 2020 in connection with European Patent Application No. EP17865713.6.
Extended European Search Report dated Sep. 11, 2020 in connection with European Patent Application No. EP17865713.6.
Invitation to Pay Additional Fees dated Jan. 19, 2018 in connection with International Patent Application No. PCT/US2017/058579.

\* cited by examiner

HIGHLY ACTIVE SELF-SUFFICIENT NITRATION BIOCATALYSTS

CROSS REFERENCE TO RELATED APPLICATION(S)

This application is a National Stage filing under 35 U.S.C. § 371 of International Application Number PCT/US2017/058579, filed Oct. 26, 2017, and claims priority under 35 U.S.C. § 119(e) to U.S. Provisional Patent Application No. 62/413,228, filed Oct. 26, 2016, the entire contents of each of which is incorporated herein.

STATEMENT OF RIGHTS TO INVENTIONS MADE UNDER FEDERALLY SPONSORED RESEARCH

This invention was made with government support under FA9550-16-1-0186 awarded by the United States Air Force Office of Scientific Research. The government has certain rights to the invention.

BACKGROUND

Nitro ($-NO_2$) compounds, particularly nitro aromatic and heterocyclic derivatives, are important industrial chemicals, with an estimated annual production of greater than 108 tons (Kulkarni and Chaudhari 2007). Their applications span a broad range such as food additives, pesticides, herbicides, polymers, explosives, and dyes (Ju and Parales 2010). The nitro group is also an important functional unit in pharmaceuticals such as chloramphenicol, nilutamine, tolcapone, metronidazole, and the recently approved anti-tuberculosis drug delamanid (Martino et al. 2003). Its therapeutic relevance is further illustrated by nitro-containing lead drug candidates such as 9-nitro-noscapine for the treatment of multidrug resistant cancers (Anej a et al. 2006) and 5-nitro-2-furancarboxylamides in treating neglected parasitic protozoa infections (Zhou et al. 2013).

Aromatic nitration is a widely used organic reaction (Yan and Yang 2013). Industrial scale reactions usually include a mixture of nitric acid and sulfuric acid or sometimes nitric acid with other acids. In these reactions, the nitronium ion, $NO_2^+$, is believed to be the active species, albeit the potential minor contribution of a radical mechanism (Olah et al. 1978). Currently used methods and materials present several challenges, such as poor selectivity, low yield, generation of multiple isomers and by-products, and low functional group tolerance frequently occur and limit their uses in generating products with specific requirements. In addition, currently used methods are not environmentally sound. Accordingly, there is a need to develop environmentally benign, selective, practical and efficient direct aromatic nitration approaches.

SUMMARY

Aromatic nitration, addition of a nitro ($NO_2$) group to an aromatic molecule, is an important chemical reaction in a variety of industries. Current industrial methods of aromatic nitration utilize chemical catalysts, for example the mixing of strong acids (e.g., nitric acid and sulfuric acid). However, this approach is inefficient, leading to low yield of desirable products, as well as being environmentally unsound.

The instant invention, in some aspects, overcomes these issues by providing a biocatalyst-based approach for aromatic nitration. The disclosure is based, in part, on the inventors' unexpected discovery that TxtE-Bm3 fusion proteins comprising linkers having a certain length (e.g., 11, 12, 14, 15, 16, 17, etc. amino acids in length) exhibit improved function (e.g., increased nitration activity, coupling efficiency, total turnover number (TTN), etc.) compared to previously described self-sufficient cytochrome p450 enzymes. Thus, the invention provides novel enzymes, novel methods, and novel substituted indoles (e.g., tryptophans).

Accordingly, in some aspects, the disclosure provides a fusion protein comprising: (i) a TxtE enzyme; (ii) an amino acid linker that is 11, 12, or between 14 and 27 amino acids in length; and, (iii) a catalytic domain of a CYP102A1 (P450BM3) reductase enzyme, wherein the linker joins (iii) to a terminus of (i).

In some embodiments, the disclosure provides a fusion protein comprising: (i) a TxtE enzyme; (ii) an amino acid linker that is 13 amino acids in length; and, (iii) a catalytic domain of a CYP102A1 (P450BM3) reductase enzyme; wherein the linker joins (iii) to a terminus of (i), and wherein the amino acid linker is not set forth in SEQ ID NO: 44.

In some embodiments, the terminus is a C-terminus.

In some embodiments, the TxtE enzyme is defined as: (i) TxtE; (ii) a portion of TxtE which catalyzes transfer of a nitro functional group to a compound of Formulae Ia, IVa, VIIa, IXa, or XVa on its indole ring; or, (iii) an enzyme which catalyzes transfer of a nitro functional group to a compound of Formulae Ia, IVa, VIIa, IXa, or XVa and is at least 95% homologous to the amino acid sequence of TxtE. In some embodiments, the TxtE enzyme shares at least 90% amino acid sequence similarity with a polypeptide encoded by region 3613916-3615136 of Genbank Accession No. FN554889 (e.g., Genbank Accession No. CBG70284.1).

In some embodiments, the TxtE enzyme comprises or consists of a sequence set forth in SEQ ID NO: 56.

In some embodiments, the catalytic domain comprises or consists of a sequence set forth in SEQ ID NO: 57.

In some embodiments, the amino acid linker is 11 or 12 amino acids in length. In some embodiments, the amino acid linker is 14, 15, 16, 17, 18, 19, 20, 21, 22, 23, 24, 25, 26 or 27 amino acids in length. In some embodiments, the amino acid linker is 14 amino acids in length.

In some embodiments, the amino acid linker is derived from a TxtE enzyme or a CYP102A1 (P450BM3) reductase enzyme.

In some embodiments, the fusion protein is not produced by overlap PCR.

In some embodiments, the amino acid linker comprises or consists of a sequence set forth in any one of SEQ ID NO:26-43 or 45-55.

In some embodiments, the amino acid linker is selected from the group consisting of flexible amino acid linker, rigid amino acid linker and cleavable amino acid linker.

In some aspects, the disclosure provides a fusion protein comprising: (i) a TxtE enzyme, wherein the TxtE enzyme comprises a sequence set forth in SEQ ID NO: 57; (ii) an amino acid linker; and, (iii) a catalytic domain of a CYP102A1 (P450BM3) reductase enzyme; wherein the linker joins (iii) to a terminus of (i).

In some embodiments, the amino acid linker is 13 amino acids in length. In some embodiments, the amino acid linker comprises a sequence set forth in SEQ ID NO: 44.

In some aspects, the disclosure relates to an expression construct comprising a nucleic acid encoding a fusion protein as described by the disclosure. In some aspects, the disclosure provides an isolated nucleic acid encoding a fusion protein as described by the disclosure. In some aspects, the disclosure provides a host cell comprising an expression construct as described by the disclosure or an isolated nucleic acid as described by the disclosure.

In some aspects, the disclosure relates to a method for producing a nitro-substituted indole (e.g., a compound of any one of Formulae I-XVI), the method comprising contacting the indole, in the presence of NAD(P)H, with a fusion protein as described by the disclosure. In some embodiments the indole is substituted with a substituent(s) other than a nitro group. In some embodiments, the indole is singly-substituted and the resulting nitro-substituted indole (e.g., a compound of any one of Formulae I-XVI) is a di-substituted nitro indole. In some embodiments, the method further comprises isolating the nitrated indole (e.g., a compound of any one of Formulae I-XVI).

In some aspects, the disclosure provides compounds produced by nitration of indoles. In some embodiments, the indole is substituted. In some aspects, the disclosure provides compounds produced by nitration of a compound of Formulae Ia, IVa, VIIa, IXa, XIIa, and XVa to afford a compound of Formulae I-XVI. In some embodiments, at least one of $X^1$, $X^2$, or $X^3$ in Formula Ia, IVa, or Va, or at least one of $Y^1$, $Y^2$, or $Y^3$ in Formulae IIa, IIIa, VIa, VIIa, VIIIa, or IXa, is not hydrogen. Accordingly, in some aspects the disclosure relates to a compound represented by Formulae I-XVI.

In embodiments, the disclosure is directed to a compound of Formula I, or a pharmaceutically acceptable salt, prodrug, hydrate, or solvate thereof:

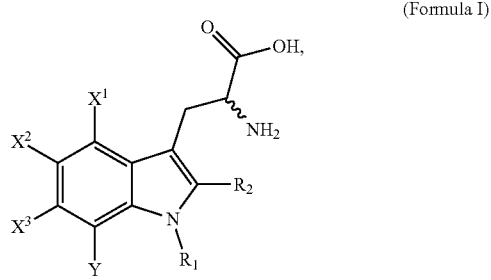

(Formula I)

wherein:
$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $OR^{Ala}$, $N(R^{Ala})_2$, or $SR^{Ala}$,
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;
each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $SR^{Ala}$,
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl; and
Y is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some aspects, the compound disclosure relates to a compound of Formula I, wherein at least one of $X^1$, $X^2$, or $X^3$ is a "weakly deactivating group", a "weakly activating group", a "moderately activating group", or a "strongly activating group", as known in the art and as defined herein. In other aspects, at least one of $X^1$, $X^2$, or $X^3$ is H, halogen (e.g., F, Cl, Br, I), substituted or unsubstituted $C_{1-6}$ alkyl (e.g., methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $SR^{Ala}$.

In another aspect, $X^1$ is halogen (e.g., F, Cl, Br, I), substituted or unsubstituted $C_{1-6}$ alkyl (e.g., methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $SR^{Ala}$; and $X^2$ and $X^3$ are each independently H, halogen (e.g., F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $SR^{Ala}$. In another aspect, $X^1$ is halogen or $C_{1-6}$ alkyl (e.g., methyl, $CH_3$). In another aspect, $X^1$ is halogen. In another aspect, $X^1$ is $C_{1-6}$ alkyl (e.g., methyl, $CH_3$). In another aspect, $X^1$ is halogen or $C_{1-6}$ alkyl (e.g., methyl, $CH_3$) and at least one of $X^2$ and $X^3$ is hydrogen. In another aspect, $X^1$ is halogen and each of $X^2$ and $X^3$ is hydrogen. In another aspect, $X^1$ if fluorine and each of $X^2$ and $X^3$ is hydrogen. In another aspect, $X^1$ is $C_{1-6}$ alkyl and each of $X^2$ and $X^3$ is hydrogen. In another aspect, $X^1$ is methyl and each of $X^2$ and $X^3$ is hydrogen.

In certain embodiments, the compound of Formula I is a compound of Formula II:

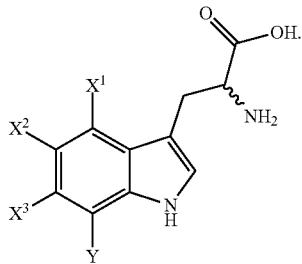

(Formula II)

In certain embodiments, the compound of Formula I is a compound of Formula III:

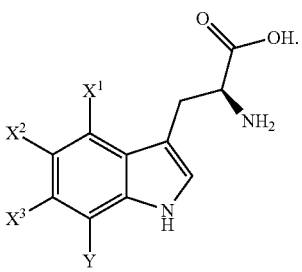

(Formula III)

In embodiments, the disclosure is directed to a compound of Formula IV, or a pharmaceutically acceptable salt, prodrug, hydrate, or solvate thereof:

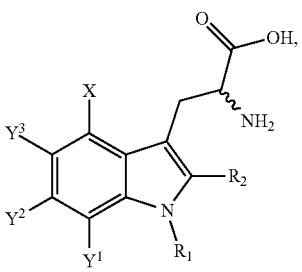

(Formula IV)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$(R^{Ala})_2$, or $SR^{Ala}$, wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some aspects, the compound disclosure relates to a compound of Formula IV, wherein at least one of $Y^1$, $Y^2$, or $Y^3$ is a "weakly deactivating group", a "weakly activating group", a "moderately activating group", or a "strongly activating group", as known in the art and as defined herein. In other aspects, at least one of $Y^1$, $Y^2$, or $Y^3$ is H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or $SR^{Ala}$.

In embodiments, $Y^1$, $Y^2$, or $Y^3$ is halogen and the halogen is fluorine. In embodiments, $Y^1$, $Y^2$, or $Y^3$ is unsubstituted $C_1$-$C_6$ alkyl. In embodiments, the unsubstituted $C_1$-$C_6$ alkyl is methyl (—$CH_3$). In embodiments, two of $Y^1$, $Y^2$ and $Y^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In some aspects, the disclosure relates to a compound of Formula IV, wherein at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$SR^{Ala}$; or and $Y^1$ and $Y^2$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or $SR^{Ala}$. In another aspect, $Y^3$ is is halogen or $C_{1-6}$ alkyl (e.g. methyl, $CH_3$). In another aspect, $Y^3$ is halogen or $C_{1-6}$ alkyl (e.g. methyl, $CH_3$) and at least one of $Y^1$ and $Y^2$ is hydrogen. In another aspect, $Y^3$ is halogen or $C_{1-6}$ alkyl (e.g. methyl, $CH_3$) and $Y^1$ and $Y^2$ are each hydrogen. In another aspect, $Y^3$ is halogen. In another aspect, $Y^3$ is halogen and at least one of $Y^1$ and $Y^2$ is hydrogen. In another aspect, $Y^3$ is halogen and $Y^1$ and $Y^2$ are each hydrogen. In certain embodiments, $Y^3$ is fluorine and at least one of $Y^1$ and $Y^2$ is hydrogen. In another aspect, $Y^3$ is fluorine and $Y^1$ and $Y^2$ are each hydrogen. In another aspect, $Y^3$ is $C_{1-6}$ alkyl. In another aspect, $Y^3$ is $C_{1-6}$ alkyl and at least one of $Y^1$ and $Y^2$ is hydrogen. In another aspect, $Y^3$ is $C_{1-6}$ alkyl and $Y^1$ and $Y^2$ are each hydrogen. In certain embodiments, $Y^3$ is methyl and at least one of $Y^1$ and $Y^2$ is hydrogen. In another aspect, $Y^3$ is methyl and $Y^1$ and $Y^2$ are each hydrogen.

In certain embodiments, the compound of Formula IV is a compound of Formula V:

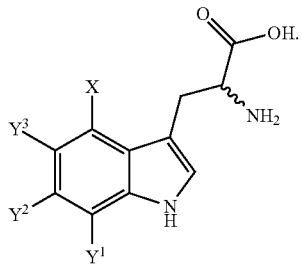

(Formula V)

In certain embodiments, the compound of Formula IV is a compound of Formula VI:

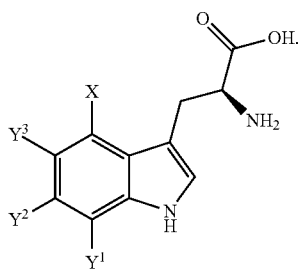

(Formula VI)

In another aspect, the invention is directed to a compound of Formulae I-VI, wherein the compound is:

(S)-2-amino-3-(4-methyl-5-nitro-1H-indol-3-yl)propanoic acid;
(S)-2-amino-3-(5-methyl-4-nitro-1H-indol-3-yl)propanoic acid;
(S)-2-amino-3-(6-methyl-4-nitro-1H-indol-3-yl)propanoic acid;
(S)-2-amino-3-(7-methyl-4-nitro-1H-indol-3-yl)propanoic acid;
(S)-2-amino-3-(4-methyl-7-nitro-1H-indol-3-yl)propanoic acid;
(S)-2-amino-3-(5-fluoro-4-nitro-1H-indol-3-yl)propanoic acid;
(S)-2-amino-3-(6-fluoro-4-nitro-1H-indol-3-yl)propanoic acid;
(S)-2-amino-3-(7-fluoro-4-nitro-1H-indol-3-yl)propanoic acid;
(S)-2-amino-3-(4-fluoro-7-nitro-1H-indol-3-yl)propanoic acid;
(S)-2-amino-3-(5-chloro-4-nitro-1H-indol-3-yl)propanoic acid;
(S)-2-amino-3-(6-chloro-4-nitro-1H-indol-3-yl)propanoic acid;
(S)-2-amino-3-(7-chloro-4-nitro-1H-indol-3-yl)propanoic acid;
(S)-2-amino-3-(4-chloro-7-nitro-1H-indol-3-yl)propanoic acid;
(S)-2-amino-3-(5-bromo-4-nitro-1H-indol-3-yl)propanoic acid;
(5)-2-amino-3-(6-bromo-4-nitro-1H-indol-3-yl)propanoic acid;
(S)-2-amino-3-(7-bromo-4-nitro-1H-indol-3-yl)propanoic acid;
(S)-2-amino-3-(4-bromo-7-nitro-1H-indol-3-yl)propanoic acid;
(S)-2-amino-3-(5-methoxy-4-nitro-1H-indol-3-yl)propanoic acid;
(S)-2-amino-3-(6-methoxy-4-nitro-1H-indol-3-yl)propanoic acid;
(S)-2-amino-3-(7-methoxy-4-nitro-1H-indol-3-yl)propanoic acid;
(S)-2-amino-3-(4-methoxy-7-nitro-1H-indol-3-yl)propanoic acid;
(S)-2-amino-3-(5-amino-4-nitro-1H-indol-3-yl)propanoic acid;
(S)-2-amino-3-(6-amino-4-nitro-1H-indol-3-yl)propanoic acid;
(S)-2-amino-3-(7-amino-4-nitro-1H-indol-3-yl)propanoic acid;
(5)-2-amino-3-(4-amino-7-nitro-1H-indol-3-yl)propanoic acid;
(S)-2-amino-3-(5-hydroxy-4-nitro-1H-indol-3-yl)propanoic acid;
(S)-2-amino-3-(6-hydroxy-4-nitro-1H-indol-3-yl)propanoic acid;
(S)-2-amino-3-(7-hydroxy-4-nitro-1H-indol-3-yl)propanoic acid;
(S)-2-amino-3-(4-hydroxy-7-nitro-1H-indol-3-yl)propanoic acid;
(S)-2-amino-3-(4-nitro-5-phenyl-1H-indol-3-yl)propanoic acid;
(S)-2-amino-3-(4-nitro-6-phenyl-1H-indol-3-yl)propanoic acid;
(S)-2-amino-3-(4-nitro-7-phenyl-1H-indol-3-yl)propanoic acid;
(S)-2-amino-3-(7-nitro-4-phenyl-1H-indol-3-yl)propanoic acid;
(S)-2-amino-3-(5-cyclopropyl-4-nitro-1H-indol-3-yl)propanoic acid;
(S)-2-amino-3-(6-cyclopropyl-4-nitro-1H-indol-3-yl)propanoic acid;
(S)-2-amino-3-(7-cyclopropyl-4-nitro-1H-indol-3-yl)propanoic acid;
(S)-2-amino-3-(4-cyclopropyl-7-nitro-1H-indol-3-yl)propanoic acid;
(S)-2-amino-3-(4-nitro-5-vinyl-1H-indol-3-yl)propanoic acid;
(S)-2-amino-3-(4-nitro-6-vinyl-1H-indol-3-yl)propanoic acid;
(S)-2-amino-3-(4-nitro-7-vinyl-1H-indol-3-yl)propanoic acid;
(S)-2-amino-3-(7-nitro-4-vinyl-1H-indol-3-yl)propanoic acid;
(S)-2-amino-3-(5-ethynyl-4-nitro-1H-indol-3-yl)propanoic acid;
(S)-2-amino-3-(6-ethynyl-4-nitro-1H-indol-3-yl)propanoic acid;
(S)-2-amino-3-(7-ethynyl-4-nitro-1H-indol-3-yl)propanoic acid;
(S)-2-amino-3-(4-ethynyl-7-nitro-1H-indol-3-yl)propanoic acid;
(S)-2-amino-3-(5-morpholino-4-nitro-1H-indol-3-yl)propanoic acid;
(S)-2-amino-3-(6-morpholino-4-nitro-1H-indol-3-yl)propanoic acid;

(S)-2-amino-3-(7-morpholino-4-nitro-1H-indol-3-yl)propanoic acid;
(S)-2-amino-3-(4-morpholino-7-nitro-1H-indol-3-yl)propanoic acid;
(S)-2-amino-3-(5-(methylthio)-4-nitro-1H-indol-3-yl)propanoic acid;
(S)-2-amino-3-(6-(methylthio)-4-nitro-1H-indol-3-yl)propanoic acid;
(S)-2-amino-3-(7-(methylthio)-4-nitro-1H-indol-3-yl)propanoic acid;
(S)-2-amino-3-(4-(methylthio)-7-nitro-1H-indol-3-yl)propanoic acid;
(S)-2-amino-3-(4-nitro-5-(pyridin-4-yl)-1H-indol-3-yl)propanoic acid;
(S)-2-amino-3-(4-nitro-6-(pyridin-4-yl)-1H-indol-3-yl)propanoic acid;
(S)-2-amino-3-(4-nitro-7-(pyridin-4-yl)-1H-indol-3-yl)propanoic acid;
(S)-2-amino-3-(7-nitro-4-(pyridin-4-yl)-1H-indol-3-yl)propanoic acid;
2-amino-3-(4-methyl-5-nitro-1H-indol-3-yl)propanoic acid;
2-amino-3-(5-methyl-4-nitro-1H-indol-3-yl)propanoic acid;
2-amino-3-(6-methyl-4-nitro-1H-indol-3-yl)propanoic acid;
2-amino-3-(7-methyl-4-nitro-1H-indol-3-yl)propanoic acid;
2-amino-3-(4-methyl-7-nitro-1H-indol-3-yl)propanoic acid;
2-amino-3-(6-fluoro-4-nitro-1H-indol-3-yl)propanoic acid;
2-amino-3-(7-fluoro-4-nitro-1H-indol-3-yl)propanoic acid;
2-amino-3-(4-fluoro-7-nitro-1H-indol-3-yl)propanoic acid;
2-amino-3-(5-chloro-4-nitro-1H-indol-3-yl)propanoic acid;
2-amino-3-(6-chloro-4-nitro-1H-indol-3-yl)propanoic acid;
2-amino-3-(7-chloro-4-nitro-1H-indol-3-yl)propanoic acid;
2-amino-3-(4-chloro-7-nitro-1H-indol-3-yl)propanoic acid;
2-amino-3-(5-bromo-4-nitro-1H-indol-3-yl)propanoic acid;
2-amino-3-(6-bromo-4-nitro-1H-indol-3-yl)propanoic acid;
2-amino-3-(7-bromo-4-nitro-1H-indol-3-yl)propanoic acid;
2-amino-3-(4-bromo-7-nitro-1H-indol-3-yl)propanoic acid;
2-amino-3-(5-methoxy-4-nitro-1H-indol-3-yl)propanoic acid;
2-amino-3-(6-methoxy-4-nitro-1H-indol-3-yl)propanoic acid;
2-amino-3-(7-methoxy-4-nitro-1H-indol-3-yl)propanoic acid;
2-amino-3-(4-methoxy-7-nitro-1H-indol-3-yl)propanoic acid;
2-amino-3-(5-amino-4-nitro-1H-indol-3-yl)propanoic acid;
2-amino-3-(6-amino-4-nitro-1H-indol-3-yl)propanoic acid;
2-amino-3-(7-amino-4-nitro-1H-indol-3-yl)propanoic acid;
2-amino-3-(4-amino-7-nitro-1H-indol-3-yl)propanoic acid;
2-amino-3-(5-hydroxy-4-nitro-1H-indol-3-yl)propanoic acid;
2-amino-3-(6-hydroxy-4-nitro-1H-indol-3-yl)propanoic acid;
2-amino-3-(7-hydroxy-4-nitro-1H-indol-3-yl)propanoic acid;
2-amino-3-(4-hydroxy-7-nitro-1H-indol-3-yl)propanoic acid;
2-amino-3-(4-nitro-5-phenyl-1H-indol-3-yl)propanoic acid;
2-amino-3-(4-nitro-6-phenyl-1H-indol-3-yl)propanoic acid;
2-amino-3-(4-nitro-7-phenyl-1H-indol-3-yl)propanoic acid;
2-amino-3-(7-nitro-4-phenyl-1H-indol-3-yl)propanoic acid;
2-amino-3-(5-cyclopropyl-4-nitro-1H-indol-3-yl)propanoic acid;
2-amino-3-(6-cyclopropyl-4-nitro-1H-indol-3-yl)propanoic acid;
2-amino-3-(7-cyclopropyl-4-nitro-1H-indol-3-yl)propanoic acid;
2-amino-3-(4-cyclopropyl-7-nitro-1H-indol-3-yl)propanoic acid;
2-amino-3-(4-nitro-5-vinyl-1H-indol-3-yl)propanoic acid;
2-amino-3-(4-nitro-6-vinyl-1H-indol-3-yl)propanoic acid;
2-amino-3-(4-nitro-7-vinyl-1H-indol-3-yl)propanoic acid;
2-amino-3-(7-nitro-4-vinyl-1H-indol-3-yl)propanoic acid;
2-amino-3-(5-ethynyl-4-nitro-1H-indol-3-yl)propanoic acid;
2-amino-3-(6-ethynyl-4-nitro-1H-indol-3-yl)propanoic acid;
2-amino-3-(7-ethynyl-4-nitro-1H-indol-3-yl)propanoic acid;
2-amino-3-(4-ethynyl-7-nitro-1H-indol-3-yl)propanoic acid;
2-amino-3-(5-morpholino-4-nitro-1H-indol-3-yl)propanoic acid;
2-amino-3-(6-morpholino-4-nitro-1H-indol-3-yl)propanoic acid;
2-amino-3-(7-morpholino-4-nitro-1H-indol-3-yl)propanoic acid;
2-amino-3-(4-morpholino-7-nitro-1H-indol-3-yl)propanoic acid;
2-amino-3-(5-(methylthio)-4-nitro-1H-indol-3-yl)propanoic acid;
2-amino-3-(6-(methylthio)-4-nitro-1H-indol-3-yl)propanoic acid;
2-amino-3-(7-(methylthio)-4-nitro-1H-indol-3-yl)propanoic acid;
2-amino-3-(4-(methylthio)-7-nitro-1H-indol-3-yl)propanoic acid;
2-amino-3-(4-nitro-5-(pyridin-4-yl)-1H-indol-3-yl)propanoic acid;
2-amino-3-(4-nitro-6-(pyridin-4-yl)-1H-indol-3-yl)propanoic acid;
2-amino-3-(4-nitro-7-(pyridin-4-yl)-1H-indol-3-yl)propanoic acid;
2-amino-3-(7-nitro-4-(pyridin-4-yl)-1H-indol-3-yl)propanoic acid;
2-amino-3-(1,5-dimethyl-4-nitro-1H-indol-3-yl)propanoic acid;
2-amino-3-(1,6-dimethyl-4-nitro-1H-indol-3-yl)propanoic acid;
2-amino-3-(1,7-dimethyl-4-nitro-1H-indol-3-yl)propanoic acid;
2-amino-3-(1,4-dimethyl-7-nitro-1H-indol-3-yl)propanoic acid;
2-amino-3-(6-fluoro-1-methyl-4-nitro-1H-indol-3-yl)propanoic acid;
2-amino-3-(7-fluoro-1-methyl-4-nitro-1H-indol-3-yl)propanoic acid;
2-amino-3-(4-fluoro-1-methyl-7-nitro-1H-indol-3-yl)propanoic acid;
2-amino-3-(5-chloro-1-methyl-4-nitro-1H-indol-3-yl)propanoic acid;
2-amino-3-(6-chloro-1-methyl-4-nitro-1H-indol-3-yl)propanoic acid;
2-amino-3-(7-chloro-1-methyl-4-nitro-1H-indol-3-yl)propanoic acid;
2-amino-3-(4-chloro-1-methyl-7-nitro-1H-indol-3-yl)propanoic acid;
2-amino-3-(5-bromo-1-methyl-4-nitro-1H-indol-3-yl)propanoic acid;
2-amino-3-(6-bromo-1-methyl-4-nitro-1H-indol-3-yl)propanoic acid;
2-amino-3-(7-bromo-1-methyl-4-nitro-1H-indol-3-yl)propanoic acid;

2-amino-3-(4-bromo-1-methyl-7-nitro-1H-indol-3-yl)propanoic acid;
2-amino-3-(5-methoxy-1-methyl-4-nitro-1H-indol-3-yl)propanoic acid;
2-amino-3-(6-methoxy-1-methyl-4-nitro-1H-indol-3-yl)propanoic acid;
2-amino-3-(7-methoxy-1-methyl-4-nitro-1H-indol-3-yl)propanoic acid;
2-amino-3-(4-methoxy-1-methyl-7-nitro-1H-indol-3-yl)propanoic acid;
2-amino-3-(5-amino-1-methyl-4-nitro-1H-indol-3-yl)propanoic acid;
2-amino-3-(6-amino-1-methyl-4-nitro-1H-indol-3-yl)propanoic acid;
2-amino-3-(7-amino-1-methyl-4-nitro-1H-indol-3-yl)propanoic acid;
2-amino-3-(4-amino-1-methyl-7-nitro-1H-indol-3-yl)propanoic acid;
2-amino-3-(5-hydroxy-1-methyl-4-nitro-1H-indol-3-yl)propanoic acid;
2-amino-3-(6-hydroxy-1-methyl-4-nitro-1H-indol-3-yl)propanoic acid;
2-amino-3-(7-hydroxy-1-methyl-4-nitro-1H-indol-3-yl)propanoic acid;
2-amino-3-(4-hydroxy-1-methyl-7-nitro-1H-indol-3-yl)propanoic acid;
2-amino-3-(1-methyl-4-nitro-5-phenyl-1H-indol-3-yl)propanoic acid;
2-amino-3-(1-methyl-4-nitro-6-phenyl-1H-indol-3-yl)propanoic acid;
2-amino-3-(1-methyl-4-nitro-7-phenyl-1H-indol-3-yl)propanoic acid;
2-amino-3-(1-methyl-7-nitro-4-phenyl-1H-indol-3-yl)propanoic acid;
2-amino-3-(5-cyclopropyl-1-methyl-4-nitro-1H-indol-3-yl)propanoic acid;
2-amino-3-(6-cyclopropyl-1-methyl-4-nitro-1H-indol-3-yl)propanoic acid;
2-amino-3-(7-cyclopropyl-1-methyl-4-nitro-1H-indol-3-yl)propanoic acid;
2-amino-3-(4-cyclopropyl-1-methyl-7-nitro-1H-indol-3-yl)propanoic acid;
2-amino-3-(1-methyl-4-nitro-5-vinyl-1H-indol-3-yl)propanoic acid;
2-amino-3-(1-methyl-4-nitro-6-vinyl-1H-indol-3-yl)propanoic acid;
2-amino-3-(1-methyl-4-nitro-7-vinyl-1H-indol-3-yl)propanoic acid;
2-amino-3-(1-methyl-7-nitro-4-vinyl-1H-indol-3-yl)propanoic acid;
2-amino-3-(5-ethynyl-1-methyl-4-nitro-1H-indol-3-yl)propanoic acid;
2-amino-3-(6-ethynyl-1-methyl-4-nitro-1H-indol-3-yl)propanoic acid;
2-amino-3-(7-ethynyl-1-methyl-4-nitro-1H-indol-3-yl)propanoic acid;
2-amino-3-(4-ethynyl-1-methyl-7-nitro-1H-indol-3-yl)propanoic acid;
2-amino-3-(1-methyl-5-morpholino-4-nitro-1H-indol-3-yl)propanoic acid;
2-amino-3-(1-methyl-6-morpholino-4-nitro-1H-indol-3-yl)propanoic acid;
2-amino-3-(1-methyl-7-morpholino-4-nitro-1H-indol-3-yl)propanoic acid;
2-amino-3-(1-methyl-4-morpholino-7-nitro-1H-indol-3-yl)propanoic acid;
2-amino-3-(1-methyl-5-(methylthio)-4-nitro-1H-indol-3-yl)propanoic acid;
2-amino-3-(1-methyl-6-(methylthio)-4-nitro-1H-indol-3-yl)propanoic acid;
2-amino-3-(1-methyl-7-(methylthio)-4-nitro-1H-indol-3-yl)propanoic acid;
2-amino-3-(1-methyl-4-(methylthio)-7-nitro-1H-indol-3-yl)propanoic acid;
2-amino-3-(1-methyl-4-nitro-5-(pyridin-4-yl)-1H-indol-3-yl)propanoic acid;
2-amino-3-(1-methyl-4-nitro-6-(pyridin-4-yl)-1H-indol-3-yl)propanoic acid;
2-amino-3-(1-methyl-4-nitro-7-(pyridin-4-yl)-1H-indol-3-yl)propanoic acid;
2-amino-3-(1-methyl-7-nitro-4-(pyridin-4-yl)-1H-indol-3-yl)propanoic acid;
2-amino-3-(2,5-dimethyl-4-nitro-1H-indol-3-yl)propanoic acid;
2-amino-3-(2,6-dimethyl-4-nitro-1H-indol-3-yl)propanoic acid;
2-amino-3-(2,7-dimethyl-4-nitro-1H-indol-3-yl)propanoic acid;
2-amino-3-(2,4-dimethyl-7-nitro-1H-indol-3-yl)propanoic acid;
2-amino-3-(6-fluoro-2-methyl-4-nitro-1H-indol-3-yl)propanoic acid;
2-amino-3-(7-fluoro-2-methyl-4-nitro-1H-indol-3-yl)propanoic acid;
2-amino-3-(4-fluoro-2-methyl-7-nitro-1H-indol-3-yl)propanoic acid;
2-amino-3-(5-chloro-2-methyl-4-nitro-1H-indol-3-yl)propanoic acid;
2-amino-3-(6-chloro-2-methyl-4-nitro-1H-indol-3-yl)propanoic acid;
2-amino-3-(7-chloro-2-methyl-4-nitro-1H-indol-3-yl)propanoic acid;
2-amino-3-(4-chloro-2-methyl-7-nitro-1H-indol-3-yl)propanoic acid;
2-amino-3-(5-bromo-2-methyl-4-nitro-1H-indol-3-yl)propanoic acid;
2-amino-3-(6-bromo-2-methyl-4-nitro-1H-indol-3-yl)propanoic acid;
2-amino-3-(7-bromo-2-methyl-4-nitro-1H-indol-3-yl)propanoic acid;
2-amino-3-(4-bromo-2-methyl-7-nitro-1H-indol-3-yl)propanoic acid;
2-amino-3-(5-methoxy-2-methyl-4-nitro-1H-indol-3-yl)propanoic acid;
2-amino-3-(6-methoxy-2-methyl-4-nitro-1H-indol-3-yl)propanoic acid;
2-amino-3-(7-methoxy-2-methyl-4-nitro-1H-indol-3-yl)propanoic acid;
2-amino-3-(4-methoxy-2-methyl-7-nitro-1H-indol-3-yl)propanoic acid;
2-amino-3-(5-amino-2-methyl-4-nitro-1H-indol-3-yl)propanoic acid;
2-amino-3-(6-amino-2-methyl-4-nitro-1H-indol-3-yl)propanoic acid;
2-amino-3-(7-amino-2-methyl-4-nitro-1H-indol-3-yl)propanoic acid;
2-amino-3-(4-amino-2-methyl-7-nitro-1H-indol-3-yl)propanoic acid;
2-amino-3-(5-hydroxy-2-methyl-4-nitro-1H-indol-3-yl)propanoic acid;
2-amino-3-(6-hydroxy-2-methyl-4-nitro-1H-indol-3-yl)propanoic acid;

2-amino-3-(7-hydroxy-2-methyl-4-nitro-1H-indol-3-yl)propanoic acid;
2-amino-3-(4-hydroxy-2-methyl-7-nitro-1H-indol-3-yl)propanoic acid;
2-amino-3-(2-methyl-4-nitro-5-phenyl-1H-indol-3-yl)propanoic acid;
2-amino-3-(2-methyl-4-nitro-6-phenyl-1H-indol-3-yl)propanoic acid;
2-amino-3-(2-methyl-4-nitro-7-phenyl-1H-indol-3-yl)propanoic acid;
2-amino-3-(2-methyl-7-nitro-4-phenyl-1H-indol-3-yl)propanoic acid;
2-amino-3-(5-cyclopropyl-2-methyl-4-nitro-1H-indol-3-yl)propanoic acid;
2-amino-3-(6-cyclopropyl-2-methyl-4-nitro-1H-indol-3-yl)propanoic acid;
2-amino-3-(7-cyclopropyl-2-methyl-4-nitro-1H-indol-3-yl)propanoic acid;
2-amino-3-(4-cyclopropyl-2-methyl-7-nitro-1H-indol-3-yl)propanoic acid;
2-amino-3-(2-methyl-4-nitro-5-vinyl-1H-indol-3-yl)propanoic acid;
2-amino-3-(2-methyl-4-nitro-6-vinyl-1H-indol-3-yl)propanoic acid;
2-amino-3-(2-methyl-4-nitro-7-vinyl-1H-indol-3-yl)propanoic acid;
2-amino-3-(2-methyl-7-nitro-4-vinyl-1H-indol-3-yl)propanoic acid;
2-amino-3-(5-ethynyl-2-methyl-4-nitro-1H-indol-3-yl)propanoic acid;
2-amino-3-(6-ethynyl-2-methyl-4-nitro-1H-indol-3-yl)propanoic acid;
2-amino-3-(7-ethynyl-2-methyl-4-nitro-1H-indol-3-yl)propanoic acid;
2-amino-3-(4-ethynyl-2-methyl-7-nitro-1H-indol-3-yl)propanoic acid;
2-amino-3-(2-methyl-5-morpholino-4-nitro-1H-indol-3-yl)propanoic acid;
2-amino-3-(2-methyl-6-morpholino-4-nitro-1H-indol-3-yl)propanoic acid;
2-amino-3-(2-methyl-7-morpholino-4-nitro-1H-indol-3-yl)propanoic acid;
2-amino-3-(2-methyl-4-morpholino-7-nitro-1H-indol-3-yl)propanoic acid;
2-amino-3-(2-methyl-5-(methylthio)-4-nitro-1H-indol-3-yl)propanoic acid;
2-amino-3-(2-methyl-6-(methylthio)-4-nitro-1H-indol-3-yl)propanoic acid;
2-amino-3-(2-methyl-7-(methylthio)-4-nitro-1H-indol-3-yl)propanoic acid;
2-amino-3-(2-methyl-4-(methylthio)-7-nitro-1H-indol-3-yl)propanoic acid;
2-amino-3-(2-methyl-4-nitro-5-(pyridin-4-yl)-1H-indol-3-yl)propanoic acid;
2-amino-3-(2-methyl-4-nitro-6-(pyridin-4-yl)-1H-indol-3-yl)propanoic acid;
2-amino-3-(2-methyl-4-nitro-7-(pyridin-4-yl)-1H-indol-3-yl)propanoic acid;
2-amino-3-(2-methyl-7-nitro-4-(pyridin-4-yl)-1H-indol-3-yl)propanoic acid;
2-amino-3-(1,2,5-trimethyl-4-nitro-1H-indol-3-yl)propanoic acid;
2-amino-3-(1,2,6-trimethyl-4-nitro-1H-indol-3-yl)propanoic acid;
2-amino-3-(1,2,7-trimethyl-4-nitro-1H-indol-3-yl)propanoic acid;
2-amino-3-(1,2,4-trimethyl-7-nitro-1H-indol-3-yl)propanoic acid;
2-amino-3-(6-fluoro-1,2-dimethyl-4-nitro-1H-indol-3-yl)propanoic acid;
2-amino-3-(7-fluoro-1,2-dimethyl-4-nitro-1H-indol-3-yl)propanoic acid;
2-amino-3-(4-fluoro-1,2-dimethyl-7-nitro-1H-indol-3-yl)propanoic acid;
2-amino-3-(5-chloro-1,2-dimethyl-4-nitro-1H-indol-3-yl)propanoic acid;
2-amino-3-(6-chloro-1,2-dimethyl-4-nitro-1H-indol-3-yl)propanoic acid;
2-amino-3-(7-chloro-1,2-dimethyl-4-nitro-1H-indol-3-yl)propanoic acid;
2-amino-3-(4-chloro-1,2-dimethyl-7-nitro-1H-indol-3-yl)propanoic acid;
2-amino-3-(5-bromo-1,2-dimethyl-4-nitro-1H-indol-3-yl)propanoic acid;
2-amino-3-(6-bromo-1,2-dimethyl-4-nitro-1H-indol-3-yl)propanoic acid;
2-amino-3-(7-bromo-1,2-dimethyl-4-nitro-1H-indol-3-yl)propanoic acid;
2-amino-3-(4-bromo-1,2-dimethyl-7-nitro-1H-indol-3-yl)propanoic acid;
2-amino-3-(5-methoxy-1,2-dimethyl-4-nitro-1H-indol-3-yl)propanoic acid;
2-amino-3-(6-methoxy-1,2-dimethyl-4-nitro-1H-indol-3-yl)propanoic acid;
2-amino-3-(7-methoxy-1,2-dimethyl-4-nitro-1H-indol-3-yl)propanoic acid;
2-amino-3-(4-methoxy-1,2-dimethyl-7-nitro-1H-indol-3-yl)propanoic acid;
2-amino-3-(5-amino-1,2-dimethyl-4-nitro-1H-indol-3-yl)propanoic acid;
2-amino-3-(6-amino-1,2-dimethyl-4-nitro-1H-indol-3-yl)propanoic acid;
2-amino-3-(7-amino-1,2-dimethyl-4-nitro-1H-indol-3-yl)propanoic acid;
2-amino-3-(4-amino-1,2-dimethyl-7-nitro-1H-indol-3-yl)propanoic acid;
2-amino-3-(5-hydroxy-1,2-dimethyl-4-nitro-1H-indol-3-yl)propanoic acid;
2-amino-3-(6-hydroxy-1,2-dimethyl-4-nitro-1H-indol-3-yl)propanoic acid;
2-amino-3-(7-hydroxy-1,2-dimethyl-4-nitro-1H-indol-3-yl)propanoic acid;
2-amino-3-(4-hydroxy-1,2-dimethyl-7-nitro-1H-indol-3-yl)propanoic acid;
2-amino-3-(1,2-dimethyl-4-nitro-5-phenyl-1H-indol-3-yl)propanoic acid;
2-amino-3-(1,2-dimethyl-4-nitro-6-phenyl-1H-indol-3-yl)propanoic acid;
2-amino-3-(1,2-dimethyl-4-nitro-7-phenyl-1H-indol-3-yl)propanoic acid;
2-amino-3-(1,2-dimethyl-7-nitro-4-phenyl-1H-indol-3-yl)propanoic acid;
2-amino-3-(5-cyclopropyl-1,2-dimethyl-4-nitro-1H-indol-3-yl)propanoic acid;
2-amino-3-(6-cyclopropyl-1,2-dimethyl-4-nitro-1H-indol-3-yl)propanoic acid;
2-amino-3-(7-cyclopropyl-1,2-dimethyl-4-nitro-1H-indol-3-yl)propanoic acid;
2-amino-3-(4-cyclopropyl-1,2-dimethyl-7-nitro-1H-indol-3-yl)propanoic acid;
2-amino-3-(1,2-dimethyl-4-nitro-5-vinyl-1H-indol-3-yl)propanoic acid;

2-amino-3-(1,2-dimethyl-4-nitro-6-vinyl-1H-indol-3-yl)
propanoic acid;
2-amino-3-(1,2-dimethyl-4-nitro-7-vinyl-1H-indol-3-yl)
propanoic acid;
2-amino-3-(1,2-dimethyl-7-nitro-4-vinyl-1H-indol-3-yl)
propanoic acid;
2-amino-3-(5-ethynyl-1,2-dimethyl-4-nitro-1H-indol-3-yl)
propanoic acid;
2-amino-3-(6-ethynyl-1,2-dimethyl-4-nitro-1H-indol-3-yl)
propanoic acid;
2-amino-3-(7-ethynyl-1,2-dimethyl-4-nitro-1H-indol-3-yl)
propanoic acid;
2-amino-3-(4-ethynyl-1,2-dimethyl-7-nitro-1H-indol-3-yl)
propanoic acid;
2-amino-3-(1,2-dimethyl-5-morpholino-4-nitro-1H-indol-3-yl)propanoic acid;
2-amino-3-(1,2-dimethyl-6-morpholino-4-nitro-1H-indol-3-yl)propanoic acid;
2-amino-3-(1,2-dimethyl-7-morpholino-4-nitro-1H-indol-3-yl)propanoic acid;
2-amino-3-(1,2-dimethyl-4-morpholino-7-nitro-1H-indol-3-yl)propanoic acid;
2-amino-3-(1,2-dimethyl-5-(methylthio)-4-nitro-1H-indol-3-yl)propanoic acid;
2-amino-3-(1,2-dimethyl-6-(methylthio)-4-nitro-1H-indol-3-yl)propanoic acid;
2-amino-3-(1,2-dimethyl-7-(methylthio)-4-nitro-1H-indol-3-yl)propanoic acid;
2-amino-3-(1,2-dimethyl-4-(methylthio)-7-nitro-1H-indol-3-yl)propanoic acid;
2-amino-3-(1,2-dimethyl-4-nitro-5-(pyridin-4-yl)-1H-indol-3-yl)propanoic acid;
2-amino-3-(1,2-dimethyl-4-nitro-6-(pyridin-4-yl)-1H-indol-3-yl)propanoic acid;
2-amino-3-(1,2-dimethyl-4-nitro-7-(pyridin-4-yl)-1H-indol-3-yl)propanoic acid; or
2-amino-3-(1,2-dimethyl-7-nitro-4-(pyridin-4-yl)-1H-indol-3-yl)propanoic acid;
and a pharmaceutically acceptable salt, prodrug, hydrate, or solvate thereof.

In embodiments, the disclosure is directed to a compound of Formula VII, or a pharmaceutically acceptable salt, prodrug, hydrate, or solvate thereof:

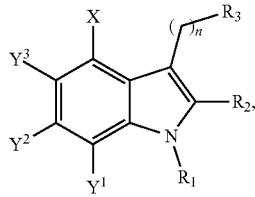

(Formula VII)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $—SR^{Ala}$,
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl;
$R_3$ is

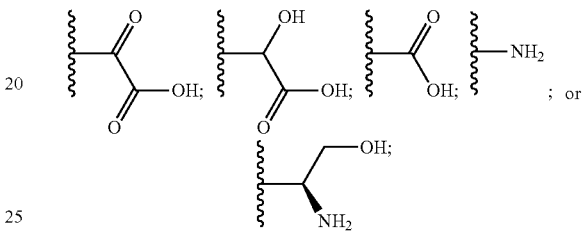

n is 0, 1, 2, or 3; and
X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H. In another aspect, $Y^1$ is H. In another aspect, $Y^2$ is H. In another aspect, $Y^3$ is H or OH. In another aspect, each of $Y^1$, $Y^2$, and $Y^3$ is H. In another aspect, $Y^1$ and $Y^2$ are each H; and $Y^3$ is OH.

In some aspects, the compound disclosure relates to a compound of Formula VII, wherein at least one of $Y^1$, $Y^2$, or $Y^3$ is a "weakly deactivating group", a "weakly activating group", a "moderately activating group", or a "strongly activating group", as known in the art and as defined herein. In other aspects, at least one of $Y^1$, $Y^2$, or $Y^3$ is H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{Ala}$, $—N(R^{Ala})_2$, or $—SR^{Ala}$.

In embodiments, $Y^1$, $Y^2$, or $Y^3$ is halogen and the halogen is fluorine. In embodiments, $Y^1$, $Y^2$, or $Y^3$ is unsubstituted $C_1$-$C_6$ alkyl. In embodiments, the unsubstituted $C_1$-$C_6$ alkyl is methyl (—$CH_3$). In embodiments, two of $Y^1$, $Y^2$ and $Y^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In some aspects, the disclosure relates to a compound of Formula VII, wherein at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$; or and Y$^1$ and Y$^2$ are each independently H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$. In another aspect, Y$^3$ is halogen or C$_{1-6}$ alkyl (e.g. methyl, CH$_3$). In another aspect, Y$^3$ is halogen or C$_{1-6}$ alkyl (e.g. methyl, CH$_3$) and at least one of Y$^1$ and Y$^2$ is hydrogen. In another aspect, Y$^3$ is halogen or C$_{1-6}$ alkyl (e.g. methyl, CH$_3$) and Y$^1$ and Y$^2$ are each hydrogen. In another aspect, Y$^3$ is halogen. In another aspect, Y$^3$ is halogen and at least one of Y$^1$ and Y$^2$ is hydrogen. In another aspect, Y$^3$ is halogen and Y$^1$ and Y$^2$ are each hydrogen. In certain embodiments, Y$^3$ is fluorine and at least one of Y$^1$ and Y$^2$ is hydrogen. In another aspect, Y$^3$ is fluorine and Y$^1$ and Y$^2$ are each hydrogen. In another aspect, Y$^3$ is C$_{1-6}$ alkyl. In another aspect, Y$^3$ is C$_{1-6}$ alkyl and at least one of Y$^1$ and Y$^2$ is hydrogen. In another aspect, Y$^3$ is C$_{1-6}$ alkyl and Y$^1$ and Y$^2$ are each hydrogen. In certain embodiments, Y$^3$ is methyl and at least one of Y$^1$ and Y$^2$ is hydrogen. In another aspect, Y$^3$ is methyl and Y$^1$ and Y$^2$ are each hydrogen.

In certain embodiments, the compound of Formula VII is a compound of Formula VIII:

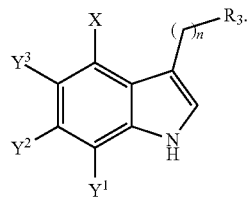

(Formula VIII)

In another aspect, the compound of Formula VII or Formula VIII is:
(3-(4-nitro-1H-indol-3-yl)-2-oxopropanoic acid;
2-hydroxy-3-(4-nitro-1H-indol-3-yl)propanoic acid;
2-(4-nitro-1H-indol-3-yl)acetic acid;
2-(4-nitro-1H-indol-3-yl)ethan-1-amine;
3-(2-aminoethyl)-4-nitro-1H-indol-5-ol; or
4-nitro-1H-indole-3-carboxylic acid;
and a pharmaceutically acceptable salt, prodrug, hydrate, or solvate thereof.

In embodiments, the disclosure is directed to a compound of Formula IX, or a pharmaceutically acceptable salt, prodrug, hydrate, or solvate thereof:

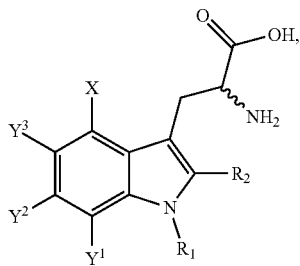

(Formula IX)

wherein:
each of Y$^2$ and Y$^3$ is, independently, hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$,
wherein each R$^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{Ala}$ are joined to form a substituted or unsubstituted, heterocyclic ring, or substituted or unsubstituted, heteroaryl ring;
R$_1$ is H or optionally substituted alkyl;
R$_2$ is H, optionally substituted alkyl, optionally substituted alkenyl, optionally substituted alkynyl, optionally substituted aryl, or optionally substituted heteroaryl; and
X is NO$_2$. In another aspect, R$_1$ is H or alkyl. In another aspect, R$_1$ is H. In another aspect, R$_1$ is alkyl. In another aspect, R$_1$ is H or methyl. In another aspect, R$_2$ is H. In another aspect, R$_1$ and R$_2$ are each H. In another aspect, R$_1$ is alkyl and R$_2$ is H. In another aspect, R$_1$ is methyl and R$_2$ is H. In another aspect, Y$^2$ is H. In another aspect, Y$^3$ is H. In another aspect, each of Y$^2$ and Y$^3$ is H.

In some aspects, the compound disclosure relates to a compound of Formula IX, wherein at least one of Y$^2$ or Y$^3$ is a "weakly deactivating group", a "weakly activating group", a "moderately activating group", or a "strongly activating group", as known in the art and as defined herein. In other aspects, at least one of Y$^2$ or Y$^3$ is H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$.

In embodiments, Y$^2$ or Y$^3$ is halogen and the halogen is fluorine. In embodiments, Y$^2$ or Y$^3$ is unsubstituted C$_1$-C$_6$ alkyl. In embodiments, the unsubstituted C$_1$-C$_6$ alkyl is methyl (—CH$_3$). In embodiments, both of Y$^2$ and Y$^3$ are hydrogen.

In some aspects, the disclosure relates to a compound of Formula IX, wherein at least one of Y$^2$ or Y$^3$ is halogen or C$_{1-6}$ alkyl (e.g. methyl, CH$_3$). In another aspect, Y$^3$ is halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$; or and Y$^1$ and Y$^2$ are each independently H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$. In another aspect, Y$^3$ is halogen or C$_{1-6}$ alkyl (e.g. methyl, CH$_3$). In another aspect, Y$^3$ is halogen or C$_{1-6}$ alkyl (e.g. methyl, CH$_3$) and Y$^2$ is hydrogen. In certain embodiments, Y$^3$ is fluorine and Y$^2$ is hydrogen. In another aspect, Y$^3$ is C$_{1-6}$ alkyl. In another aspect, Y$^3$ is C$_{1-6}$ alkyl and Y$^2$ is hydrogen. In certain embodiments, Y$^3$ is methyl and Y$^2$ is hydrogen.

In certain embodiments, the compound of Formula IX is a compound of Formula X:

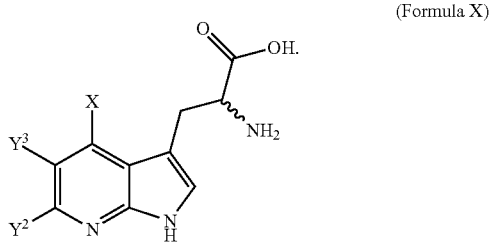

(Formula X)

In certain embodiments, the compound of Formula IX is a compound of Formula XI:

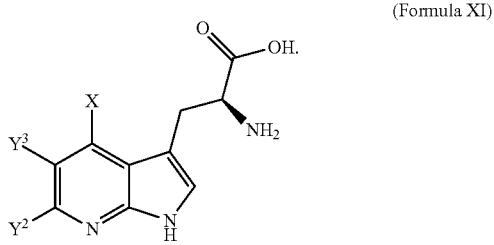

(Formula XI)

In another aspect, the compound of any one of Formulae IX-XI is 2-amino-3-(4-nitro-1H-pyrrolo[2,3-b]pyridin-3-yl)propanoic acid;

and a pharmaceutically acceptable salt, prodrug, hydrate, or solvate thereof.

In embodiments, the disclosure is directed to a compound of Formula XII, or a pharmaceutically acceptable salt, prodrug, hydrate, or solvate thereof:

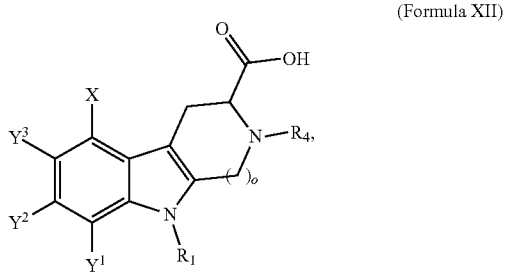

(Formula XII)

wherein:
each of Y$^1$, Y$^2$, and Y$^3$ is, independently, hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$, wherein each R$^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{Ala}$ are joined to form a substituted or unsubstituted, heterocyclic ring, or substituted or unsubstituted, heteroaryl ring;

R$_1$ is H or optionally substituted alkyl;
R$_4$ is H or optionally substituted alkyl;
o is 0, 1, 2, or 3; and
X is NO$_2$. In another aspect, R$_1$ is H or alkyl. In another aspect, R$_1$ is H. In another aspect, R$_1$ is alkyl. In another aspect, R$_1$ is H or methyl. In another aspect, R$_4$ is H or alkyl. In another aspect, R$_4$ is H. In another aspect, R$_1$ and R$_4$ are each H. In another aspect, R$_1$ is alkyl and R$_4$ is H. In another aspect, R$_1$ is methyl and R$_4$ is H. In another aspect, R$_1$ is H and R$_4$ is alkyl. In another aspect, R$_1$ is H and R$_4$ is methyl. In another aspect, Y$^1$ is H. In another aspect, Y$^2$ is H. In another aspect, Y$^3$ is H. In another aspect, each of Y$^1$, Y$^2$, and Y$^3$ is H. In another aspect, o is 1.

In embodiments, Y$^1$, Y$^2$, or Y$^3$ is halogen and the halogen is fluorine. In embodiments, Y$^1$, Y$^2$, or Y$^3$ is unsubstituted C$_1$-C$_6$ alkyl. In embodiments, the unsubstituted C$_1$-C$_6$ alkyl is methyl (—CH$_3$). In embodiments, two of Y$^1$, Y$^2$ and Y$^3$ are hydrogen. In embodiments, Y$^2$ and Y$^3$ are hydrogen. In embodiments, Y$^1$ and Y$^3$ are hydrogen. In embodiments, Y$^1$ and Y$^2$ are hydrogen.

In some aspects, the compound disclosure relates to a compound of Formula XII, wherein at least one of Y$^1$, Y$^2$, or Y$^3$ is a "weakly deactivating group", a "weakly activating group", a "moderately activating group", or a "strongly activating group", as known in the art and as defined herein. In other aspects, at least one of Y$^1$, Y$^2$, or Y$^3$ is H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$.

In embodiments, Y$^1$, Y$^2$, or Y$^3$ is halogen and the halogen is fluorine. In embodiments, Y$^1$, Y$^2$, or Y$^3$ is unsubstituted C$_1$-C$_6$ alkyl. In embodiments, the unsubstituted C$_1$-C$_6$ alkyl is methyl (—CH$_3$). In embodiments, two of Y$^1$, Y$^2$ and Y$^3$ are hydrogen. In embodiments, Y$^2$ and Y$^3$ are hydrogen. In embodiments, Y$^1$ and Y$^3$ are hydrogen. In embodiments, Y$^1$ and Y$^2$ are hydrogen.

In some aspects, the disclosure relates to a compound of Formula XII, wherein at least one of Y$^1$, Y$^2$ or Y$^3$ is halogen or C$_{1-6}$ alkyl (e.g. methyl, CH$_3$). In another aspect, Y$^3$ is halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$; and Y$^1$ and Y$^2$ are each independently H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$. In another aspect, Y$^3$ is halogen or C$_{1-6}$ alkyl (e.g. methyl, CH$_3$). In another aspect, Y$^3$ is halogen or C$_{1-6}$ alkyl (e.g. methyl, CH$_3$) and at least one of Y$^1$ and Y$^2$ is hydrogen. In another aspect, Y$^3$ is halogen or C$_{1-6}$ alkyl (e.g. methyl, CH$_3$) and Y$^1$ and Y$^2$ are each hydrogen. In another aspect, Y$^3$ is halogen. In another aspect, Y$^3$ is halogen and at least one of Y$^1$ and Y$^2$ is hydrogen. In another aspect, Y$^3$ is halogen and Y$^1$ and Y$^2$ are each hydrogen. In certain embodiments, Y$^3$ is fluorine and at least one of Y$^1$ and Y$^2$ is hydrogen. In another aspect, Y$^3$ is fluorine and Y$^1$ and Y$^2$ are each hydrogen. In another aspect, Y$^3$ is C$_{1-6}$ alkyl. In another aspect, Y$^3$ is C$_{1-6}$ alkyl and at least one of Y$^1$ and Y$^2$ is hydrogen. In another aspect, Y$^3$ is C$_{1-6}$ alkyl and Y$^1$ and Y$^2$ are each hydrogen. In certain embodiments, Y$^3$ is methyl and at least one of Y$^1$ and Y$^2$ is hydrogen. In another aspect, Y$^3$ is methyl and Y$^1$ and Y$^2$ are each hydrogen.

In certain embodiments, the compound of Formula XII is a compound of Formula XIII:

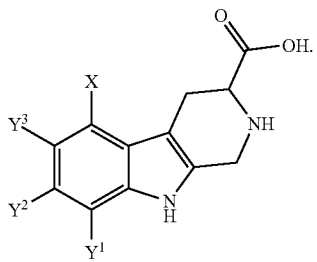

(Formula XIII)

In certain embodiments, the compound of Formula XII is a compound of Formula XIV:

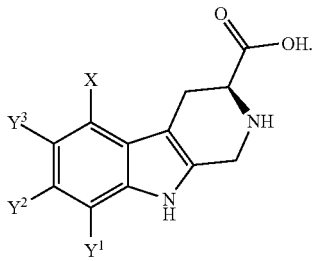

(Formula XIV)

In another aspect, the compound of any one of Formulae XII-XIV is 5-nitro-2,3,4,9-tetrahydro-1H-pyrido[3,4-b]indole-3-carboxylic acid;

and a pharmaceutically acceptable salt, prodrug, hydrate, or solvate thereof.

In embodiments, the disclosure is directed to a compound of Formula XV, or a pharmaceutically acceptable salt, prodrug, hydrate, or solvate thereof:

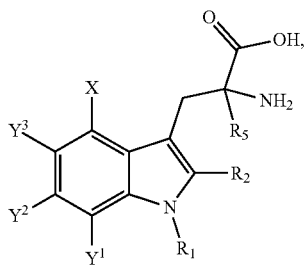

(Formula XV)

wherein:
each of Y$^1$, Y$^2$, and Y$^3$ is, independently, hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or —SR$^{Ala}$, wherein each R$^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{Ala}$ are joined to form a substituted or unsubstituted, heterocyclic ring, or substituted or unsubstituted, heteroaryl ring;

R$_1$ is H or optionally substituted alkyl;
R$_2$ is H, optionally substituted alkyl, optionally substituted alkenyl, optionally substituted alkynyl, optionally substituted aryl, or optionally substituted heteroaryl;
R$_5$ is optionally substituted alkyl; and
X is NO$_2$. In another aspect, R$_1$ is H or alkyl. In another aspect, R$_1$ is H. In another aspect, R$_1$ is alkyl. In another aspect, R$_1$ is H or methyl. In another aspect, R$_2$ is H. In another aspect, R$_1$ and R$_2$ are each H. In another aspect, R$_1$ is alkyl and R$_2$ is H. In another aspect, R$_1$ is methyl and R$_2$ is H. In another aspect, R$_5$ is alkyl. In another aspect, R$_5$ is methyl. In another aspect, R$_1$ is alkyl, R$_2$ is H, and R$_5$ is alkyl. In another aspect, R$_1$ is H, R$_2$ is H, and R$_5$ is alkyl. In another aspect, R$_1$ is H, R$_2$ is H, and R$_5$ is methyl.

In some aspects, the compound disclosure relates to a compound of Formula XV, wherein at least one of Y$^1$, Y$^2$, or Y$^3$ is a "weakly deactivating group", a "weakly activating group", a "moderately activating group", or a "strongly activating group", as known in the art and as defined herein. In other aspects, at least one of Y$^1$, Y$^2$, or Y$^3$ is H, halogen (e.g. F, Cl, Br, I), substituted or unsubstituted C$_{1-6}$ alkyl (e.g. methyl, CH$_3$), substituted or unsubstituted C$_{2-6}$ alkenyl, substituted or unsubstituted C$_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{Ala}$, —N(R$^{Ala}$)$_2$, or SR$^{Ala}$.

In embodiments, Y$^1$, Y$^2$, or Y$^3$ is halogen and the halogen is fluorine. In embodiments, Y$^1$, Y$^2$, or Y$^3$ is unsubstituted C$_1$-C$_6$ alkyl. In embodiments, the unsubstituted C$_1$-C$_6$ alkyl is methyl (—CH$_3$). In embodiments, two of Y$^1$, Y$^2$ and Y$^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In some aspects, the disclosure relates to a compound of Formula XV, wherein at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{Ala}$, $-N(R^{Ala})_2$, $-SR^{Ala}$; or and $Y^1$ and $Y^2$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{Ala}$, $-N(R^{Ala})_2$, or $-SR^{Ala}$. In another aspect, $Y^3$ is is halogen or $C_{1-6}$ alkyl (e.g. methyl, $CH_3$). In another aspect, $Y^3$ is halogen or $C_{1-6}$ alkyl (e.g. methyl, $CH_3$) and at least one of $Y^1$ and $Y^2$ is hydrogen. In another aspect, $Y^3$ is halogen or $C_{1-6}$ alkyl (e.g. methyl, $CH_3$) and $Y^1$ and $Y^2$ are each hydrogen. In another aspect, $Y^3$ is halogen. In another aspect, $Y^3$ is halogen and at least one of $Y^1$ and $Y^2$ is hydrogen. In another aspect, $Y^3$ is halogen and $Y^1$ and $Y^2$ are each hydrogen. In certain embodiments, $Y^3$ is fluorine and at least one of $Y^1$ and $Y^2$ is hydrogen. In another aspect, $Y^3$ is fluorine and $Y^1$ and $Y^2$ are each hydrogen. In another aspect, $Y^3$ is $C_{1-6}$ alkyl. In another aspect, $Y^3$ is $C_{1-6}$ alkyl and at least one of $Y^1$ and $Y^2$ is hydrogen. In another aspect, $Y^3$ is $C_{1-6}$ alkyl and $Y^1$ and $Y^2$ are each hydrogen. In certain embodiments, $Y^3$ is methyl and at least one of $Y^1$ and $Y^2$ is hydrogen. In another aspect, $Y^3$ is methyl and $Y^1$ and $Y^2$ are each hydrogen.

In certain embodiments, the compound of Formula XV is a compound of Formula XVI:

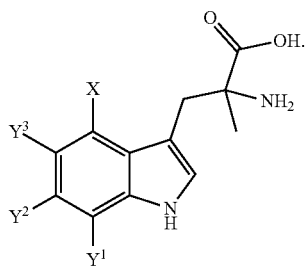

(Formula XVI)

In another aspect, the compound of Formula XV or Formula XVI is 2-amino-2-methyl-3-(4-nitro-1H-indol-3-yl)propanoic acid;
and a pharmaceutically acceptable salt, prodrug, hydrate, or solvate thereof.

In some aspects, the disclosure relates to a composition comprising the compound of Formulae IXVI, or a pharmaceutically acceptable salt, prodrug, hydrate, or solvate thereof, that is produced by a method described by the disclosure. In some embodiments, the composition further comprises a pharmaceutically acceptable carrier. In some aspects, the disclosure provides a polypeptide comprising the compound of Formulae IXVI, or a pharmaceutically acceptable salt, prodrug, hydrate, or solvate thereof. In some aspects, the disclosure relates to a cell comprising a compound of IXVI, or a pharmaceutically acceptable salt, prodrug, hydrate, or solvate thereof.

In some aspects, the disclosure relates to methods of producing a compound of Formulae I-XVI, or a pharmaceutically acceptable salt, prodrug, hydrate, or solvate thereof. In some aspects, the method comprises contacting a compound of Formulae Ia, IVa, VIIa, IXa, or XVa with (i) at least one reductase enzyme; and, (ii) a cytochrome P450 enzyme which catalyzes transfer of a nitro functional group to a compound of Formulae Ia, IVa, VIIa, IXa, or XVa, in the presence of NAD(P)H.

In another aspect, the disclosure is related to a method of producing a compound of Formula I, or a pharmaceutically acceptable salt, prodrug, hydrate, or solvate thereof, the method comprising contacting a compound of Formula Ia:

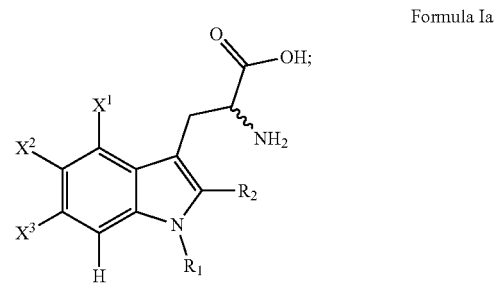

Formula Ia with any of the TxtE-BM3R fusion proteins described herein to produce a compound of Formula I:

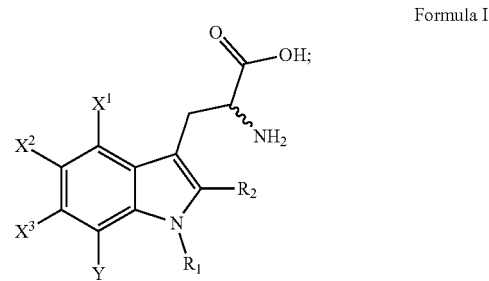

Formula I wherein:
each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{Ala}$, $-N(R^{Ala})_2$, or $SR^{Ala}$;
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring; each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or $SR^{Ala}$;

wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;

Y is $NO_2$;

$R_1$ is H or optionally substituted alkyl; and $R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In another aspect, the disclosure is related to a method of producing a compound of Formula IV, or a pharmaceutically acceptable salt, prodrug, hydrate, or solvate thereof, the method comprising contacting a compound of Formula IVa:

Formula IVa with any of the TxtE-BM3R fusion proteins described herein to produce a compound of Formula IV:

Formula IV wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$R(R^{Ala})_2$, or —$SR^{Ala}$; and wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;

X is $NO_2$;

$R_1$ is H or optionally substituted alkyl; and $R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In another aspect, the disclosure is related to a method of producing a compound of Formula VII, or a pharmaceutically acceptable salt, prodrug, hydrate, or solvate thereof, the method comprising contacting a compound of Formula VIIa:

Formula VIIa with any of the TxtE-BM3R fusion proteins described herein to produce a compound of Formula VII:

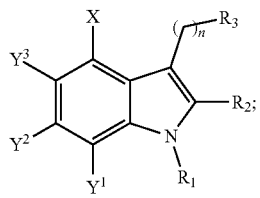

Formula VII

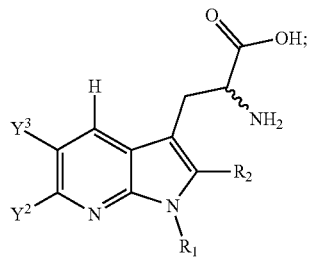

Formula IXa wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$R^{Ala}$, wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl;

$R_3$ is

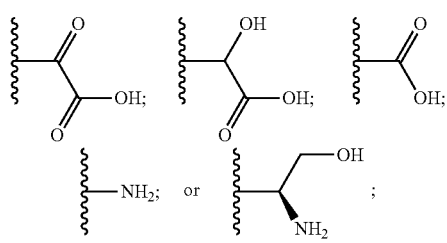

n is 0, 1, 2, or 3; and

X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H. In another aspect, $Y^1$ is H. In another aspect, $Y^2$ is H. In another aspect, $Y^3$ is H or OH. In another aspect, each of $Y^1$, $Y^2$, and $Y^3$ is H. In another aspect, $Y^1$ and $Y^2$ are each H; and $Y^3$ is OH.

In another aspect, the disclosure is related to a method of producing a compound of Formula IX, or a pharmaceutically acceptable salt, prodrug, hydrate, or solvate thereof, the method comprising contacting a compound of Formula IXa:

with any of the TxtE-BM3R fusion proteins described herein to produce a compound of Formula IX:

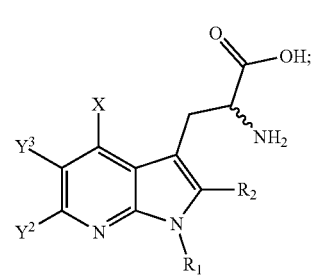

Formula IX wherein:

each of $Y^2$ and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$SR^{Ala}$, wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H. In another aspect, $Y^2$ is H. In another aspect, $Y^3$ is H. In another aspect, each of $Y^2$ and $Y^3$ is H.

In another aspect, the disclosure is related to a method of producing a compound of Formula XII, or a pharmaceutically acceptable salt, prodrug, hydrate, or solvate thereof, the method comprising contacting a compound of Formula XIIa:

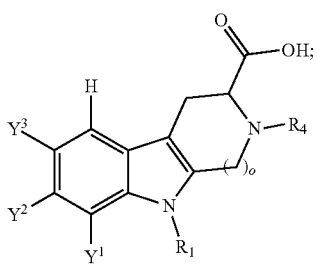

Formula XIIa with any of the TxtE-BM3R fusion proteins described herein to produce a compound of Formula XII:

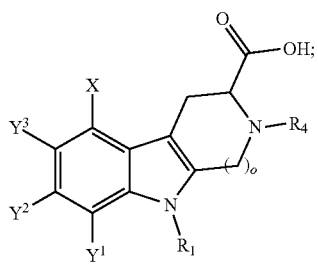

Formula XII wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$SR^{Ala}$,
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;
$R_1$ is H or optionally substituted alkyl;
$R_4$ is H or optionally substituted alkyl;
o is 0, 1, 2, or 3; and
X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_4$ is H or alkyl. In another aspect, $R_4$ is H. In another aspect, $R_1$ and $R_4$ are each H. In another aspect, $R_1$ is alkyl and $R_4$ is H. In another aspect, $R_1$ is methyl and $R_4$ is H. In another aspect, $R_1$ is H and $R_4$ is alkyl. In another aspect, $R_1$ is H and $R_4$ is methyl. In another aspect, $Y^1$ is H. In another aspect, $Y^2$ is H. In another aspect, $Y^3$ is H. In another aspect, each of $Y^1$, $Y^2$, and $Y^3$ is H. In another aspect, o is 1. In embodiments, $Y^1$, $Y^2$, or $Y^3$ is halogen and the halogen is fluorine. In embodiments, $Y^1$, $Y^2$, or $Y^3$ is unsubstituted $C_1$-$C_6$ alkyl. In embodiments, the unsubstituted $C_1$-$C_6$ alkyl is methyl (—$CH_3$). In embodiments, two of $Y^1$, $Y^2$ and $Y^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In another aspect, the disclosure is related to a method of producing a compound of Formula XV, or a pharmaceutically acceptable salt, prodrug, hydrate, or solvate thereof, the method comprising contacting a compound of Formula XVa:

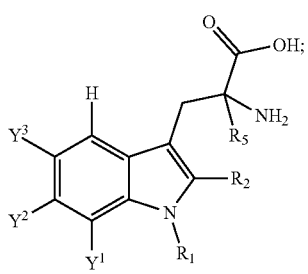

Formula XVa with any of the TxtE-BM3R fusion proteins described herein to produce a compound of Formula XV:

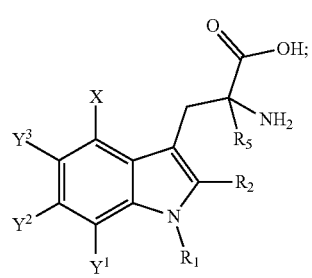

Formula XV wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$SR^{Ala}$,
wherein each $R^{Ala}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{Ala}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl;
$R_5$ is optionally substituted alkyl; and
X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H. In another aspect, $R_5$ is alkyl. In another aspect, $R_5$ is methyl. In another aspect, $R_1$ is alkyl, $R_2$ is H, and $R_5$ is alkyl. In another aspect, $R_1$ is H, $R_2$ is H, and $R_5$ is alkyl. In another aspect, $R_1$ is H, $R_2$ is H, and $R_5$ is methyl.

BRIEF DESCRIPTION OF DRAWINGS

FIG. 3A shows identification of a notable length difference at the loop connecting J and K helices after superimposing crystal structures of TxtE (PDB: 4TPO) (left) and P450BM3 heme domain (PDB: 1ZO9) (right). FIG. 3B shows a schematic depiction of the interface between BM3 heme and FMN-binding domains. The loop connecting J and K helices is shown on the left side of the structure and its basic residues are shown as sticks. Acidic residues in the loop motif of FMN-binding domain are also shown.

FIG. 7A shows the chemical structures of Trp and its analogs that induced type I spectral shift of TxtE and TB14. FIG. 7B shows the structures of compounds that had no detectable level of interactions with TxtE and TB14.

DETAILED DESCRIPTION

Figure 1:
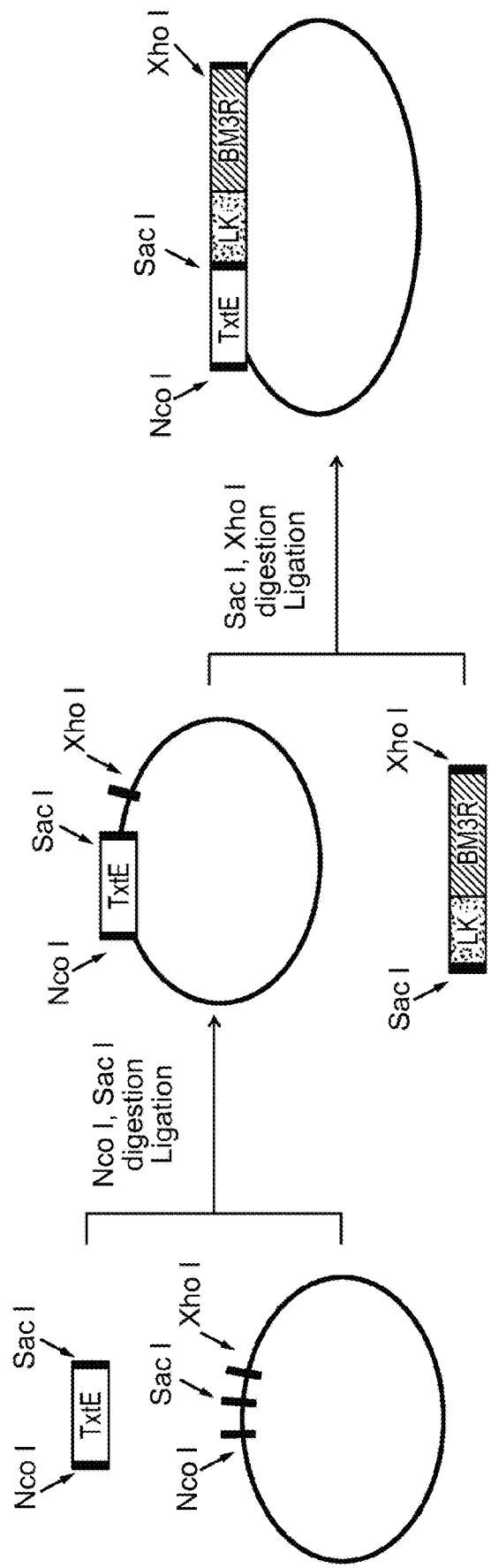
FIG. 1 shows a schematic depiction of stepwise construction of TxtE chimeras with variable lengths. The expression vector backbone is pET28b.

Aromatic nitration is an essential chemical reaction for the production of a variety of important industrial chemicals. For example, nitro compounds are used in the production of food additives, herbicides and pharmaceuticals. However, currently used technologies to perform aromatic nitration on an industrial scale are hampered by challenges ranging from lack of reaction efficiency to the production of environmentally unfriendly by-products. Therefore, new approaches for direct aromatic nitration must be developed.

Without wishing to be bound by any particular theory, aromatic nitration using biocatalysts offers a number of distinct advantages, such as high efficiency, high degree of selectivity, mild reaction conditions, and environmental friendliness, over currently used chemical catalysis. Accordingly, provided herein are methods and compositions for nitration of aromatic compounds. In some aspects, the present invention relates to the use of a biocatalyst for aromatic nitration. In some embodiments, the biocatalyst is a cytochrome P450 enzyme. As discussed above, it is believed that the active nitration species in the nitration processes delineated herein is the nitronium ion, $NO_{2+}$. Thus, it is believed that the nitration processes presented herein proceed via an electrophilic aromatic substitution mechanism. Therefore, as is well established in the art for processes involving electrophilic aromatic substitution, substituents on the aromatic system (e.g., $X^1$, $X^2$, $X^3$ in Formulae I, Ia, II, III, IV, IVa, V, or VI; $Y^1$, $Y^2$, $Y^3$ in Formulae VII, VIIa, VIII, XII, XIIa, XIII, XIV, XV, XVa, or XVI; and $Y^2$, $Y^3$ in Formulae IX, IXa, X, or XI) that increase the electron density of the aromatic system are well-known in the art as "activating groups", and increase the rate of electrophilic aromatic substitution (e.g., nitration) relative to the unsubstituted aromatic system, while substituents that decrease the electron density of the aromatic system are well-known in the art as "deactivating groups", and decrease the rate of electrophilic aromatic substitution relative to the unsubstituted aromatic system. The "activating groups" are further classified as "weakly activating groups" (i.e., groups that weakly increase reaction rate), "moderately activating groups" (i.e., groups that moderately increase reaction rate), and "strongly activating groups" (i.e., groups that strongly increase reaction rate), while "deactivating groups" are further classified as "weakly deactivating groups" (i.e., groups that weakly decrease reaction rate), "moderately deactivating groups" (i.e., groups that moderately decrease reaction rate), and "strongly deactivating groups" (i.e., groups that strongly decrease reaction rate).

Non-limiting examples of "weakly activating groups" are alkyl groups (e.g., methyl, ethyl, and the like), aryl groups (e.g., phenyl, naphthyl, and the like), and unsaturated hydrocarbon moieties (e.g., alkenyl, alkynyl, and the like). Non-limiting examples of "moderately activating groups" are N-attached amides (—NHCOR) and O-attached esters (—OCOR). Non-limiting examples of "strongly activating groups" are —$NH_2$, —NHR, —$NR_2$, —OR (e.g., —OMe, —OEt, and the like), and —OH. Non-limiting examples of "weakly deactivating groups" are halogen groups (e.g., —F, —Cl, —Br, and the like). Non-limiting examples of "moderately deactivating groups" are formyl (e.g., —CHO), ketones (—COR), carboxylic acid (—COOH), C-attached carboxylic esters (—COOR), carboxylic acid halides (e.g., —COCl, and the like), and C-attached amides (—$CONH_2$, —CONHR, —$CONHR_2$, and the like). Non-limiting examples of "strongly deactivating groups" are trihaloalkyl moieties (e.g., —$CF_3$, and the like), —CN, S-attached sulfonates (e.g., —$SO_3R$, and the like), quaternary ammonium salts (e.g., —$NH_3^+$, —$NR_3^+$, and the like), and —$NO_2$.

In some aspects, the disclosure relates to the use of a biocatalyst for aromatic nitration. In some embodiments, the biocatalyst is a self-sufficient cytochrome P450 enzyme. Previously described self-sufficient cytochrome P450 enzymes typically comprise (i) a cytochrome P450 enzyme which catalyzes transfer of a nitro functional group to aromatic moieties (e.g., indole); (ii) an amino acid linker; and, (iii) a catalytic domain of a reductase enzyme. For example, TxtE-P450BM3 (also referred to herein as TB13-Q) is described in PCT Publication WO 2016/134145, the entire contents of which are incorporated by reference herein. However, previously described self-sufficient P450 enzymes, in some embodiments, exhibit reduced activity (e.g., lower electron coupling efficiency, total turnover number (TTN), etc.) compared to wild-type cytochrome P450 enzymes which catalyze transfer of a nitro functional group to a L-tryptophan (e.g., wild-type TxtE).

In certain aspects, the invention is based, in part, upon the surprising discovery that altering linker length of certain TxtE-BM3R fusion proteins results in improved catalytic turnover, coupling efficiency and substrate specificity relative to previously described TxtE-BM3 fusion proteins. Therefore, in some aspects, the disclosure provides a fusion protein comprising: (i) a TxtE enzyme; (ii) an amino acid linker that is 11, 12, or between 14 and 27 amino acids in length; and, (iii) a catalytic domain of a CYP102A1 (P450BM3) reductase enzyme, wherein the linker joins (iii) to a terminus of (i).

As used herein, the term "TxtE enzyme" refers to a (i) polypeptide comprising the entire amino acid sequence of TxtE, (ii) a portion of TxtE which maintains the function of catalyzing transfer of a nitro functional group to aromatic moieties (e.g., indole), or (iii) an enzyme which catalyzes transfer of a nitro functional group to aromatic moieties (e.g., indole) and is at least 95% homologous to the amino acid sequence of TxtE. For example, in some embodiments, a TxtE enzyme comprises or consists of a sequence set forth in Genebank Accession No. CBG70284.1 or a portion thereof (e.g., SEQ ID NO: 56).

The skilled artisan recognizes that for a portion of TxtE to maintain the nitration function, the portion must include active site residues of TxtE, for example Arg59, Asn293, Thr296 and Glu394. However, genetic modification of residues at a location of the TxtE polypetide remote from the active site may maintain the activity of the enzyme. As used herein, the term "genetic modification" refers to amino acid substitution (conservative, missense and/or non-sense), deletion and/or insertion. Thus in some embodiments, a portion of TxtE comprises at least 1, at least 2, at least 3, at least 4, at least 5, at least 10, at least 20, at least 30, at least 40, at least 50, at least 75, or at least 100 genetic modifications relative to wild-type TxtE. In some embodiments a portion of TxtE is truncated relative to wild-type TxtE. Truncations may occur at the N-terminus or C-terminus of the portion of TxtE. For example, a portion of TxtE may be truncated by 1, 2, 3, 4, 5, 10, 20, 30, 40, 50, 75, 100 or 200 amino acids at it N-terminus or C-terminus relative to wild-type TxtE.

In some embodiments, the disclosure provides a TxtE enzyme in which the loop region corresponding to residues A274 to V279 of Genebank Accession No. CBG70284.1 are replaced by the heme domain (e.g. loops "j" and "k") of CYP102A1 (e.g., P450BM3, PDB ID: 1BVY). In some embodiments, a TxtE enzyme comprises or consists of the sequence set forth in SEQ ID NO: 58.

Methods of genetically modifying TxtE or portions thereof and screening for renention of functional activity are known in the art and available to the skilled artisan. For example, TxtE may be modified by directed evolution or random mutagenesis and biochemcially assayed for the capability to transfer a nitro group to aromatic moieties (e.g., indole). In some embodiments, a TxtE enzyme may be an enzyme which catalyzes transfer of a nitro functional group to aromatic moieties (e.g., indole) and has less than 95% homologous to the amino acid sequence of TxtE. In some embodiments, the enzyme has about 90%, about 80%, about 70%, about 60% or about 50% homology to the amino acid sequence of TxtE.

In some aspects, the disclosure provides fusion proteins comprising a catalytic domain of a reductase enzyme. As used herein, the term "reductase enzyme" refers to an enzyme that catalyzes a reduction reaction. Non-limiting examples of reductase enzymes include thioredoxn reductase, cytochrome P450 reductase and flavin adenine dinucleotide (FAD) reductase. In some embodiments, the reductase enzyme is a prokaryotic reductase enzyme. In some embodiments, the reductase enzyme is a bacterial reducatase enzyme. In some embodiments, the bacterial reductase enzyme naturally occurs in a self-sufficient cytochrome P450, for example CYP102A1 (P450BM3) reductase or a P450RhF reductase. In some embodiments, the catalytic domain of a reductase enzyme comprises or consists of the sequence set forth in SEQ ID NO: 57.

In some embodiments, the fusion protein comprises an amino acid linker. As used herein, the term "linker" refers to an amino acid sequence that joins two larger polypeptide domains to form a single fusion polypeptide. Amino acid linkers are well known to those skilled in the art and include flexible linkers (e.g. glycine rich linkers such as [GGGS]$_n$ where n>2), rigid linkers (e.g. poly-proline rich linkers) and cleavable linkers (e.g. photocleavable and enzyme-sensitive linkers). In some embodiments, an amino acid linker is derived from a TxtE enzyme or a reductase enzyme (e.g., CYP102A1). For example, in some embodiments, an amino acid linker may comprise between about 3 and about 27 continuous (e.g., covalently linked) amino acids of a reductase enzyme (e.g., between about 3 and about 27 contiguous amino acids the sequence set forth in UniProtKB/Swiss-Prot Accession No. P14779.2. In some embodiments, an amino acid linker comprises between about 3 and about 27 contiguous amino acids of SEQ ID NO: 57.

In some embodiments, amino acid linker length affects the folding and orientation of fusion polypeptides. For example, a linker that is too long can prevent the interaction of a reductase domain with the cytochrome P450 enzyme to which it is linked. (It is also known that long linkers can fold and take on specific orientations that can be desirable.) Conversely, a linker that is too short can cause a reductase enzyme to sterically inhibit binding of substrate to the active site of the P450 enzyme to which it is linked. The disclosure is based, in part, on the surprising discovery that TxtE-Bm3 fusion proteins comprising linkers having a certain length (e.g., 11, 12, 14, 15, 16, 17, etc. amino acids in length) exhibit improved function (e.g., increased nitration activity, coupling efficiency, total turnover number (TTN), etc.) compared to previously described self-sufficient cytochrome p450 enzymes. Accordingly, in some embodiments, a fusion protein described by the disclosure comprises an amino acid linker between about 3 and about 27 amino acids in length. In some embodiments, an amino acid linker is between about 11 and about 17 amino acids in length. In some embodiments, an amino acid linker is between about 14 and 16 amino acids in length. In some embodiments, the length of the linker is 11, 12, 14, 15, 16, 17, 18, 19, 20, 21, 22, 23, 24, 25, 26, or 27 amino acids in length.

In some embodiments, the amino acid linker joins a catalytic domain of a reductase enzyme to a terminus of a cytochrome P450 enzyme. As used herein, the term "terminus" refers to the ends of a polypeptide sequence relative to the start codon of said polypeptide. For example, the N-terminus of a polypeptide is the end of the polypeptide containing the start codon (AUG) of the polypeptide, whereas the C-terminus of the polypeptide is the end of the polypeptide opposite of the start codon. In some embodiments, the amino acid linker joins the a catalytic domain of a reductase enzyme to the C-terminus of a cytochrome P450 enzyme. In some embodiments, the amino acid linker joins CYP102A1 (P450BM3) reductase or P450RhF reductase to the C-terminus of a TxtE enzyme.

Generally, fusion proteins described by the disclosure can be produced by any suitable means known in the art. For example, in some embodiments, a fusion protein is produced by an overlap PCR method. As used herein, "overlap PCR" refers to the splicing (e.g., joining together) of two or more oligonucleotides by polymerase chain reaction employing primers that share complementarity with the terminus of each of the oligonucleotides, for example as described by Higuchi et al. (1988) Nucleic Acids Res. 16 (15): 7351-67. In some embodiments, fusion proteins described by the disclosure are not produced by overlap PCR. In some embodiments, fusion proteins described by the disclosure are produced by a restriction digest-based method (e.g., traditional cloning), for example as described in Molecular Cloning: A Laboratory Manual, J. Sambrook, et al., eds., Second Edition, Cold Spring Harbor Laboratory Press, Cold Spring Harbor, N.Y., 1989.

In some aspects, the disclosure relates to an expression construct comprising a fusion protein as described by the disclosure. As used herein, the term "expression construct" refers to an artificially constructed molecule comprising a nucleic acid (e.g. DNA) capable of artificially carrying foreign genetic material into another cell (for example, a bacterial cell). In some embodiments, vectors carry common functional elements including an origin of replication, a multicloning site, a selectable marker and, optionally a promoter sequence. In some embodiments, the selectable marker is a bacterial resistance gene, for example kanamycin, chloramphenicol or β-lactamase. Non-limiting examples of vectors include plasmids, viral vectors, cosmids, and artificial chromosomes. In some embodiments, the vector is a high-copy plasmid. In some embodiments, the vector is a low-copy plasmid. In some embodiments, the vectors of the disclosure are maintained inside cells. In some embodiments, the vectors of the disclosure are maintained in a non-cellular environment, for example as part of a kit. Methods of introducing vectors into bacteria are well known in the art and described, for example, in Current Protocols in Molecular Biology, Ausubel et al. (Eds), John Wiley and Sons, New York, 2007.

In some aspects, the disclosure relates to isolated nucleic acids encoding the fusion proteins described herein. As used herein "nucleic acid" refers to a DNA or RNA molecule. Nucleic acids are polymeric macromolecules comprising a plurality of nucleotides. In some embodiments, the nucleotides are deoxyribonucleotides or ribonucleotides. In some embodiments, the nucleotides comprising the nucleic acid are selected from the group consisting of adenine, guanine, cytosine, thymine, uracil and inosine. In some embodiments, the nucleotides comprising the nucleic acid are modified nucleotides. Non-limiting examples of natural nucleic acids include genomic DNA and plasmid DNA. In some embodiments, the nucleic acids of the instant disclosure are synthetic. As used herein, the term "synthetic nucleic acid" refers to a nucleic acid molecule that is constructed via joining nucleotides by a synthetic or non-natural method. One non-limiting example of a synthetic method is solid-phase oligonucleotide synthesis. In some embodiments, the nucleic acids of the instant disclosure are isolated.

In some aspects, the disclosure relates to the transfer of a nitro group ($NO_2$) to an aromatic molecule. In some embodiments, the aromatic molecule is an indole. In some embodiments, the aromatic molecule is L-tryptophan or a substituted tryptophan. In some embodiments, the aromatic molecule is substituted. In some embodiments, the aromatic molecule is substituted on its indole ring. In some embodiments, the aromatic molecule is substituted on the benzoid portion of an indole moiety (i.e., at the 4-, 5-, 6-, or 7-position). In some embodiments, the substituted aromatic molecule is a compound of Formulae Ia, IVa, VIIa, IXa, XIIa, or XVa. The substitution may be halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3-to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{Ala}$, —$N(R^{Ala})_2$, or —$SR^{Ala}$, provided that the substitution does not comprise a "moderately deactivating group", a "strongly deactivating group", or does not sterically hinder interaction between the P450 enzyme and the reductase enzyme catalytic domain. As used herein, the terms "moderately deactivating group" and "strongly deactivating group" refer to a functional moiety that moderately or strongly reduces the rate of electrophilic aromatic substitution (e.g., nitration), respectively, relative to the corresponding unsubstituted aromatic moiety, as is well-known in the art. Non-limiting examples of "moderately deactivating groups" are formyl (e.g., —CHO), ketones, carboxylic acid (—COOH), C-attached carboxylic esters, carboxylic acid halides (e.g., —COCl, and the like), and C-attached amides. Non-limiting examples of "strongly deactivating groups" are trihaloalkyl moieties (e.g., —$CF_3$, and the like), —CN, S-attached sulfonates, quaternary ammonium salts, and —$NO_2$. Steric hindrance may occur if the substitution on the indole ring comprises a large molecule that impedes access of the substrate to the active site of P450 enzyme or prevents interaction of reductase with P450 enzyme.

In certain aspects, each of $X^1$, $X^2$, $X^3$, $Y^1$, $Y^2$, and $Y^3$ is independently —H, a "weakly deactivating group", a "weakly activating group", a "moderately activating group", or a "strongly activating group". Non-limiting examples of "weakly activating groups" are alkyl groups (e.g., methyl, ethyl, and the like), aryl groups (e.g., phenyl, naphthyl, and the like), and unsaturated hydrocarbon moieties (e.g., alkenyl, alkynyl, and the like). Non-limiting examples of "moderately activating groups" are N-attached amides and O-attached esters. Non-limiting examples of "strongly activating groups" are —$NH_2$, secondary amines, tertiary amines, alkoxy (e.g., —OMe, —OEt, and the like), and —OH. Non-limiting examples of "weakly deactivating groups" are halogen groups (e.g., —F, —Cl, —Br, and the like).

In some aspects, the disclosure relates to compounds produced by aromatic nitration. Certain aspects of the disclosure relate to unnatural compounds produced by the transfer of a nitro group to a compound of any of Formulae Ia, IVa, VIIa, IXa, XIIa, or XVa by TxtE-BM3R fusion proteins described herein. Accordingly, in some aspects the disclosure provides a method for producing a compound of any of the Formulae I-XVI using any of the methods described herein Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In general, alkyl, alkenyl, and alkynyl groups contain 1-20 aliphatic carbon atoms. In embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$—cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkyl" in general refers to a radical of a straight-chain or branched saturated hydrocarbon group having from 1 to 20 carbon atoms ("$C_{1-20}$ alkyl"). In embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents (e.g., halogen, such as F). In certain embodiments, the alkyl group is unsubstituted $C_{1-10}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —$CF_3$, Bn).

"Alkenyl", in general, refers to a radical of a straight-chain or branched hydrocarbon group having from 2 to 20 carbon atoms, one or more carbon-carbon double bonds, and no triple bonds ("$C_{2-20}$ alkenyl"). In embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

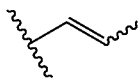

) may be an (E)- or (Z)-double bond.

"Alkynyl", in general, refers to a radical of a straight-chain or branched hydrocarbon group having from 2 to 20 carbon atoms, one or more carbon-carbon triple bonds, and optionally one or more double bonds ("$C_{2-20}$ alkynyl"). In embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic", in general, refers to a radical of a non-aromatic cyclic hydrocarbon group having from 3 to 10 ring carbon atoms ("$C_{3-10}$ carbocyclyl") and zero heteroatoms in the non-aromatic ring system. In embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like.

Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ to carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

A heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). A heteroaryl group can be a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$+X, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-5}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_6$10 aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)$^+$X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-5}$ alkyl), —C(=S)SC$_{1-5}$ alkyl, —SC(=S)SC$_{1-5}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, carborane anions (e.g., CB$_{11}$H$_{12}$$^-$ or (HCB$_{11}$MesBr$_6$)), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^a$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group described herein is Bn, Boc, Cbz, Fmoc, trifluoroacetyl, triphenylmethyl, acetyl, or Ts.

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group described herein is silyl, TBDPS, TBDMS, TIPS, TES, TMS, MOM, THP, t-Bu, Bn, allyl, acetyl, pivaloyl, or benzoyl.

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. In certain embodiments, a sulfur protecting group described herein is acetamidomethyl, t-Bu, 3-nitro-2-pyridine sulfenyl, 2-pyridine-sulfenyl, or triphenylmethyl.

The disclosure also relates to pharmaceutical compositions comprising a compound of any of Formulae I-XV, and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

In some embodiments, a compound of any of Formulae I-XVI is incorporated into a polypeptide. For example, nitration of a compound of Formulae Ia, IVa, VIIa, IXa, XIIa, or XVa results in formation of a compound of Formulae I-XVI. It is known in the art that L-tryptophan and its derivatives (e.g., compounds of Formulae I-XVI) may be incorporated into polypeptides to form artificial or unnatural proteins, for example as disclosed by *Methods in Molecular Biology*, vol. 32: *Protein Engineering Protocols*, Arndt and Müller (Eds.), Humana Press, N J, 2007.

In some aspects, the disclosure relates to methods for producing a compound of Formulae I-XVI. In some embodiments, the method comprises contacting a compound of Formulae Ia, IVa, VIIa, IXa, XIIa, or XVa with any of the TxtE-BM3R fusion proteins described herein to produce a compound of Formulae I-XVI in the presence of NADPH. In some embodiments, the compound of Formulae Ia, IVa, VIIa, IXa, XIIa, or XVa is contacted with any of the TxtE-BM3R fusion proteins described herein, in the presence of NAD(P)H to produce a compound of Formulae I-XVI.

In aspects the method further comprises isolating the indole portion of a compound of Formulae I-XVI. Methods of removing or isolating indole rings are known in the art. For example, the enzyme tryptophanase may be used to deanimate tryptophan to produce an indole ring.

In another aspect, the invention is directed to compounds of Formulae I, Ia, II, III, IV, IVa, V, VI, VII, VIIa, VIII, IX, IXa, X, XII, XIIa, XIII, XIV, XV, XVa, XVI, and their use in any of the processes or methods delineated herein. Compounds of Formulae Ia, IVa, VIIa, IXa, XIIa, and XVa can be purchased or prepared according to any synthetic methods known in the art [e.g., Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987]. For example, tryptophan derivatives (e.g., compounds of Formulae Ia, IVa, IXa, and XVa) can be prepared from the corresponding indole, Formulae Ib, IVb, and IXb, via reaction with serine and acetic acid/acetic anhydride, as outlined in Blaser, G. et al. (2008) Tetrahedron letters., 49 (17). pp. 2795-2798. Other chemical and enzymatic methods are also known for converting indoles (e.g., Formulae Ib, IVb, and IXb) to the corresponding tryptophan derivatives (e.g., compounds of Formulae Ia, IVa, IXa, and XVa) [Eto et al., *Bull. Chem. Soc. Japan* (1989), 62(3), pages 961-963; Li et al., *Tetrahedron* (2014), 70(42), pages 7753-7762; Wartmann et al., *Eur. J. Org. Chem.* (2013), 2013(9), pages 1649-1652; Murai et al., *J. Org. Chem.* (2012), 77(19), pages 8581-8587; Mollica et al., *Tet. Lett.* (2011), 52(20), pages 2583-2585; Heemstra et al., *J. Am. Chem. Soc.*, (2008), 130(43), pages 14024-14025; Yamada et al., *Chem. Pharm. Bull.* (2005), 53(10), pages 1277-1290; Li et al., *Tet. Lett.* (2004), 45(46), pages 8569-8573; Kim et al., *Syn. Comm.* (2004), 34(16), pages 2931-2943; Konda-Yamada et al., *Tetrahedron* (2002), 58(39), pages 7851-7861; WO2001094345; Zhang et al., *Tet. Lett.* (1995), 36(41), pages 7411-7314; Filler et al., *Can. J. Chem.* (1989), 67(11), pages 1837-1841; Ojima et al., *J. Org. Chem.* (1989), 54(19), pages 4511-4522; Schmidt et al., *Liebigs Annalen der Chemie* (1985), 4, pages 785-793; Petrovic et al., *Amino Acids* (2013), 44(5), pages 1329-1336; Frese et al., *ChemCatChem* (2014), 6(5), pages 1270-1276; Smith et al., *Org. Lett.* (2014), 16(10), pages 2622-2625].

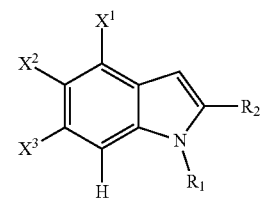

Formula Ib

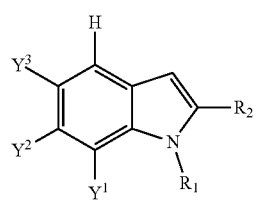

Formula IVb

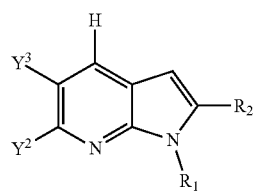

Formula IXb

Indoles of Formulae Ib-IVb can be purchased from commercial sources or can be prepared by any methods known in the art for preparing and/or modifying indoles. Non-limiting examples of such processes are Bartoli indole synthesis, Mannich reaction, Fischer indole synthesis, Nenitzescu indole synthesis, and the like.

The present invention is further illustrated by the following Examples, which in no way should be construed as further limiting.

EXAMPLES

Example 1: Materials and Methods

General Chemicals, DNA Sub-Cloning, and Bacterial Strains

Molecular biology reagents and enzymes were supplied by Fisher Scientific. Primers were ordered from Sigma-Aldrich. 4-Me-DL-Tryptophan was from MP Biomedicals (Santa Ana, Calif.), while NOC-5 (3-(Aminopropyl)-1-hydroxy-3-isopropyl-2-oxo-1-triazene) was purchased from EMD Millipore. Other chemicals and solvents were purchased from Fisher Scientific and Sigma-Aldrich. *Escherichia coli* DH5α (Life Technologies) was used for cloning and plasmid harvesting, while *E. coli* BL21-GOLD (DE3) (Agilent) was used for protein overexpression. *E. coli* strains were grown in Luria-Bertani broth or Terrific broth. Preparation and manipulation of plasmid DNA from *E. coli* was performed subsequently, DNA sequencing was performed.

A Shimadzu Prominence UHPLC system (Kyoto, Japan) fitted with an Agilent Poroshell 120 EC-C18 column (2.7 μm, 3.0×50 mm), coupled with a PDA detector was used for HPLC analysis. For semi-preparative HPLC, YMC-Pack Ph column (5 μm, 4.6×250 mm) was used. All NMR spectra were recorded in 100 mM DCl in $D_2O$ on a Bruker 600 MHz spectrometer using a 5 mm TXI Cryoprobe. The instrument was operated at 600.17 MHz for 1H NMR and 150.9 MHz for $^{13}C$ NMR. Spectroscopy data were collected using Topspin 3.5 software. HRMS data were obtained using a Thermo Fisher Q Exactive Focus mass spectrometer equipped with electrospray probe on Universal Ion Max API source.

Construction of TxtE-BM3R Variants

TxtE gene (Genbank: FN554889 REGION: 3613916 . . . 3615136; e.g., Genbank Accession No. CBG70284.1) was amplified from genomic DNA of S. scabies 87.22 (NRRL B-24449) using a pair of SELKnco-F and SELKsac-R primers (Table 1). The PCR mixture (50 μL) contained 50 ng template, 2 μM of each primer, 0.1 mM of dNTP, 3% dimethyl sulfoxide, and 0.5 μl Phusion high fidelity DNA polymerase in 1×GC reaction buffer. Reaction conditions consisted of an initial denaturation step at 98° C. for 30 s followed by 30 cycles of 98° C. for 10 s, 70° C. for 20 s, and 72° C. for 30 s, and a final extension of 72° C. for 5 min. The PCR product was analyzed by agarose gel and extracted with a GeneJET Gel Extraction Kit (Thermo). Purified PCR products and pET28b were digested with the restriction enzymes NcoI and SacI, and corresponding linear DNAs were ligated to generate expression construct pET28b-TxtEs. To further create the TxtE-BM3R variants with variable linker length, BM3R domain with selected linker lengths was amplified from P450BM3 gene by a set of primer pairs (Table 1). Purified PCR products and pET28b-TxtE construct were then digested with the restriction enzymes SacI and XhoI, and corresponding linear DNAs were ligated to generate pET28b-TxtE-BM3R expression constructs (FIG. 1). To create the P450BM3 standalone reductase (BM3R) expression constructs, BM3R gene was amplified using a pair of BM3R-F and BM3R-R primers. Purified PCR products and pET28b were digested with the restriction enzymes NdeI and XhoI, and corresponding linear DNAs were ligated to create pET28b-BM3R. To create TB13S fusion variant, TB13-Q template was PCR amplified with primers of TxtESF and TxtESR to obtain the TxtES fragment (Table 1), and the S13BM3R fragment was amplified with primers of FW-V1 and RV (Table 1). P450BM3 gene was used as the template to amplify JKL insert using primers of V1-3-F and V1-3-R. After purification, these fragments were fused by overlapping PCR technology. The full-length TB13S was cloned into the expression vector. All inserts in the constructs were sequenced to exclude mutations introduced during PCR amplification and gene manipulation.

TABLE 1

Primers for gene expression

| Name | Sequence (5'→3') | Function | SEQ ID NO: |
|---|---|---|---|
| SELKnco-F | ATACCATGGTGACCGTCCCCTCGCCG | TxtE cloning | 1 |
| SELKsac-R | ATAGAGCTCGCGGAGGCTGAGCGGCAG | TxtE cloning | 2 |
| BM3R-F | CTACATATGTCTGCTAAAAAAGTACGCAA | BM3R fusion | 3 |
| BM3R-R | ATCCTCGAGCCCAGCCCACACGTCTTTTG | BM3R fusion | 4 |
| BM3LKsac3-F | tctGAGCTCAACGCTCATAATACGCCGCTG | TxtE-BM3R fusion F primer | 5 |
| BM3LKsac6-F | tctGAGCTCAAGGCAGAAAACGCTCATAATACG | TxtE-BM3R fusion F primer | 6 |
| BM3LKsac9-F | tctGAGCTCGTACGCAAAAAGGCAGAAAACG | TxtE-BM3R fusion F primer | 7 |
| BM3LKsac11-F | tctGAGCTCAAAAAAGTACGCAAAAAGGCAG | TxtE-BM3R fusion F primer | 8 |
| BM3LKsac12-F | tctGAGCTCGCTAAAAAAGTACGCAAAAAGGCAG | TxtE-BM3R fusion F primer | 9 |
| BM3LKsac13-F | tctGAGCTCTCTGCTAAAAAAGTACGCAAAAAGGCAG | TxtE-BM3R fusion F primer | 10 |

TABLE 1-continued

Primers for gene expression

| Name | Sequence (5'→3') | Function | SEQ ID NO: |
|---|---|---|---|
| BM3LKsac14-F | tctGAGCTCCAGTCTGCTAAAAAAGTACGCAAAAAG | TxtE-BM3R fusion F primer | 11 |
| BM3LKsac15-F | tctGAGCTCGAACAGTCTGCTAAAAAAGTAC | TxtE-BM3R fusion F primer | 12 |
| BM3LKsac16-F | tctGAGCTCACTGAACAGTCTGCTAAAAAAG | TxtE-BM3R fusion F primer | 13 |
| BM3LKsac17-F | tctGAGCTCAGCACTGAACAGTCTGCTAAAAAAG | TxtE-BM3R fusion F primer | 14 |
| BM3LKsac19-F | tctGAGCTCTCACCTAGCACTGAACAGTCTGC | TxtE-BM3R fusion F primer | 15 |
| BM3LKsac22-F | tctGAGCTCGGTATTCCTTCACCTAGCACTGAAC | TxtE-BM3R fusion F primer | 16 |
| BM3LKsac24-F | tctGAGCTCCTTGGCGGTATTCCTTCACCTAG | TxtE-BM3R fusion F primer | 17 |
| BM3LKsac27-F | tctGAGCTCAAAATTCCGCTTGGCGGTATTC | TxtE-BM3R fusion F primer | 18 |
| BM3LKxho-R | atcCTCGAGCCCAGCCCACACGTCTTTTGC | TxtE-BM3R fusion R primer | 19 |
| TxtESF | CACCCATGGTGACCGTCCCCTCGCCGCTC | TxtES fusion F primer | 20 |
| TxtESR | CGGGTTGCGGGCGAACGC | TxtES fusion R primer | 21 |
| V1-3-F | GCGTTCGCCCGCAACCCGCATGTATTACAAAAAGCAGCAGAAGAAGC | JKLoop insert F primer | 22 |
| V1-3-R | GGCCGCGACGCGCCAAGGAGCAGTTGGCCATAAGCG | JKLoop insert R primer | 23 |
| FW-V1 | ACCTGGCGCGTCGCGGC | S13BM3R fusion F primer | 24 |
| RV | GACCCAGCCCACACGTCTTTTGC | S13BM3R fusion R primer | 25 |

Heterologous Expression and Purification of Recombinant Proteins

Expression constructs were transformed into E. coli BL21 (DE3)-GOLD competent cells for protein expression. Cells harboring the constructs were cultured in Terrific Broth medium 5 supplemented with kanamycin (50 µg/ml) and 1× trace metal solution (1000× stock solution: 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mm $Na_2MoO_4$, and 2 mM $H_3BO_3$). Cultures were grown at 37° C., 250 rpm until $OD_{600}$ reached 0.6. Protein expression was then induced by isopropyl-β3-D-thiogalactopyranoside (IPTG) with a final concentration of 0.1 mM. The cultures were further grown at 16° C., 250 rpm for 16 hours. After centrifugation (5,000 g, 10 min, and 4° C.), cell pellets were stored in −80° C. or directly used for protein purification. For protein purification, cell pellets were first resuspended in the suitable volumes of lysis buffer (cell biomass: volume=1:4) [25 mM Tris-HCl, pH 8.0, 100 mM NaCl, 20 mM imidazole, 3 mM (3-mercaptoethanol (BME) and 10% glycerol]. Soluble proteins were released by sonication. After centrifugation at 35,000×g at 4° C. for 30 min, the clear supernatants were incubated with pre-equilibrated Ni-NTA agarose resin (Thermo) at 4° C. for 2 h. The resins were washed with 10 volumes of lysis buffer with 30 mM imidazole, and recombinant P450s were then eluted in lysis buffer with 50 to 320 mM imidazole. After SDS-PAGE analysis, elution solution fractions containing P450s were combined and concentrated. The proteins were then exchanged into storage buffer (25 mM Tris-HCl, pH8.0, 100 mM NaCl, 3 mM (βME, and 10% glycerol) using PD-10 column, aliquoted and stored at −80° C. until needed. The concentrations of functional P450s were accurately measured by CO difference spectroscopy.

Spectral Analysis of Chimeric TxtE-BM3R Variants

Purified TxtE and its chimeric fusions were spectrally analyzed following a previous protocol. Briefly, the absorbance spectra (400-600 nm) of TxtE variants (3 µM) in Tris-HCl (25 mM, pH 8) buffer were recorded with a Shimadzu UV2700 dual beam UV-Vis spectrophotometer. The ferric heme of enzymes was then saturated with carbon monoxide (Airgas) through bubbling and the spectra of the saturated enzyme solutions were recorded. Immediately, sodium dithionite solution (30 µL, 0.5 M) was added to reduce ferric ion, and reduced spectra were taken subsequently. CO reduced difference spectra of all enzymes were created by subtracting the CO binding spectra from the reduced spectra. Data were further analyzed by Excel. Substrate binding affinities to P450s were measured using 1.5 μM of enzyme solutions in 25 mM Tris-HCl, pH 8.0. Not more than 10 μl of substrate stock solutions prepared in the above buffer were added to the sample cuvette with an interval of 0.5 μl, and the spectra were recorded from 300 nm to 500 nm each time. The equal volume of buffer was added to the reference cuvette. The changes in absorbance (ΔA) were determined by subtracting the absorbance at ~420 nm from that at ~390 nm. Data were then fitted to the equation of $\Delta A = \Delta A_{max}[L]/(K_d+[L])$ using GraphPad Prism 4.

Catalytic Activities of Chimeric TxtE-BM3R Variants

P450 reactions (100 μl) contained 0.5 mM substrate, 1 mM NADP+, 1 mM glucose, ~10 units/mL self-prepared glucose dehydrogenase crude extract, 1 mM NOC-5 in 100 μL of Tris-HCl buffer (100 mM, pH 8.0). As the positive control, the TxtE reaction was also re-constructed in the above mixture further supplemented with 0.43 μM spinach Fer and 0.33 μM Frd. The reactions were initiated by adding 1.5 μM P450s, and incubated at 20° C., 300 rpm on a thermostat (Eppendorf) for 30 or 45 minutes. Methanol (200 μl) was then added to stop the reactions. After centrifugation, 10 μl solutions were analyzed by HPLC. Total turnover number (TTN) was reported as nmol product per nmol P450. The 4-NO2-L-tryptophan was synthesized in a large-scale enzymatic reaction to establish a standard curve for product quantification. To determine the coupling efficiency, NADPH (2 mM) was used to replace the NADPH regeneration system in the reaction mixture. NADPH consumption in enzyme reactions was measured at 340 nm (c=6.22 mM$^{-1}$ cm$^{-1}$) with a Shimadzu UV2700 dual beam UV-Vis spectrophotometer. Non-enzymatic oxidation of NADPH was subtracted as the background. The quantity of nitrated product was determined by HPLC analysis as described above. Coupling efficiency (%) was determined as product (nmol)/consumed NADPH (nmol)×100%. All reactions were independently repeated at least three times. Conversion rate (%) was calculated as product (nmol)/(product+substrate) (nmol)×100%. All experiments were performed at least in triplicate.

Large-Scale Enzymatic Synthesis of Nitrated Trp Analogs

To isolate sufficient amount of nitrated 4-Me-Trp analogues for structural determination, 18 μM TB14 was used in a 10-mL reaction mixture containing 1.5 mM 4-Me-Trp, 3 mM NADP+, 3 mM glucose, ~30 units/mL self-prepared glucose dehydrogenase crude extract, 3 mM NOC-5 in 100 mM Tris-HCl buffer (pH 8.0). The reactions in a 200-ml flask were incubated at 20° C., 250 rpm overnight, and then terminated by 20 mL methanol or acidification to pH 1.0 with 6 M HCl. After centrifugation, the supernatants were concentrated in vacuo and then freeze-dried. The products were redissolved in 3 ml methanol. Semi-preparation was performed with an YMC-Pack Ph column (5 m, 4.6×250 mm).

Analytical and Semi-Preparative HPLC Analysis

For analytical analysis, the HPLC column kept at 40° C. was eluted first with 1% solvent B (acetonitrile with 0.1% formic acid) for 0.5 min and then with a linear gradient of 1-20% solvent B in 2 min, followed by another linear gradient of 20-99% solvent B in 0.5 min. The column was further cleaned with 99% solvent B for 0.5 min and then re-equilibrated with 1% solvent B for 2 min. The flow rate was set as 1.5 mL/min, and the products were detected at 211 nm with a PDA detector. All enzyme reactions were performed at least in triplicate.

For semi-preparative HPLC, the column kept at 30° C. was eluted first with 20% solvent B (acetonitrile with 0.1% formic acid) for 3 min and then with a linear gradient of 20-50% solvent B for 8 min, followed by a linear gradient of 50-99% solvent B for 1 min. The column was then cleaned by 99% solvent B for 2 min and re-equilibrated with 20% solvent B for 4 min. The flow rate was set at 1 mL/min, and the products were detected at 211 nm with a PDA detector. All isolates were combined, concentrated, freeze-dried, and then weighed.

NMR Analysis

In NMR analysis, chemical shifts were reported in parts per million (ppm) downfield from tetramethylsilane. Proton coupling patterns were described as singlet (s), doublet (d), double doublet (dd), triplet (t), and multiplet (m).

4-Me-5-nitro-L-tryptophan: H NMR (600 MHz, 100 mM DCl in D$_2$O) δ 7.22 (d, J=9.0 Hz, 1H), 6.88 (s, 1H), 6.84 (d, J=8.9 Hz, 1H), 3.80 (dd, J=10.1, 5.1 Hz, 1H), 3.22 (dd, J=15.6, 5.1 Hz, 1H), 2.84 (dd, J=15.7, 10.1 Hz, 1H), 2.23 (s, 3H). C NMR (151 MHz, D$_2$O) δ 170.56, 154.71, 142.20, 138.27, 128.39, 127.74, 124.17, 118.79, 109.77, 109.69, 58.96, 53.66, 27.77, 15.15. HRMS (ESI+): calc. for C$_{12}$H$_{13}$N$_3$O$_4$ [M+H]$^+$: 264.0906, found: 264.0892.

4-Me-7-nitro-L-tryptophan: 1H NMR (600 MHz, 100 mM DCl in D$_2$O) δ 6.80 (d, J=8.3 Hz, 1H), 6.63 (d, J=8.1 Hz, 1H), 3.92 (dd, J=10.7, 5.4 Hz, 1H), 3.22 (dd, J=16.2, 5.4 Hz, 1H), 2.98 (dd, J=16.2, 10.8 Hz, 1H), 2.10 (s, 3H). HRMS (ESI+): calc. for C$_{12}$H$_{13}$N$_3$O$_4$ [M+H]$^+$: 264.0906, found: 264.0893.

Marfey's Derivatization

4-Me-Trp and nitrated 4-Me-Trp from enzyme reactions were reacted with Marfey's reagent. Derivatized products were analyzed by LC-MS with A SHIMADZU Prominence UPLC system fitted with a Waters SymmetryShield™ RP-C18 column (3.5 am, 4.6×100 mm) and a Linear Ion Trap Quadrupole LC/MS/MS Mass Spectrometer system. The column was eluted with 90% solvent A (0.05 M triethylammonium acetate, pH 3.0), 10% solvent B (acetonitrile) for 2 min and then with a linear gradient of 10-50% solvent B in 60 min. The column was then cleaned by 50% solvent B for 5 min and re-equilibrated with 10% solvent B for 2 min. The flow rate was 0.5 mL/min. For MS detection, the turbo spray conditions were the same as described above.

Example 2: Characterization of Self-Sufficient P450 Enzymes

Attempts have been made to expand the biocatalytic toolbox by developing nitration biocatalysts. One example is TxtE, a cytochrome P450 enzyme that uses nitric oxide (NO) and O$_2$ to nitrate C4 of the L-tryptophan (Trp) indole in the thaxtomin biosynthetic pathway. P450s catalyse a wide array of oxygenation reactions under mild conditions and have impressive biotechnological potential. However, the requirement of auxiliary redox proteins and low activity and electron coupling efficiency are common limitations that constrain frequent industrial implementation of P450s. TxtE fused with the reductase domain (BM3R) of naturally self-sufficient P450 P450BM3 has been described, for example in WO2016/134135. The chimera outperformed TxtE supplemented with spinach ferredoxin (Fer) and ferredoxin reductase (Frd) in terms of catalytic activity, and was subsequently utilized in the biocatalytic syntheses of two nitro-Trp analogues. However, both electron coupling efficiency and total turnover number (TTN) of the developed chimeric enzyme were 20% lower than TxtE.

Figure 2:
FIG. 2 shows a schematic depiction of chimeric TxtE-BM3R constructs with variable linker length or a swapped loop (arrow). The structure of human NADPH-cytochrome P450 reductase (PDB: 3QE2, right) represented not-available BM3R structure along with TxtE (PDB: 4TPO, left). The 25-AA linker of P450BM3 is shown as a dashed line (middle) along with the amino acid sequence (SEQ ID NO: 27).
Figure 3A:
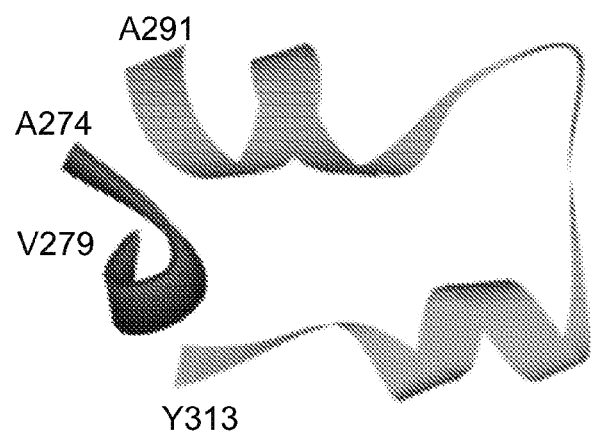
FIGS. 3A-3B show schematic depictions of chimeric TxtE-BM3R constructs.
Figure 3B:
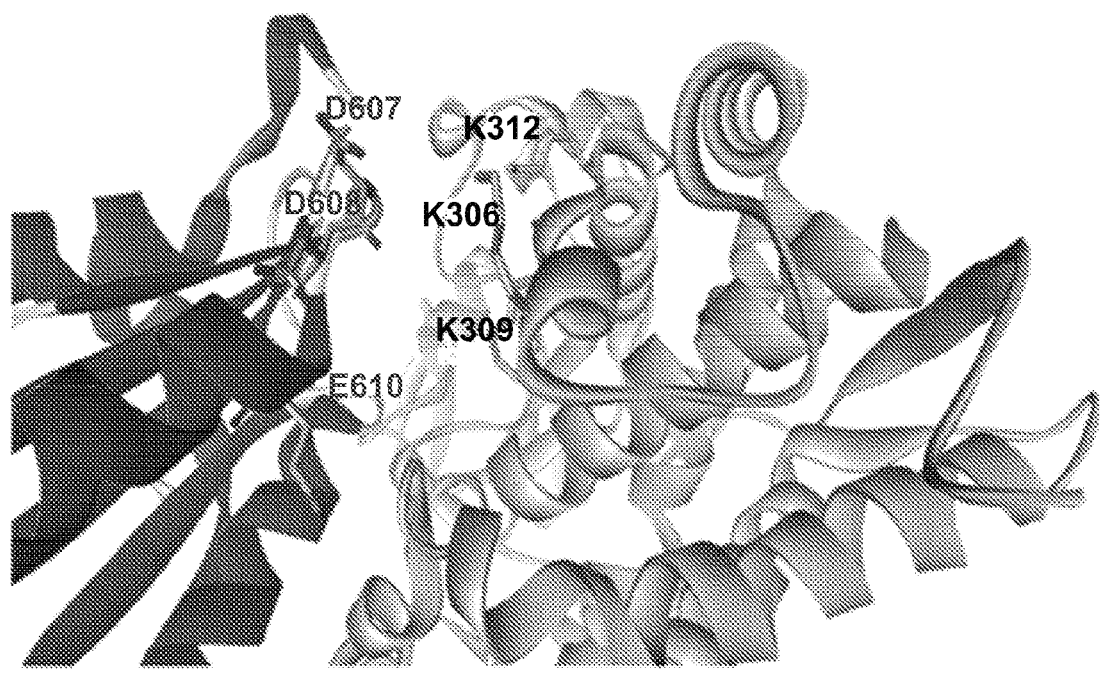

This example describes the characterization of 15 new chimeric TxtE-BM3R biocatalysts. These chimeras were developed by varying the length of a linker connecting TxtE and BM3R, and swapping a putative interfacial loop on the TxtE to improve interactions with the reductase domain (FIG. 2). These studies have yielded TxtE-BM3R constructs with improved catalytic turnover, coupling efficiency, and broad substrate specificity.

Design and Production of Chimeric TxtE-BM3R Variants

Figure 4:
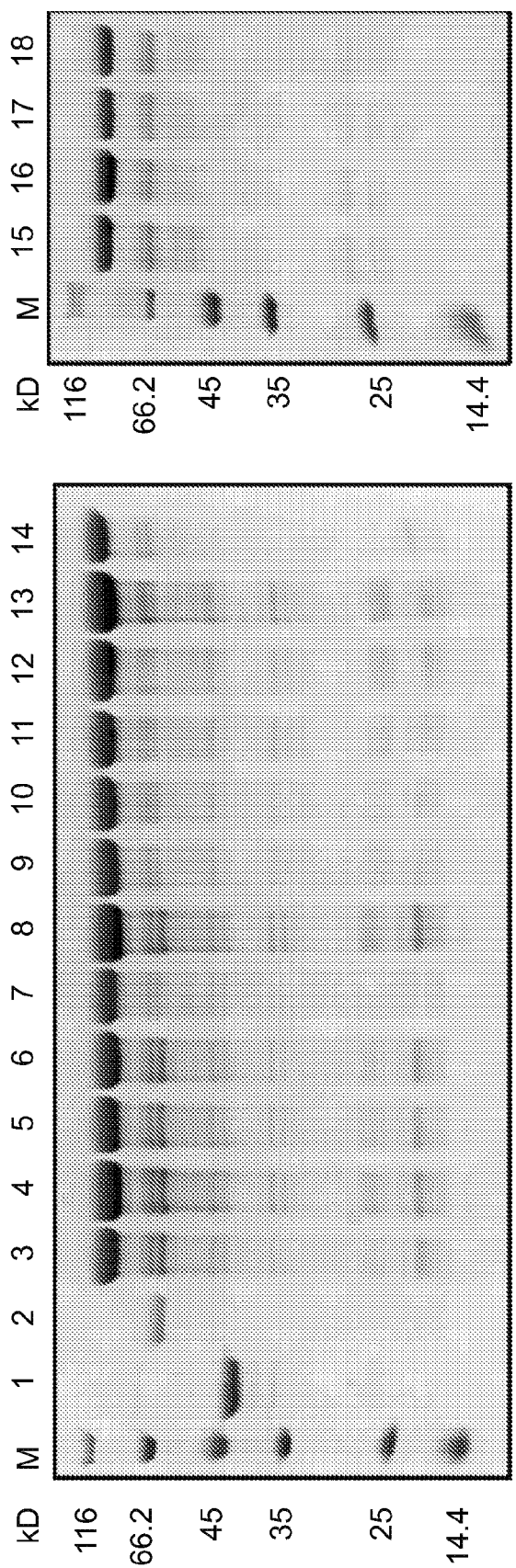
FIG. 4 shows SDS-PAGE analysis of purified recombinant proteins. M: protein marker; Lane 1-14: TxtE, BM3R, TB3, TB6, TB9, TB11, TB13-Q, TB14, TB17, TB19, TB22, TB24, TB27, and TB13S. Lane 15-18: TB12, TB13, TB15, and TB16.
Figure 5:
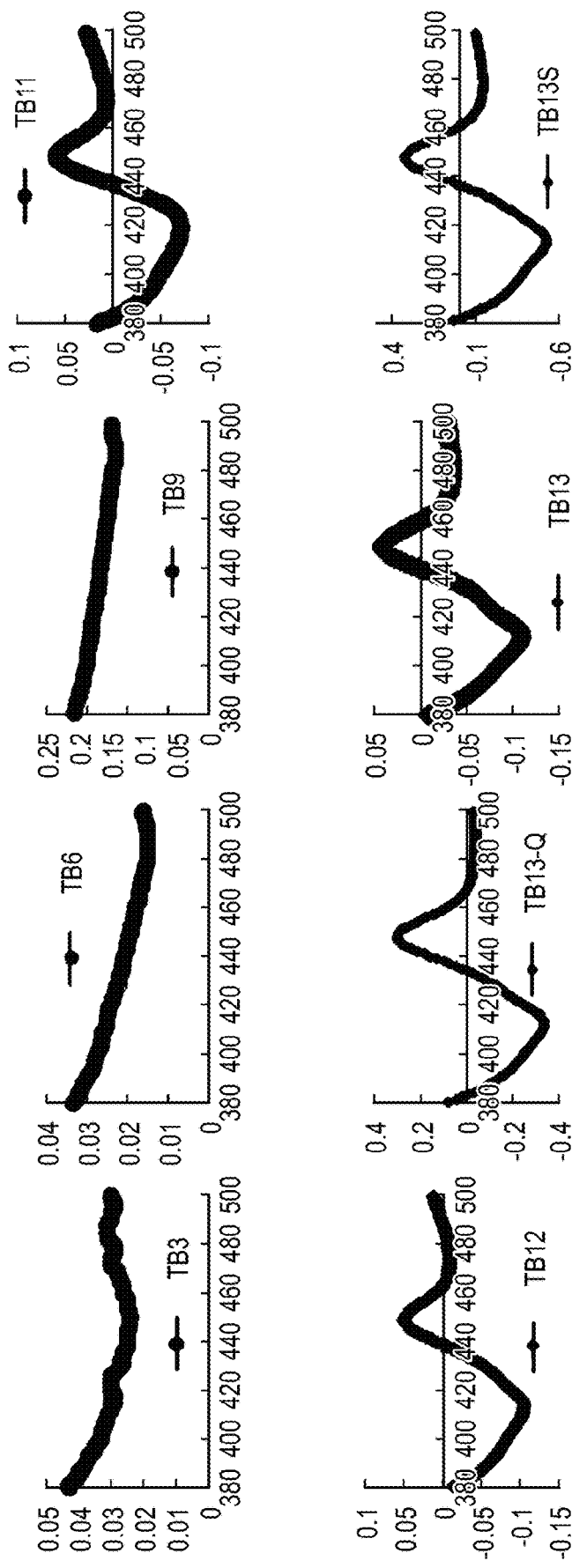
FIG. 5 shows representative data for CO-reduced difference spectra of chimeric TxtE fusion constructs and TxtE. A peak at around 450 nm indicates the properly folded, active P450.
Figure 5:
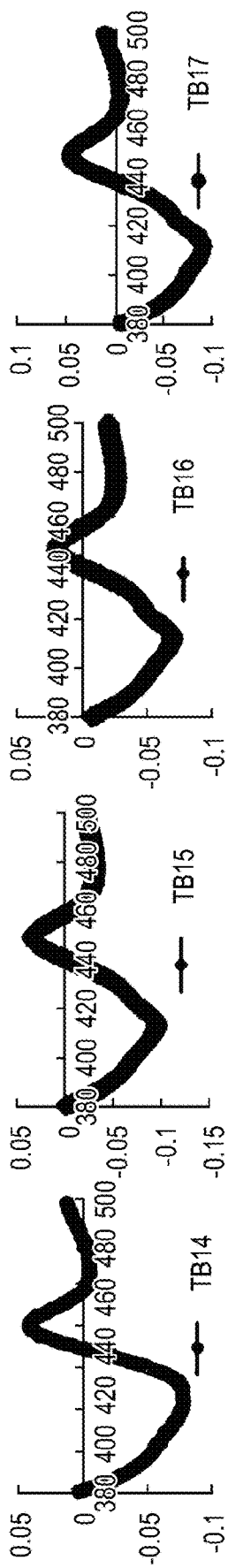
Figure 5:
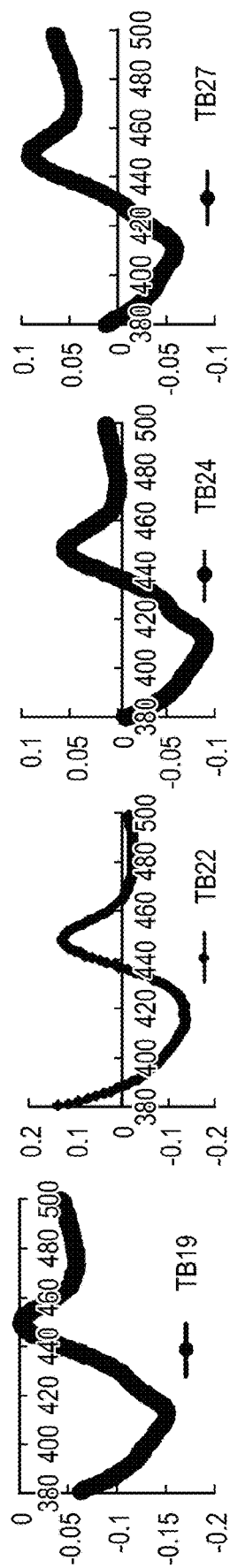
Figure 5:
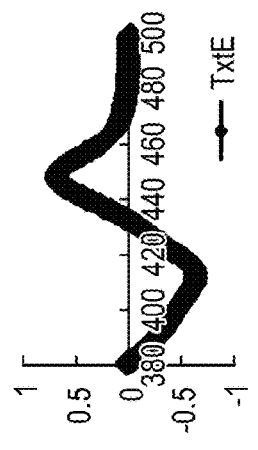
Figure 6:
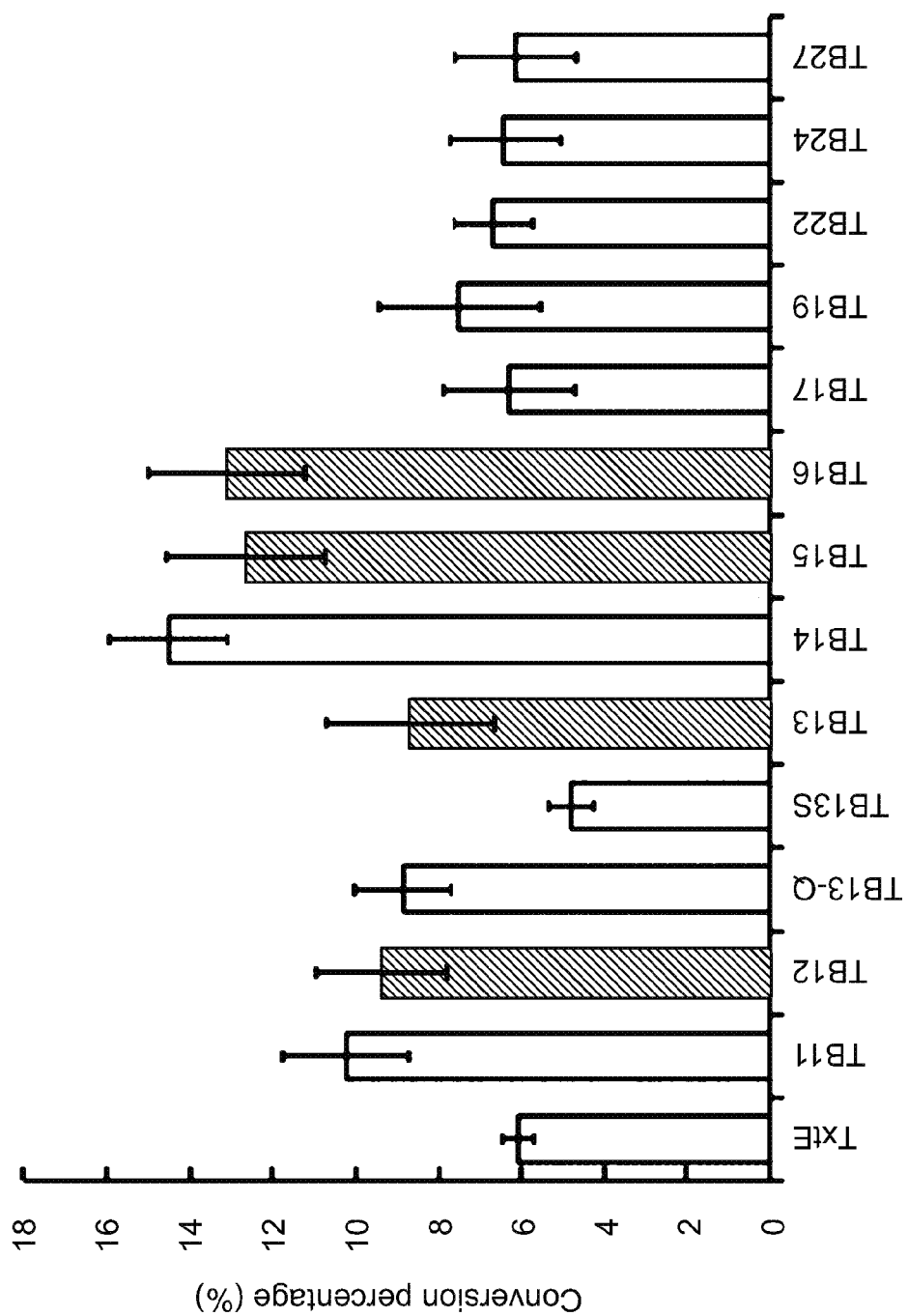
FIG. 6 shows relative nitration activity of TxtE and chimeric TxtE-BM3R variants. All reactions contained 0.5 mM Trp and 1.5 µM P450. The TxtE reaction was further supplemented with 0.43 µM spinach Fer and 0.33 µM Frd. The reactions were incubated at 20° C., 300 rpm for 30 minutes. All experiments were repeated at least three times. The results of TB12, TB13, TB15, and TB16 were shown as black bars.
Figure 7A:
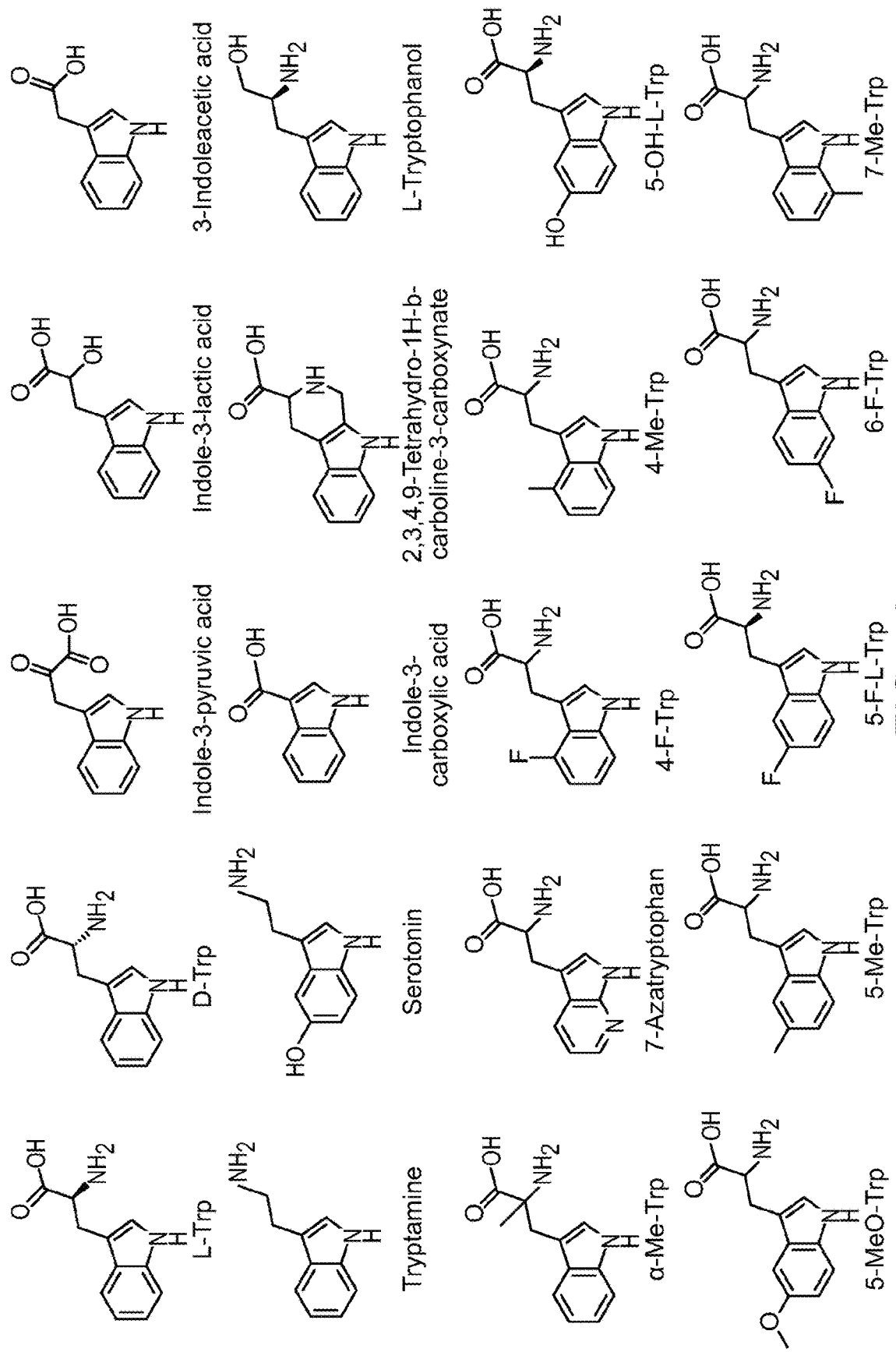
FIGS. 7A-7B show representative data for characterization of TxtE and TB14.
Figure 7B:
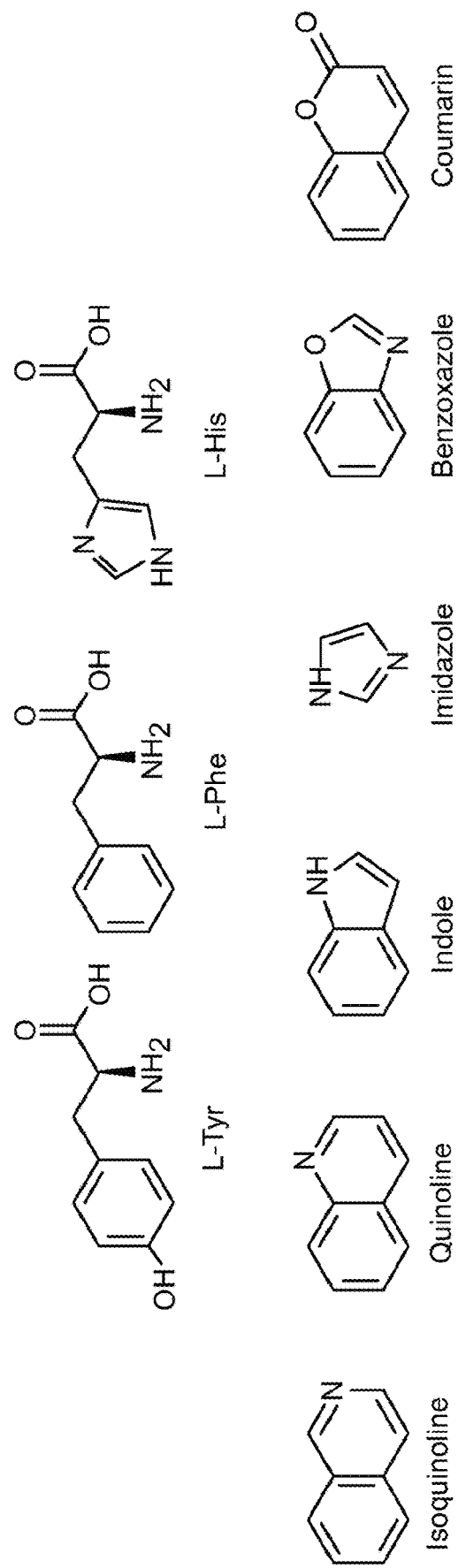

Three self-sufficient TxtE constructs were previously described. Of the two reductase domains that were evaluated, the di-flavin reductase BM3R homologous to eukaryotic cytochrome P450 reductase conferred superior TxtE nitration activity compared with the P450RhF reductase domain (RhFRED), a natural fusion of Frd and Fer. However, the electron coupling efficiency and total turnover number (TTN) of the developed chimeric enzyme were 20% lower than wild-type TxtE.

Here, a stepwise cloning approach (FIG. 1) was used to produce, chimeric TxtE-BM3R variants with linker lengths of 3, 6, 9, 11, 14, 17, 19, 22, 24, and 27 amino acids (AA) (Table 2) to evaluate influences of linker length on enzyme nitration performance. Additional variants with linker lengths of 12, 13, 15, and 16 were also produced and evaluated. Hereafter, these TxtE-BM3R variants are designated as TB-linker length, so for example, the TxtE-BM3R variant AA linker of P450BM3 containing a 13-AA linker that bears EQ at its N-terminus (Table 2) is denoted TB13-Q in this study. Superimposition of the crystal structure of TxtE (PDB: 4TPO) with the P450 heme domain of P450BM3 (PDB: 1BVY) revealed an additional opportunity to potentially improve the chimera's catalytic activity. A loop connecting two helices (J and K, FIG. 3A) of P450BM3 putatively contributes to the interface of heme and reductase domains. This basic-residue-rich loop (A291 to Y313) is about 7 Å away from the acidic residues of the FMN-binding domain and can provide a specific protein-protein interaction for efficient electron transfer (FIG. 3B). This stretch of amino acids is significantly different from those in TxtE (FIG. 3A). The effect of replacing those residues in TxtE with the corresponding residues in P450BM3 on the coupling efficiency between the domains was examined (FIG. 2). The rationally swapped chimera (TB13S) carrying the JK loop from P450BM3 was constructed with overlapping PCR using TB13-Q and P450BM3 as the templates. All constructs were expressed in *E. coli* and purified to homogeneity by a single $Ni^{2+}$-NTA affinity chromatography (FIG. 4). All chimeras except TB3, TB6 and TB9 showed a peak at around 450 nm in their reduced-carbon monoxide (CO) difference spectra (FIG. 5), indicating the production of active P450s. A minimal effect of variable linker length on the solubility of both active and inactive chimeras was observed. The concentrations of active chimeras and TxtE in purified proteins were quantitated using an extinction coefficient of $\Delta\varepsilon_{450\text{-}490\ nm}$ of 91 $mM^{-1}$ $cm^{-1}$ for the ferrous P450-CO complex.

TABLE 2

Description of TxtE chimeras with variable linker lengths:

| Variant name | Linker length | Linker sequence | SEQ ID NO: |
|---|---|---|---|
| TB27 | 27 | EL KIPLGGIPSPSTEQSAKKVRKKAEN | 26, 27 |
| TB24 | 24 | EL LGGIPSPSTEQSAKKVRKKAEN | 28, 29 |
| TB22 | 22 | EL GIPSPSTEQSAKKVRKKAEN | 30, 31 |
| TB19 | 19 | EL SPSTEQSAKKVRKKAEN | 32, 33 |
| TB17 | 17 | EL STEQSAKKVRKKAEN | 34, 35 |
| TB16 | 16 | EL TEQSAKKVRKKAEN | 36, 37 |
| TB15 | 15 | EL SQSAKKVRKKAEN | 38, 39 |
| TB 14 | 14 | EL QSAKKVRKKAEN | 40, 41 |
| TB 13 | 13 | EL SAKKVRKKAEN | 42, 43 |
| TB 13-Q | 13 | EQ SAKKVRKKAEN | 44, 45 |
| TB 12 | 12 | EL AKKVRKKAEN | 46, 47 |
| TB 11 | 11 | EL KKVRKKAEN | 48, 49 |
| TB 9 | 9 | EL VRKKAEN | 50, 51 |
| TB 6 | 6 | EL KAEN | 52, 53 |
| TB 3 | 3 | ELN | 54, 55 |

Nitration Performance of Chimeric TxtE-BM3R Variants

The catalytic performance of TB11, TB13-Q, TB13S, TB14, TB17, TB19, TB22, TB24, and TB27 was measured to quickly assess the potential effects of linker length (FIG. 6 and Table 3). TxtE coupled with spinach Fer and Frd served as the control. HPLC analysis revealed that all fusion enzymes nitrated Trp to a different extent (FIG. 6). After 30 min, TxtE (1.5 μM) converted 6.1% of Trp (0.5 mM) into 4-$NO_2$-L-Trp, and this rate was lower than all tested chimeric constructs (1.5 μM). Compared with TxtE, the nitration activity of the most active chimera, TB14, was improved by 2.4 times to reach 14.5% conversion. The second most active enzyme was TB11 (10.2%), followed by TB13-Q (8.9%). The nitration activity of chimeras with longer linker length from 17 to 27 AAs were similar to one another (6.2 to 7.5%) and lower than TB14 (FIG. 6). Next, TB12, TB13, TB15, and TB16 were further investigated (Table 2). The activity of both TB15 and TB16 was higher than TB11 and TB17 and was only slightly lower than TB14 (FIG. 6). On the other hand, TB12 and TB13 retained about 60% of TB14's activity. These results demonstrated the preferred linker length to be about 14 to 16 AAs. Moreover, the similar activity of TB13 and TB13-Q (Table 3) indicated that linker content played a minor role in determining activity (FIG. 6). Additionally, standalone BM3R (FIG. 4) in solution was unable to support TxtE for nitration, indicating the necessity of the linker in modulating proper interactions between TxtE and BM3R.

Figure 8:
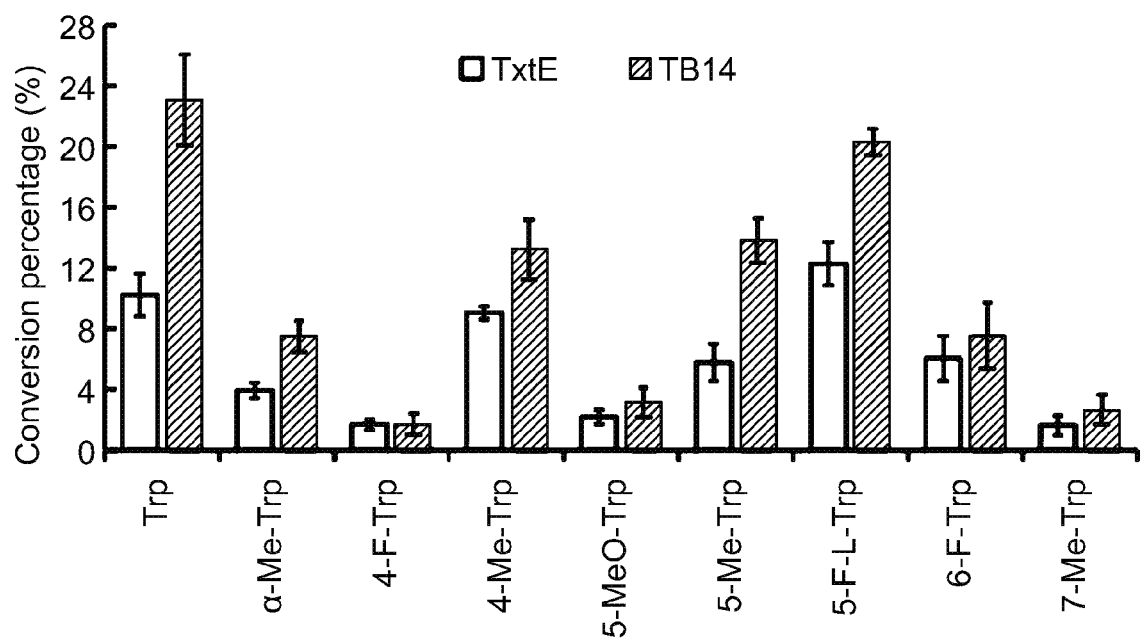
FIG. 8 shows the for degree of nitration of Trp and its analogues by TxtE and TB14. The reactions were prepared and then incubated at 20° C., 300 rpm for 45 minutes. All experiments were repeated at least three times.

The nitration activity of rationally designed TB13S (4.8%) was lower than TxtE and TB13-Q (FIG. 6). The observed catalytic activity, however, clearly demonstrated that TxtE is a robust scaffold for chimerogenesis engineering that has potential to greatly expand fitness and improve catalytic properties of nitration biocatalysts.

To yield mechanistic insights to account for the observed activity changes, the binding affinities of Trp toward all active chimeras were assessed by UV-Vis difference spectroscopy (Table 3). All fusions showed Type I spectral shift of the Soret peak from 420 to around 390 nm after adding Trp, and demonstrated the overly similar level of binding affinity ($K_d$=~20 μM). This result indicated that linker length or structural swapping minimally influenced substrate binding. Next coupling efficiency was determined to evaluate the extent to which linker length and structural swapping affect electron transfer compatibility during nitration reaction (Table 3).

TABLE 3

Binding affinity toward Trp, coupling efficiency and total turnover numbers of TxtE and its chimeras:

| Chimeras | $K_d$ (μM) | Coupling (%) | TTN |
|---|---|---|---|
| TxtE | 24.8 ± 1.1 | 2.4 ± 0.3 | 378 ± 17 |
| TB11 | 16.2 ± 0.6 | 5.2 ± 0.5 | 535 ± 28 |
| TB12 | 22.3 ± 1.4 | 1.8 ± 0.2 | 332 ± 40 |
| TB13-Q | 21.5 ± 0.8 | 2.0 ± 0.1 | 308 ± 18 |
| TB13S | 19.3 ± 0.6 | 2.6 ± 0.2 | 202 ± 20 |
| TB13 | 21.3 ± 0.4 | 2.2 ± 0.3 | 342 ± 29 |
| TB14 | 17.4 ± 1.0 | 5.3 ± 0.5 | 707 ± 16 |
| TB15 | 21.4 ± 0.9 | 3.9 ± 0.4 | 658 ± 33 |
| TB16 | 18.9 ± 1.0 | 2.7 ± 0.2 | 351 ± 39 |
| TB17 | 15.5 ± 0.6 | 2.1 ± 0.3 | 348 ± 24 |
| TB19 | 16.0 ± 0.8 | 2.4 ± 0.5 | 464 ± 21 |
| TB22 | 27.1 ± 1.3 | 2.4 ± 0.5 | 408 ± 32 |
| TB24 | 14.9 ± 0.3 | 2.3 ± 0.1 | 381 ± 15 |
| TB27 | 16.2 ± 1.1 | 2.0 ± 0.6 | 548 ± 17 |

Coupling efficiency of TB11 (5.2%) and TB14 (5.3%) were about 2.2 times higher than TxtE (2.4%), indicating that improvement in their activity was driven by more effective electron transfer. TB15 (3.9%) and TB16 (2.7%) also showed improved coupling efficiency in comparison with TxtE. Coupling efficiency of the other fusions was similar to that of TxtE. Of note, the positive influence of the swapped JK loop from P450BM3 was reflected by improved electron transfer efficiency of TB13S (2.6% vs 2.0% of TB13-Q). Additionally, a total turnover number (TTN) as nmol product per nmol P450 in all reactions (Table 3) was determined. TB14 had the highest TTN at 707 that was 1.9 times and 2.3 times of values of TxtE and TB13-Q, respectively. TTNs of TB11, TB15, and TB16 were also substantially higher than TxtE, indicating their higher nitration activity (FIG. 6). A high TTN of TB27 was also observed. On the other hand, TTN of TB13S decreased from 308 of TB13-Q to 202, indicating the less efficient use of electrons in its nitration.

Substrate Scope of TB14

Next, the substrate promiscuity of the most active chimera TB14, as well as TxtE with a library of 29 chemicals that carry substitutions and moderate alterations on the amine, carboxylate, or indole moieties of Trp was characterized (FIG. 7A-7B). In spectroscopic analysis, 20 Trp analogues (FIG. 7A) induced the Type I spectral shift of TB14 indicating binding, while simple aromatics such as indole and other aromatic amino acids (FIG. 7B) had no detectable level of interaction with the enzymes. There was no significant difference between TB14 and TxtE in terms of binding affinities (Table 4), further confirming the minimal effect of fused BM3R on substrate binding (Table 3). Compounds with modified amine or carboxylate moiety generally showed weaker interactions than those with substitutions on the indole. The nitration activity of TB14 and TxtE toward all library members was examined. To generate sufficient products for HPLC detection, the reactions were incubated for 45 min. Besides Trp and α-Me-DL-Trp, both enzymes nitrated seven Trp analogues with substitutions on the C4, C5, C6, and C7 of the indole (FIG. 7A, FIG. 8). TB14 showed the higher activity toward all substrates. Both enzymes showed good activity toward 4-Me-DL-Trp, 5-Me-DL-Trp, 5-F-L-Trp and 6-F-DL-Trp but not α-Me-DL-Trp, 4-F-DL-Trp, 5-MeO-DL-Trp and 7-Me-DL-Trp. 5-F-L-Trp emerged as the best substrate of TxtE and was comparable to Trp in the TB14 reaction. Nonetheless, these results supported improved performance of TB14 across a variety of substrate analogues and underlined its immediate applications to produce unnatural nitro-Trp compounds. These compounds can have broad applications in synthesizing numerous bioactive peptidic compounds and in analysing macromolecule structures and dynamics.

TABLE 4

Binding affinities of 20 Trp analogues toward TxtE and TB14:

| Substrate analogs | TxtE $K_d$ (μM) | TB14 $K_d$ (μM) |
|---|---|---|
| L-Trp | 24.84 ± 1.11 | 17.37 ± 0.95 |
| D-Trp | 432.30 ± 17.23 | 469.82 ± 25.33 |
| Indole-3-pyruvic acid | 386.10 ± 42.45 | 478.43 ± 31.61 |
| Indole-3-lactic acid | >7 mM | >7 mM |
| 3-Indoleacetic acid | >17 mM | >17 mM |
| Tryptamine | 68.36 ± 6.19 | 59.83 ± 7.88 |
| Serotonin | 322.30 ± 31.43 | 309.59 ± 38.51 |
| Indole-3-carboxylic acid | >9 mM | >9 mM |
| 2,3,4,9-Tetrahydro-1H-β-carboline-3-carboxynate | 579.20 ± 44.42 | 730.80 ± 85.98 |
| L-tryptophanol | 221.50 ± 32.43 | 280.34 ± 43.21 |
| α-Me-Trp | 100.10 ± 4.30 | 94.69 ± 8.52 |
| 7-Azatryptophan | 16.83 ± 0.28 | 25.46 ± 0.58 |
| 4-F-Trp | 189.20 ± 11.14 | 175.22 ± 12.90 |
| 4-Me-Tr | 9.58 ± 0.36 | 13.48 ± 0.98 |
| 5-OH-L-Trp | 340.90 ± 26.39 | 452.58 ± 15.47 |
| 5-MeO-Trp | 29.13 ± 1.16 | 25.77 ± 1.84 |
| 5-Me-Trp | 34.66 ± 0.99 | 29.86 ± 1.03 |
| 5-F-L-Trp | 84.18 ± 4.37 | 77.48 ± 5.74 |
| 6-F-Trp | 73.39 ± 6.06 | 65.31 ± 4.49 |
| 7-Me-Trp | 12.93 ± 0.99 | 10.64 ± 0.75 |

Binding affinities of chemicals to P450s were measured using 1.5 μM of enzymes in 25 mM Tris-HCl, pH 8.0. All experiments were repeated at least three times. Data were fitted to the Michaelis-Menten equation.

Regio-Specificity of TB14 in Nitration

A remarkable plasticity of TB13-Q to selectively nitrate C7 when C4 of its substrate indole is occupied by an F substitution has been observed. To further probe the extent to which physiochemical properties of the substituted group at C4 impact enzyme regio-selectivity, TB14 was produced in a scaled-up reaction to nitrate commercially available racemic 4-Me-DL-Trp. Compared with the fluorine replacement, the methyl group is larger in size and is electron donating in nature. Interestingly, 4-Me-DL-Trp bound to enzymes more tightly than 4-F-DL-Trp (Table 4). Additionally, TB14 favoured 4-Me-DL-Trp about 8 times more over 4-F-DL-Trp in nitration (FIG. 8).

Figure 9:
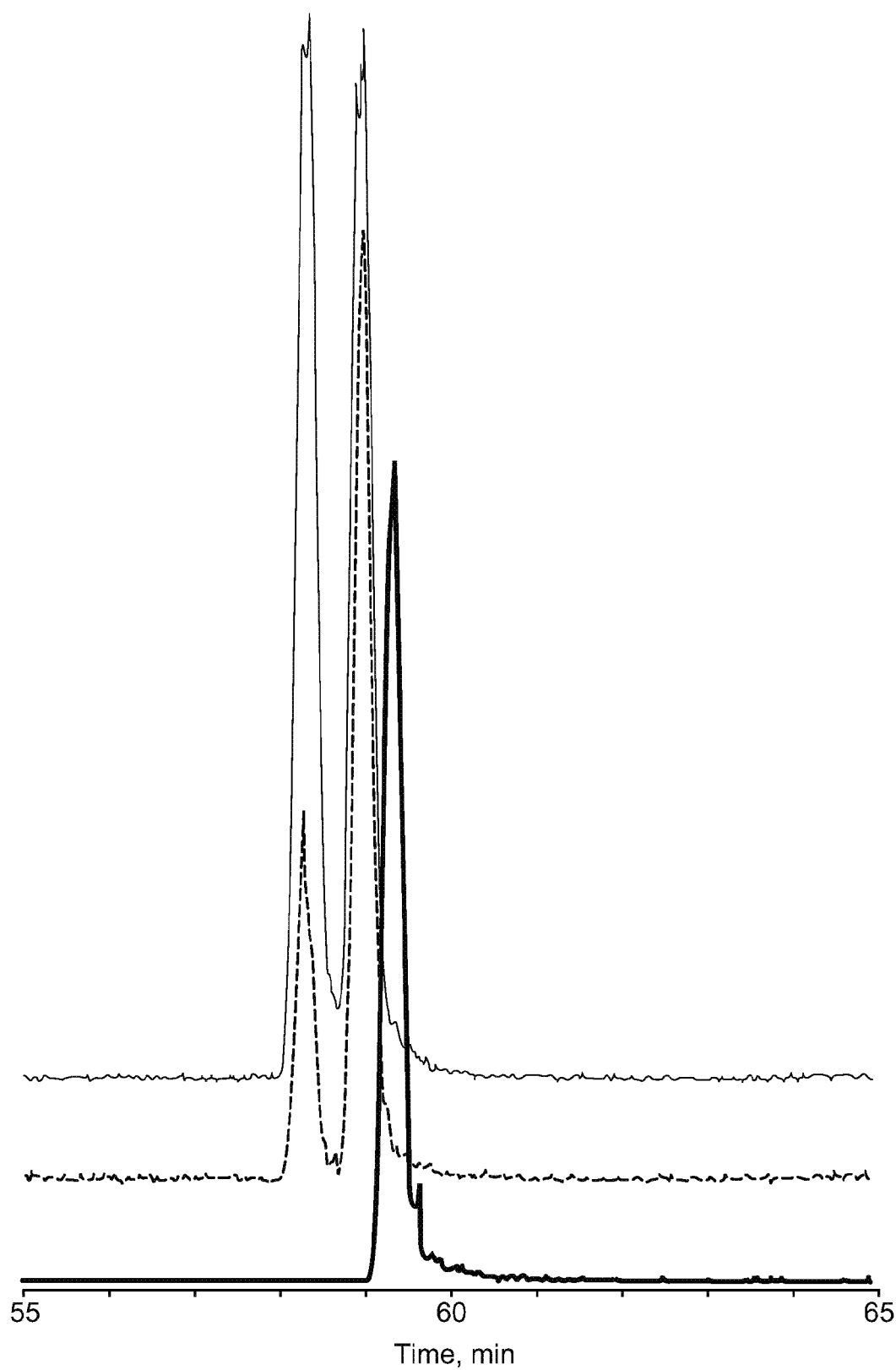
FIG. 9 shows LC-MS analysis of Marfey's derivatization of 4-Me-DL-Trp and its nitro product. Top peaks: ion extract spectrum of Marfey's derivatized 4-Me-DL-Trp; Middle peaks: ion extract spectrum of Marfey's derivatized 4-Me-DL-Trp after the enzyme reaction; and Bottom peaks: ion extract spectrum of Marfey's derivatized nitro product.
Figure 10:
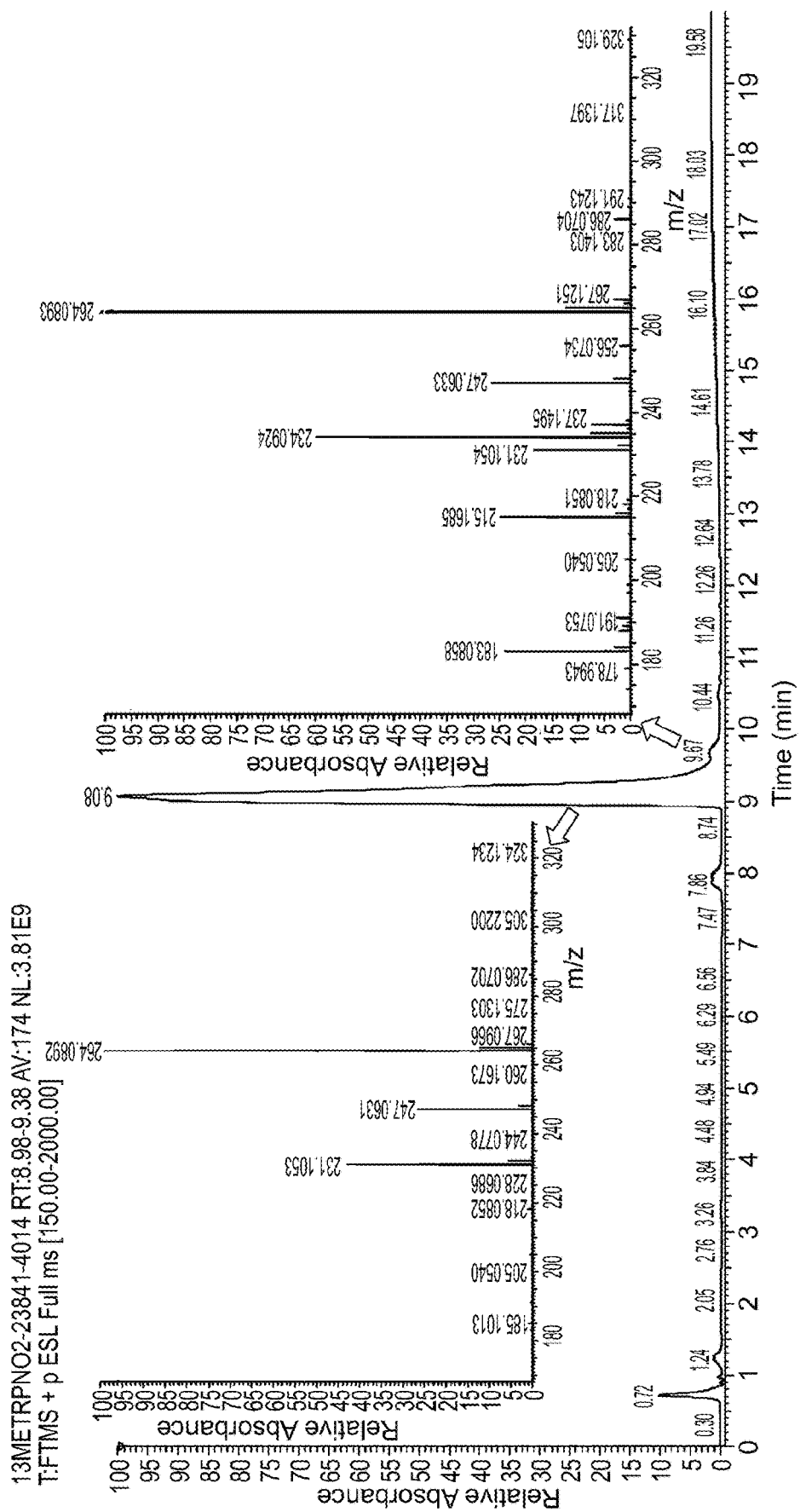
FIG. 10 shows LC-HRMS analysis of isolated nitro product of 4-Me-DL-Trp. Two peaks with the retention times of 9.06 and 9.67 min showed the same m/z value of about 264.0892.

About 0.08 mg of nitrated 4-Me-DL-Trp was isolated as a yellow powder by semi-preparative HPLC. By Marfey's derivatization, significant consumption of 4-Me-L-Trp in the reaction was observed and the nitro product was identified with L-configuration (FIG. 9). This result further confirmed the strict stereo-selectivity of TB14 in nitration. LC-high resolution (HR) MS analysis of the isolated product confirmed the nitration on the substrate by giving one major peak with the expected molecular weight of nitro product (m/z=264.0892, FIG. 10). Interestingly, one minor peak with the same molecular weight was eluted right after the major one (FIG. 10), indicating the coexistence of two structural isomers in the sample.

Figure 11:
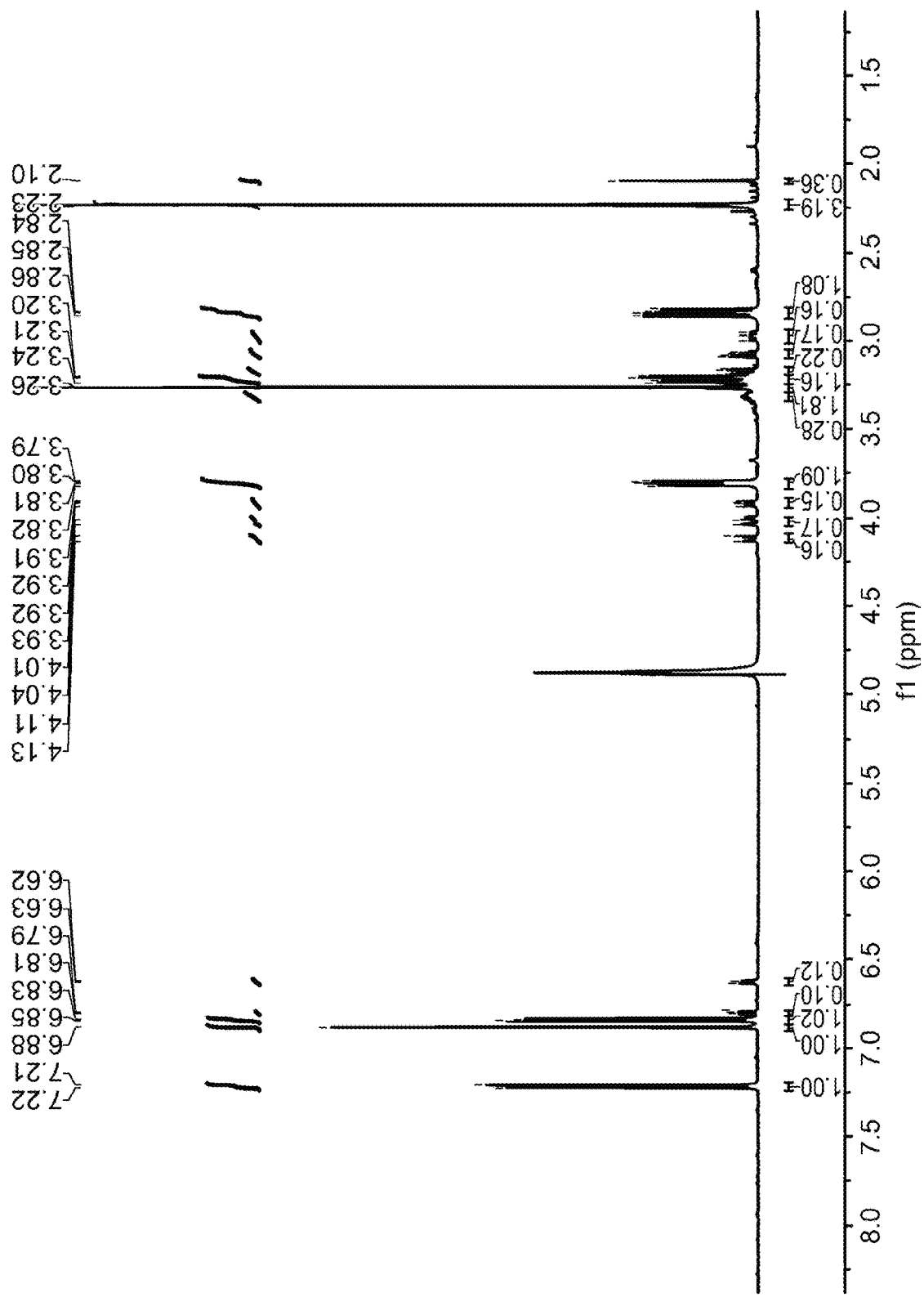
FIG. 11 shows the $^1$H NMR spectrum of isolated nitro product of 4-Me-DL-Trp.
Figure 12:
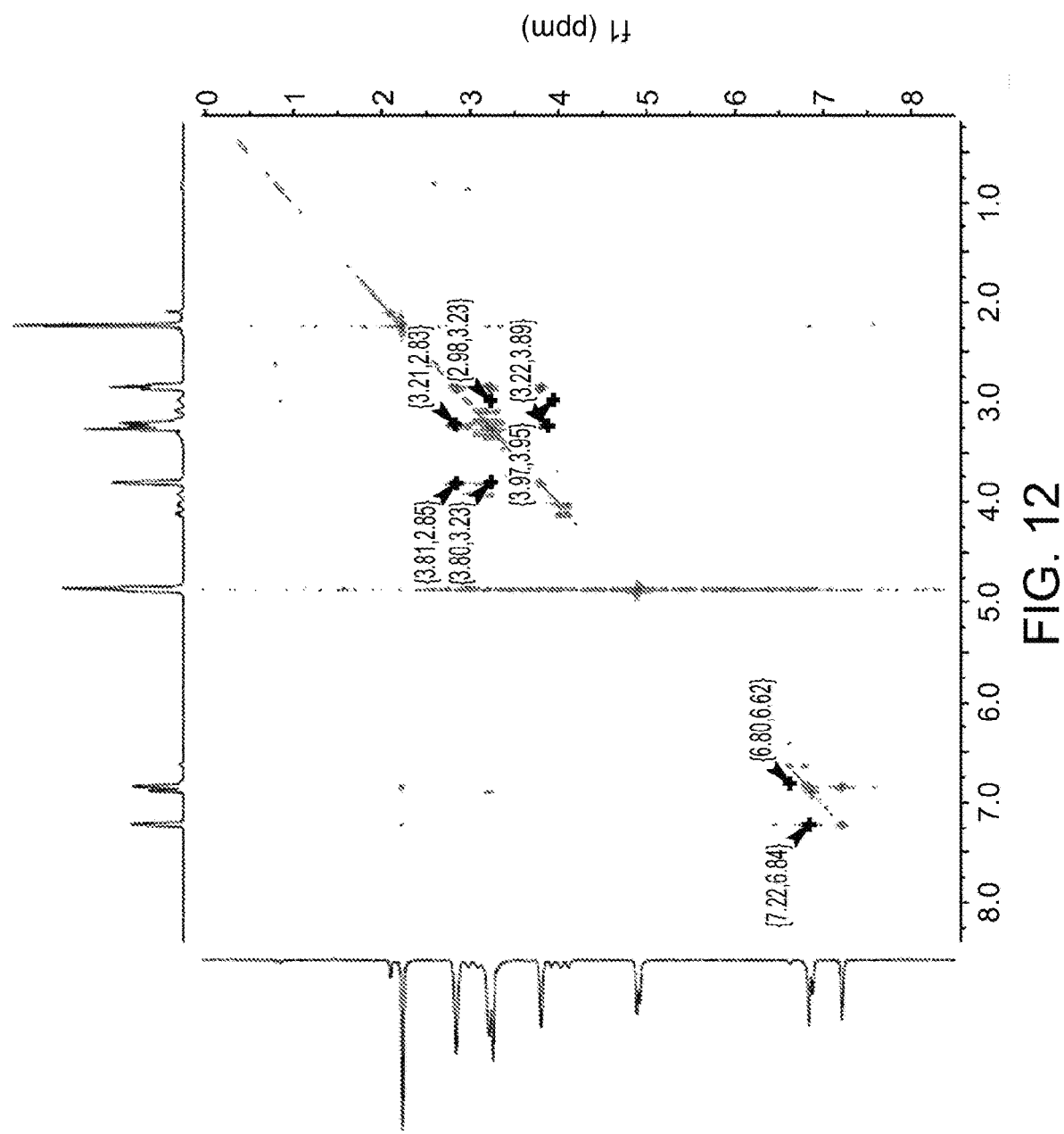
FIG. 12 shows the COSY spectrum of the isolated nitro product of 4-Me-DL-Trp.
Figure 13:
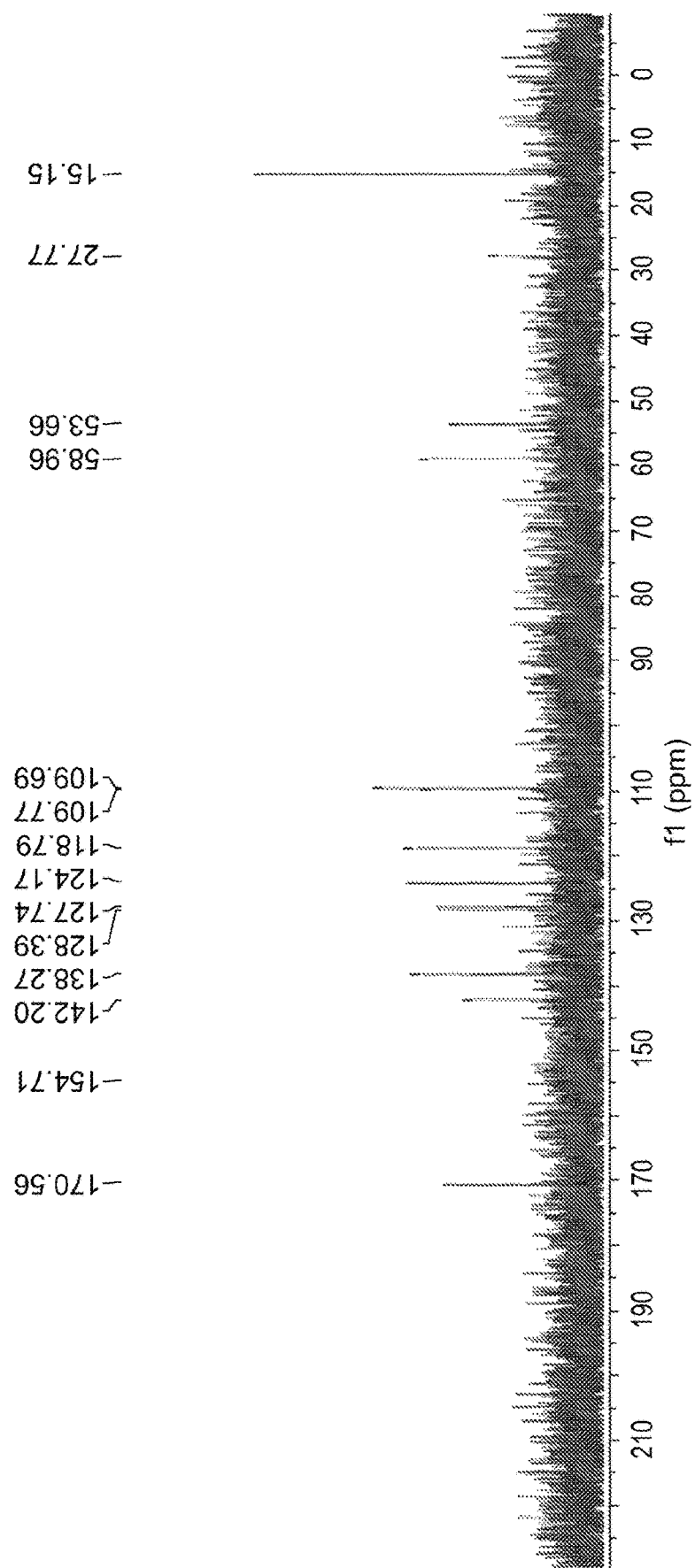
FIG. 13 shows the HSQ13C NMR spectrum of the isolated nitro product of 4-Me-DL-Trp.
Figure 14:
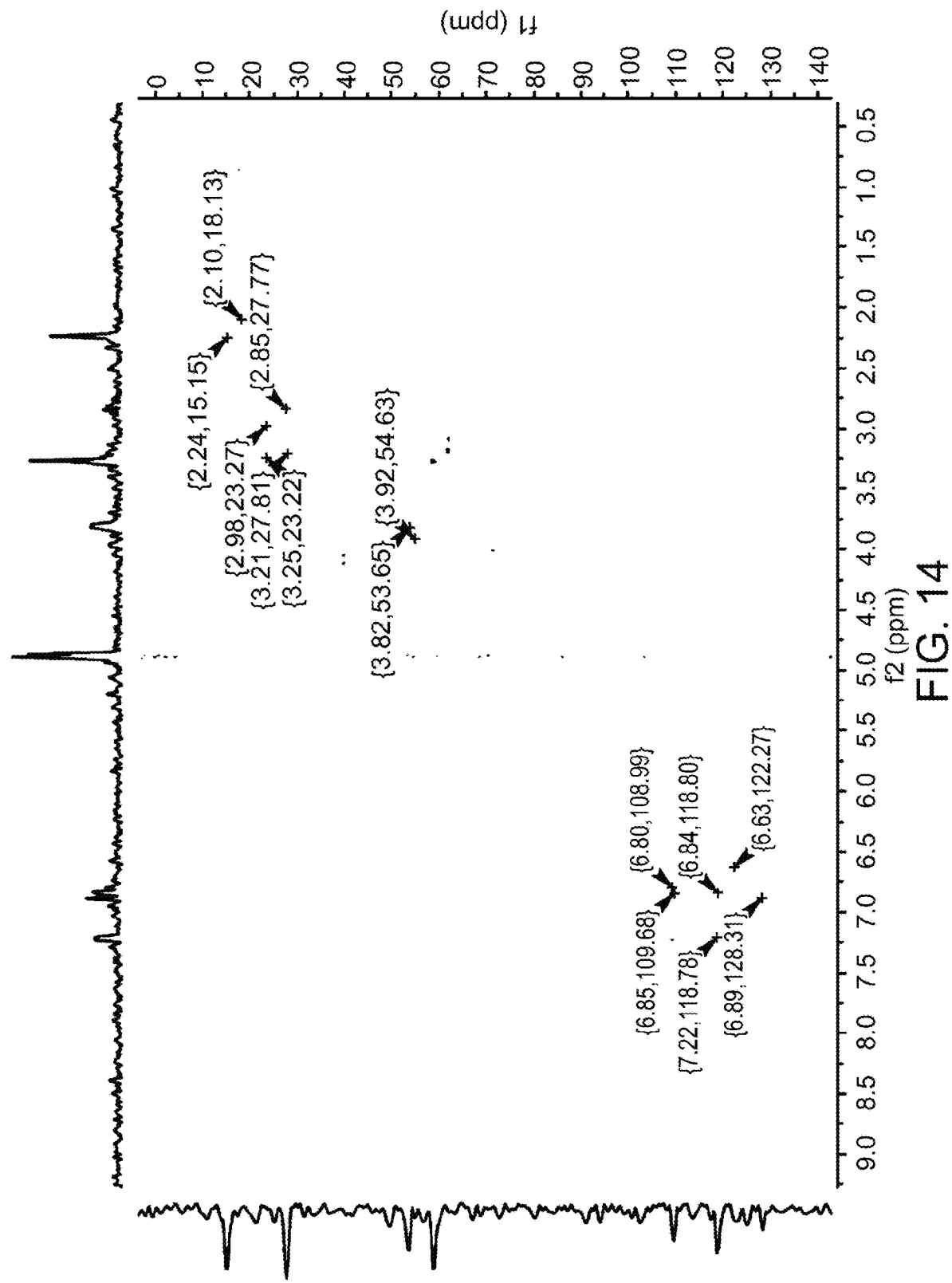
FIG. 14 shows the HMBC spectrum of the isolated nitro product of 4-Me-DL-Trp.
Figure 15:
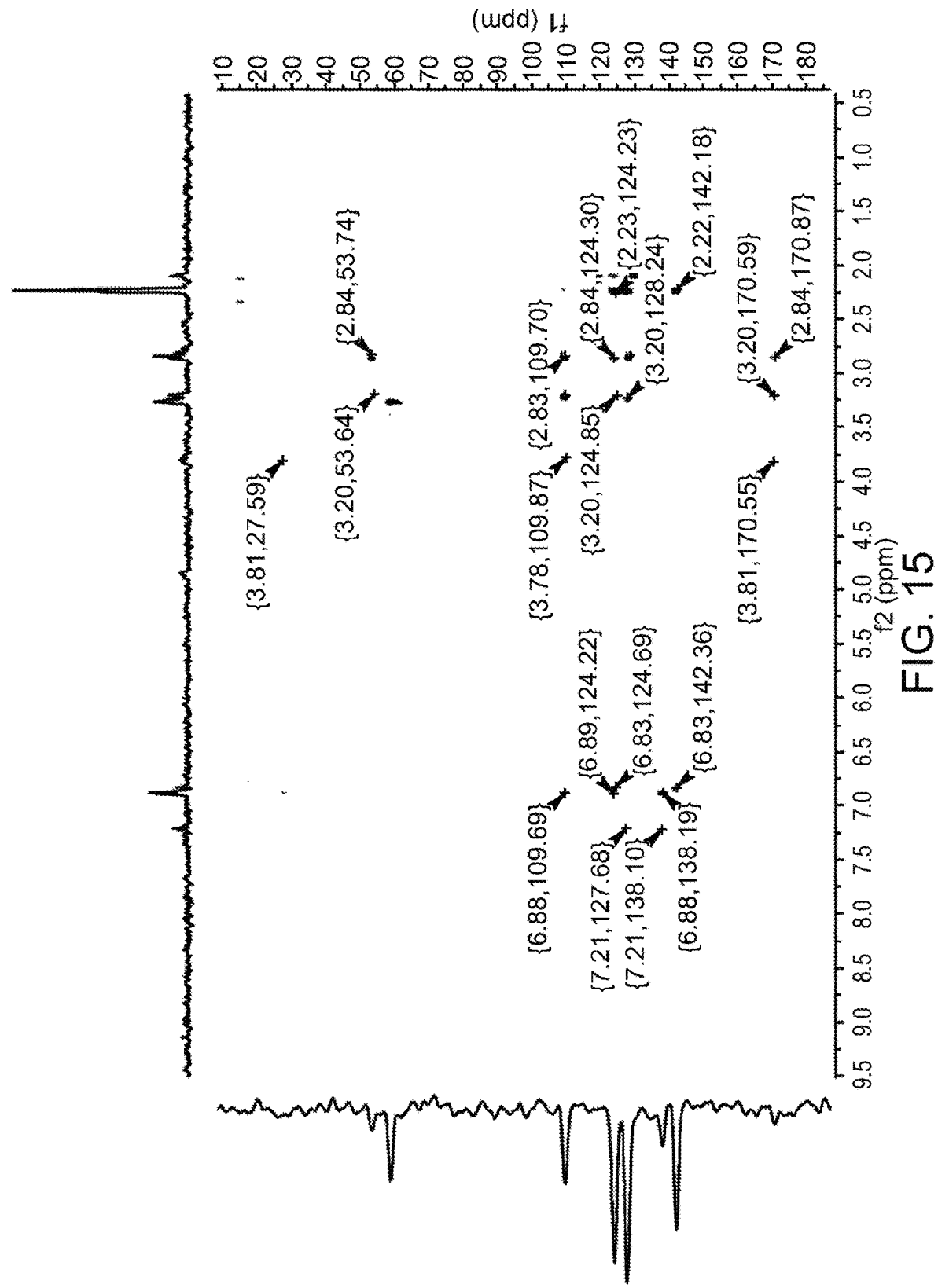
FIG. 15 shows the HMBC spectrum of the isolated nitro product of 4-Me-DL-Trp.
Figure 16:
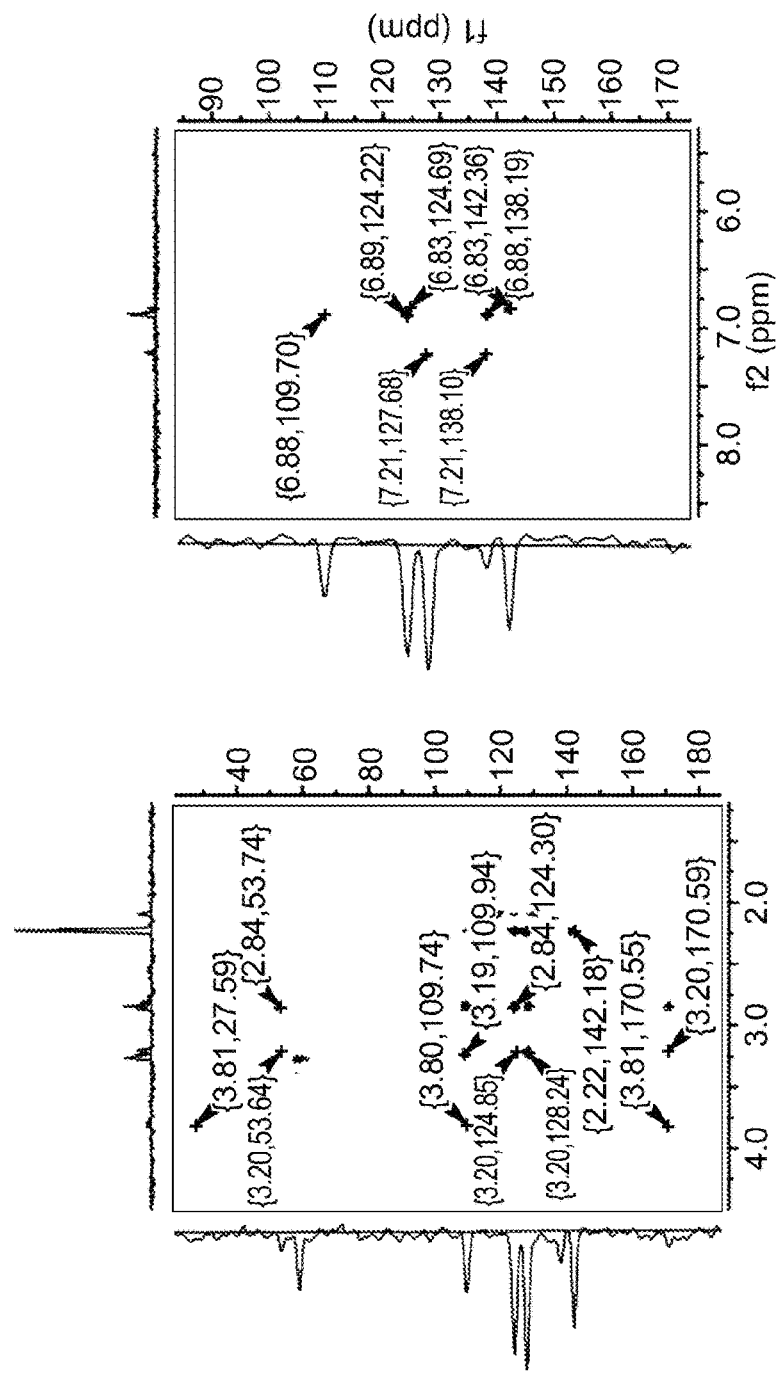
FIG. 16 shows an expansion of the HMBC spectrum in the aromatic and aliphatic regions and the representative correlations for 4-methyl-5-nitro-L-tryptophan.
Figure 16:
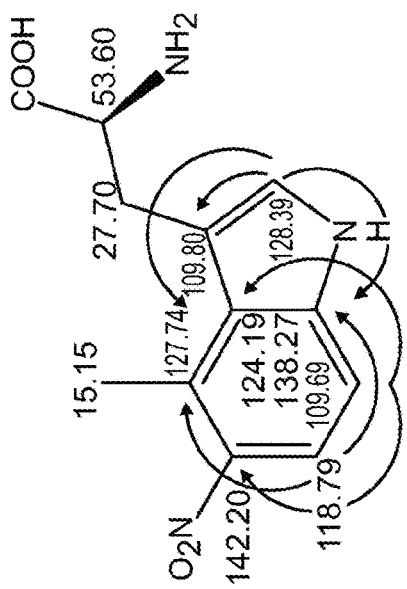
Figure 17:
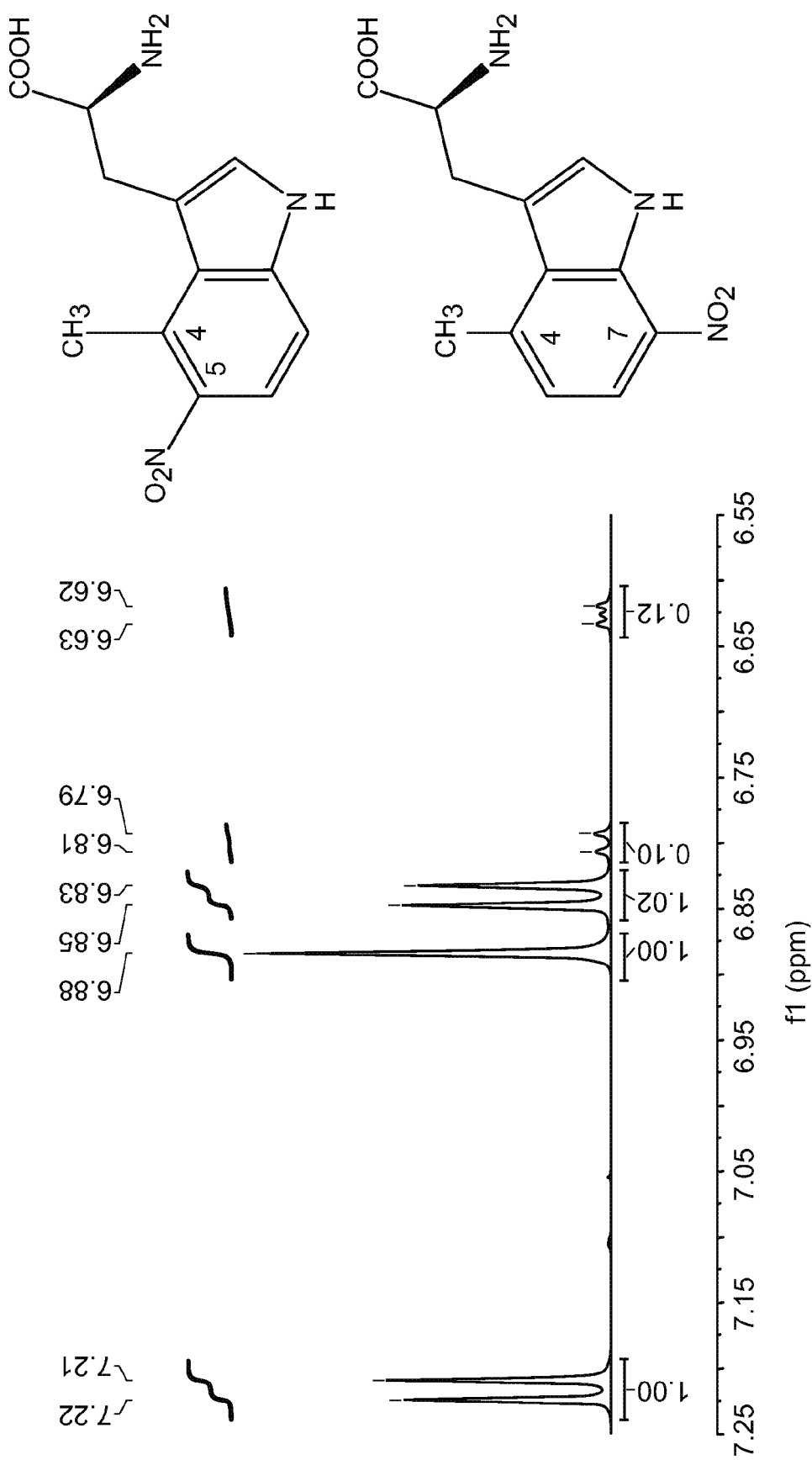
FIG. 17 shows that both 4-Me-5-$NO_2$-L-Trp and 4-Me-7-$NO_2$-L-Trp were produced in the TB14 reaction with 4-Me-DL-Trp as substrate. The aromatic region of the 1H NMR spectrum of isolated product showed the characteristic chemical shifts of aromatic protons of two products. Integrated values of these protons were also included.

Next, the isolated product was characterized by $^1$H and $^{13}$C and 2D NMR analysis (FIGS. 11-16). From the $^1$H NMR and COSY spectra (FIG. 11-12), two well separated AX coupling systems were observed in the aromatic region, clearly indicating two nitration sites in the indole. One AX coupling system involved two large doublet peaks at δ 7.22 ppm and 6.84 ppm (FIG. 17) while the other was from two small doublet peaks at δ 6.80 ppm and 6.62 ppm (FIG. 17). The large vicinal coupling constants (8-9 Hz) of the two AX coupling systems further indicate the C5 and C7 of the indole as the nitration sites (Table 5, FIG. 17). Given the larger deshielding effect of C5-$NO_2$ than C7-$NO_2$ on the C4-Me group, the methyl signal of 4-Me-5-$NO_2$-L-Trp was in the lower field (δ 2.23 ppm vs 2.10 ppm in 4-Me-7-$NO_2$-L-Trp, Table S2). Using the integration values of two methyl groups, the molar ratio of 4-Me-5-$NO_2$-L-Trp: 4-Me-7-$NO_2$-L-Trp was determined to be about 10:1 (FIG. 11). The chemical shift signals of 4-Me-5-$NO_2$-L-Trp in the $^{13}$C NMR spectrum were also observed (Table 5, FIG. 13). The determination of the product structure was further assisted by HSQC and HMBC spectra (FIGS. 14-15). In the HMBC spectrum, the C4-Me group (2.22 ppm) correlated with a significantly deshielded aromatic carbon (142.18 ppm) that became possibly only by the C5-$NO_2$ group (FIGS. 15-16). Therefore, TB14 carried a striking regio-flexibility in nitrating 4-Me-DL-Trp to produce predominantly 4-Me-5-$NO_2$-L-Trp and 4-Me-7-$NO_2$-L-Trp (FIG. 17). These results indicated that different types of substituted groups at C4 of the indole ring can affect key parameters (activity and regio-selectivity) of TxtE biocatalysts.

TABLE 5

13C and 1H NMR data of 4-Me-5-NO2-L-Trp and 4-F-7-NO2-L-Trp and 1H NMR data of 4-Me-7-NO2-L-Trp:

| | 4-Me-5-$NO_2$-L-Trp | | 4-Me-7-$NO_2$-L-Trp | | 4-F-7-$NO_2$-L-Trp | |
|---|---|---|---|---|---|---|
| Atom | $δ_C$, type | $δ_H$ (J in Hz) | $δ_C$, type | $δ_H$ (J in Hz) | $δ_C$, type | $δ_H$ (J in Hz) |
| 2 | 128.4, CH | 6.88 s | —, CH | | 128.5, CH | 7.29 s |
| 3 | 109.8, C | | —, C | | 108.3, C | |
| 3a | 124.2, C | | —, C | | 115.2, C | |
| 4 | 127.7, C | | —, C | | 151.5, C | |
| 5 | 142.2, C | | —, CH | 6.63 d (8.1) | 119.4, CH | 7.80 dd (8.1, 8.1) |
| 6 | 118.7, CH | 7.22 d (9.0) | —, CH | 6.80 d (8.3) | 108.4, CH | 7.22 d (9.1) |
| 7 | 109.7, CH | 6.84 d (8.9) | —, C | | 128.6, C | |
| 7a | 138.3, C | | —, C | | 142.3, C | |
| 1' | 171.4, C | | —, C | | 171.3, C | |
| 2' | 53.6, CH | 3.80 dd (10.1, 5.1) | —, CH | 3.92 dd (10.7, 5.4) | 53.7, CH | 4.26 m |
| 3' | 27.7, $CH_2$ | 3.22 dd (15.6, 5.1) 2.84 dd (15.7, 10.1) | —, $CH_2$ | 3.22 dd (16.2, 5.4) 2.98 dd (16.2, 10.8) | 26.7, $CH_2$ | 3.43 dd (15.2, 6.5) 3.32 dd (15.2, 8.2) |
| 4-Me | 15.15, $CH_3$ | 2.23 s | —, $CH_3$ | 2.10 s | — | — |

Data recorded at 151 MHz; data recorded at 600 MHz; 4-F-7-NO2-l-Trp data obtained from: R. Zuo, Y. Zhang, J. C. Huguet-Tapia, M. Mehta, E. Dedic, S. D. Bruner, R. Loria and Y. Ding, Biotechnol J, 2016, 11, 624-632.

The following nitro-aromatic analogs can be synthesized using any of the methods delineated herein, including the processes presented in Examples 1-2.

Example 3: Preparation of (S)-2-amino-3-(5-methyl-4-nitro-1H-indol-3-yl)propanoic Acid (3)

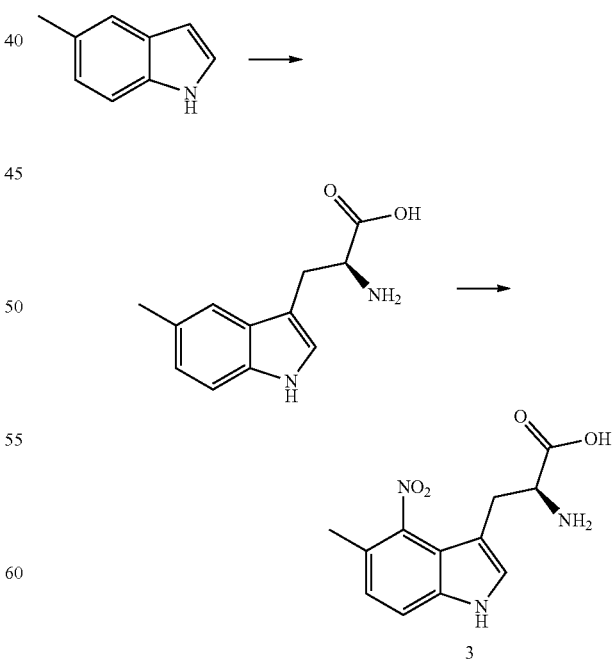

3

Example 3 can be prepared from 5-methylindole as shown above and in a similar manner as described in Examples 1-2.

Example 4: Preparation of (S)-2-amino-3-(6-methyl-4-nitro-1H-indol-3-yl)propanoic Acid (4)

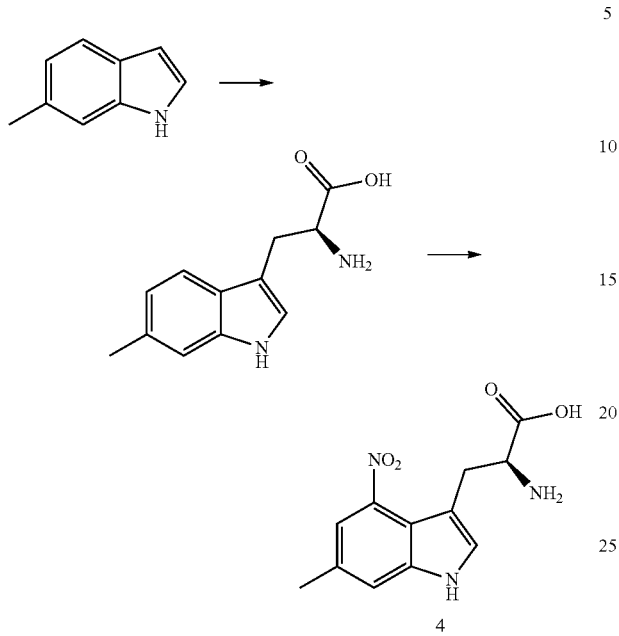

Example 4 can be prepared from 6-methylindole as shown above and in a similar manner as described in Examples 1-2.

Example 5: Preparation of (S)-2-amino-3-(7-methyl-4-nitro-1H-indol-3-yl)propanoic Acid (5)

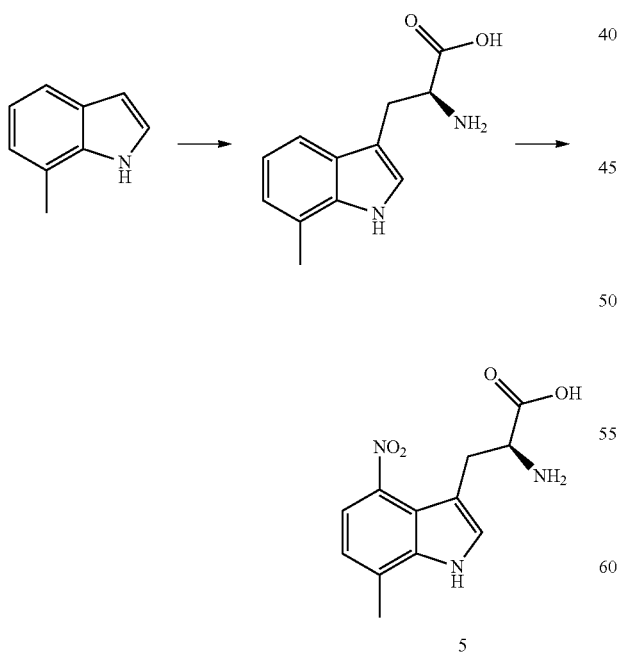

Example 5 can be prepared from 7-methylindole as shown above and in a similar manner as described in Examples 1-2.

Example 6: Preparation of (S)-2-amino-3-(5-fluoro-4-nitro-1H-indol-3-yl)propanoic Acid (6)

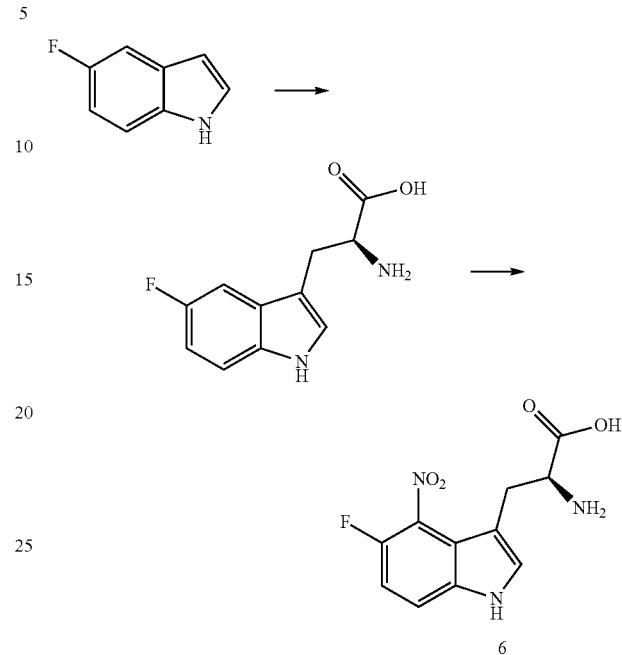

Example 6 can be prepared from 5-fluoroindole as shown above and in a similar manner as described in Examples 1-2.

Example 7: Preparation of (S)-2-amino-3-(6-fluoro-4-nitro-1H-indol-3-yl)propanoic Acid (7)

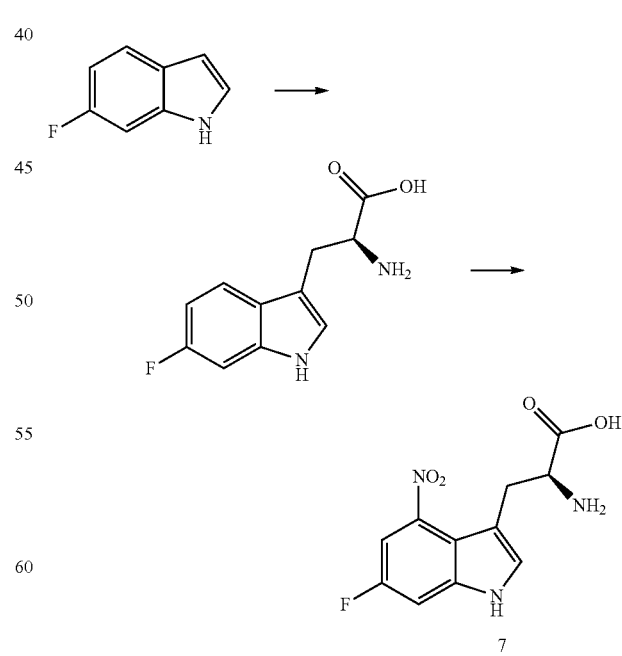

Example 7 can be prepared from 6-fluoroindole as shown above and in a similar manner as described in Examples 1-2.

Example 8: Preparation of (S)-2-amino-3-(7-fluoro-4-nitro-1H-indol-3-yl)propanoic Acid (8)

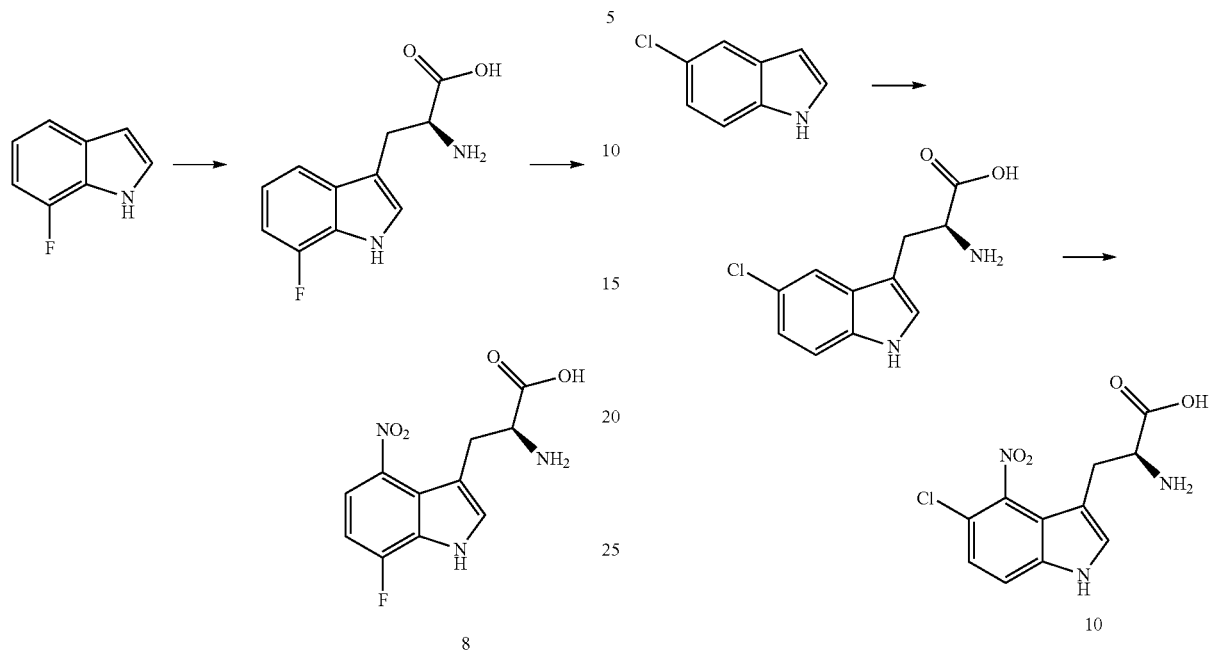

Example 8 can be prepared from 7-fluoroindole as shown above and in a similar manner as described in Examples 1-2.

Example 9: Preparation of (S)-2-amino-3-(4-fluoro-7-nitro-1H-indol-3-yl)propanoic Acid (9)

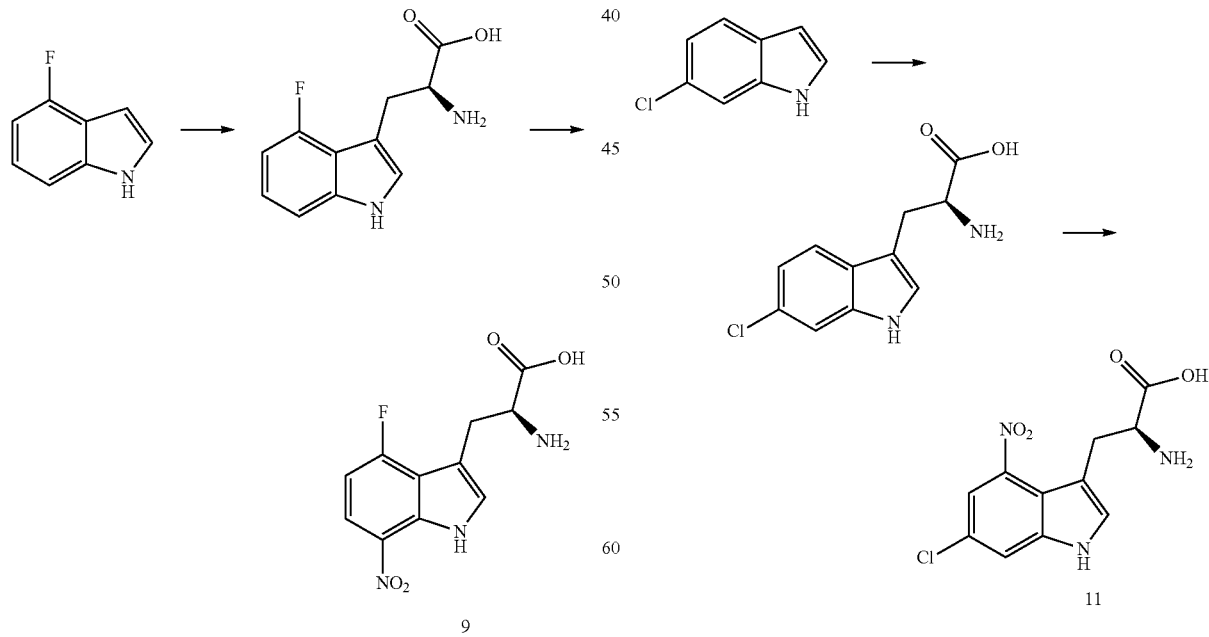

Example 9 can be prepared from 4-fluoroindole as shown above and in a similar manner as described in Examples 1-2.

Example 10: Preparation of (S)-2-amino-3-(5-chloro-4-nitro-1H-indol-3-yl)propanoic Acid

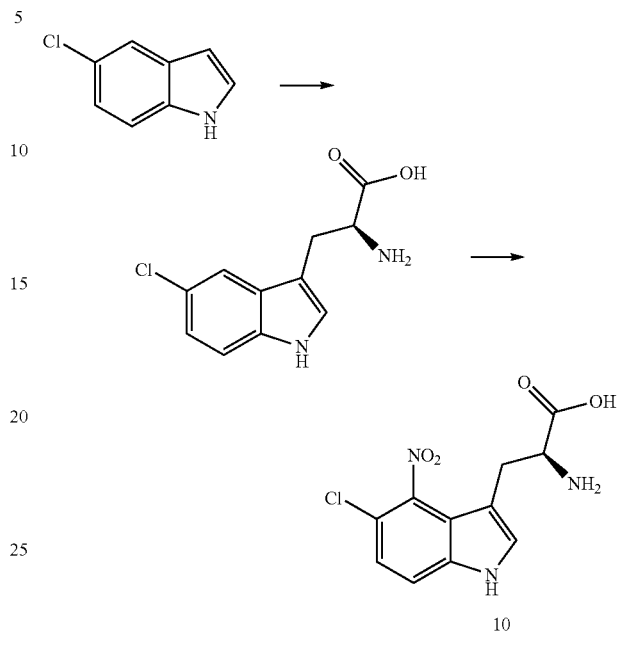

Example 10 can be prepared from 5-chloroindole as shown above and in a similar manner as described in Examples 1-2.

Example 11: Preparation of (S)-2-amino-3-(6-chloro-4-nitro-1H-indol-3-yl)propanoic Acid (11)

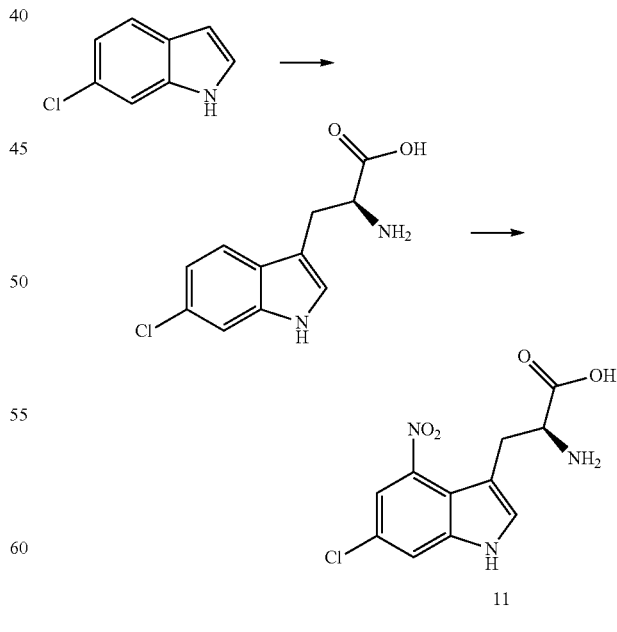

Example 11 can be prepared from 6-chloroindole as shown above and in a similar manner as described in Examples 1-2.

Example 12: Preparation of (S)-2-amino-3-(7-chloro-4-nitro-1H-indol-3-yl)propanoic Acid (12)

Example 14: Preparation of (S)-2-amino-3-(5-bromo-4-nitro-1H-indol-3-yl)propanoic Acid (14)

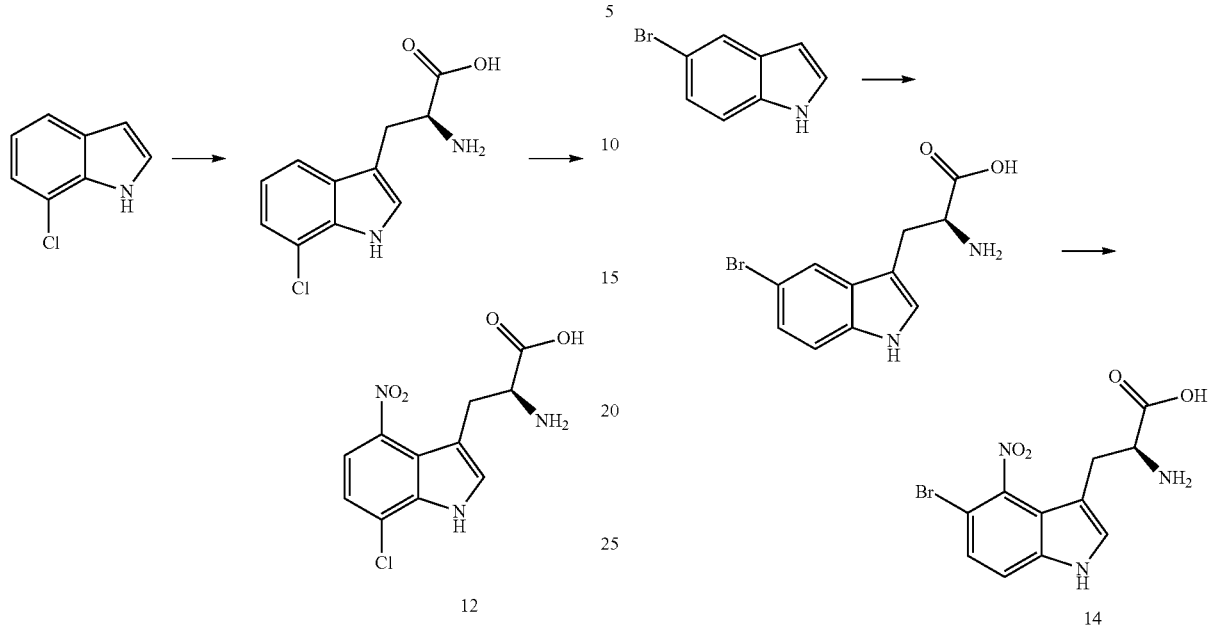

Example 12 can be prepared from 7-chloroindole as shown above and in a similar manner as described in Examples 1-2.

Example 14 can be prepared from 5-bromoindole as shown above and in a similar manner as described in Examples 1-2.

Example 13: Preparation of (S)-2-amino-3-(4-chloro-7-nitro-1H-indol-3-yl)propanoic Acid Example 15: Preparation of (S)-2-amino-3-(6-bromo-4-nitro-1H-indol-3-yl)propanoic Acid (15)

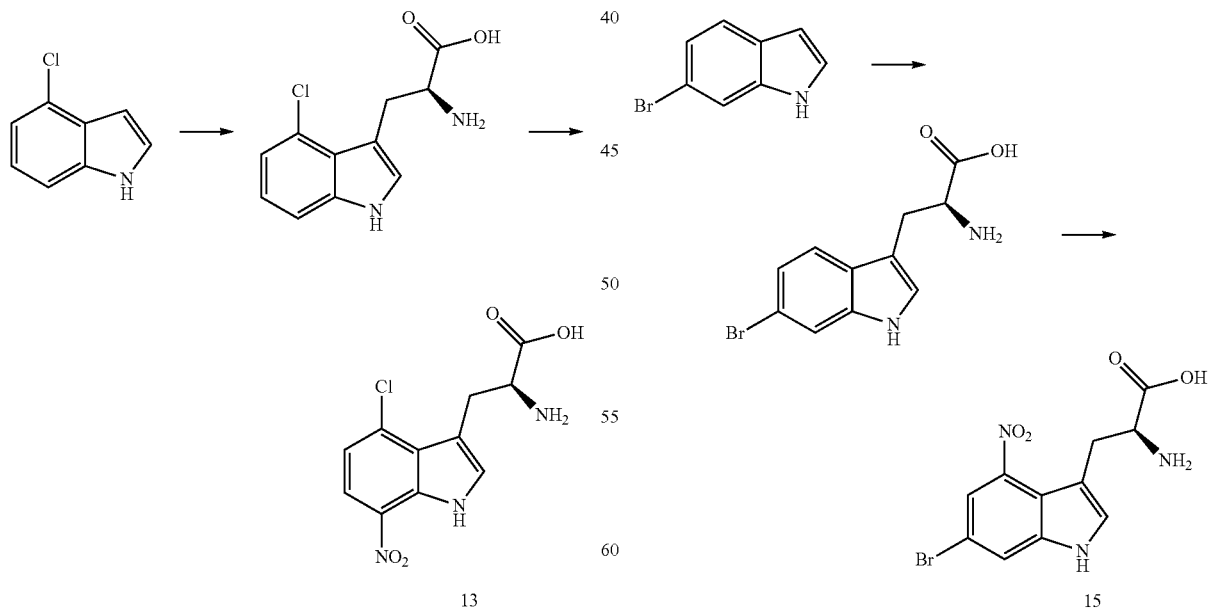

Example 13 can be prepared from 4-chloroindole as shown above and in a similar manner as described in Examples 1-2.

Example 15 can be prepared from 6-bromoindole as shown above and in a similar manner as described in Examples 1-2.

Example 16: Preparation of (S)-2-amino-3-(7-bromo-4-nitro-1H-indol-3-yl)propanoic Acid (16)

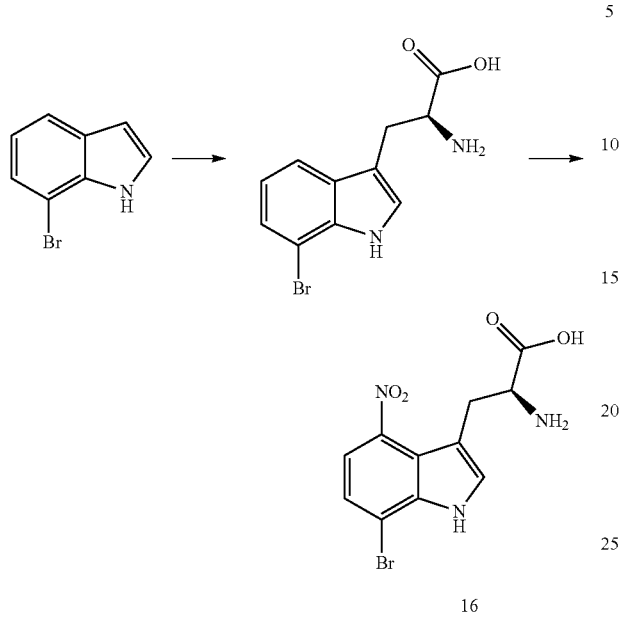

16

Example 16 can be prepared from 7-bromoindole as shown above and in a similar manner as described in Examples 1-2.

Example 17: Preparation of (S)-2-amino-3-(4-bromo-7-nitro-1H-indol-3-yl)propanoic Acid (17)

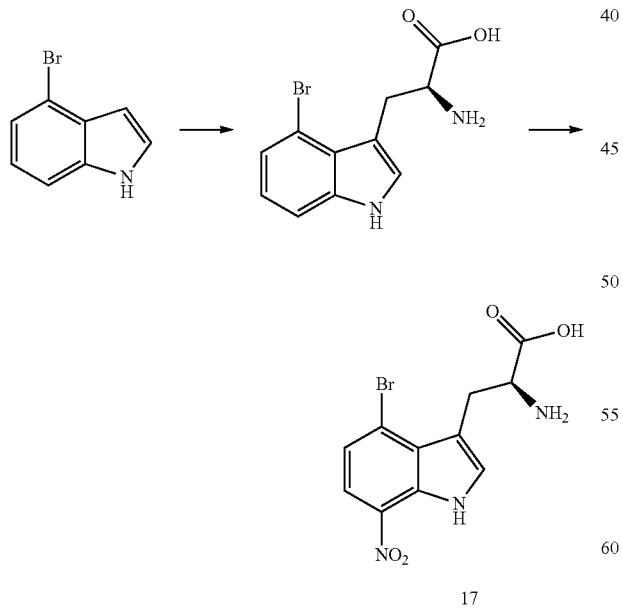

17

Example 17 can be prepared from 4-bromoindole as shown above and in a similar manner as described in Examples 1-2.

Example 18: Preparation of (S)-2-amino-3-(5-methoxy-4-nitro-1H-indol-3-yl)propanoic Acid (18)

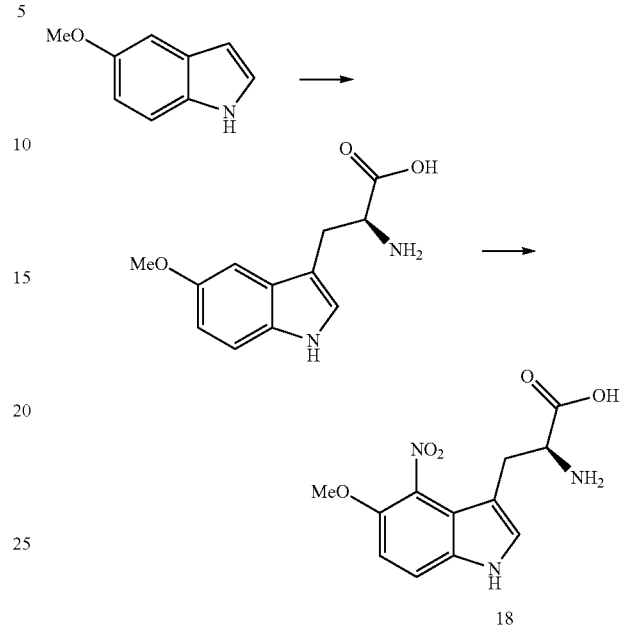

18

Example 18 can be prepared from 5-methoxyindole as shown above and in a similar manner as described in Examples 1-2.

Example 19: Preparation of (S)-2-amino-3-(6-methoxy-4-nitro-1H-indol-3-yl)propanoic Acid

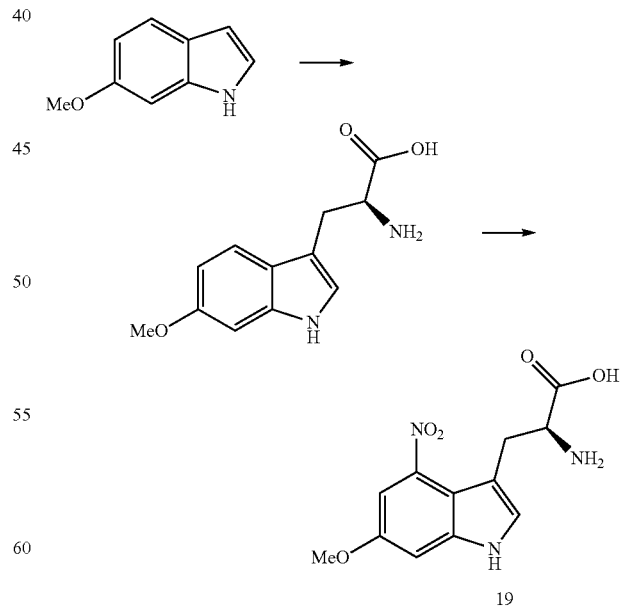

19

Example 19 can be prepared from 6-methoxyindole as shown above and in a similar manner as described in Examples 1-2.

Example 20: Preparation of (S)-2-amino-3-(7-methoxy-4-nitro-1H-indol-3-yl)propanoic Acid (20)

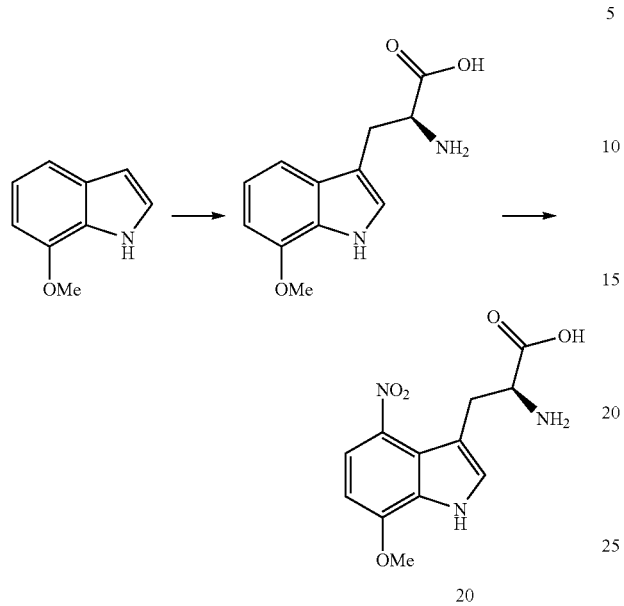

Example 20 can be prepared from 7-methoxyindole as shown above and in a similar manner as described in Examples 1-2.

Example 21: Preparation of (S)-2-amino-3-(4-methoxy-7-nitro-1H-indol-3-yl)propanoic Acid (21)

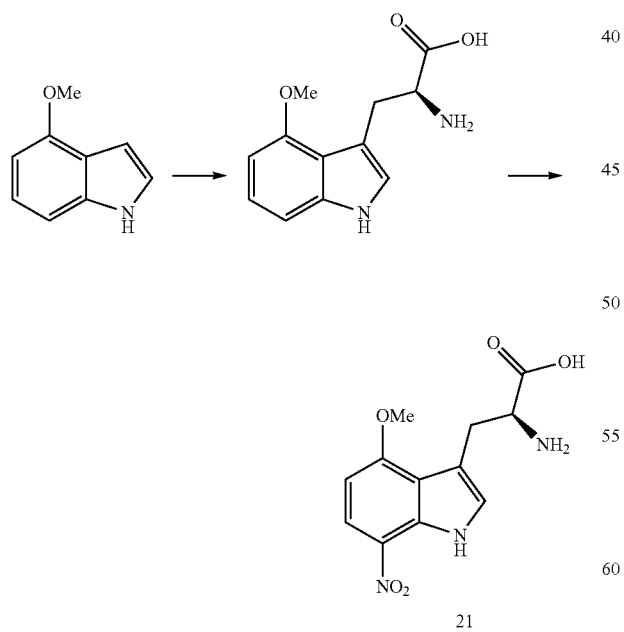

Example 21 can be prepared from 4-methoxyindole as shown above and in a similar manner as described in Examples 1-2.

Example 22: Preparation of (S)-2-amino-3-(5-amino-4-nitro-1H-indol-3-yl)propanoic Acid

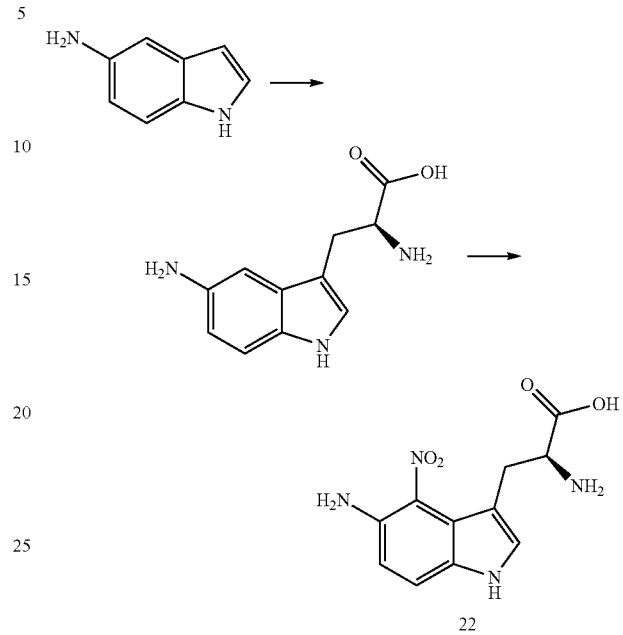

Example 22 can be prepared from 5-aminoindole as shown above and in a similar manner as described in Examples 1-2.

Example 23: Preparation of (S)-2-amino-3-(6-amino-4-nitro-1H-indol-3-yl)propanoic Acid (23)

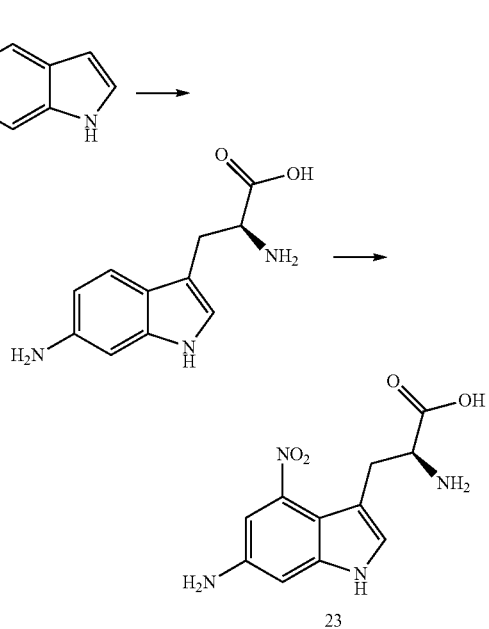

Example 23 can be prepared from 6-aminoindole as shown above and in a similar manner as described in Examples 1-2.

Example 24: Preparation of (S)-2-amino-3-(7-amino-4-nitro-1H-indol-3-yl)propanoic Acid (24)

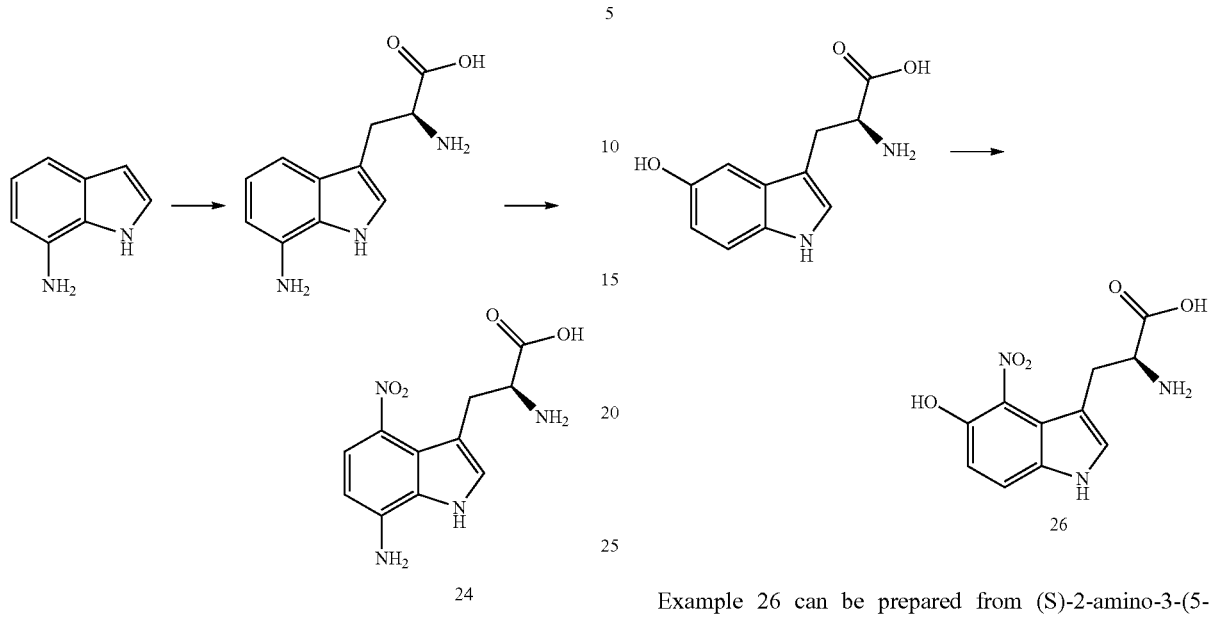

Example 24 can be prepared from 7-aminoindole as shown above and in a similar manner as described in Examples 1-2.

Example 25: Preparation of (S)-2-amino-3-(4-amino-7-nitro-1H-indol-3-yl)propanoic Acid

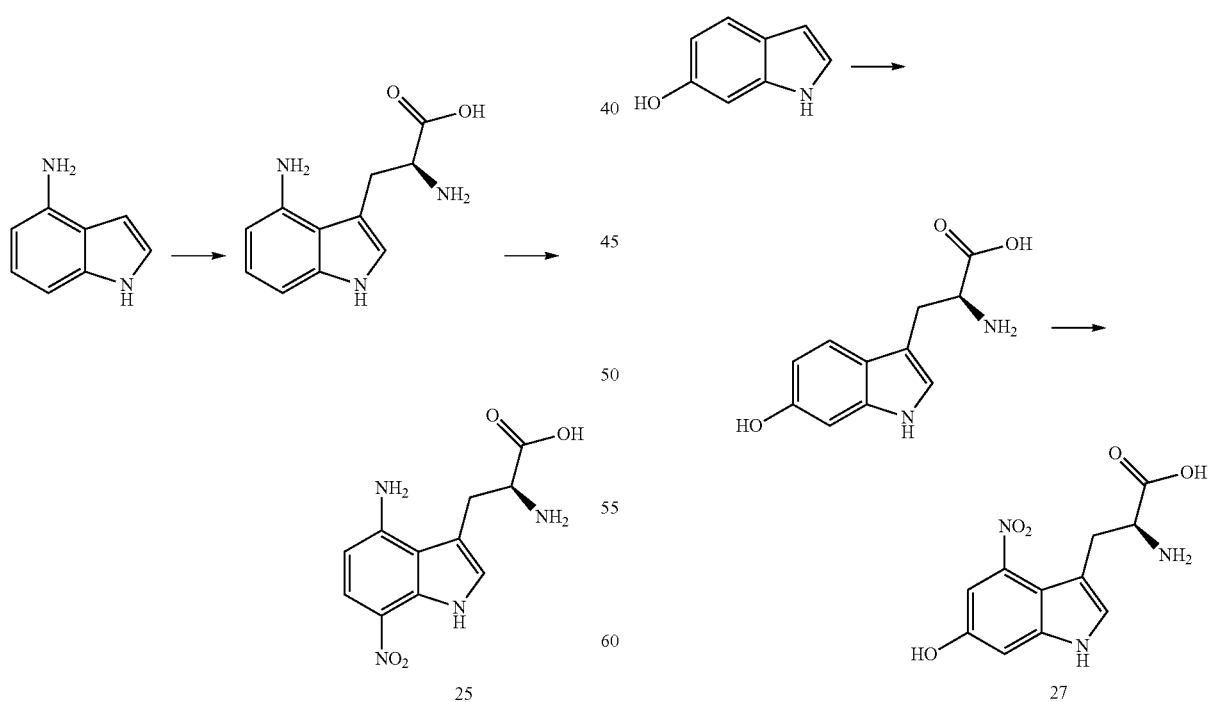

Example 25 can be prepared from 4-aminoindole as shown above and in a similar manner as described in Examples 1-2.

Example 26: Preparation of (S)-2-amino-3-(5-hydroxy-4-nitro-1H-indol-3-yl)propanoic Acid (26)

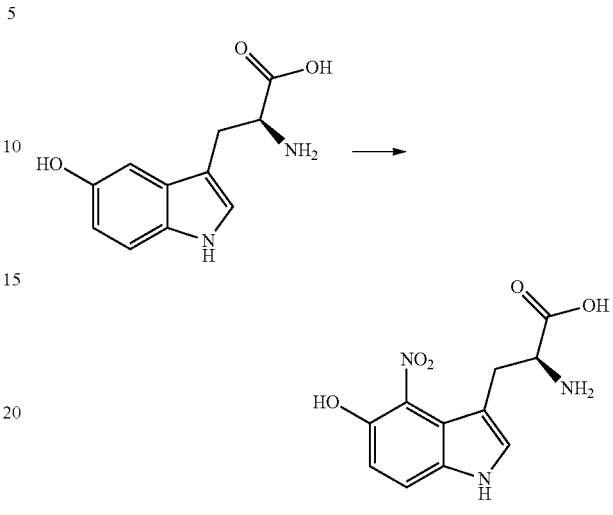

Example 26 can be prepared from (S)-2-amino-3-(5-hydroxy-1H-indol-3-yl)propanoic acid as shown above and in a similar manner as described in Examples 1-2.

Example 27: Preparation of (S)-2-amino-3-(6-hydroxy-4-nitro-1H-indol-3-yl)propanoic Acid (27)

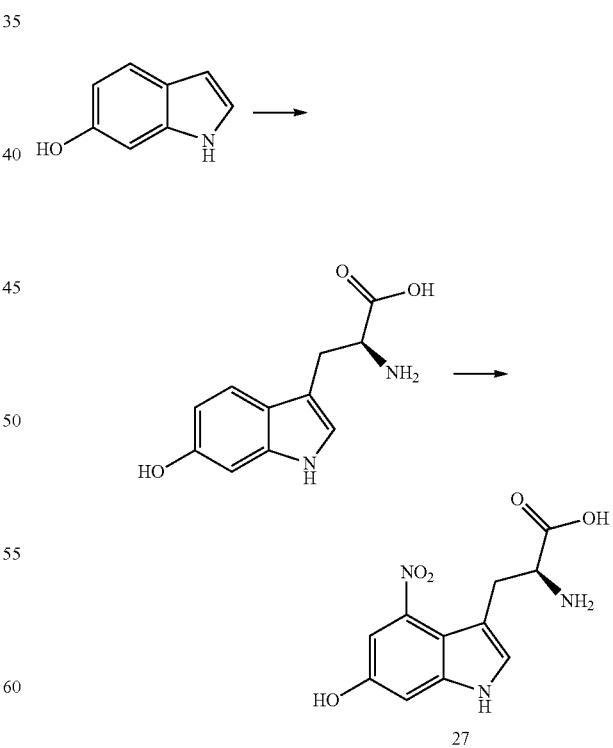

Example 27 can be prepared from 6-hydroxyindole as shown above and in a similar manner as described in Examples 1-2.

Example 28: Preparation of (S)-2-amino-3-(7-hydroxy-4-nitro-1H-indol-3-yl)propanoic Acid

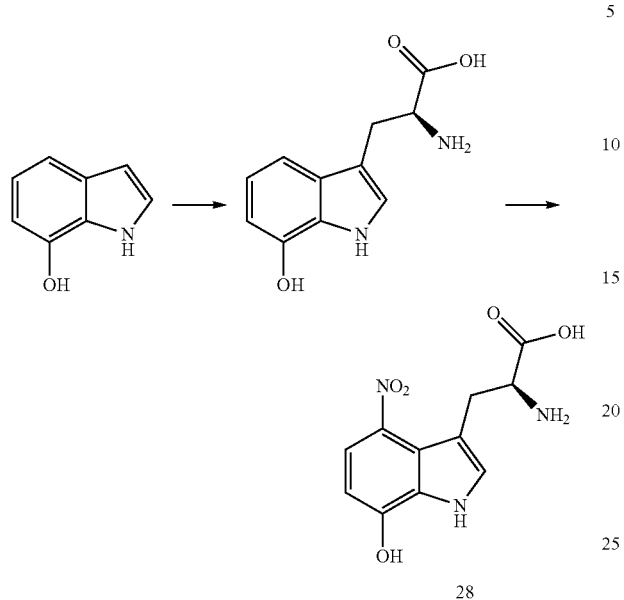

Example 28 can be prepared from 7-hydroxyindole as shown above and in a similar manner as described in Examples 1-2.

Example 29: Preparation of (S)-2-amino-3-(4-hydroxy-7-nitro-1H-indol-3-yl)propanoic Acid (29)

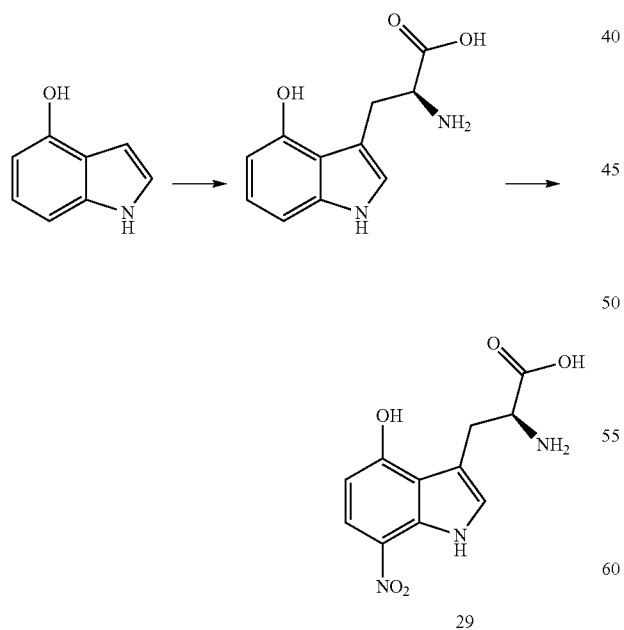

Example 29 can be prepared from 4-hydroxyindole as shown above and in a similar manner as described in Examples 1-2.

Example 30: Preparation of (S)-2-amino-3-(4-nitro-5-phenyl-1H-indol-3-yl)propanoic Acid (30)

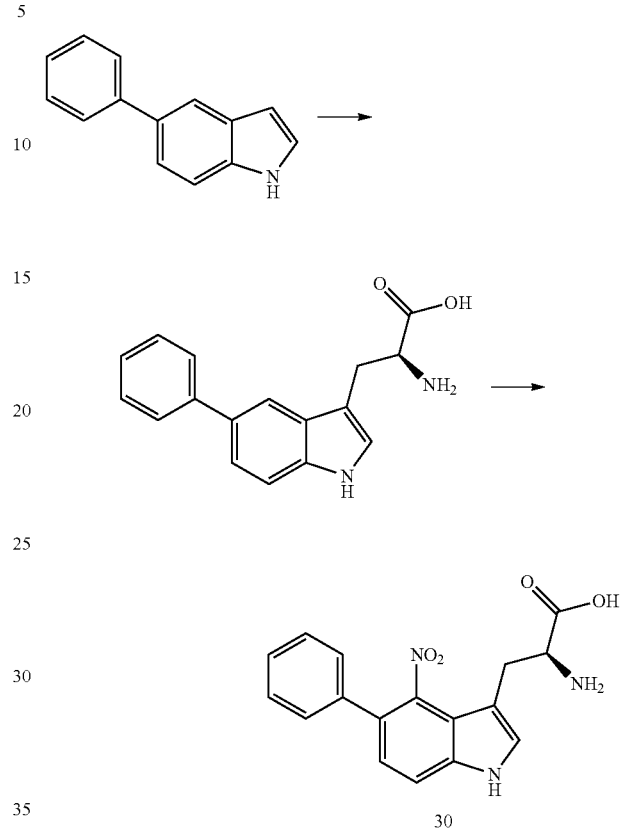

Example 30 can be prepared from 5-phenylindole as shown above and in a similar manner as described in Examples 1-2.

Example 31: Preparation of (S)-2-amino-3-(4-nitro-6-phenyl-1H-indol-3-yl)propanoic Acid

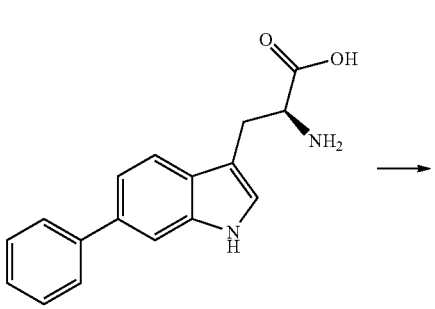

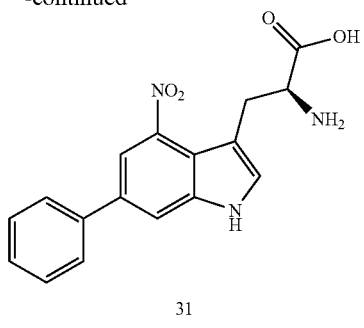

Example 31 can be prepared from 6-phenylindole as shown above and in a similar manner as described in Examples 1-2.

Example 32: Preparation of (S)-2-amino-3-(4-nitro-7-phenyl-1H-indol-3-yl)propanoic Acid (32)

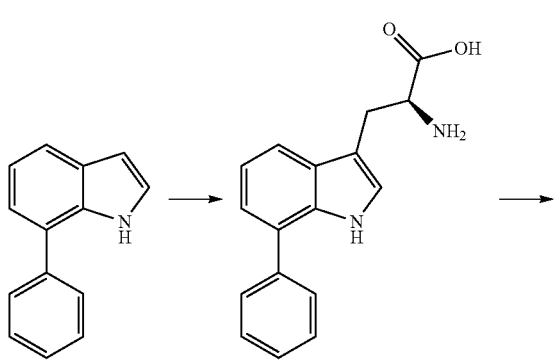

Example 32 can be prepared from 7-phenylindole as shown above and in a similar manner as described in Examples 1-2.

Example 33: Preparation of (S)-2-amino-3-(7-nitro-4-phenyl-1H-indol-3-yl)propanoic Acid (33)

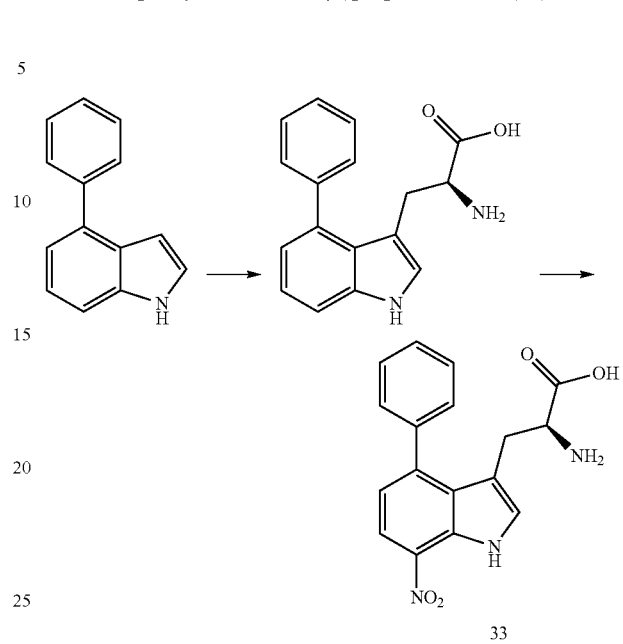

Example 33 can be prepared from 4-phenylindole as shown above and in a similar manner as described in Examples 1-2.

Example 34: Preparation of (S)-2-amino-3-(5-cyclopropyl-4-nitro-1H-indol-3-yl)propanoic Acid (34)

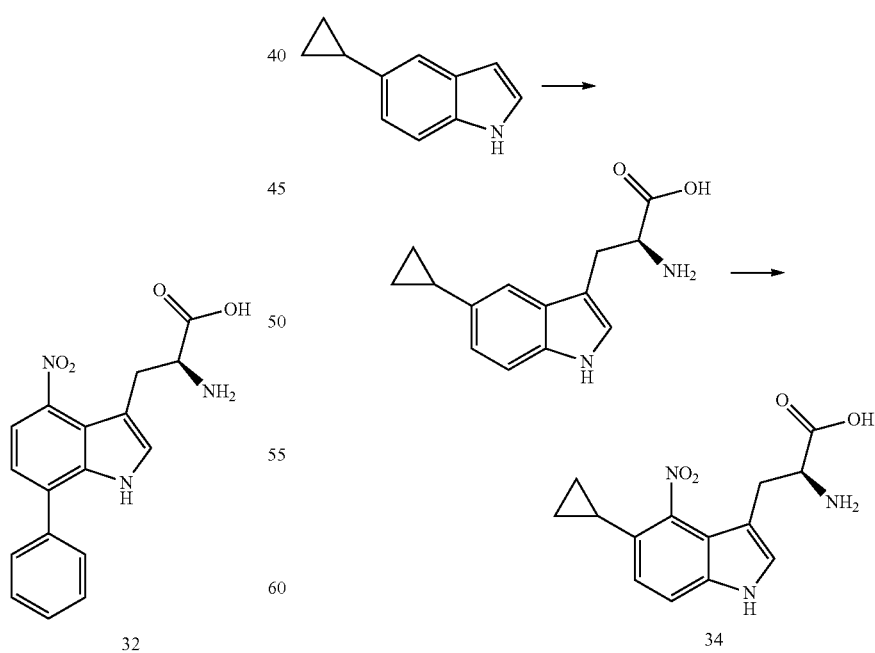

Example 34 can be prepared from 5-cyclopropylindole as shown above and in a similar manner as described in Examples 1-2.

Example 35: Preparation of (S)-2-amino-3-(6-cyclopropyl-4-nitro-1H-indol-3-yl)propanoic Acid (35)

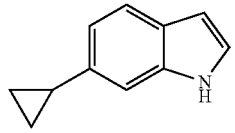

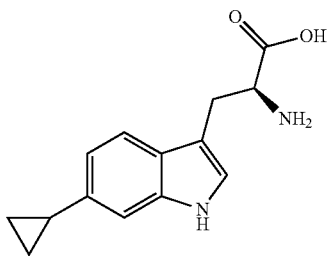

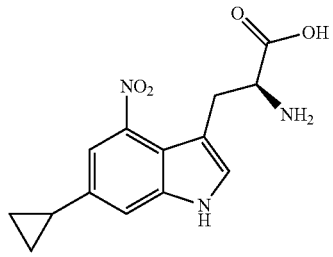

35

Example 35 can be prepared from 6-cyclopropylindole as shown above and in a similar manner as described in Examples 1-2.

Example 36: Preparation of (S)-2-amino-3-(7-cyclopropyl-4-nitro-1H-indol-3-yl)propanoic Acid (36)

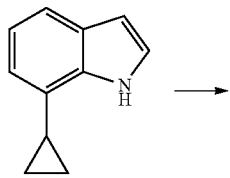

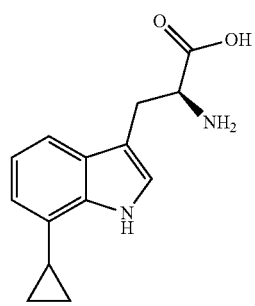

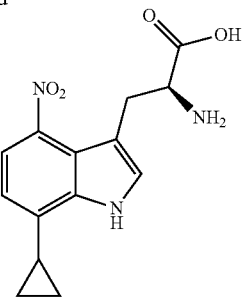

36

Example 36 can be prepared from 7-cyclopropylindole as shown above and in a similar manner as described in Examples 1-2.

Example 37: Preparation of (S)-2-amino-3-(4-cyclopropyl-7-nitro-1H-indol-3-yl)propanoic Acid (37)

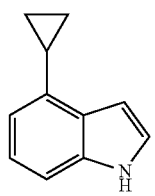

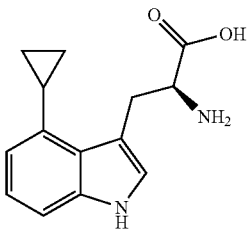

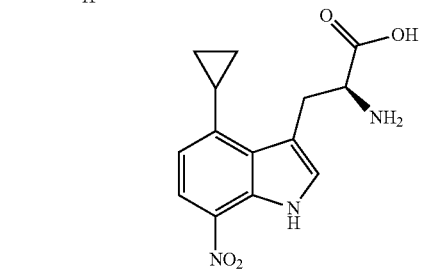

37

Example 37 can be prepared from 4-cyclopropylindole as shown above and in a similar manner as described in Examples 1-2.

Example 38: Preparation of (S)-2-amino-3-(4-nitro-5-vinyl-1H-indol-3-yl)propanoic Acid (38)

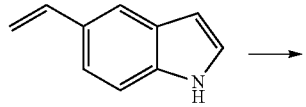

-continued

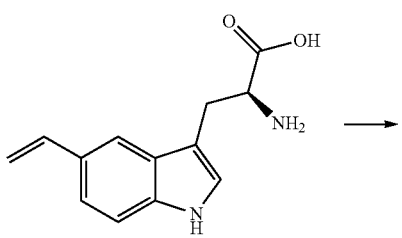

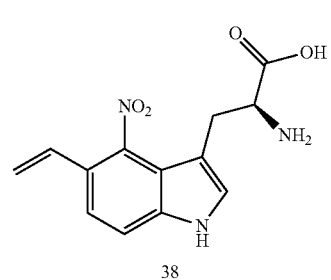

38

Example 38 can be prepared from 5-vinylindole as shown above and in a similar manner as described in Examples 1-2.

Example 39: Preparation of (S)-2-amino-3-(4-nitro-6-vinyl-1H-indol-3-yl)propanoic Acid (39)

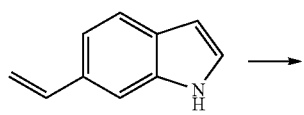

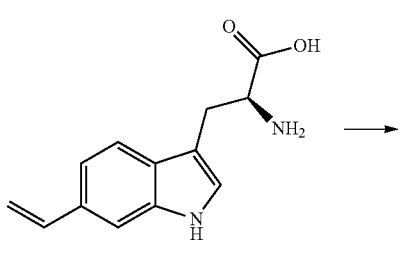

39

Example 39 can be prepared from 6-vinylindole as shown above and in a similar manner as described in Examples 1-2.

Example 40: Preparation of (S)-2-amino-3-(4-nitro-7-vinyl-1H-indol-3-yl)propanoic Acid (40)

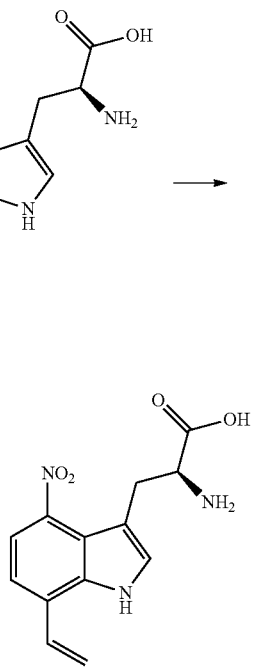

40

Example 40 can be prepared from 7-vinylindole as shown above and in a similar manner as described in Examples 1-2.

Example 41: Preparation of (S)-2-amino-3-(7-nitro-4-vinyl-1H-indol-3-yl)propanoic Acid (41)

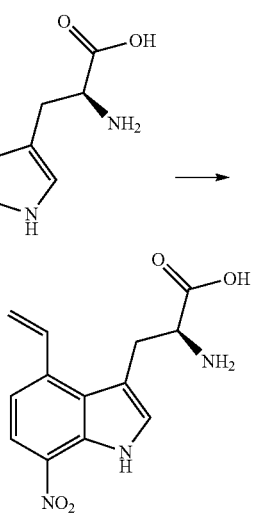

41

Example 41 can be prepared from 4-vinylindole as shown above and in a similar manner as described in Examples 1-2.

Example 42: Preparation of (S)-2-amino-3-(5-ethynyl-4-nitro-1H-indol-3-yl)propanoic Acid (42)

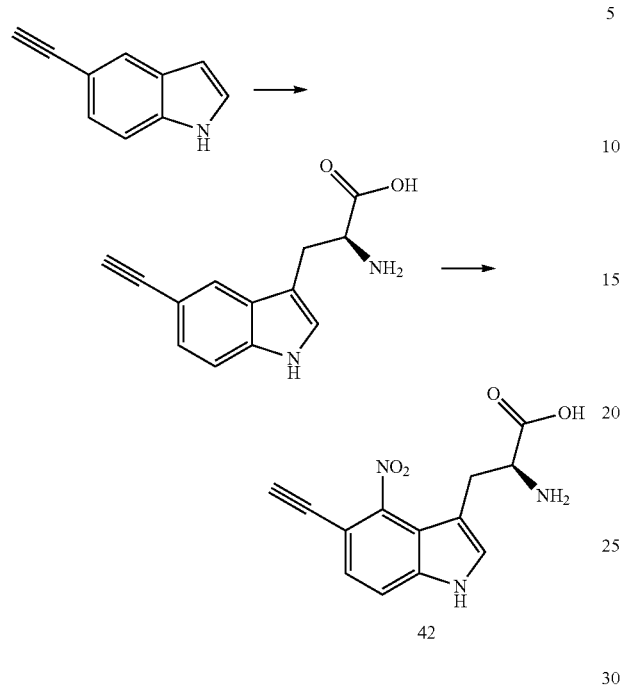

Example 42 can be prepared from 5-ethynylindole as shown above and in a similar manner as described in Examples 1-2.

Example 43: Preparation of (S)-2-amino-3-(6-ethynyl-4-nitro-1H-indol-3-yl)propanoic Acid (43)

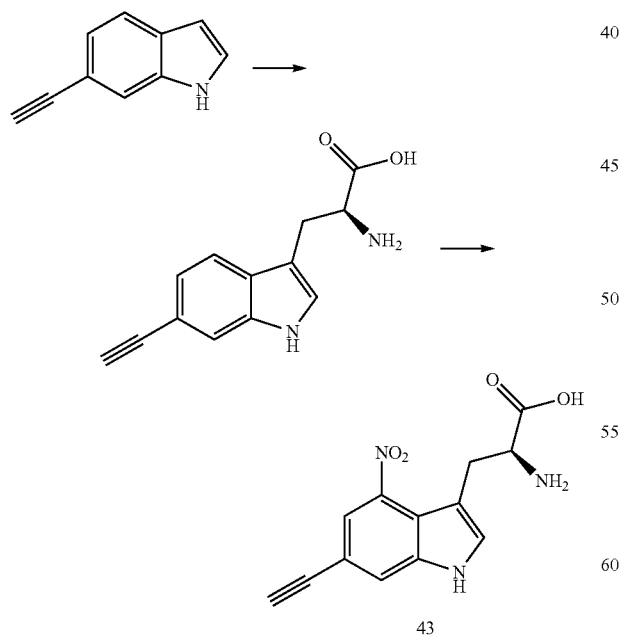

Example 43 can be prepared from 6-ethynylindole as shown above and in a similar manner as described in Examples 1-2.

Example 44: Preparation of (S)-2-amino-3-(7-ethynyl-4-nitro-1H-indol-3-yl)propanoic Acid (44)

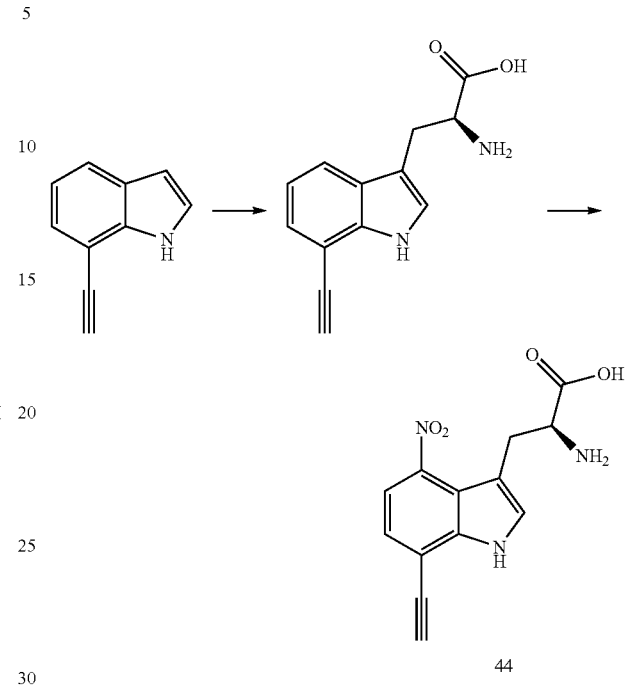

Example 44 can be prepared from 7-ethynylindole as shown above and in a similar manner as described in Examples 1-2.

Example 45: Preparation of (S)-2-amino-3-(4-ethynyl-7-nitro-1H-indol-3-yl)propanoic Acid (45)

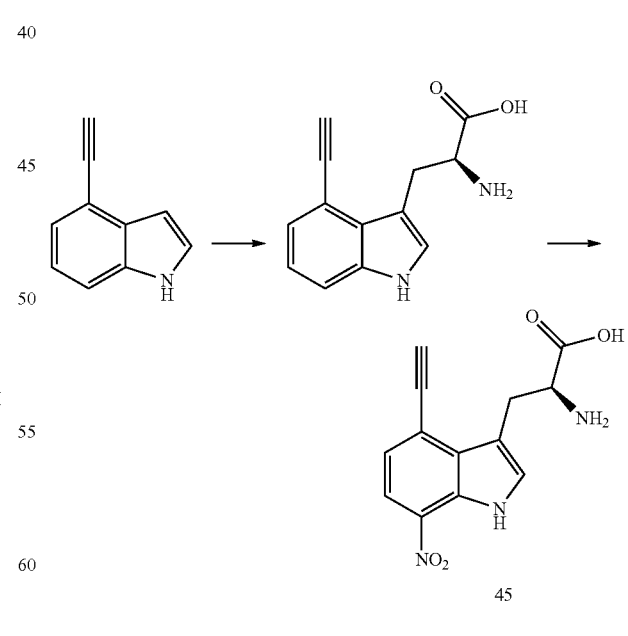

Example 45 can be prepared from 4-ethynylindole as shown above and in a similar manner as described in Examples 1-2.

Example 46: Preparation of (S)-2-amino-3-(5-morpholino-4-nitro-1H-indol-3-yl)propanoic Acid (46)

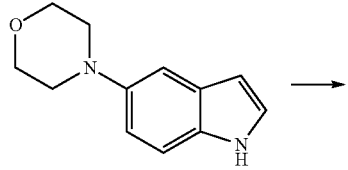

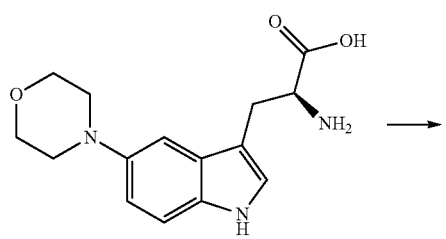

46

Example 46 can be prepared from 5-morpholinoindole as shown above and in a similar manner as described in Examples 1-2.

Example 47: Preparation of (S)-2-amino-3-(6-morpholino-4-nitro-1H-indol-3-yl)propanoic Acid (47)

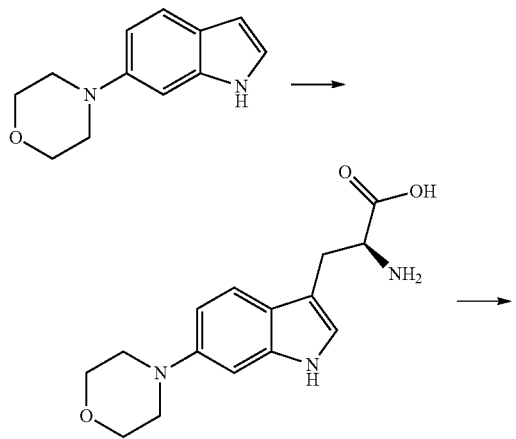

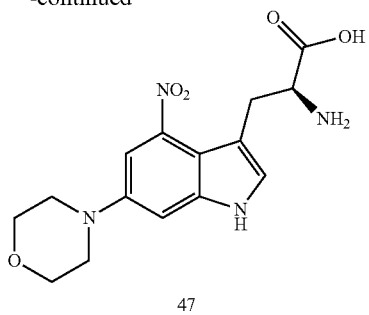

47

Example 47 can be prepared from 6-morpholinoindole as shown above and in a similar manner as described in Examples 1-2.

Example 48: Preparation of (S)-2-amino-3-(7-morpholino-4-nitro-1H-indol-3-yl)propanoic Acid (48)

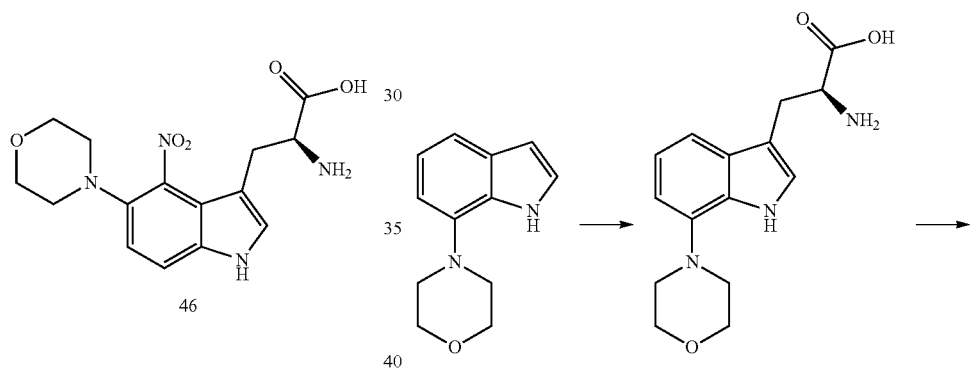

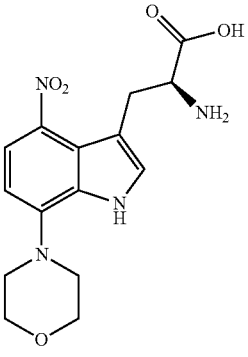

48

Example 48 can be prepared from 7-morpholinoindole as shown above and in a similar manner as described in Examples 1-2.

Example 49: Preparation of (S)-2-amino-3-(4-morpholino-7-nitro-1H-indol-3-yl)propanoic Acid (49)

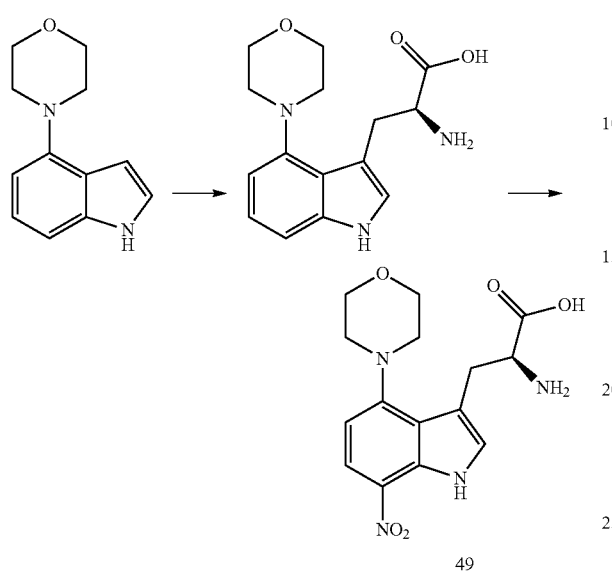

Example 49 can be prepared from 4-morpholinoindole as shown above and in a similar manner as described in Examples 1-2.

Example 50: Preparation of (S)-2-amino-3-(5-(methylthio)-4-nitro-1H-indol-3-yl)propanoic Acid (50)

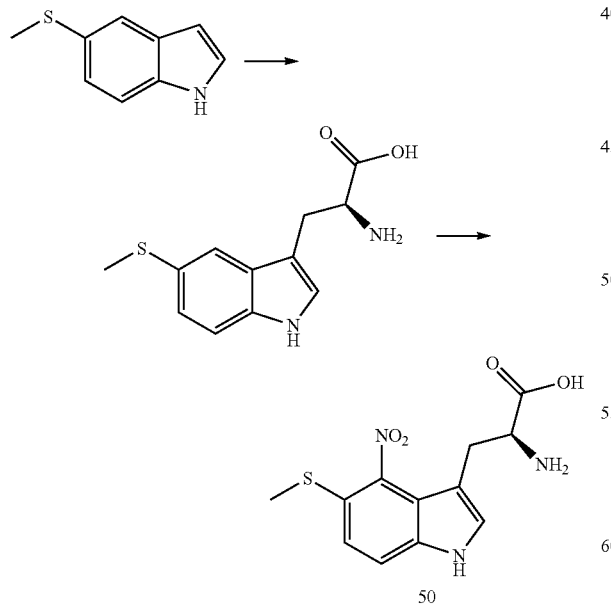

Example 50 can be prepared from 5-(methylthio)indole as shown above and in a similar manner as described in Examples 1-2.

Example 51: Preparation of (S)-2-amino-3-(6-(methylthio)-4-nitro-1H-indol-3-yl)propanoic Acid (51)

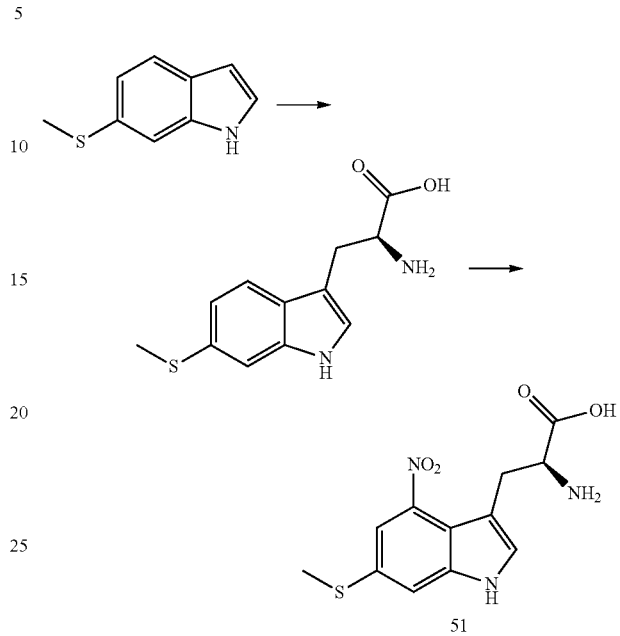

Example 51 can be prepared from 6-(methylthio)indole as shown above and in a similar manner as described in Examples 1-2.

Example 52: Preparation of (S)-2-amino-3-(7-(methylthio)-4-nitro-1H-indol-3-yl)propanoic Acid (52)

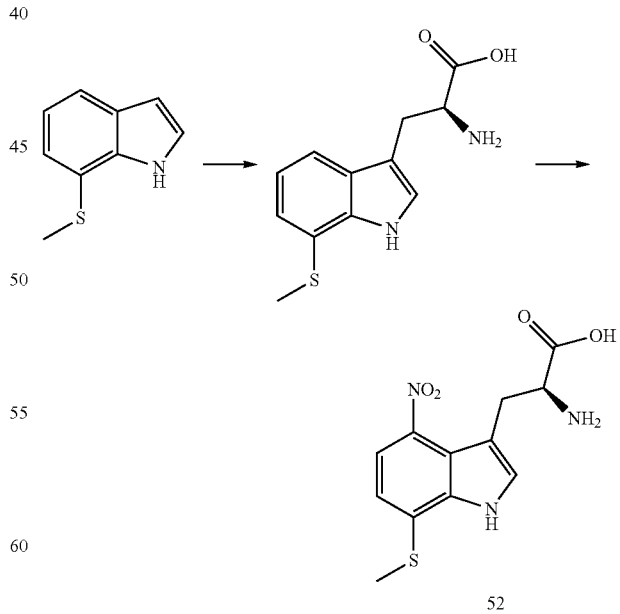

Example 52 can be prepared from 7-(methylthio)indole as shown above and in a similar manner as described in Examples 1-2.

Example 53: Preparation of (S)-2-amino-3-(4-(methylthio)-7-nitro-1H-indol-3-yl)propanoic Acid (53)

Example 55: Preparation of (S)-2-amino-3-(4-nitro-6-(pyridin-4-yl)-1H-indol-3-yl)propanoic Acid (55)

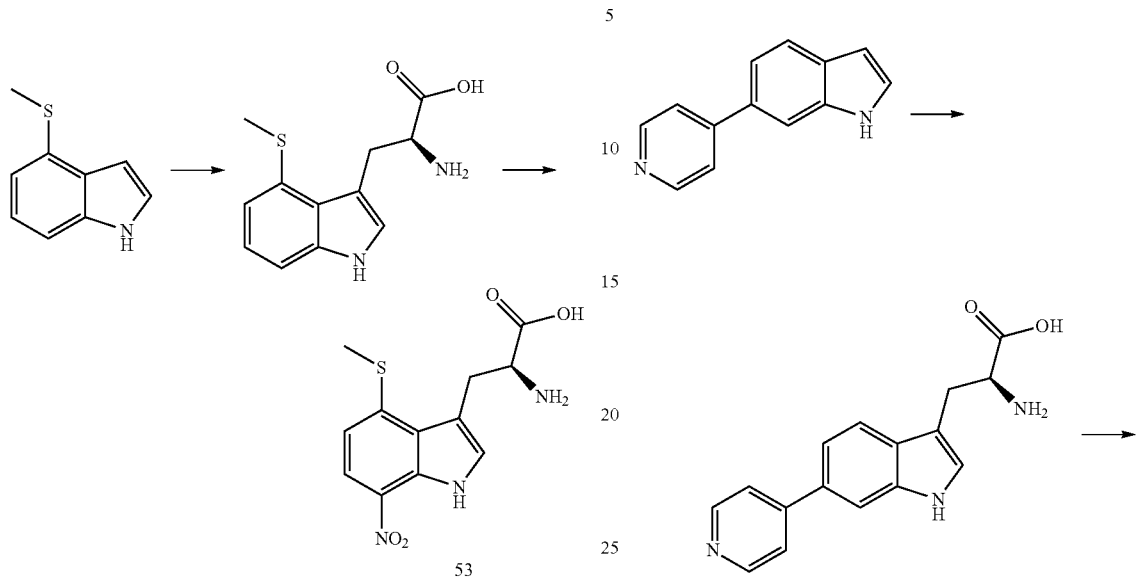

Example 53 can be prepared from 4-(methylthio)indole as shown above and in a similar manner as described in Examples 1-2.

Example 54: Preparation of (S)-2-amino-3-(4-nitro-5-(pyridin-4-yl)-1H-indol-3-yl)propanoic Acid (54)

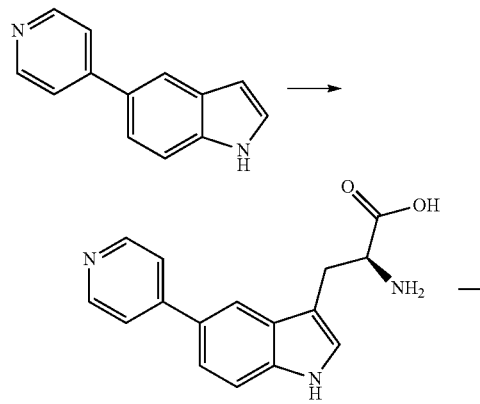

Example 55 can be prepared from 6-(pyridin-4-yl)indole as shown above and in a similar manner as described in Examples 1-2.

Example 56: Preparation of (S)-2-amino-3-(4-nitro-7-(pyridin-4-yl)-1H-indol-3-yl)propanoic Acid (56)

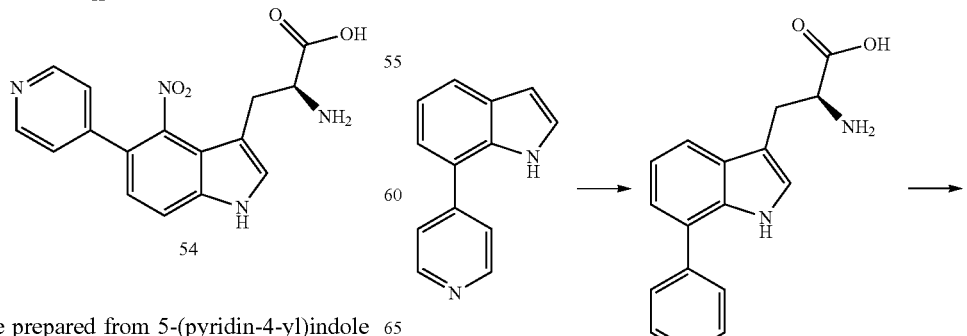

Example 54 can be prepared from 5-(pyridin-4-yl)indole as shown above and in a similar manner as described in Examples 1-2.

-continued

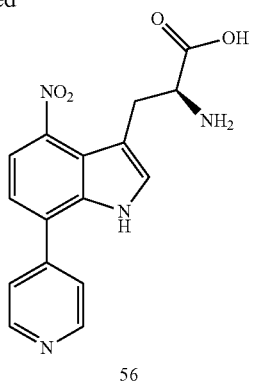

56

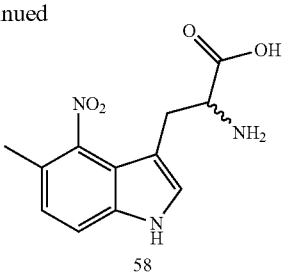

58

Example 58 can be prepared from 2-amino-3-(5-methyl-1H-indol-3-yl)propanoic acid as shown above and in a similar manner as described in Examples 1-2.

Example 56 can be prepared from 7-(pyridin-4-yl)indole as shown above and in a similar manner as described in Examples 1-2.

Example 59: Preparation of 2-amino-3-(6-methyl-4-nitro-1H-indol-3-yl)propanoic Acid (59)

Example 57: Preparation of (S)-2-amino-3-(7-nitro-4-(pyridin-4-yl)-1H-indol-3-yl)propanoic Acid (57)

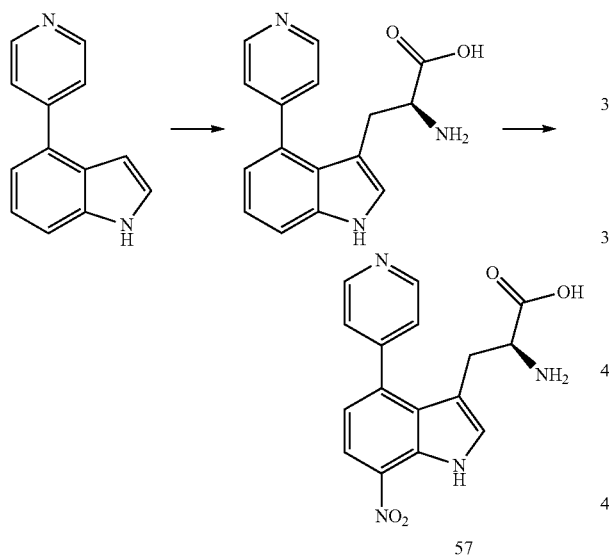

57

Example 57 can be prepared from 4-(pyridin-4-yl)indole as shown above and in a similar manner as described in Examples 1-2.

Example 58: Preparation of 2-amino-3-(5-methyl-4-nitro-1H-indol-3-yl)propanoic Acid (58)

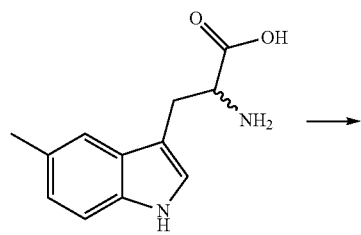

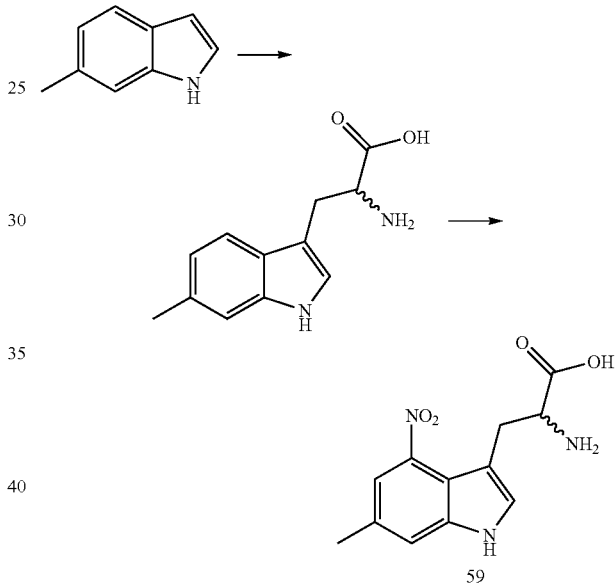

59

Example 59 can be prepared from 6-methylindole as shown above and in a similar manner as described in Examples 1-2.

Example 60: Preparation of 2-amino-3-(7-methyl-4-nitro-1H-indol-3-yl)propanoic Acid (60)

60

Example 60 can be prepared from 2-amino-3-(7-methyl-1H-indol-3-yl)propanoic acid as shown above and in a similar manner as described in Examples 1-2.

Example 61: Preparation of 2-amino-3-(4-methyl-7-nitro-1H-indol-3-yl)propanoic Acid (61)

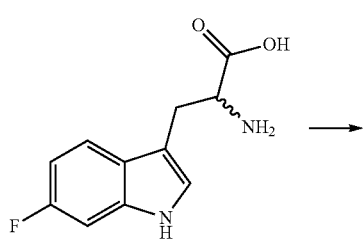

61

Example 61 was prepared from 2-amino-3-(4-methyl-1H-indol-3-yl)propanoic acid as shown above and in a similar manner as described in Examples 1-2.

Example 62: Preparation of 2-amino-3-(6-fluoro-4-nitro-1H-indol-3-yl)propanoic Acid (62)

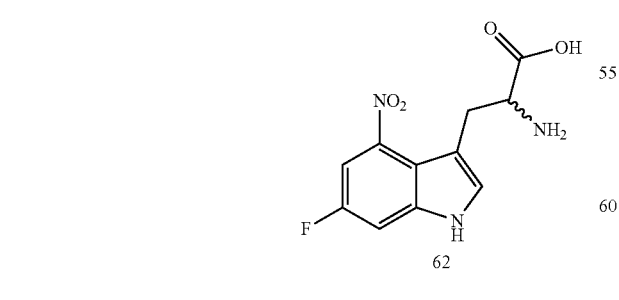

62

Example 62 can be prepared from 2-amino-3-(6-fluoro-1H-indol-3-yl)propanoic acid as shown above and in a similar manner as described in Examples 1-2.

Example 63: Preparation of 2-amino-3-(7-fluoro-4-nitro-1H-indol-3-yl)propanoic Acid (63)

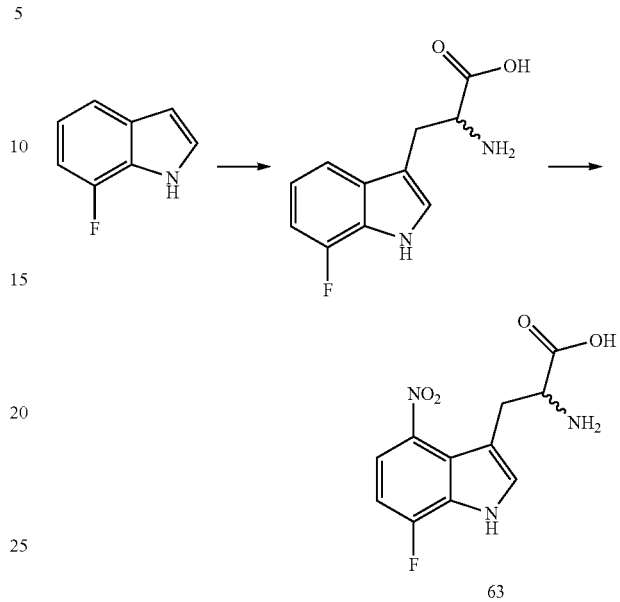

63

Example 63 can be prepared from 7-fluoroindole as shown above and in a similar manner as described in Examples 1-2.

Example 64: Preparation of 2-amino-3-(4-fluoro-7-nitro-1H-indol-3-yl)propanoic Acid (64)

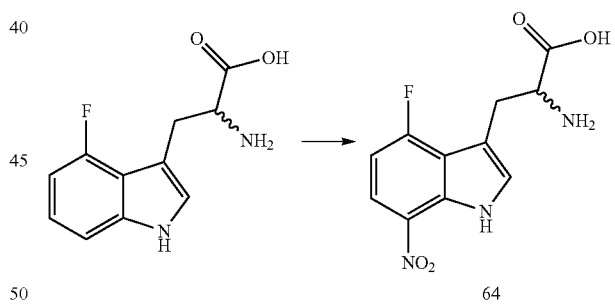

64

Example 64 can be prepared from 2-amino-3-(4-fluoro-1H-indol-3-yl)propanoic acid as shown above and in a similar manner as described in Examples 1-2.

Example 65: Preparation of 2-amino-3-(5-chloro-4-nitro-1H-indol-3-yl)propanoic Acid (65)

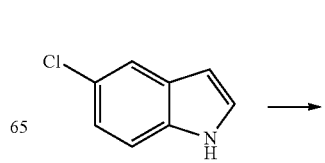

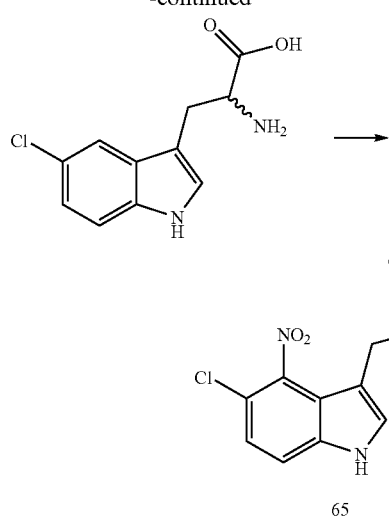

65

Example 65 can be prepared from 5-chloroindole as shown above and in a similar manner as described in Examples 1-2.

Example 66: Preparation of 2-amino-3-(6-chloro-4-nitro-1H-indol-3-yl)propanoic Acid (66)

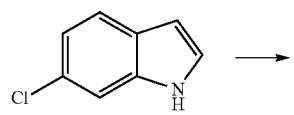

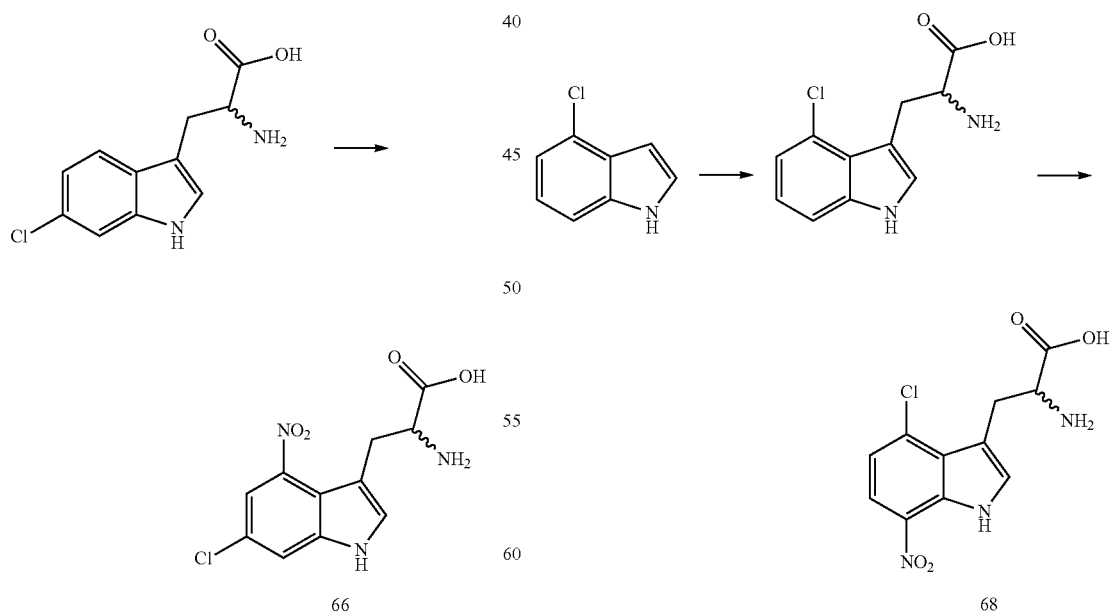

66

Example 66 can be prepared from 6-chloroindole as shown above and in a similar manner as described in Examples 1-2.

Example 67: Preparation of 2-amino-3-(7-chloro-4-nitro-1H-indol-3-yl)propanoic Acid (67)

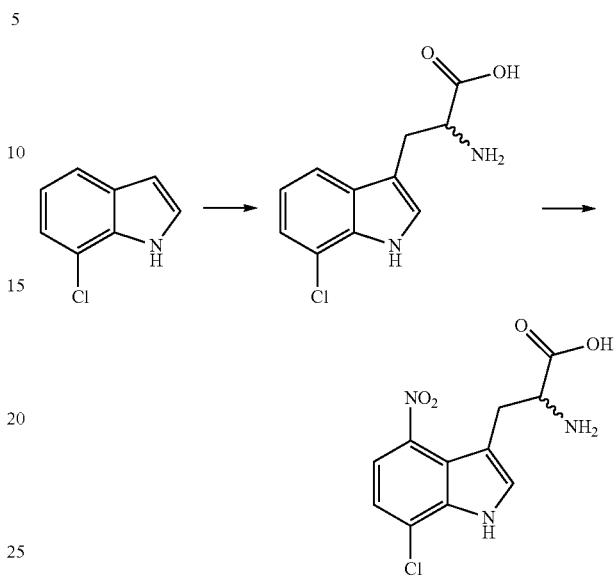

67

Example 67 can be prepared from 7-chloroindole as shown above and in a similar manner as described in Examples 1-2.

Example 68: Preparation of 2-amino-3-(4-chloro-7-nitro-1H-indol-3-yl)propanoic Acid (68)

68

Example 68 can be prepared from 4-chloroindole as shown above and in a similar manner as described in Examples 1-2.

Example 69: Preparation of 2-amino-3-(5-bromo-4-nitro-1H-indol-3-yl)propanoic Acid (69)

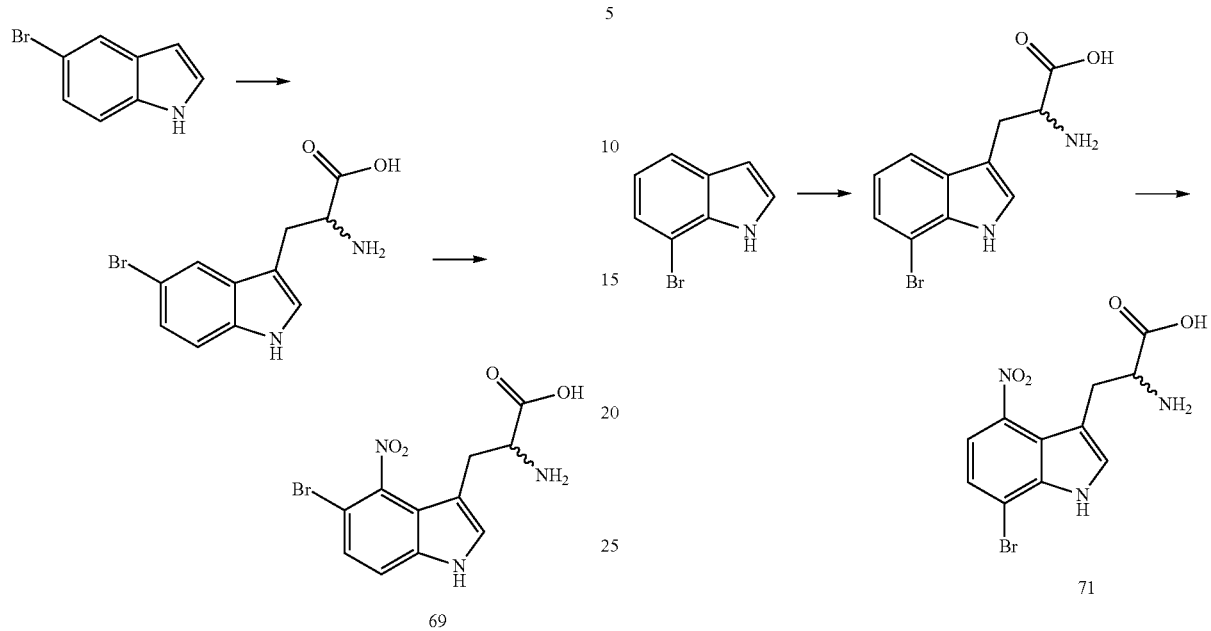

Example 69 can be prepared from 5-bromoindole as shown above and in a similar manner as described in Examples 1-2.

Example 70: Preparation of 2-amino-3-(6-bromo-4-nitro-1H-indol-3-yl)propanoic Acid (70)

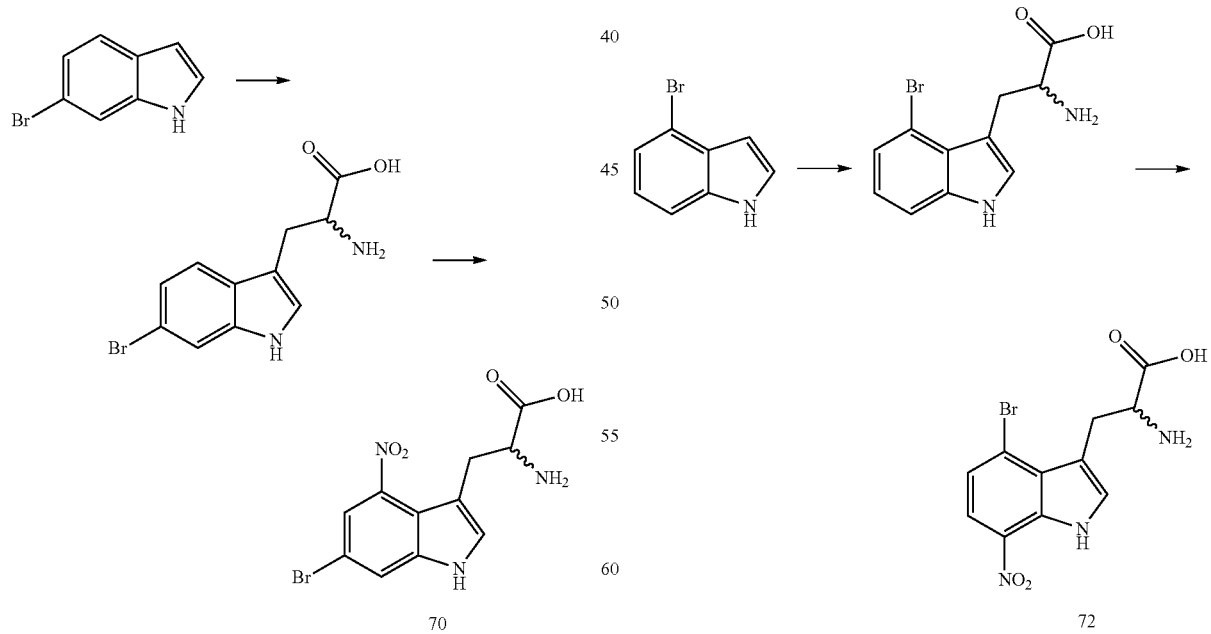

Example 70 can be prepared from 6-bromoindole as shown above and in a similar manner as described in Examples 1-2.

Example 71: Preparation of 2-amino-3-(7-bromo-4-nitro-1H-indol-3-yl)propanoic Acid (71)

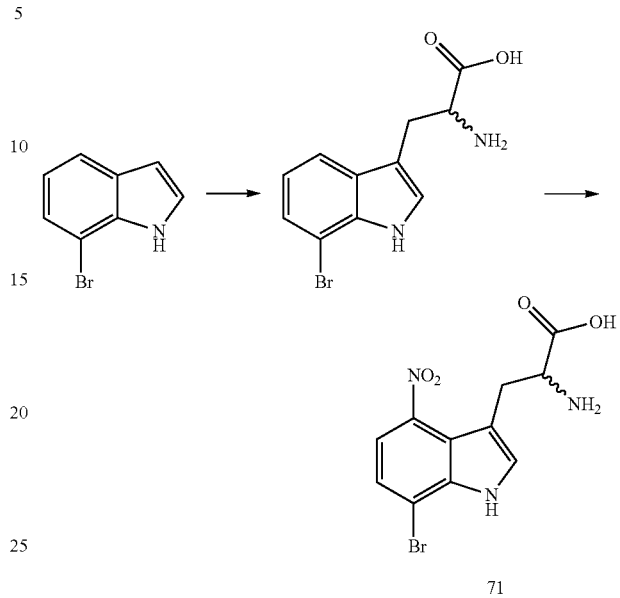

Example 71 can be prepared from 7-bromoindole as shown above and in a similar manner as described in Examples 1-2.

Example 72: Preparation of 2-amino-3-(4-bromo-7-nitro-1H-indol-3-yl)propanoic Acid (72)

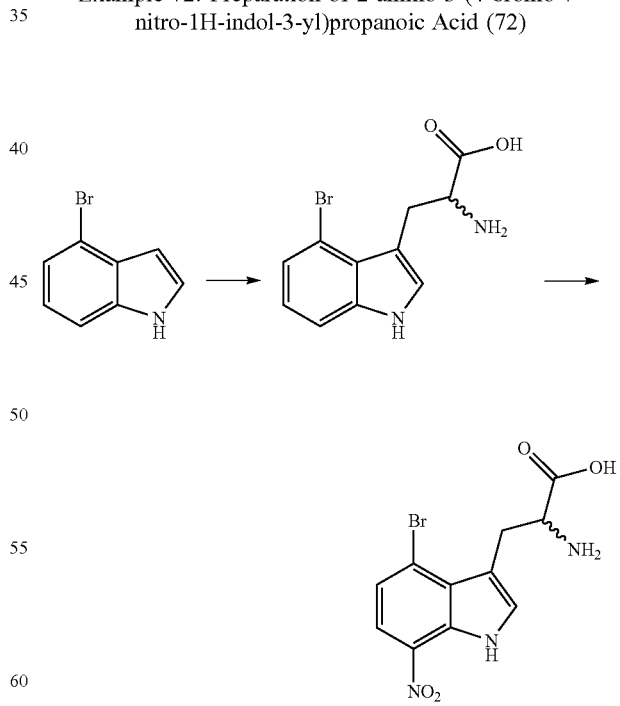

Example 72 can be prepared from 4-bromoindole as shown above and in a similar manner as described in Examples 1-2.

Example 73: Preparation of 2-amino-3-(5-methoxy-4-nitro-1H-indol-3-yl)propanoic Acid (73)

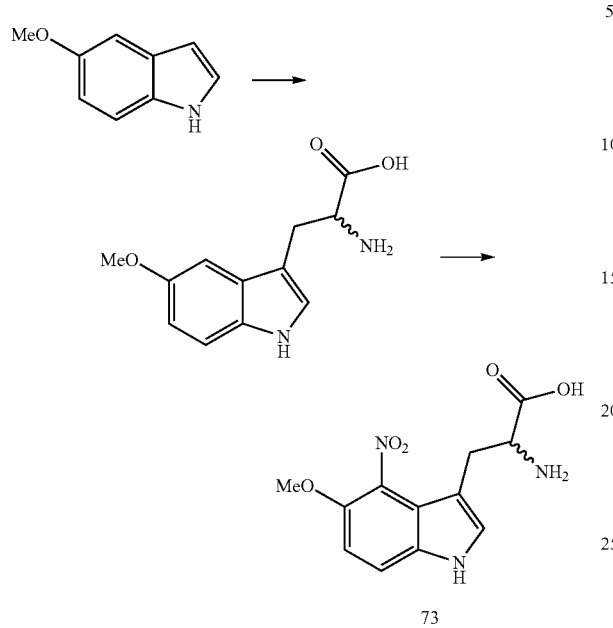

73

Example 73 can be prepared from 5-methoxyindole as shown above and in a similar manner as described in Examples 1-2.

Example 74: Preparation of 2-amino-3-(6-methoxy-4-nitro-1H-indol-3-yl)propanoic Acid (74)

74

Example 74 can be prepared from 6-methoxyindole as shown above and in a similar manner as described in Examples 1-2.

Example 75: Preparation of 2-amino-3-(7-methoxy-4-nitro-1H-indol-3-yl)propanoic Acid (75)

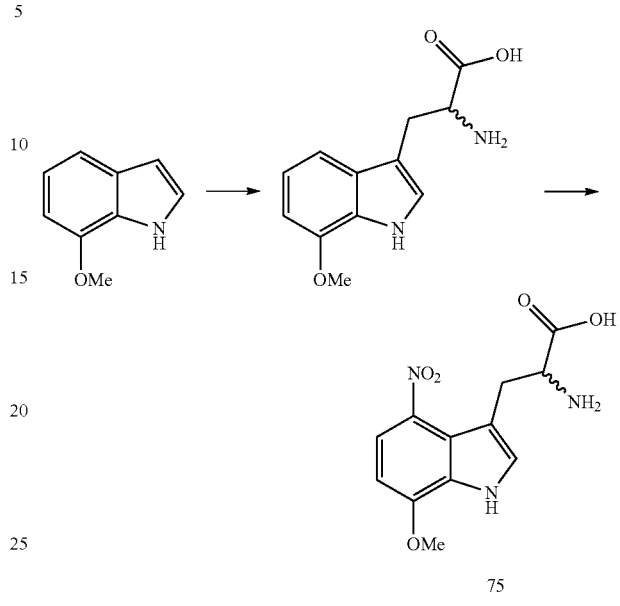

75

Example 75 can be prepared from 7-methoxyindole as shown above and in a similar manner as described in Examples 1-2.

Example 76: Preparation of 2-amino-3-(4-methoxy-7-nitro-1H-indol-3-yl)propanoic Acid (76)

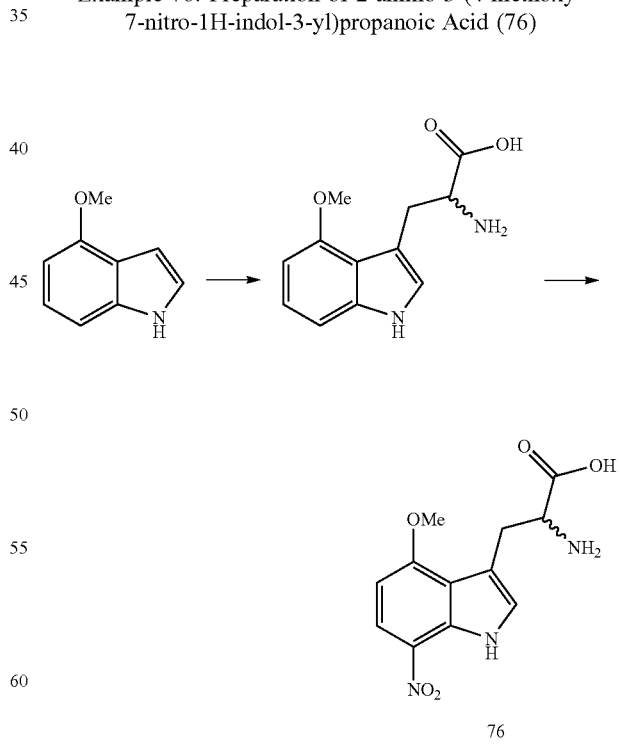

76

Example 76 can be prepared from 4-methoxyindole as shown above and in a similar manner as described in Examples 1-2.

Example 77: Preparation of 2-amino-3-(5-amino-4-nitro-1H-indol-3-yl)propanoic Acid (77)

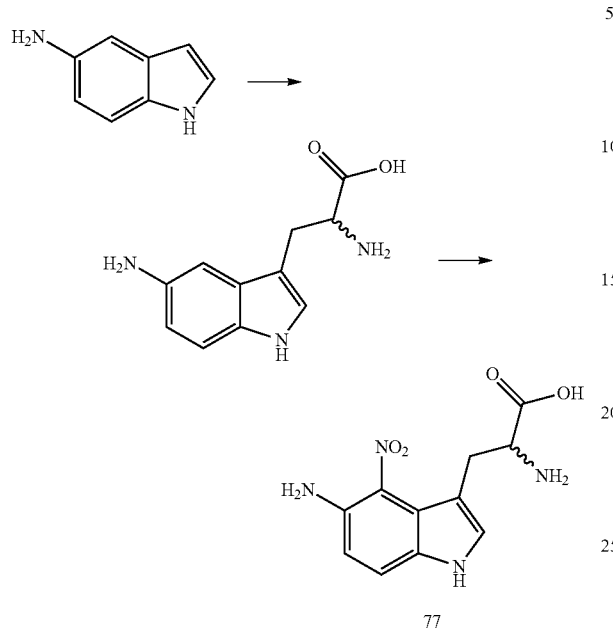

77

Example 77 can be prepared from 5-aminoindole as shown above and in a similar manner as described in Examples 1-2.

Example 78: Preparation of 2-amino-3-(6-amino-4-nitro-1H-indol-3-yl)propanoic Acid (78)

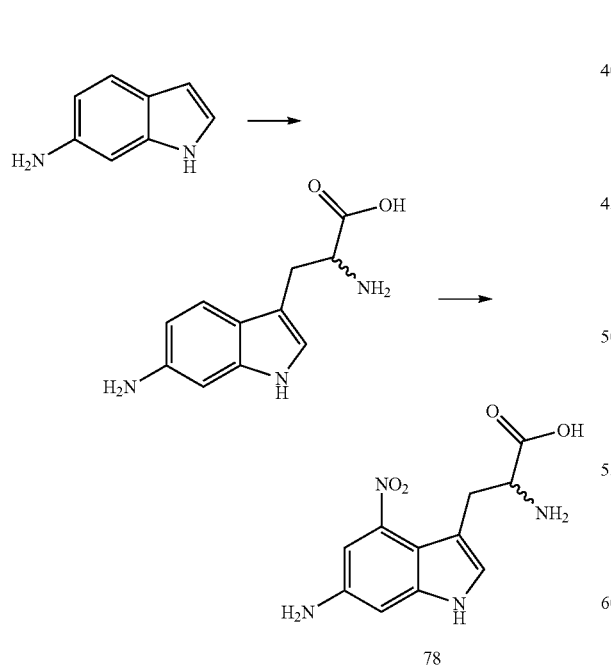

78

Example 78 can be prepared from 6-aminoindole as shown above and in a similar manner as described in Examples 1-2.

Example 79: Preparation of 2-amino-3-(7-amino-4-nitro-1H-indol-3-yl)propanoic Acid (79)

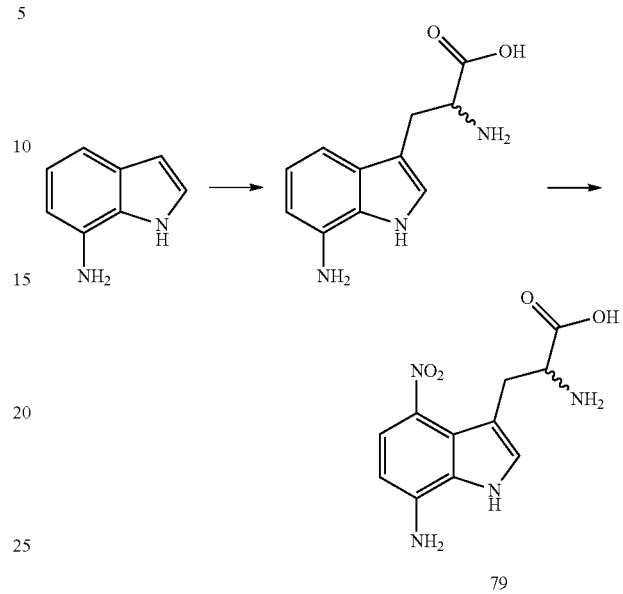

79

Example 79 can be prepared from 7-aminoindole as shown above and in a similar manner as described in Examples 1-2.

Example 80: Preparation of 2-amino-3-(4-amino-7-nitro-1H-indol-3-yl)propanoic Acid (80)

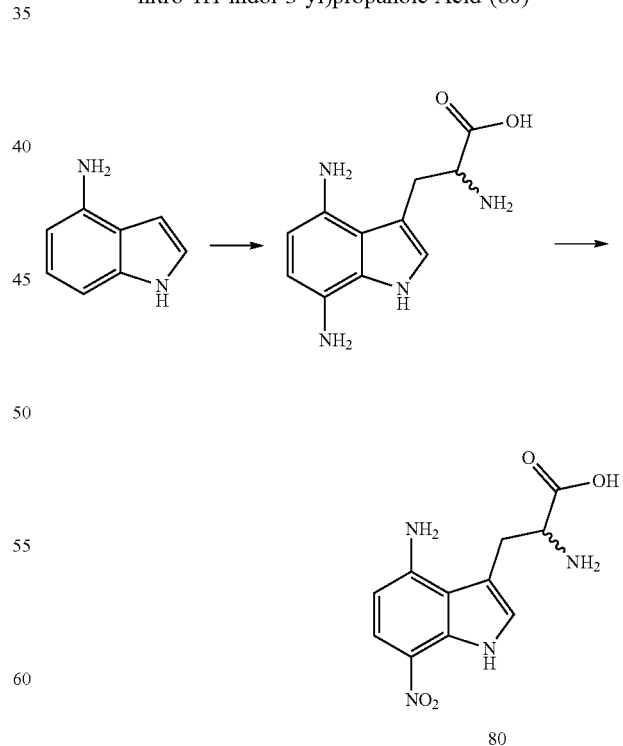

80

Example 80 can be prepared from 4-aminoindole as shown above and in a similar manner as described in Examples 1-2.

Example 81: Preparation of 2-amino-3-(5-hydroxy-4-nitro-1H-indol-3-yl)propanoic Acid (81)

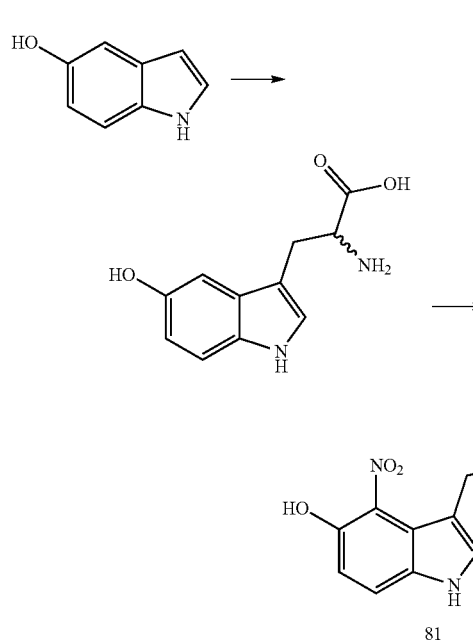

Example 81 can be prepared from 5-hydroxyindole as shown above and in a similar manner as described in Examples 1-2.

Example 82: Preparation of 2-amino-3-(6-hydroxy-4-nitro-1H-indol-3-yl)propanoic Acid (82)

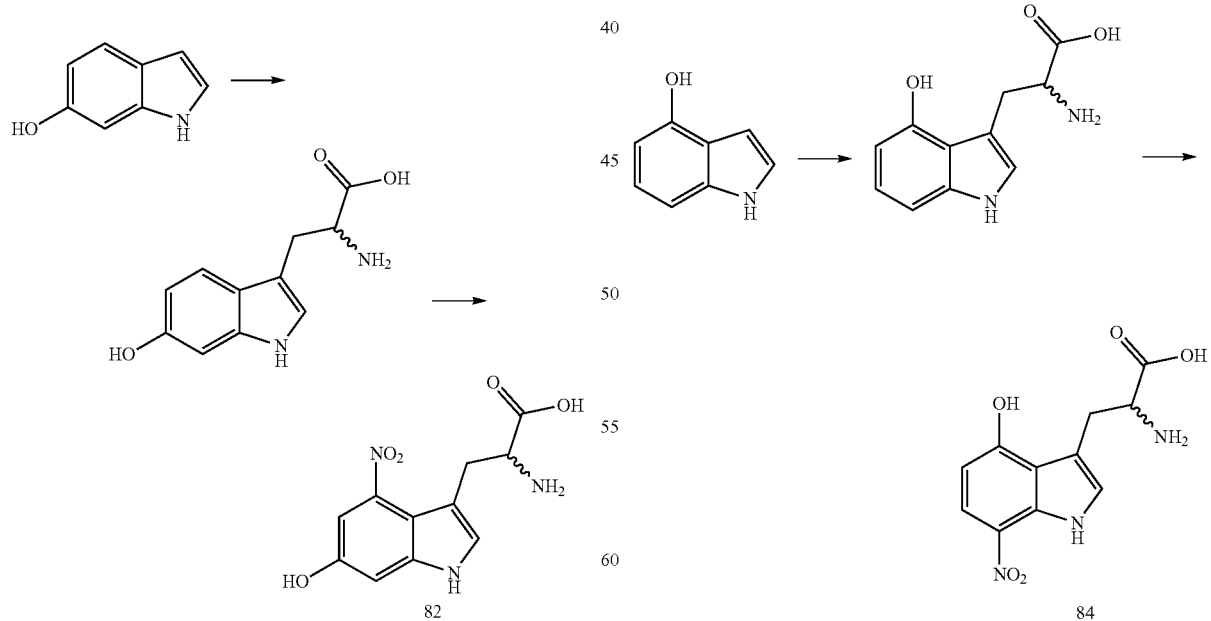

Example 82 can be prepared from 6-hydroxyindole as shown above and in a similar manner as described in Examples 1-2.

Example 83: Preparation of 2-amino-3-(7-hydroxy-4-nitro-1H-indol-3-yl)propanoic Acid (83)

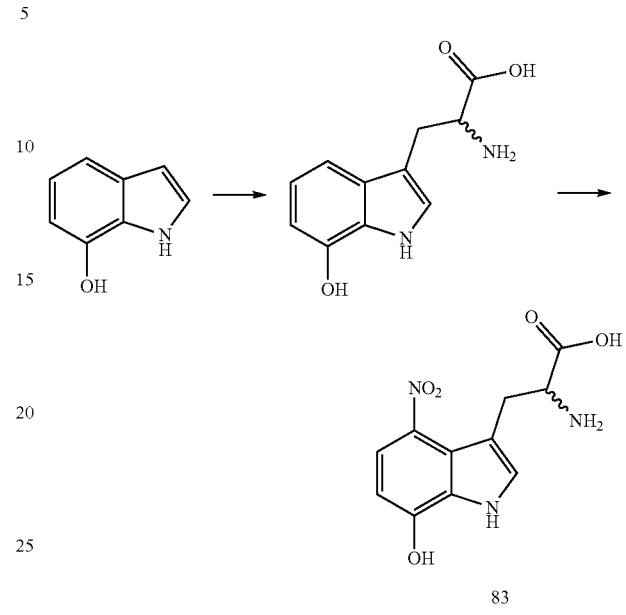

Example 83 can be prepared from 7-hydroxyindole as shown above and in a similar manner as described in Examples 1-2.

Example 84: Preparation of 2-amino-3-(4-hydroxy-7-nitro-1H-indol-3-yl)propanoic Acid (84)

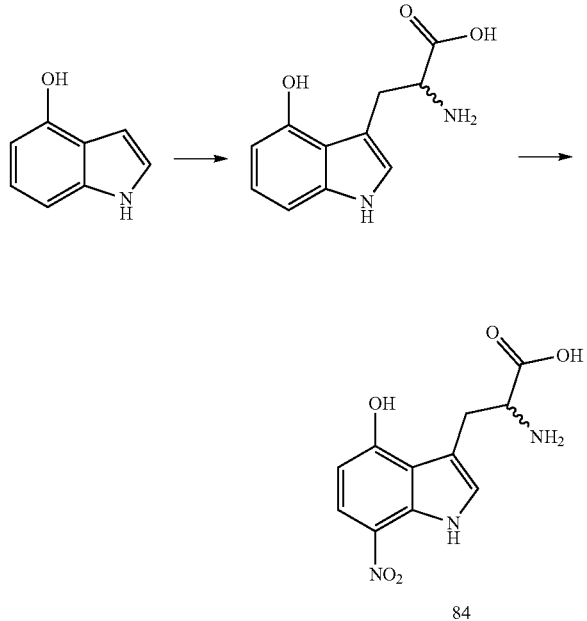

Example 84 can be prepared from 4-hydroxyindole as shown above and in a similar manner as described in Examples 1-2.

Example 85: Preparation of 2-amino-3-(4-nitro-5-phenyl-1H-indol-3-yl)propanoic Acid (85)

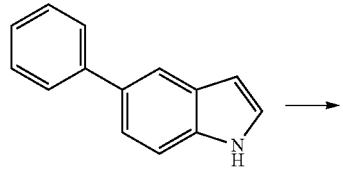

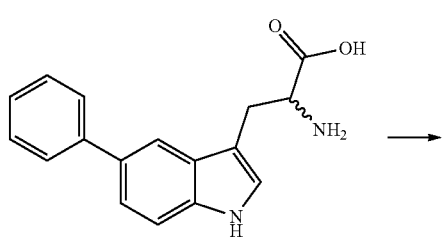

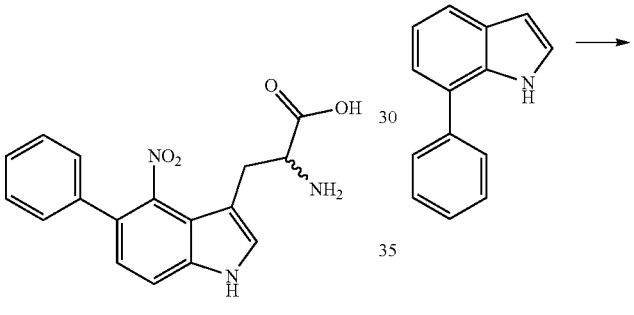

85

Example 85 can be prepared from 5-phenylindole as shown above and in a similar manner as described in Examples 1-2.

Example 86: Preparation of 2-amino-3-(4-nitro-6-phenyl-1H-indol-3-yl)propanoic Acid (86)

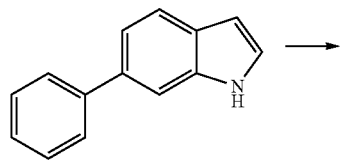

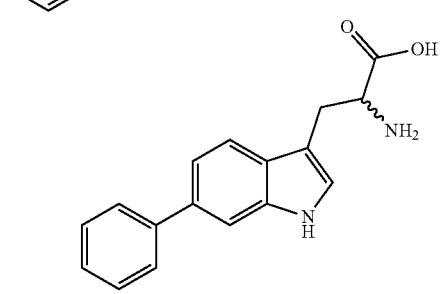

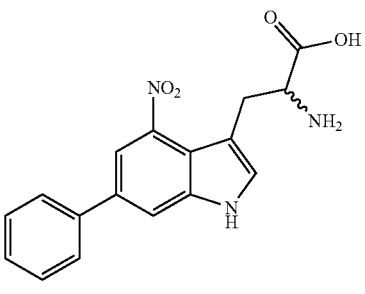

86

Example 86 can be prepared from 6-phenylindole as shown above and in a similar manner as described in Examples 1-2.

Example 87: Preparation of 2-amino-3-(4-nitro-7-phenyl-1H-indol-3-yl)propanoic Acid (87)

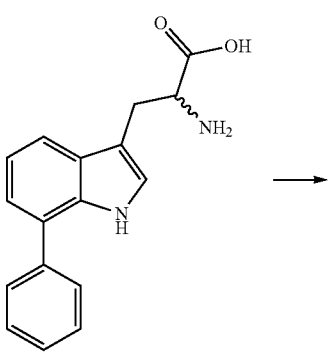

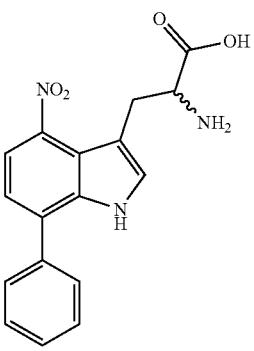

87

Example 87 can be prepared from 7-phenylindole as shown above and in a similar manner as described in Examples 1-2.

Example 88: Preparation of 2-amino-3-(7-nitro-4-phenyl-1H-indol-3-yl)propanoic Acid (88)

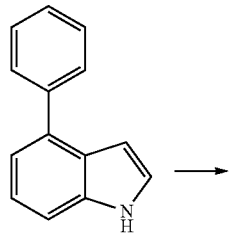

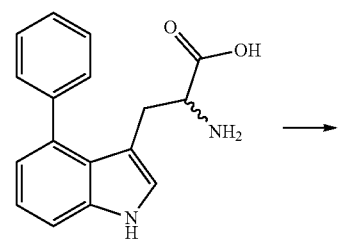

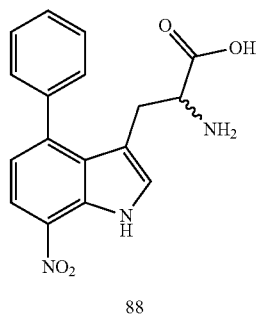

88

Example 88 can be prepared from 4-phenylindole as shown above and in a similar manner as described in Examples 1-2.

Example 89: Preparation of 2-amino-3-(5-cyclopropyl-4-nitro-1H-indol-3-yl)propanoic Acid (89)

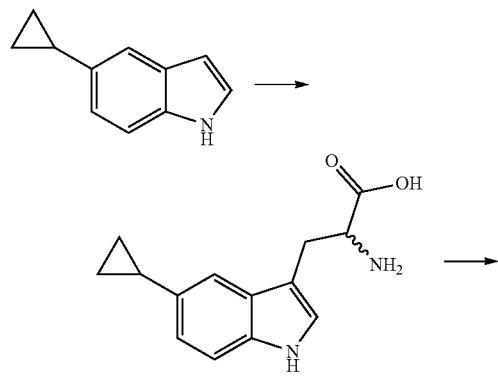

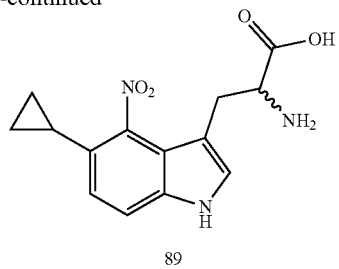

89

Example 89 can be prepared from 5-cyclopropylindole as shown above and in a similar manner as described in Examples 1-2.

Example 90: Preparation of 2-amino-3-(6-cyclopropyl-4-nitro-1H-indol-3-yl)propanoic Acid (90)

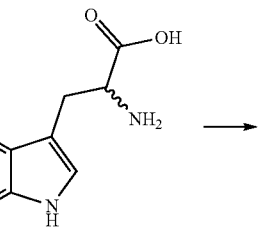

90

Example 90 can be prepared from 6-cyclopropylindole as shown above and in a similar manner as described in Examples 1-2.

Example 91: Preparation of 2-amino-3-(7-cyclopropyl-4-nitro-1H-indol-3-yl)propanoic Acid (91)

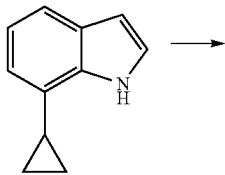

-continued

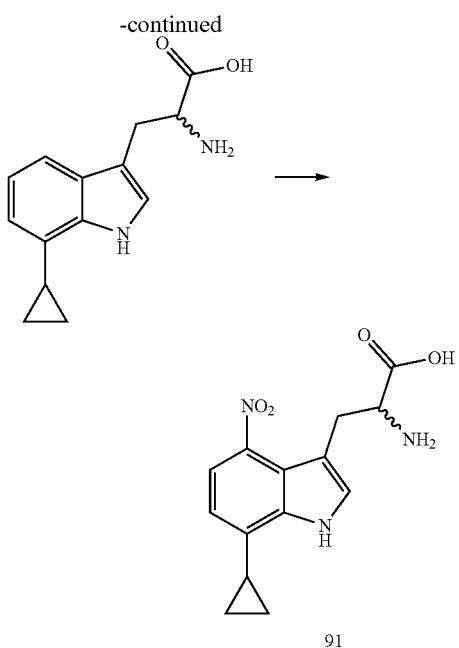

91

Example 91 can be prepared from 7-cyclopropylindole as shown above and in a similar manner as described in Examples 1-2.

Example 92: Preparation of 2-amino-3-(4-cyclopropyl-7-nitro-1H-indol-3-yl)propanoic Acid (92)

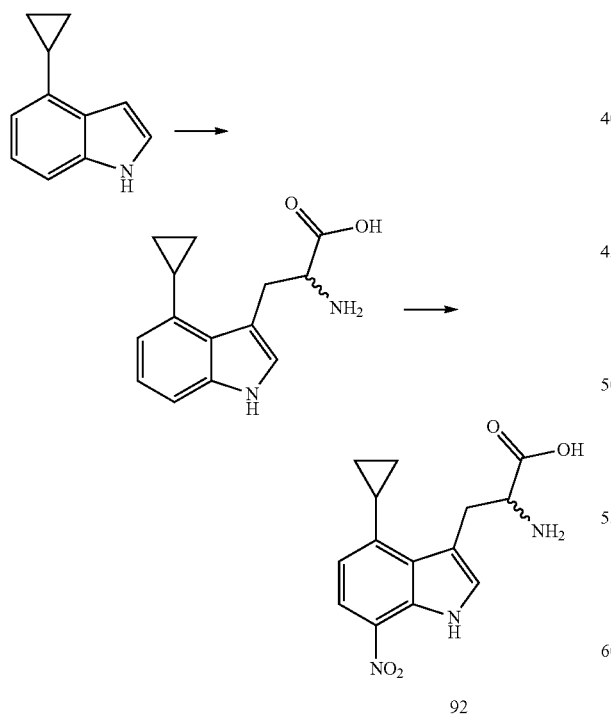

92

Example 92 can be prepared from 4-cyclopropylindole as shown above and in a similar manner as described in Examples 1-2.

Example 93: Preparation of 2-amino-3-(4-nitro-5-vinyl-1H-indol-3-yl)propanoic Acid (93)

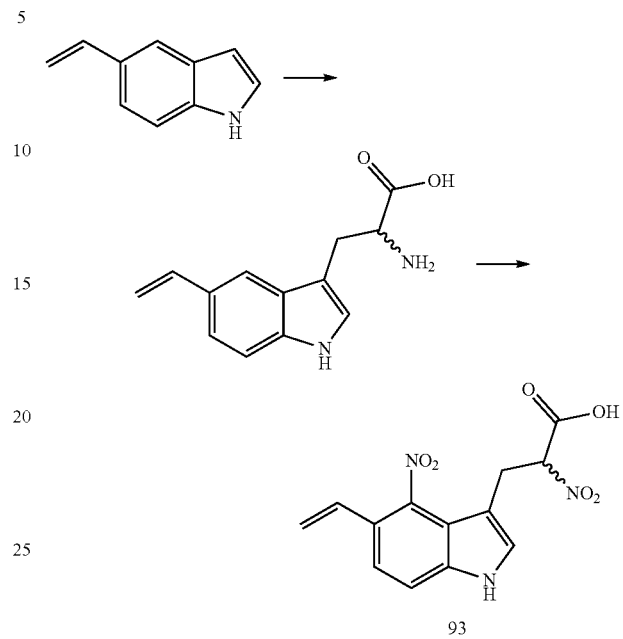

93

Example 93 can be prepared from 5-vinylindole as shown above and in a similar manner as described in Examples 1-2.

Example 94: Preparation of 2-amino-3-(4-nitro-6-vinyl-1H-indol-3-yl)propanoic Acid (94)

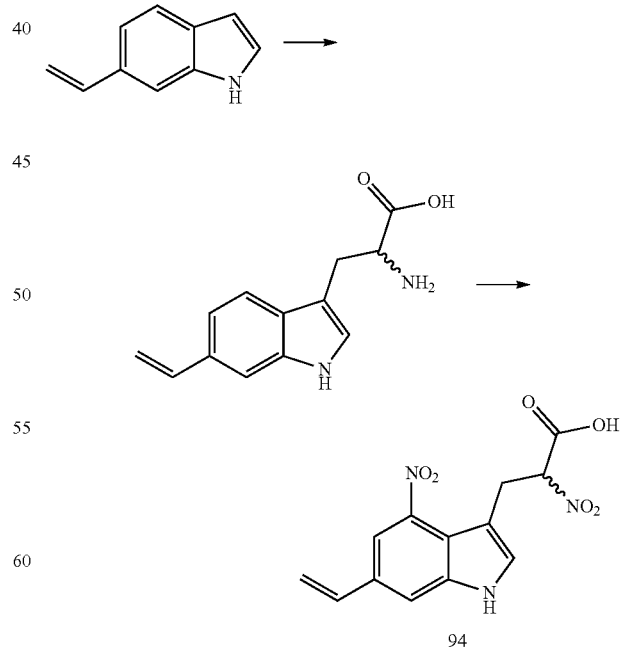

94

Example 94 can be prepared from 6-vinylindole as shown above and in a similar manner as described in Examples 1-2.

Example 95: Preparation of 2-amino-3-(4-nitro-7-vinyl-1H-indol-3-yl)propanoic Acid (95)

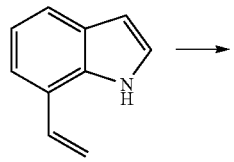

95

Example 95 can be prepared from 7-vinylindole as shown above and in a similar manner as described in Examples 1-2.

Example 96: Preparation of 2-amino-3-(7-nitro-4-vinyl-1H-indol-3-yl)propanoic Acid (96)

96

Example 96 can be prepared from 4-vinylindole as shown above and in a similar manner as described in Examples 1-2.

Example 97: Preparation of 2-amino-3-(5-ethynyl-4-nitro-1H-indol-3-yl)propanoic Acid (97)

97

Example 97 can be prepared from 5-ethynylindole as shown above and in a similar manner as described in Examples 1-2.

Example 98: Preparation of 2-amino-3-(6-ethynyl-4-nitro-1H-indol-3-yl)propanoic Acid (98)

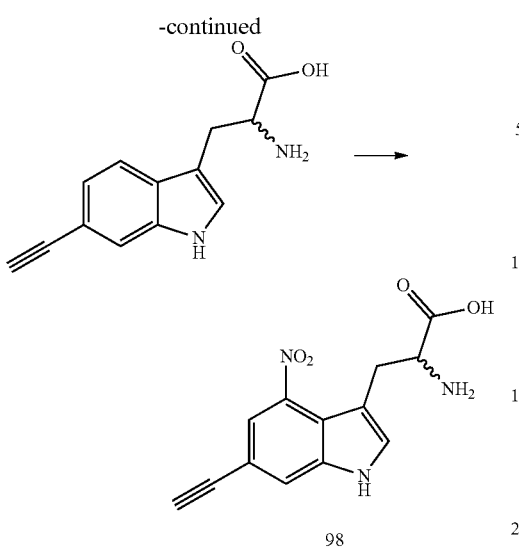

98

Example 98 can be prepared from 6-ethynylindole as shown above and in a similar manner as described in Examples 1-2.

Example 99: Preparation of 2-amino-3-(7-ethynyl-4-nitro-1H-indol-3-yl)propanoic Acid (99)

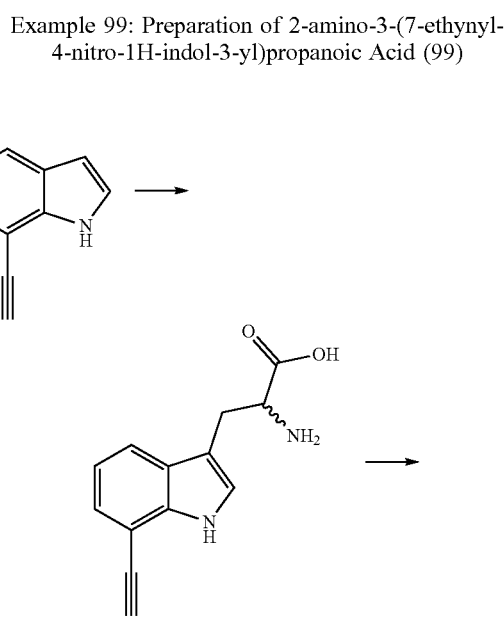

99

Example 99 can be prepared from 7-ethynylindole as shown above and in a similar manner as described in Examples 1-2.

Example 100: Preparation of 2-amino-3-(4-ethynyl-7-nitro-1H-indol-3-yl)propanoic Acid (100)

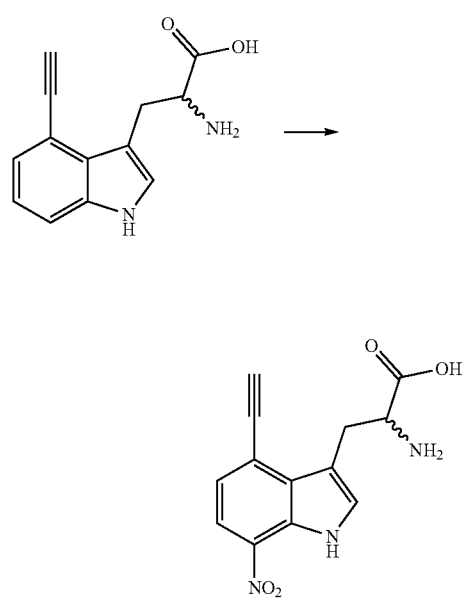

100

Example 100 can be prepared from 4-ethynylindole as shown above and in a similar manner as described in Examples 1-2.

Example 101: Preparation of 2-amino-3-(5-morpholino-4-nitro-1H-indol-3-yl)propanoic Acid

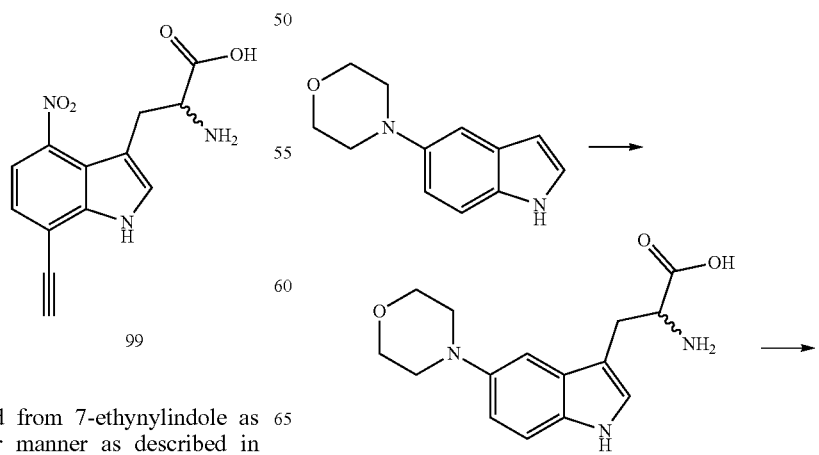

-continued

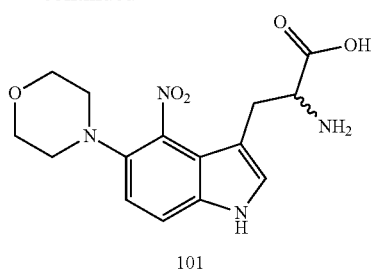

101

Example 101 can be prepared from 5-morpholinoindole as shown above and in a similar manner as described in Examples 1-2.

Example 102: Preparation of 2-amino-3-(6-morpholino-4-nitro-1H-indol-3-yl)propanoic Acid (102)

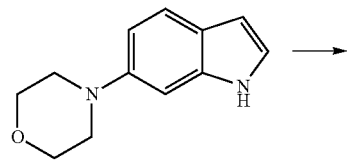

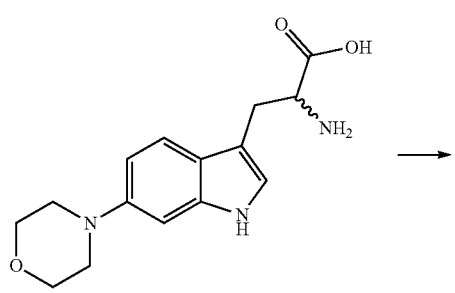

102

Example 102 can be prepared from 6-morpholinoindole as shown above and in a similar manner as described in Examples 1-2.

Example 103: Preparation of 2-amino-3-(7-morpholino-4-nitro-1H-indol-3-yl)propanoic Acid (103)

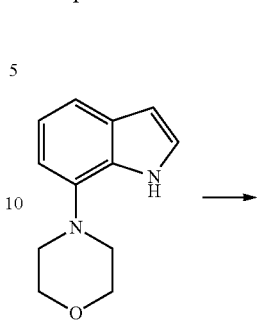

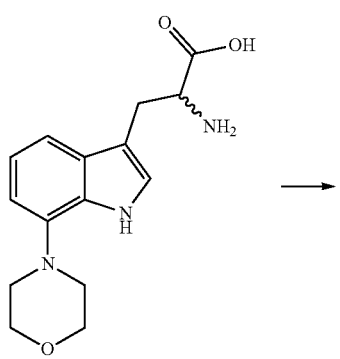

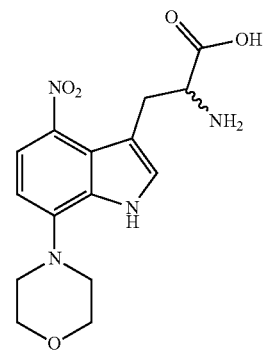

103

Example 103 can be prepared from 7-morpholinoindole as shown above and in a similar manner as described in Examples 1-2.

Example 104: Preparation of 2-amino-3-(4-morpholino-7-nitro-1H-indol-3-yl)propanoic Acid (104)

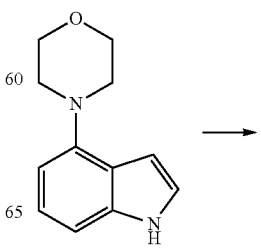

-continued

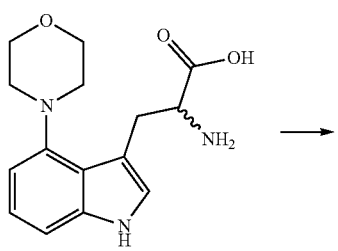

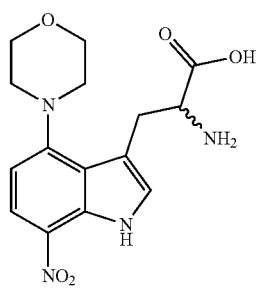

104

Example 104 can be prepared from 4-morpholinoindole as shown above and in a similar manner as described in Examples 1-2.

Example 105: Preparation of 2-amino-3-(5-(methylthio)-4-nitro-1H-indol-3-yl)propanoic Acid (105)

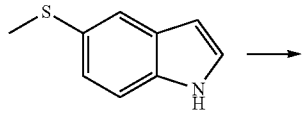

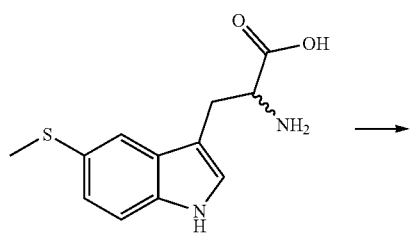

105

Example 105 can be prepared from 5-(methylthio)indole as shown above and in a similar manner as described in Examples 1-2.

Example 106: Preparation of 2-amino-3-(6-(methylthio)-4-nitro-1H-indol-3-yl)propanoic Acid (106)

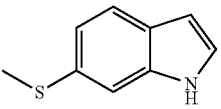

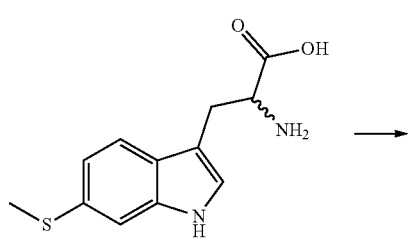

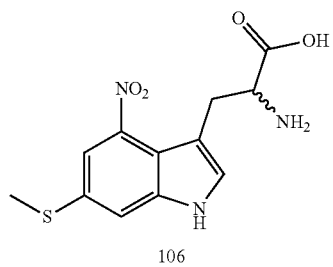

106

Example 106 can be prepared from 6-(methylthio)indole as shown above and in a similar manner as described in Examples 1-2.

Example 107: Preparation of 2-amino-3-(7-(methylthio)-4-nitro-1H-indol-3-yl)propanoic Acid (107)

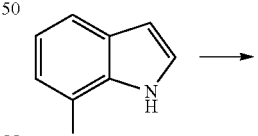

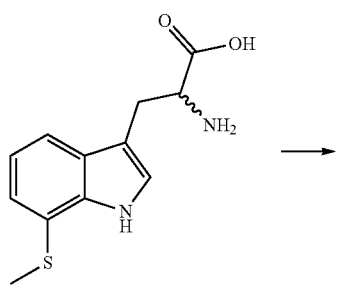

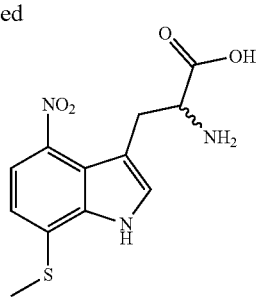

107

Example 107 can be prepared from 7-(methylthio)indole as shown above and in a similar manner as described in Examples 1-2.

Example 108: Preparation of 2-amino-3-(4-(methylthio)-7-nitro-1H-indol-3-yl)propanoic Acid (108)

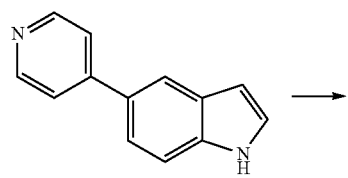

108

Example 108 can be prepared from 4-(methylthio)indole as shown above and in a similar manner as described in Examples 1-2.

Example 109: Preparation of 2-amino-3-(4-nitro-5-(pyridin-4-yl)-1H-indol-3-yl)propanoic Acid (109)

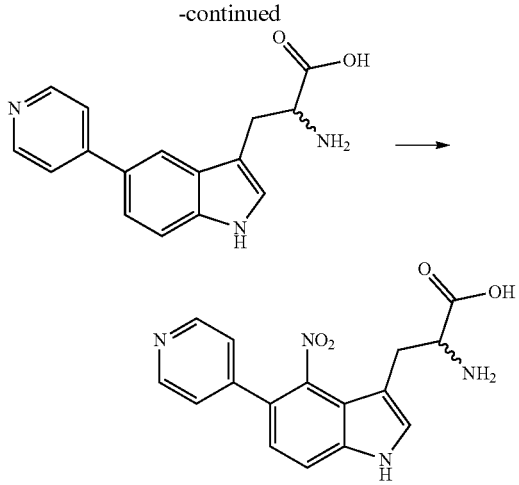

109

Example 109 can be prepared from 5-(pyridin-4-yl)indole as shown above and in a similar manner as described in Examples 1-2.

Example 110: Preparation of 2-amino-3-(4-nitro-6-(pyridin-4-yl)-1H-indol-3-yl)propanoic Acid (110)

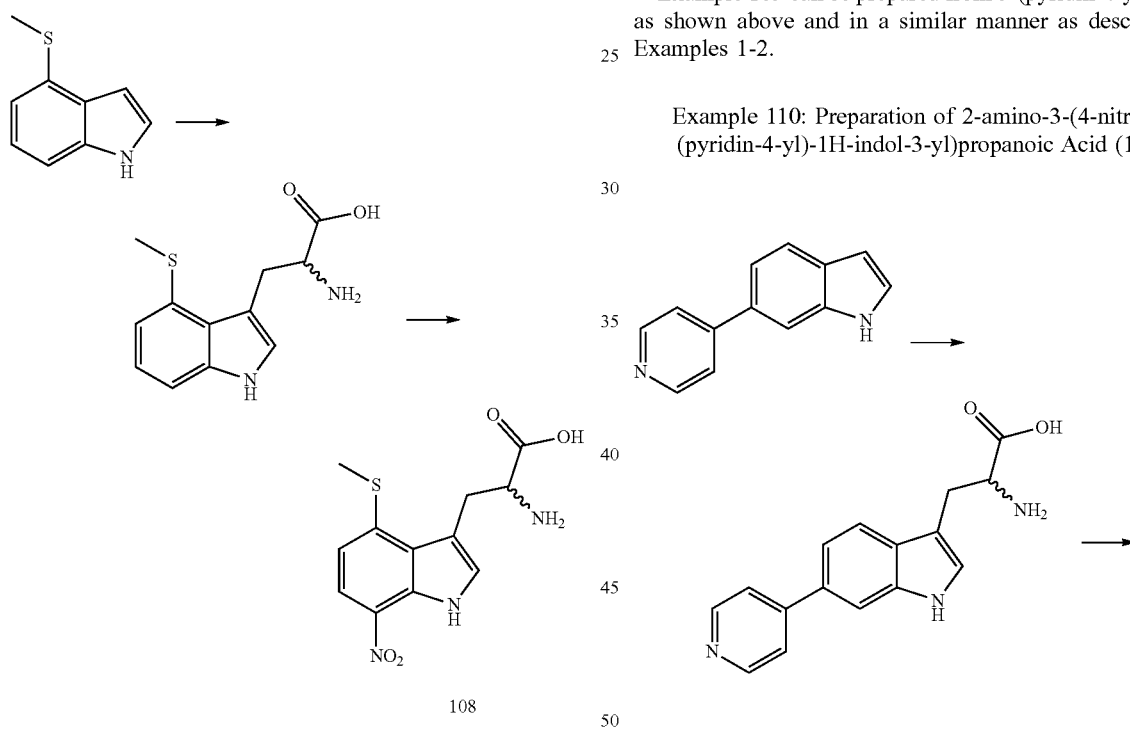

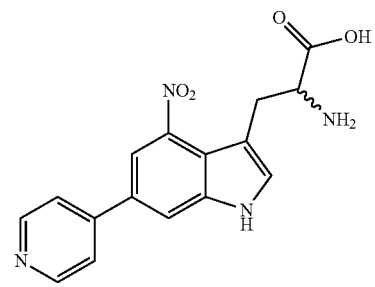

110

Example 110 can be prepared from 6-(pyridin-4-yl)indole as shown above and in a similar manner as described in Examples 1-2.

Example 111: Preparation of 2-amino-3-(4-nitro-7-(pyridin-4-yl)-1H-indol-3-yl)propanoic Acid (111)

Example 112 can be prepared from 4-(pyridin-4-yl)indole as shown above and in a similar manner as described in Examples 1-2.

Example 113: Preparation of 2-amino-3-(1,5-dimethyl-4-nitro-1H-indol-3-yl)propanoic Acid (113)

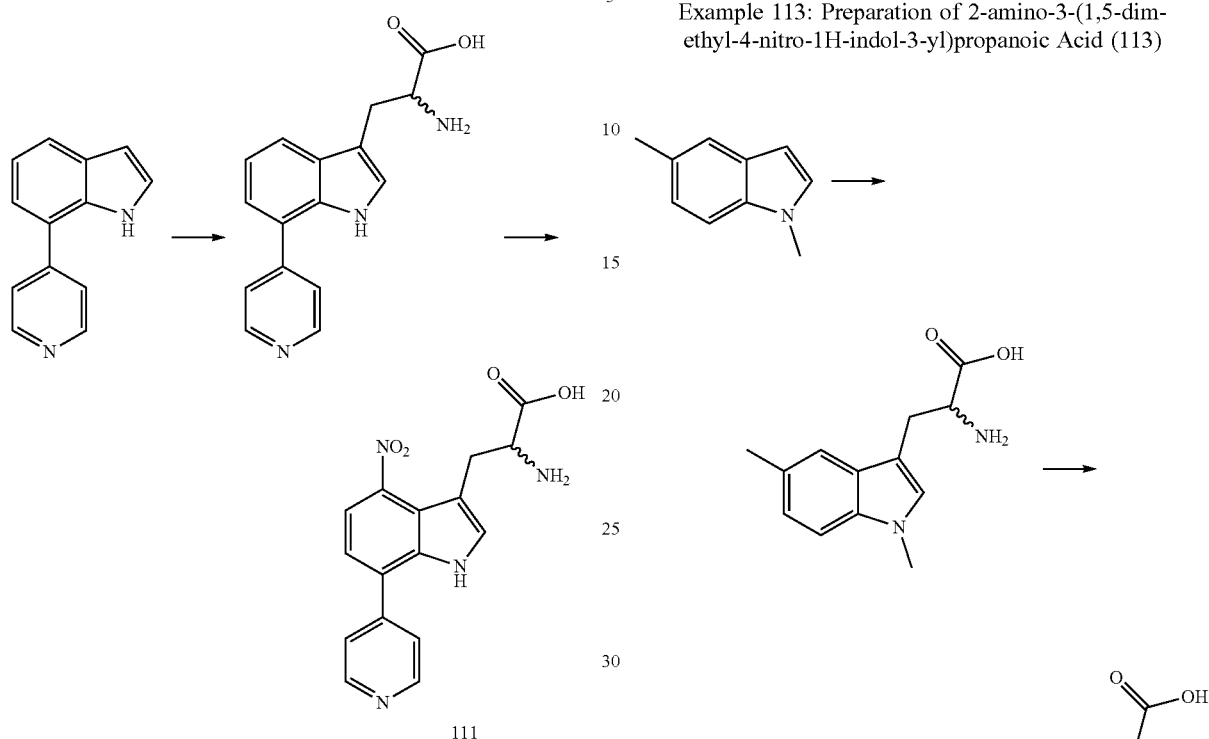

111

Example 111 can be prepared from 7-(pyridin-4-yl)indole as shown above and in a similar manner as described in Examples 1-2.

Example 112: Preparation of 2-amino-3-(7-nitro-4-(pyridin-4-yl)-1H-indol-3-yl)propanoic Acid (112)

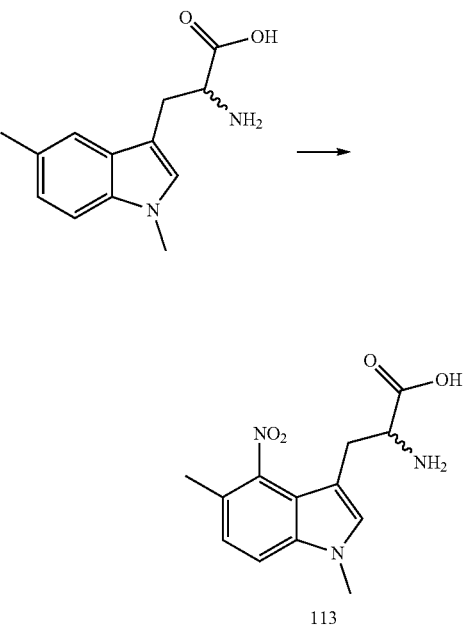

113

Example 113 can be prepared from 1,5-dimethyl-1H-indole as shown above and in a similar manner as described in Examples 1-2.

Example 114: Preparation of 2-amino-3-(1,6-dimethyl-4-nitro-1H-indol-3-yl)propanoic Acid (114)

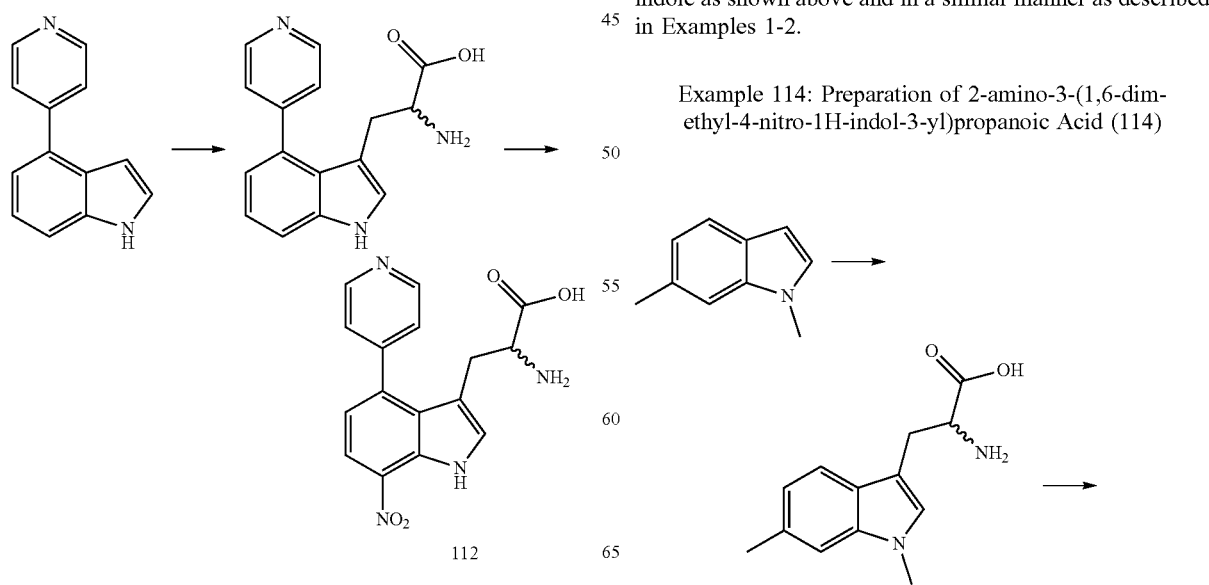

112

125
-continued

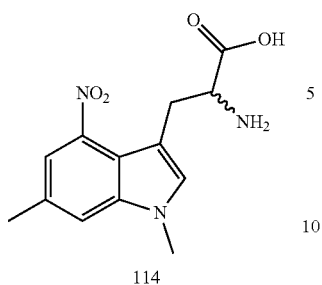

114

Example 114 can be prepared from 1,6-dimethyl-1H-indole as shown above and in a similar manner as described in Examples 1-2.

Example 115: Preparation of 2-amino-3-(1,7-dimethyl-4-nitro-1H-indol-3-yl)propanoic Acid (115)

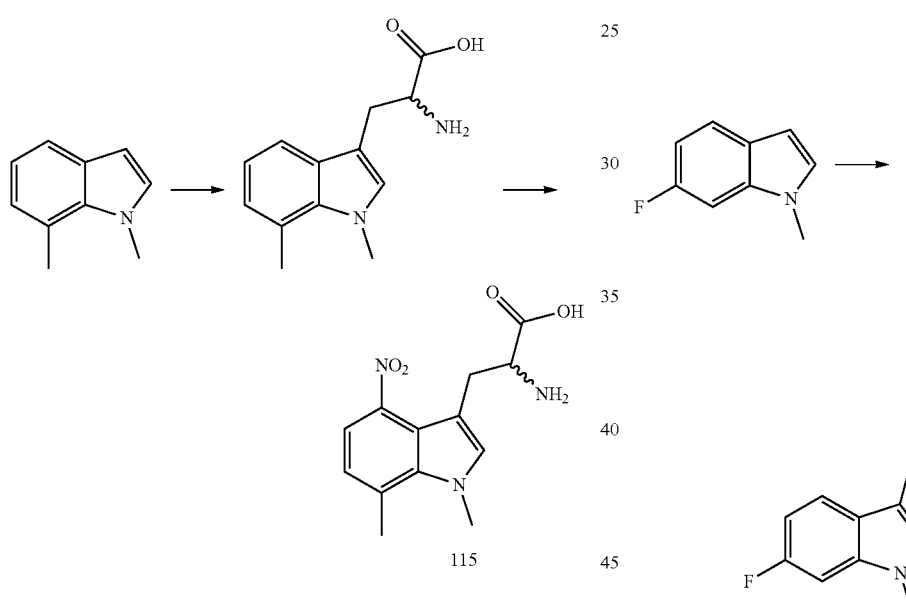

115

Example 115 can be prepared from 1,7-dimethyl-1H-indole as shown above and in a similar manner as described in Examples 1-2.

Example 116: Preparation of 2-amino-3-(1,4-dimethyl-7-nitro-1H-indol-3-yl)propanoic Acid (116)

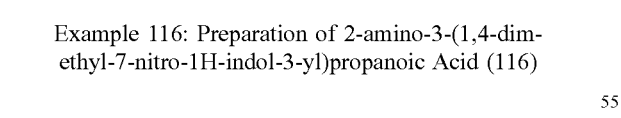

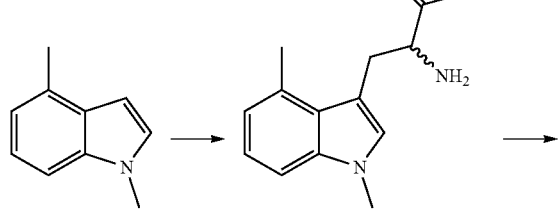

126
-continued

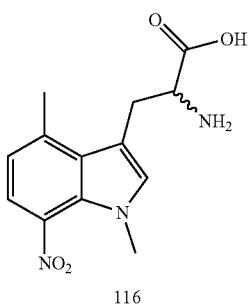

116

Example 116 can be prepared from 1,4-dimethyl-1H-indole as shown above and in a similar manner as described in Examples 1-2.

Example 117: Preparation of 2-amino-3-(6-fluoro-1-methyl-4-nitro-1H-indol-3-yl)propanoic Acid (117)

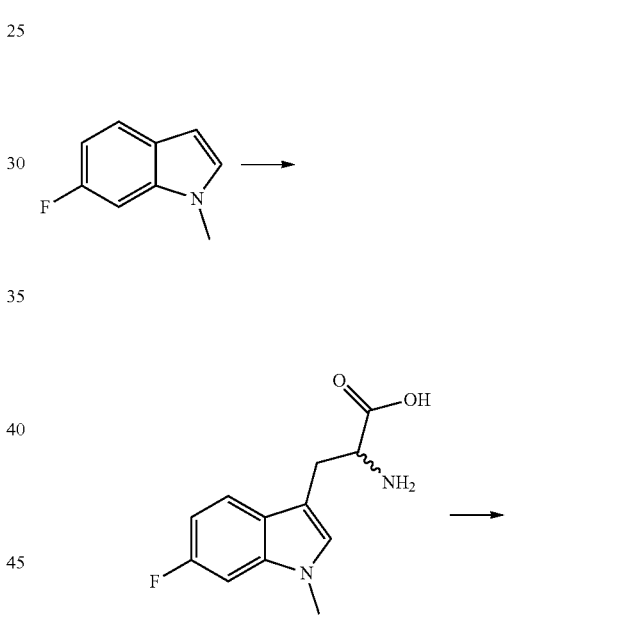

117

Example 117 can be prepared from 6-fluoro-1-methyl-1H-indole as shown above and in a similar manner as described in Examples 1-2.

Example 118: Preparation of 2-amino-3-(7-fluoro-1-methyl-4-nitro-1H-indol-3-yl)propanoic Acid (118)

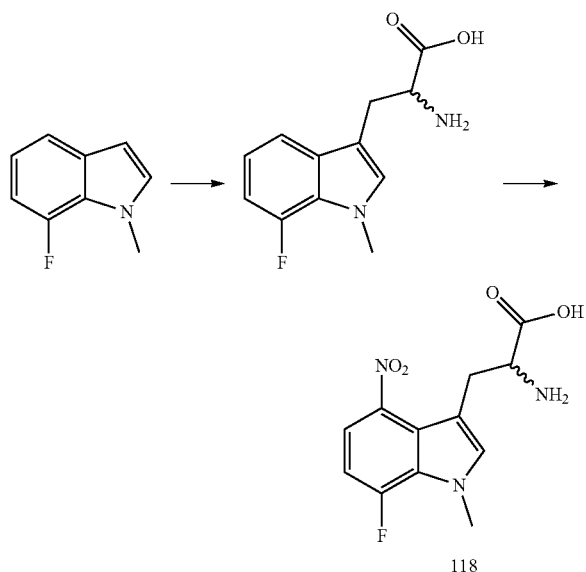

118

Example 118 can be prepared from 7-fluoro-1-methyl-indole as shown above and in a similar manner as described in Examples 1-2.

Example 119: Preparation of 2-amino-3-(4-fluoro-1-methyl-7-nitro-1H-indol-3-yl)propanoic Acid (119)

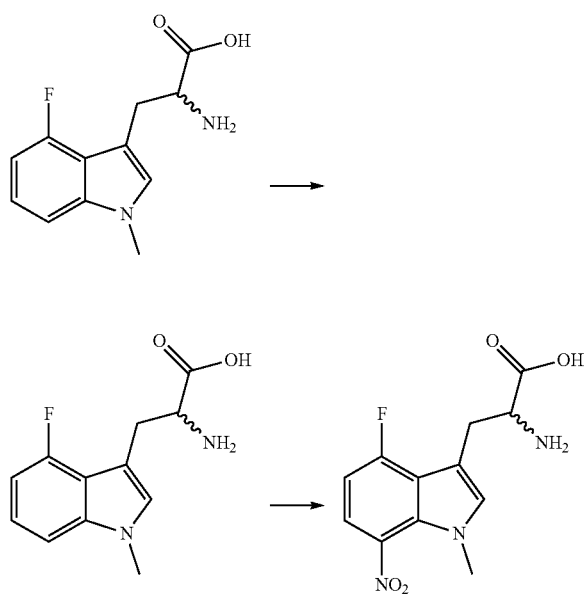

119

Example 119 can be prepared from 4-fluoro-1-methyl-indole as shown above and in a similar manner as described in Examples 1-2.

Example 120: Preparation of 2-amino-3-(5-chloro-1-methyl-4-nitro-1H-indol-3-yl)propanoic Acid (120)

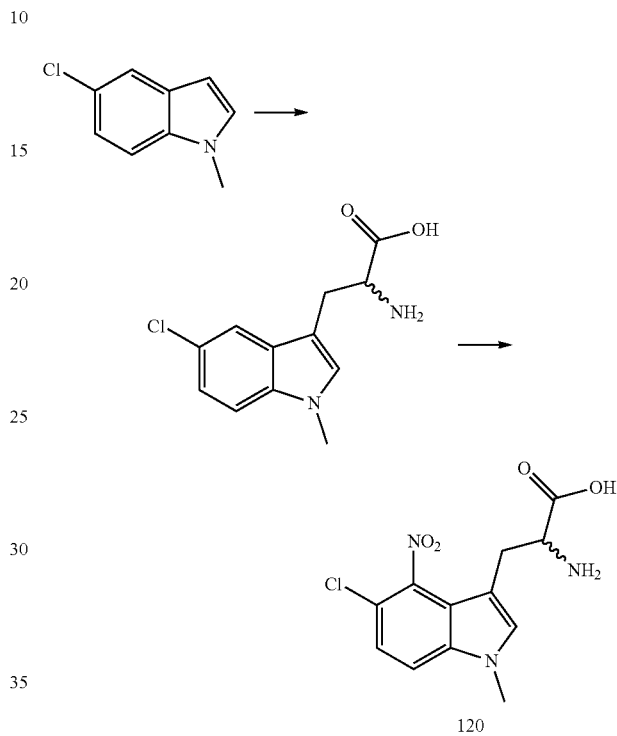

120

Example 120 can be prepared from 5-chloro-1-methyl-indole as shown above and in a similar manner as described in Examples 1-2.

Example 121: Preparation of 2-amino-3-(6-chloro-1-methyl-4-nitro-1H-indol-3-yl)propanoic Acid (121)

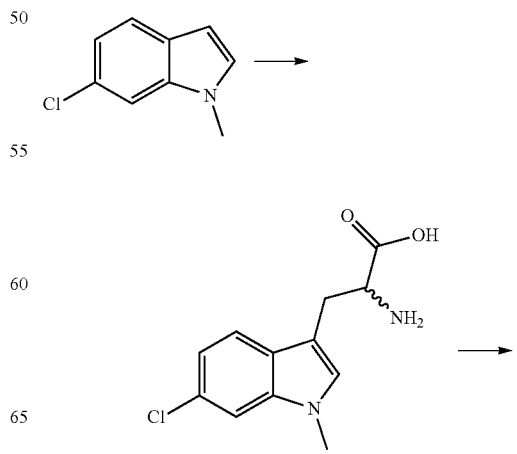

-continued

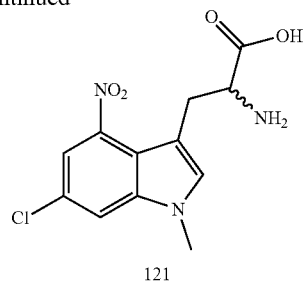
121

Example 121 can be prepared from 6-chloro-1-methyl-indole as shown above and in a similar manner as described in Examples 1-2.

Example 122: Preparation of 2-amino-3-(7-chloro-1-methyl-4-nitro-1H-indol-3-yl)propanoic Acid (122)

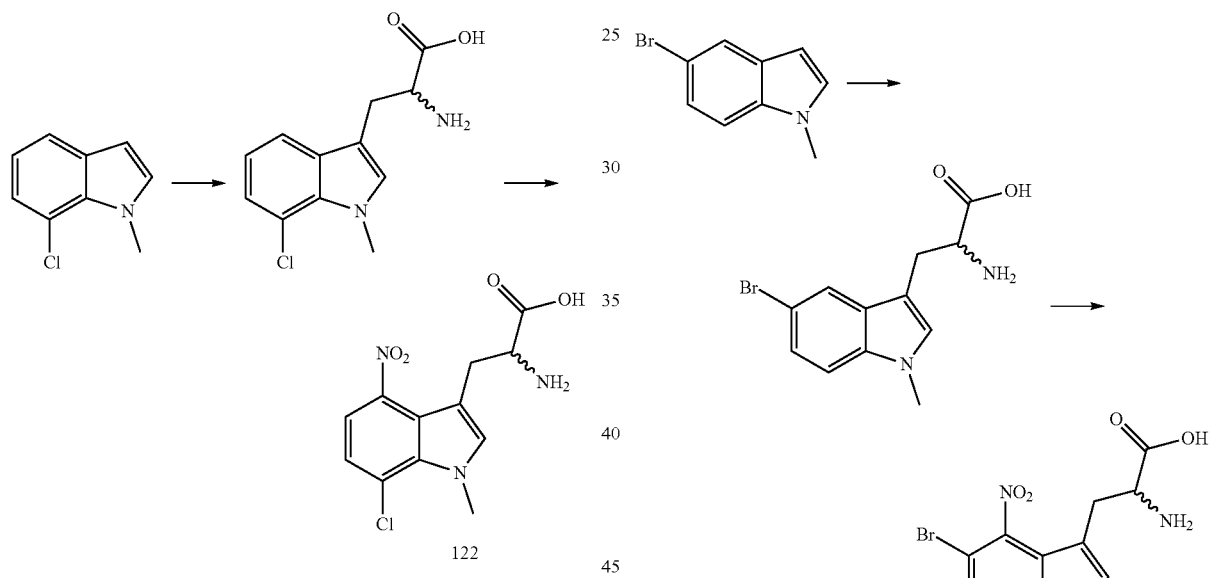

Example 122 can be prepared from 7-chloro-1-methyl-indole as shown above and in a similar manner as described in Examples 1-2.

Example 123: Preparation of 2-amino-3-(4-chloro-1-methyl-7-nitro-1H-indol-3-yl)propanoic Acid (123)

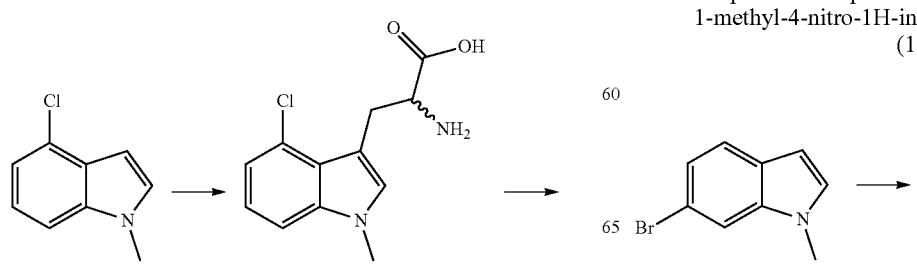

-continued

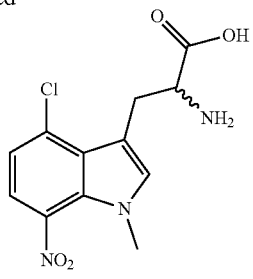
123

Example 123 can be prepared from 4-chloro-1-methyl-indole as shown above and in a similar manner as described in Examples 1-2.

Example 124: Preparation of 2-amino-3-(5-bromo-1-methyl-4-nitro-1H-indol-3-yl)propanoic Acid (124)

Example 124 can be prepared from 5-bromo-1-methyl-indole as shown above and in a similar manner as described in Examples 1-2.

Example 125: Preparation of 2-amino-3-(6-bromo-1-methyl-4-nitro-1H-indol-3-yl)propanoic Acid (125)

131

-continued

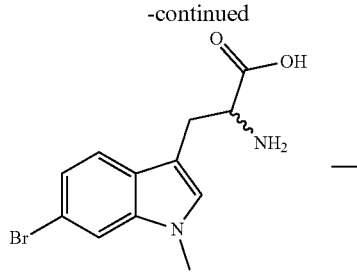

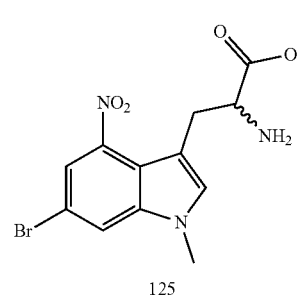
125

Example 125 can be prepared from 6-bromo-1-methyl-indole as shown above and in a similar manner as described in Examples 1-2.

Example 126: Preparation of 2-amino-3-(7-bromo-1-methyl-4-nitro-1H-indol-3-yl)propanoic Acid (126)

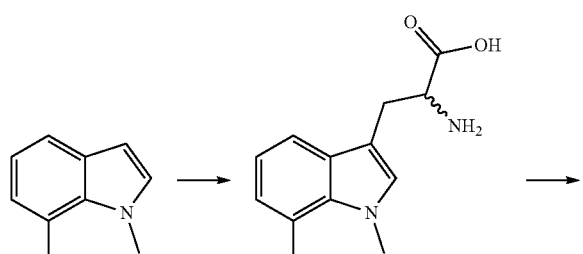
126

Example 126 can be prepared from 7-bromo-1-methyl-indole as shown above and in a similar manner as described in Examples 1-2.

132

Example 127: Preparation of 2-amino-3-(4-bromo-1-methyl-7-nitro-1H-indol-3-yl)propanoic Acid (127)

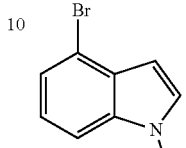

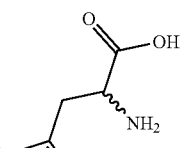

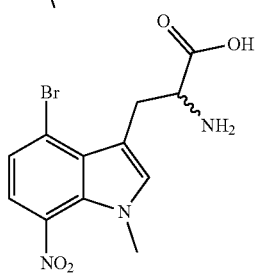
127

Example 127 can be prepared from 4-bromo-1-methyl-indole as shown above and in a similar manner as described in Examples 1-2.

Example 128: Preparation of 2-amino-3-(5-methoxy-1-methyl-4-nitro-1H-indol-3-yl)propanoic Acid (128)

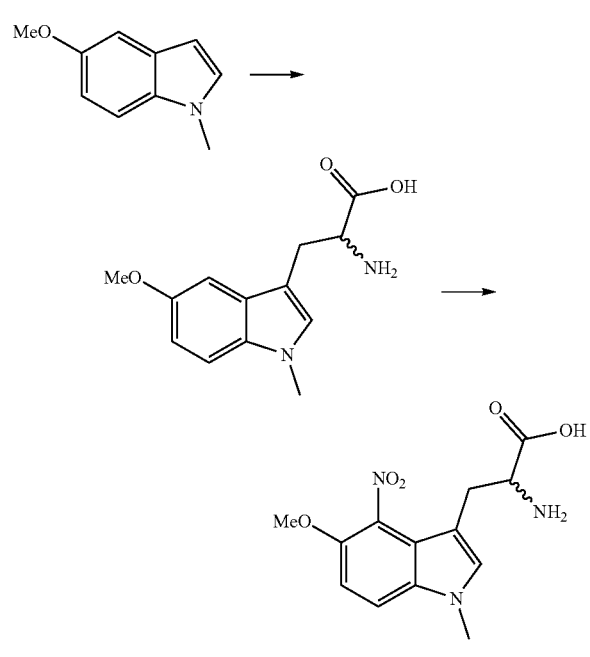
128

Example 128 can be prepared from 5-methoxy-1-methyl-indole as shown above and in a similar manner as described in Examples 1-2.

Example 129: Preparation of 2-amino-3-(6-methoxy-1-methyl-4-nitro-1H-indol-3-yl)propanoic Acid (129)

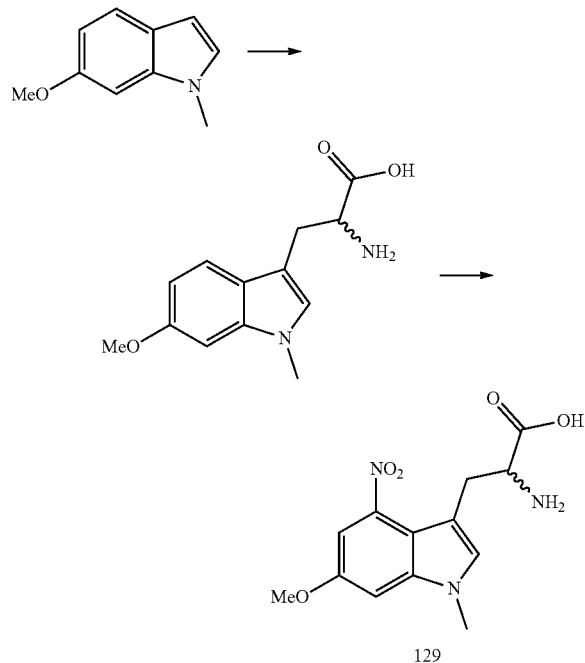

129

Example 129 can be prepared from 6-methoxy-1-methyl-indole as shown above and in a similar manner as described in Examples 1-2.

Example 130: Preparation of 2-amino-3-(7-methoxy-1-methyl-4-nitro-1H-indol-3-yl)propanoic Acid (130)

Example 130 can be prepared from 7-methoxy-1-methyl-indole as shown above and in a similar manner as described in Examples 1-2.

Example 131: Preparation of 2-amino-3-(4-methoxy-1-methyl-7-nitro-1H-indol-3-yl)propanoic Acid (131)

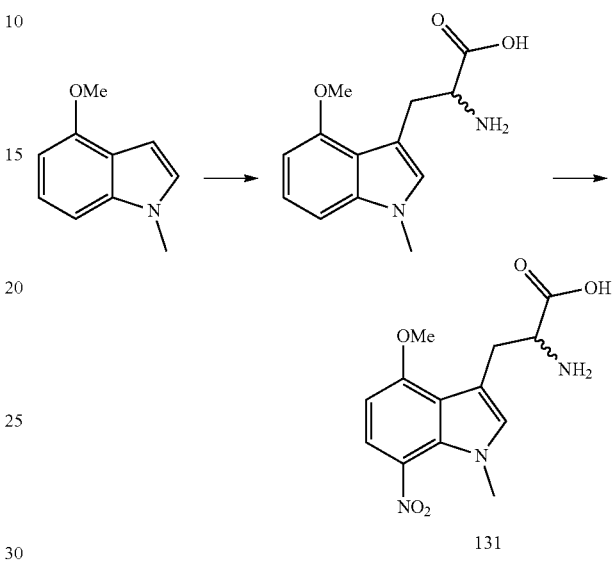

131

Example 131 can be prepared from 4-methoxy-1-methyl-indole as shown above and in a similar manner as described in Examples 1-2.

Example 132: Preparation of 2-amino-3-(5-amino-1-methyl-4-nitro-1H-indol-3-yl)propanoic Acid (132)

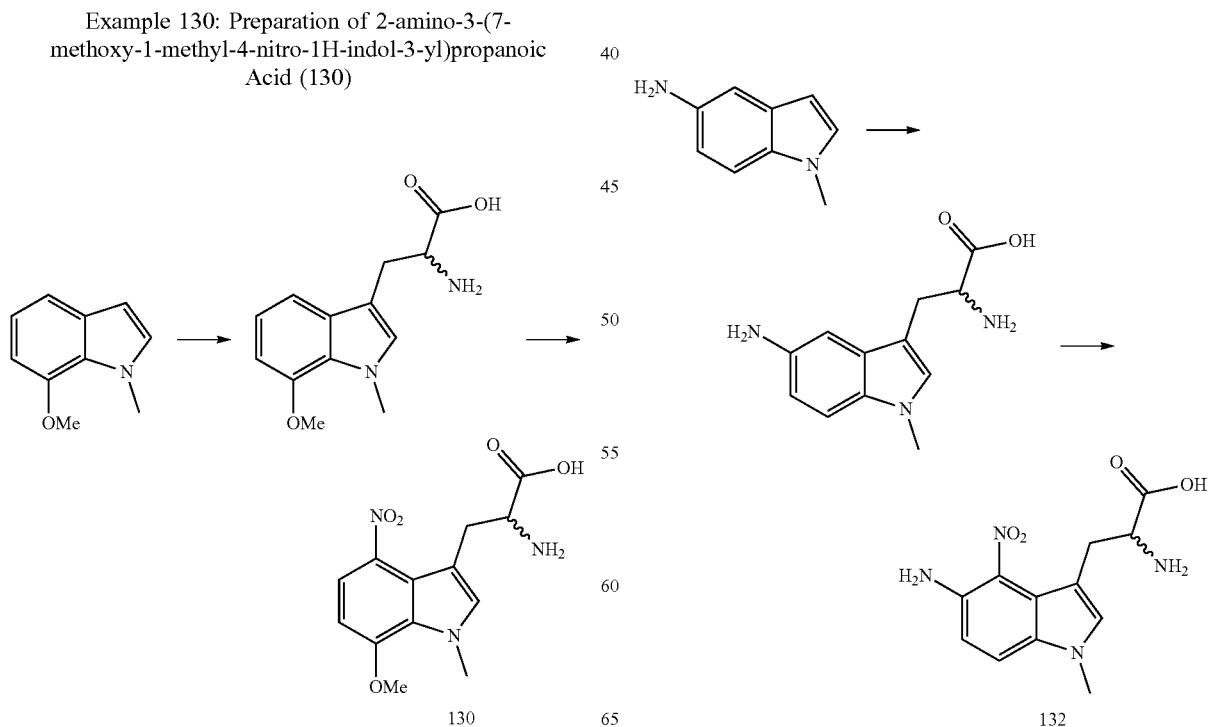

130

132

Example 132 can be prepared from 5-amino-1-methyl-indole as shown above and in a similar manner as described in Examples 1-2.

Example 133: Preparation of 2-amino-3-(6-amino-1-methyl-4-nitro-1H-indol-3-yl)propanoic Acid (133)

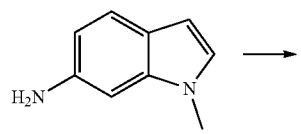

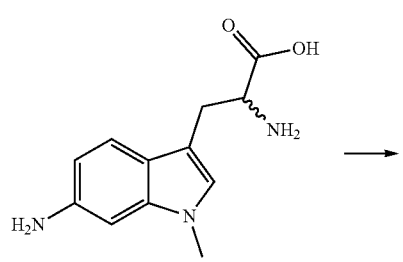

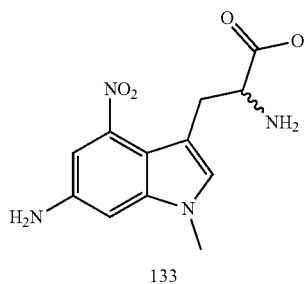

133

Example 133 can be prepared from 6-amino-1-methyl-indole as shown above and in a similar manner as described in Examples 1-2.

Example 134: Preparation of 2-amino-3-(7-amino-1-methyl-4-nitro-1H-indol-3-yl)propanoic Acid (134)

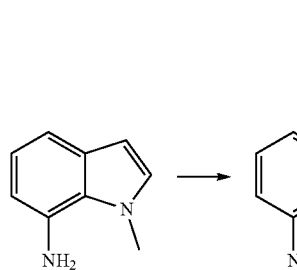

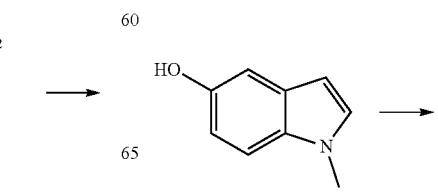

-continued

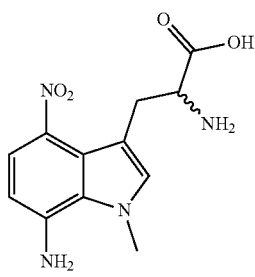

134

Example 134 can be prepared from 7-amino-1-methyl-indole as shown above and in a similar manner as described in Examples 1-2.

Example 135: Preparation of 2-amino-3-(4-amino-1-methyl-7-nitro-1H-indol-3-yl)propanoic Acid (135)

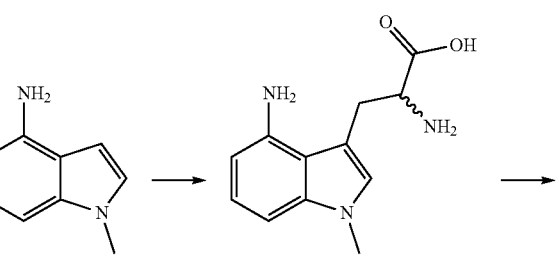

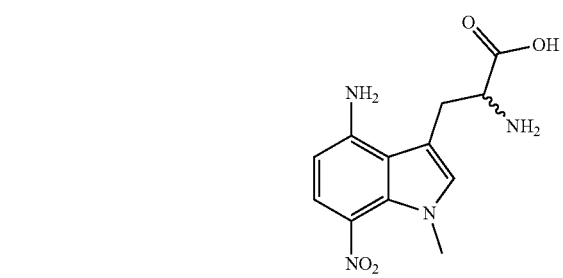

135

Example 135 can be prepared from 4-amino-1-methyl-indole as shown above and in a similar manner as described in Examples 1-2.

Example 136: Preparation of 2-amino-3-(5-hydroxy-1-methyl-4-nitro-1H-indol-3-yl)propanoic Acid (136)

-continued

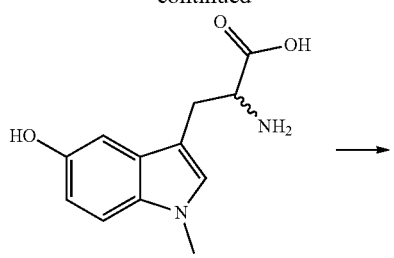

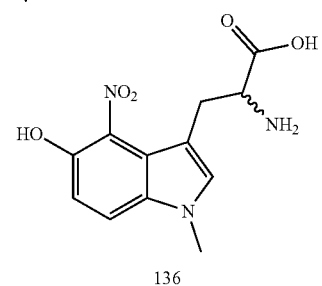

136

Example 136 can be prepared from 5-hydroxy-1-methyl-indole as shown above and in a similar manner as described in Examples 1-2.

Example 137: Preparation of 2-amino-3-(6-hydroxy-1-methyl-4-nitro-1H-indol-3-yl)propanoic Acid (137)

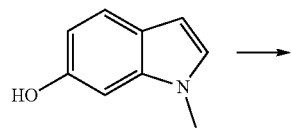

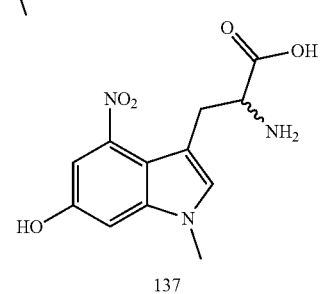

137

Example 137 can be prepared from 6-hydroxy-1-methyl-indole as shown above and in a similar manner as described in Examples 1-2.

Example 138: Preparation of 2-amino-3-(7-hydroxy-1-methyl-4-nitro-1H-indol-3-yl)propanoic Acid (138)

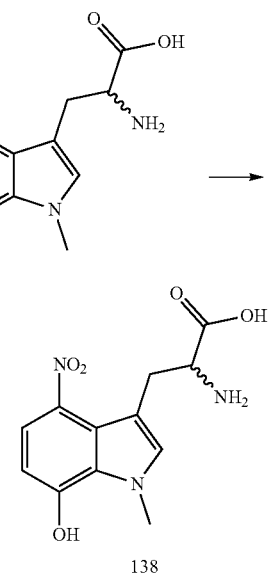

138

Example 138 can be prepared from 7-hydroxy-1-methyl-indole as shown above and in a similar manner as described in Examples 1-2.

Example 139: Preparation of 2-amino-3-(4-hydroxy-1-methyl-7-nitro-1H-indol-3-yl)propanoic Acid (139)

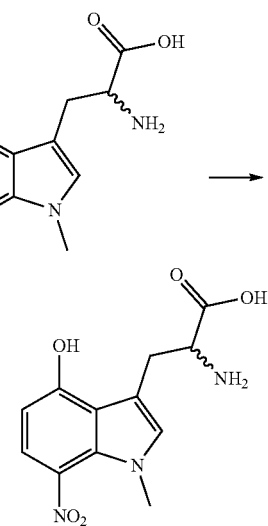

139

Example 139 can be prepared from 4-hydroxy-1-methyl-indole as shown above and in a similar manner as described in Examples 1-2.

Example 140: Preparation of 2-amino-3-(1-methyl-4-nitro-5-phenyl-1H-indol-3-yl)propanoic Acid (140)

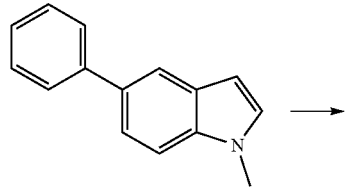

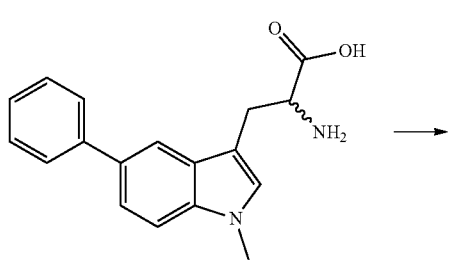

Example 140 can be prepared from 5-phenyl-1-methyl-indole as shown above and in a similar manner as described in Examples 1-2.

Example 141: Preparation of 2-amino-3-(1-methyl-4-nitro-6-phenyl-1H-indol-3-yl)propanoic Acid (141)

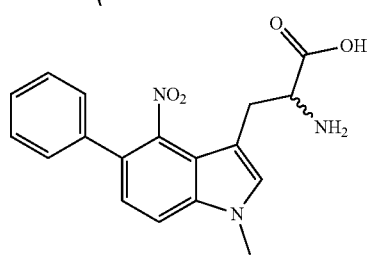

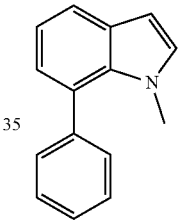

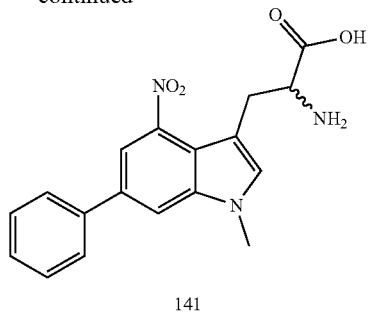

Example 141 can be prepared from 6-phenyl-1-methyl-indole as shown above and in a similar manner as described in Examples 1-2.

Example 142: Preparation of 2-amino-3-(1-methyl-4-nitro-7-phenyl-1H-indol-3-yl)propanoic Acid (142)

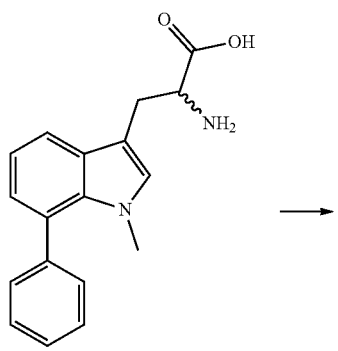

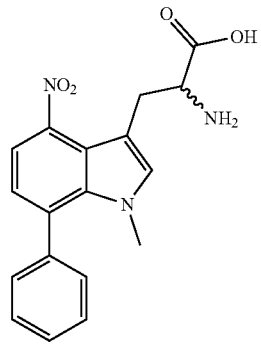

Example 142 can be prepared from 7-phenyl-1-methyl-indole as shown above and in a similar manner as described in Examples 1-2.

Example 143: Preparation of 2-amino-3-(1-methyl-7-nitro-4-phenyl-1H-indol-3-yl)propanoic Acid (143)

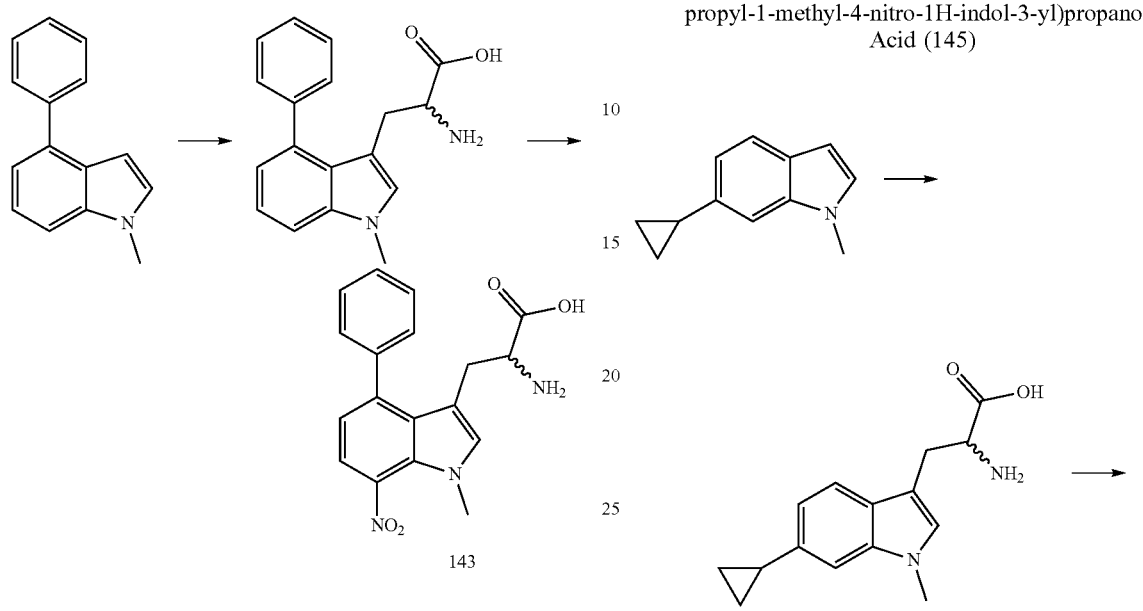

Example 143 can be prepared from 4-phenyl-1-methyl-indole as shown above and in a similar manner as described in Examples 1-2.

Example 144: Preparation of 2-amino-3-(5-cyclopropyl-1-methyl-4-nitro-1H-indol-3-yl)propanoic Acid (144)

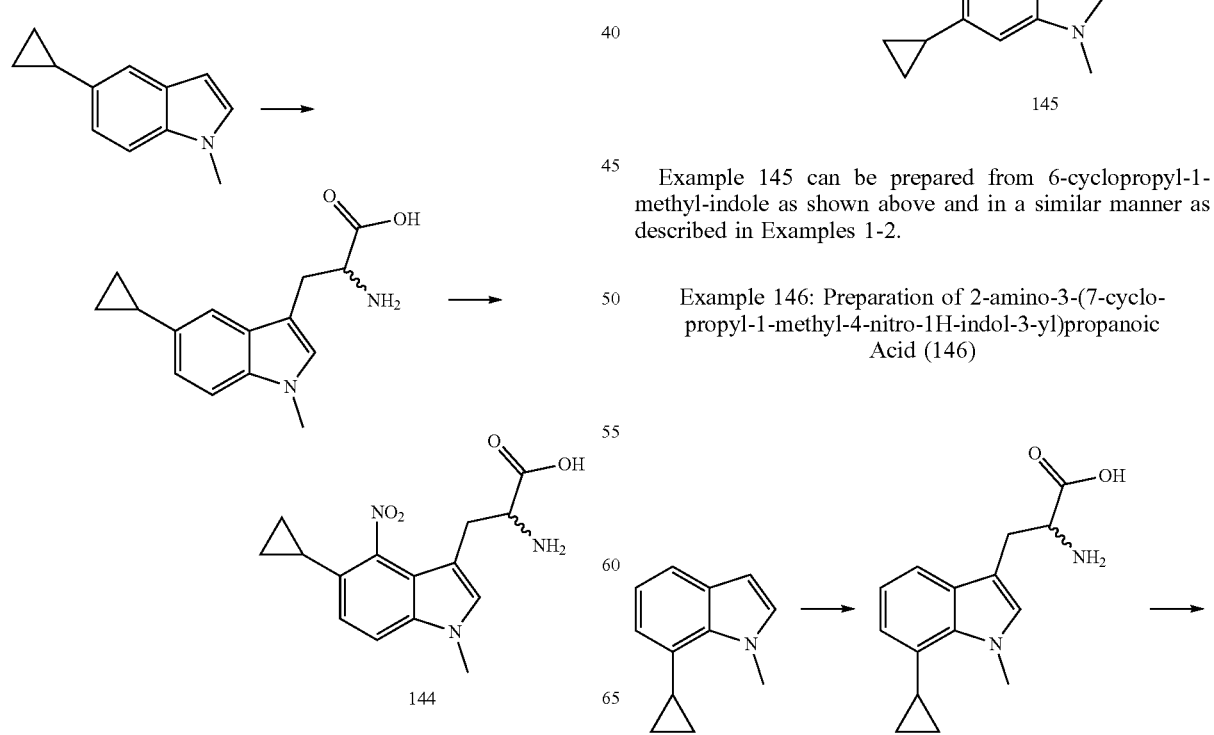

Example 144 can be prepared from 5-cyclopropyl-1-methyl-indole as shown above and in a similar manner as described in Examples 1-2.

Example 145: Preparation of 2-amino-3-(6-cyclopropyl-1-methyl-4-nitro-1H-indol-3-yl)propanoic Acid (145)

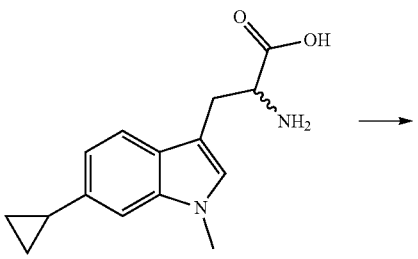

Example 145 can be prepared from 6-cyclopropyl-1-methyl-indole as shown above and in a similar manner as described in Examples 1-2.

Example 146: Preparation of 2-amino-3-(7-cyclopropyl-1-methyl-4-nitro-1H-indol-3-yl)propanoic Acid (146)

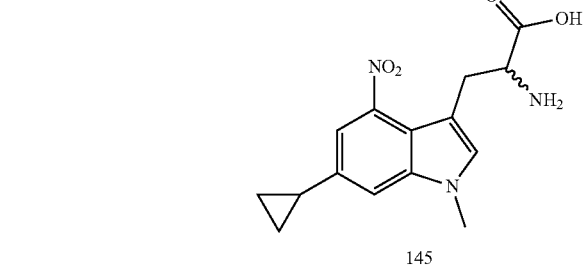

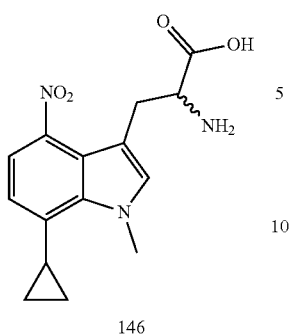

146

Example 146 can be prepared from 7-cyclopropyl-1-methyl-indole as shown above and in a similar manner as described in Examples 1-2.

Example 147: Preparation of 2-amino-3-(4-cyclopropyl-1-methyl-7-nitro-1H-indol-3-yl)propanoic Acid (147)

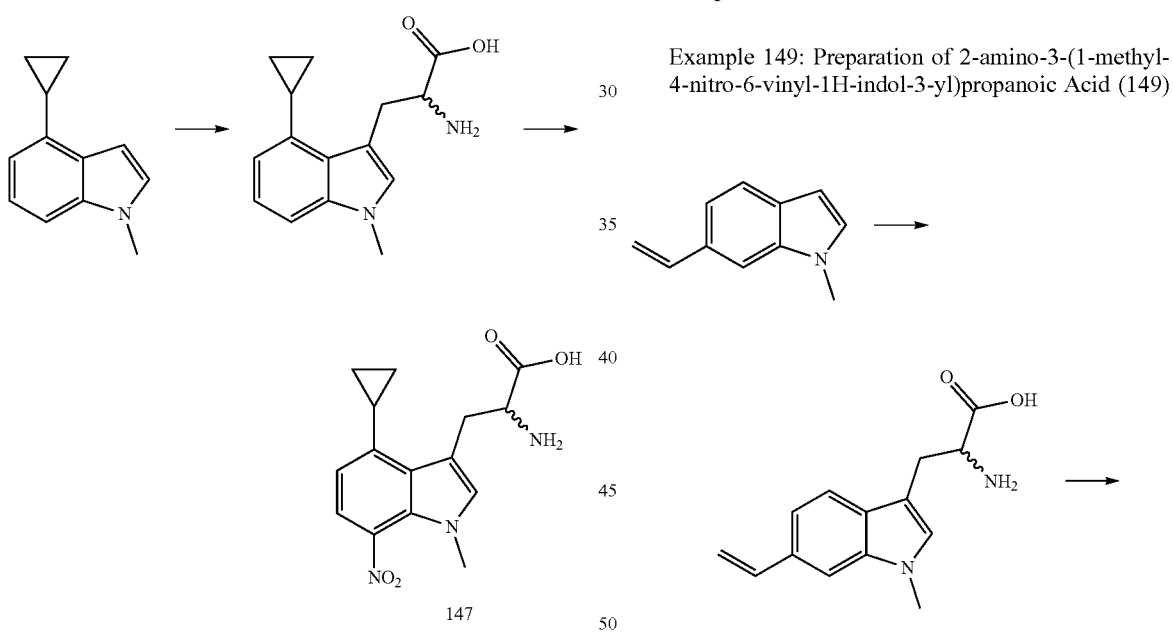

147

Example 147 can be prepared from 4-cyclopropyl-1-methyl-indole as shown above and in a similar manner as described in Examples 1-2.

Example 148: Preparation of 2-amino-3-(1-methyl-4-nitro-5-vinyl-1H-indol-3-yl)propanoic Acid (148)

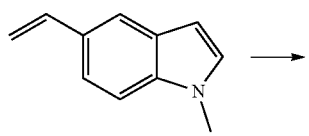

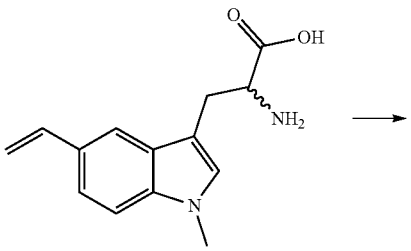

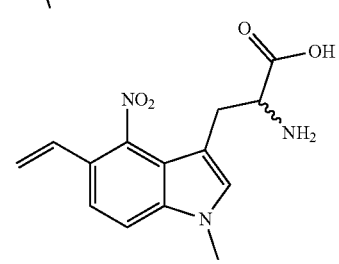

148

Example 148 can be prepared from 5-vinyl-1-methyl-indole as shown above and in a similar manner as described in Examples 1-2.

Example 149: Preparation of 2-amino-3-(1-methyl-4-nitro-6-vinyl-1H-indol-3-yl)propanoic Acid (149)

149

Example 149 can be prepared from 6-vinyl-1-methyl-indole as shown above and in a similar manner as described in Examples 1-2.

145

Example 150: Preparation of 2-amino-3-(1-methyl-4-nitro-7-vinyl-1H-indol-3-yl)propanoic Acid (150)

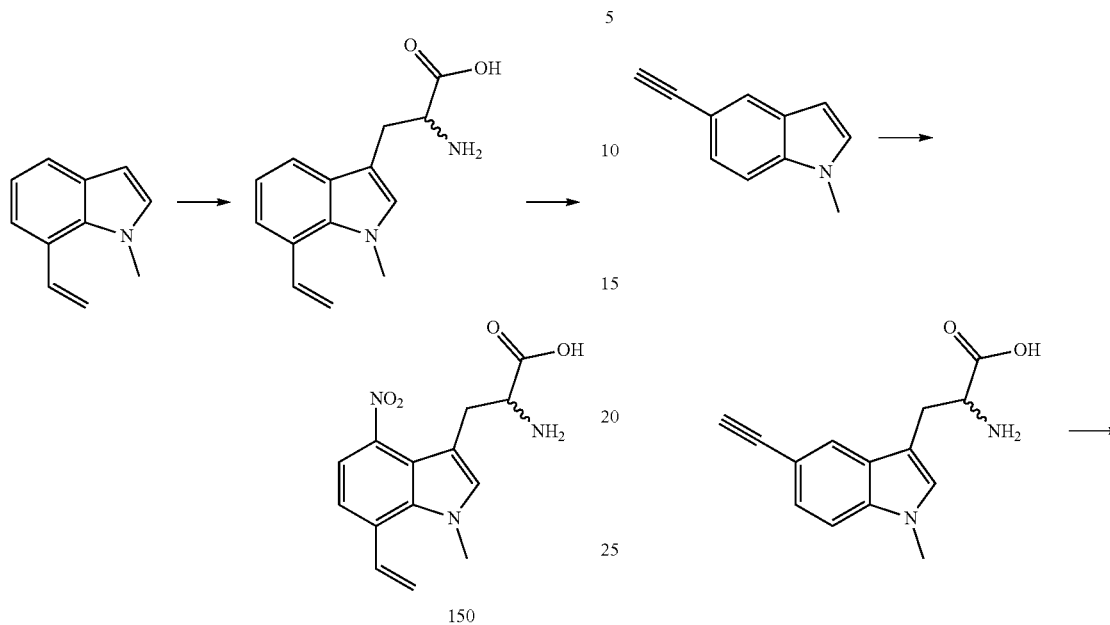

150

Example 150 can be prepared from 7-vinyl-1-methyl-indole as shown above and in a similar manner as described in Examples 1-2.

Example 151: Preparation of 2-amino-3-(1-methyl-7-nitro-4-vinyl-1H-indol-3-yl)propanoic Acid (151)

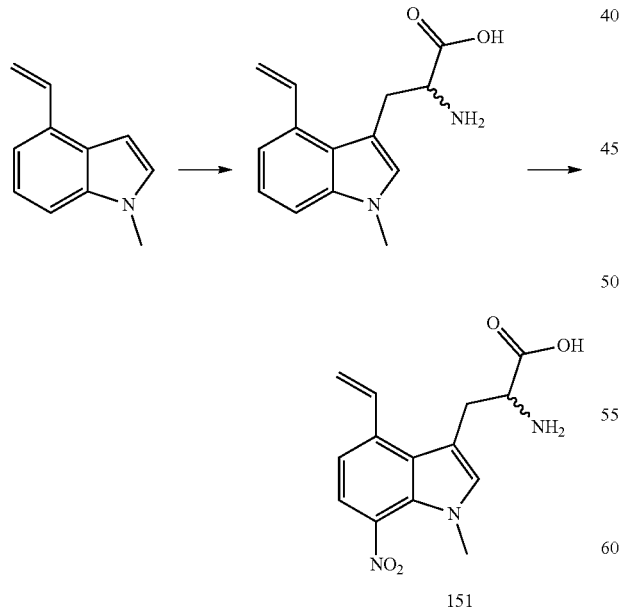

151

Example 151 can be prepared from 4-vinyl-1-methyl-indole as shown above and in a similar manner as described in Examples 1-2.

146

Example 152: Preparation of 2-amino-3-(5-ethynyl-1-methyl-4-nitro-1H-indol-3-yl)propanoic Acid (152)

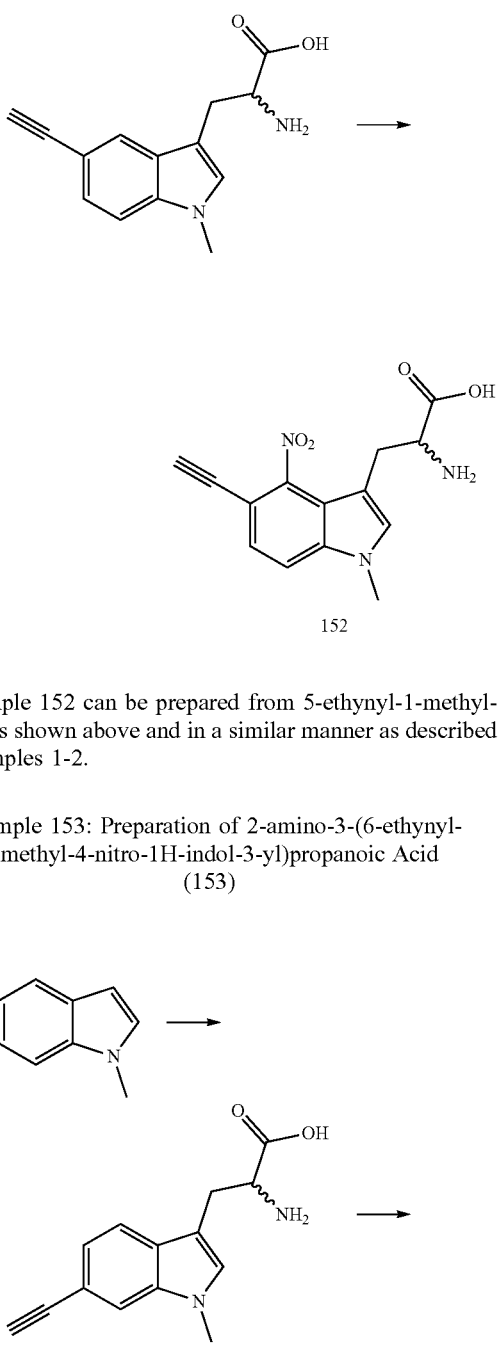

152

Example 152 can be prepared from 5-ethynyl-1-methyl-indole as shown above and in a similar manner as described in Examples 1-2.

Example 153: Preparation of 2-amino-3-(6-ethynyl-1-methyl-4-nitro-1H-indol-3-yl)propanoic Acid (153)

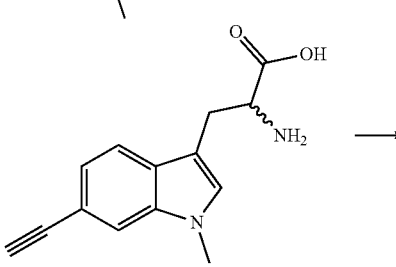

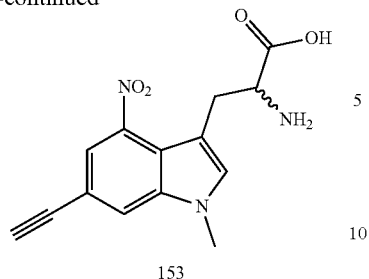

153

Example 153 can be prepared from 6-ethynyl-1-methyl-indole as shown above and in a similar manner as described in Examples 1-2.

Example 154: Preparation of 2-amino-3-(7-ethynyl-1-methyl-4-nitro-1H-indol-3-yl)propanoic Acid (154)

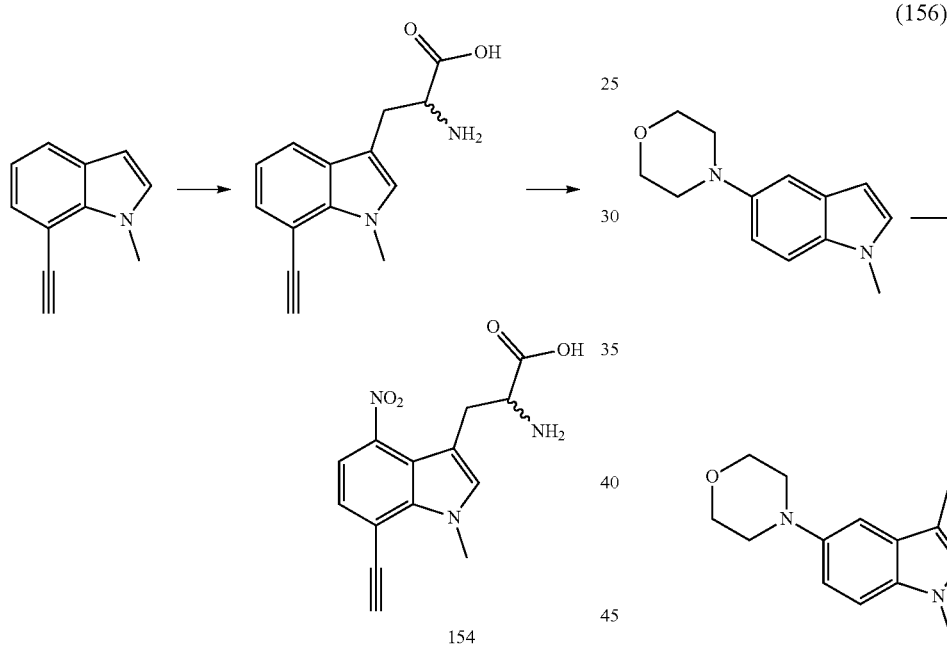

154

Example 154 can be prepared from 7-ethynyl-1-methyl-indole as shown above and in a similar manner as described in Examples 1-2.

Example 155: Preparation of 2-amino-3-(4-ethynyl-1-methyl-7-nitro-1H-indol-3-yl)propanoic Acid (155)

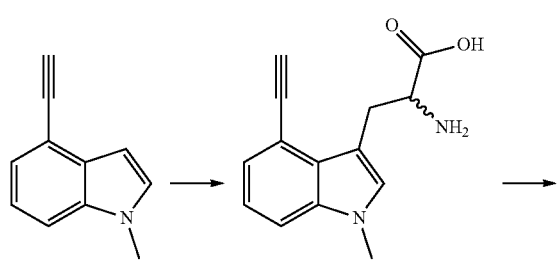

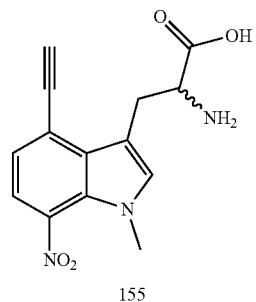

155

Example 155 can be prepared from 4-ethynyl-1-methyl-indole as shown above and in a similar manner as described in Examples 1-2.

Example 156: Preparation of 2-amino-3-(1-methyl-5-morpholino-4-nitro-1H-indol-3-yl)propanoic Acid (156)

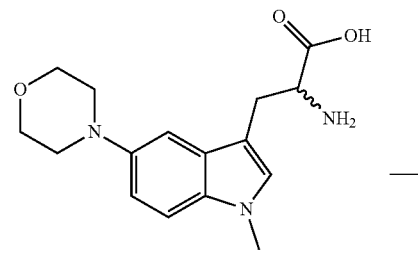

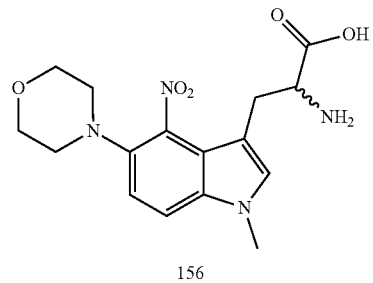

156

Example 156 can be prepared from 5-morpholino-1-methyl-indole as shown above and in a similar manner as described in Examples 1-2.

Example 157: Preparation of 2-amino-3-(1-methyl-6-morpholino-4-nitro-1H-indol-3-yl)propanoic Acid (157)

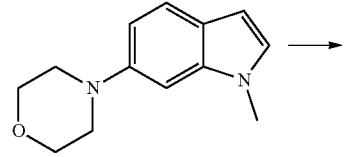

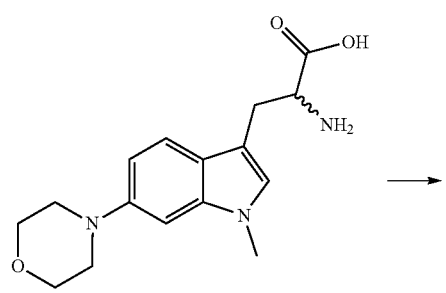

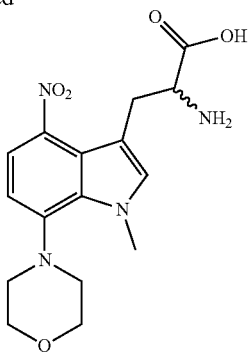

Example 157 can be prepared from 6-morpholino-1-methyl-indole as shown above and in a similar manner as described in Examples 1-2.

Example 158: Preparation of 2-amino-3-(1-methyl-7-morpholino-4-nitro-1H-indol-3-yl)propanoic Acid (158)

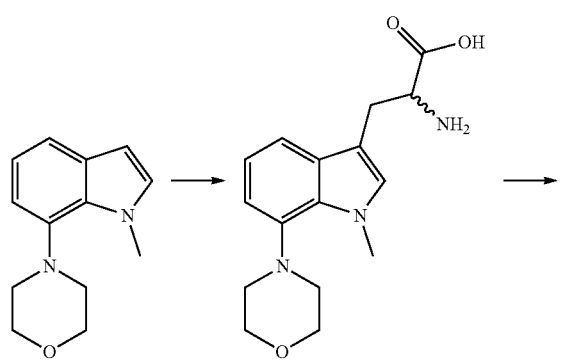

Example 158 can be prepared from 7-morpholino-1-methyl-indole as shown above and in a similar manner as described in Examples 1-2.

Example 159: Preparation of 2-amino-3-(1-methyl-4-morpholino-7-nitro-1H-indol-3-yl)propanoic Acid (159)

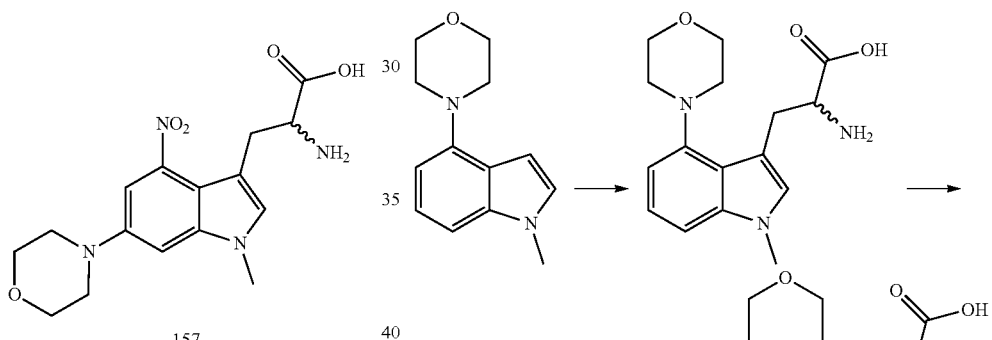

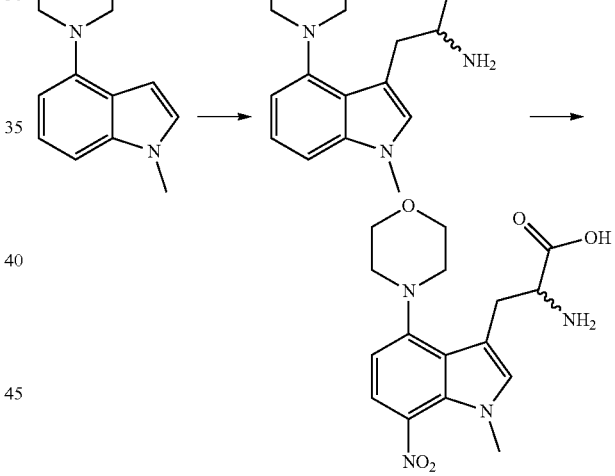

Example 159 can be prepared from 4-morpholino-1-methyl-indole as shown above and in a similar manner as described in Examples 1-2.

Example 160: Preparation of 2-amino-3-(1-methyl-5-(methylthio)-4-nitro-1H-indol-3-yl)propanoic Acid (160)

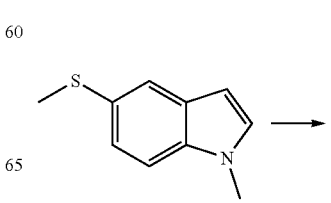

-continued

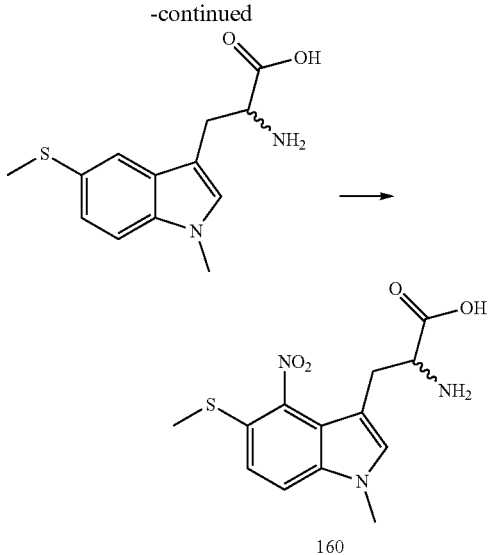

160

Example 160 can be prepared from 5-(methylthio)-1-methyl-indole as shown above and in a similar manner as described in Examples 1-2.

Example 161: Preparation of 2-amino-3-(1-methyl-6-(methylthio)-4-nitro-1H-indol-3-yl)propanoic Acid (161)

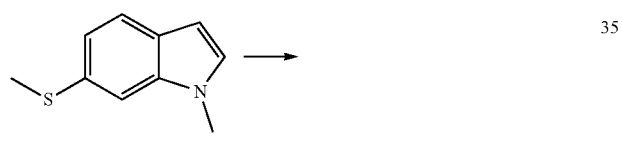

161

Example 161 can be prepared from 6-(methylthio)-1-methyl-indole as shown above and in a similar manner as described in Examples 1-2.

Example 162: Preparation of 2-amino-3-(1-methyl-7-(methylthio)-4-nitro-1H-indol-3-yl)propanoic Acid (162)

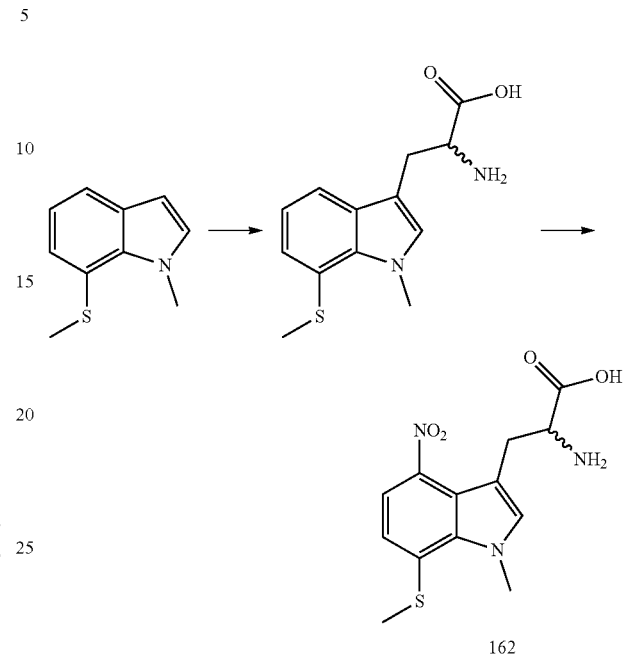

162

Example 162 can be prepared from 7-(methylthio)-1-methyl-indole as shown above and in a similar manner as described in Examples 1-2.

Example 163: Preparation of 2-amino-3-(1-methyl-4-(methylthio)-7-nitro-1H-indol-3-yl)propanoic Acid (163)

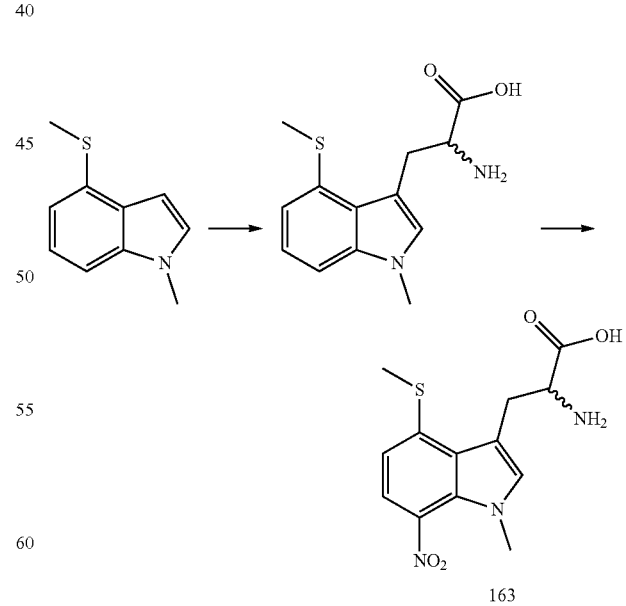

163

Example 163 can be prepared from 4-(methylthio)-1-methyl-indole as shown above and in a similar manner as described in Examples 1-2.

Example 164: Preparation of 2-amino-3-(1-methyl-4-nitro-5-(pyridin-4-yl)-1H-indol-3-yl)propanoic Acid (164)

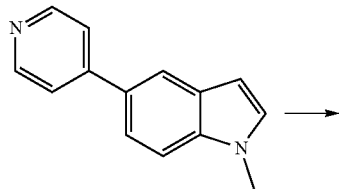

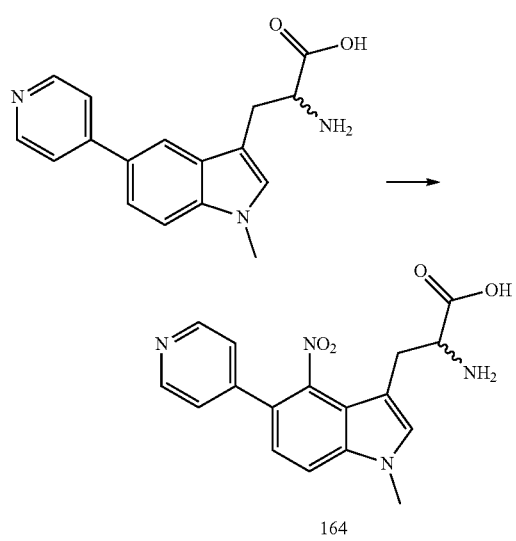

164

Example 164 can be prepared from 5-(pyridin-4-yl)-1-methyl-indole as shown above and in a similar manner as described in Examples 1-2.

Example 165: Preparation of 2-amino-3-(1-methyl-4-nitro-6-(pyridin-4-yl)-1H-indol-3-yl)propanoic Acid (165)

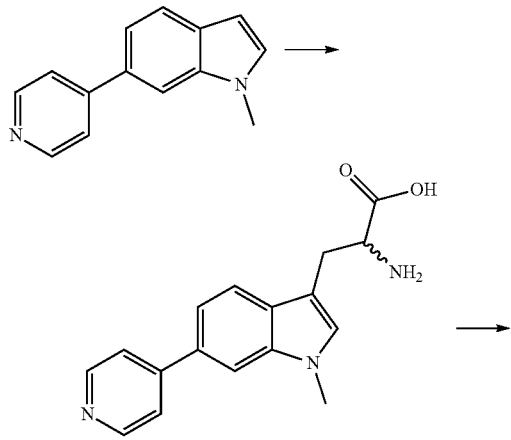

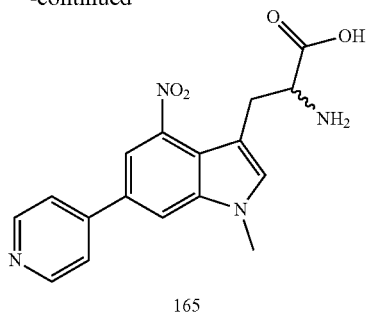

165

Example 165 can be prepared from 6-(pyridin-4-yl)-1-methyl-indole as shown above and in a similar manner as described in Examples 1-2.

Example 166: Preparation of 2-amino-3-(1-methyl-4-nitro-7-(pyridin-4-yl)-1H-indol-3-yl)propanoic Acid (166)

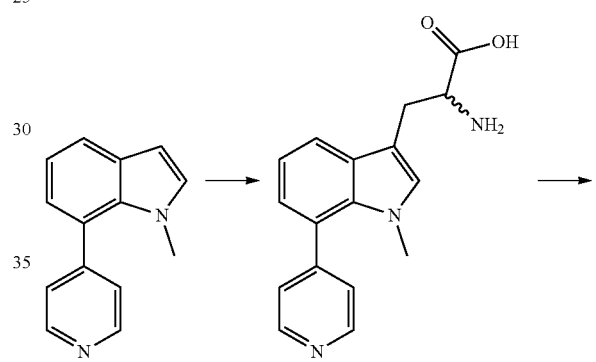

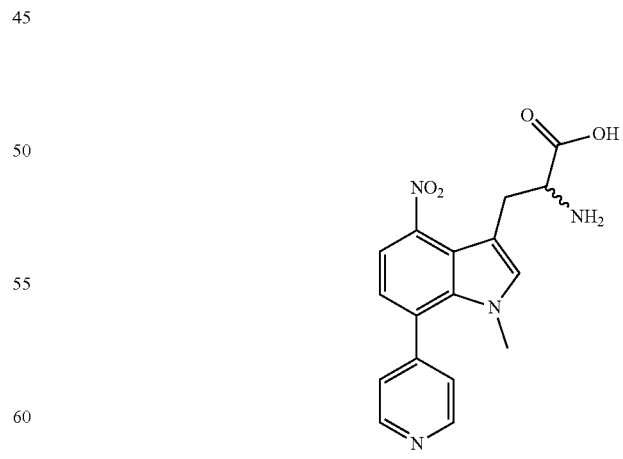

166

Example 166 can be prepared from 7-(pyridin-4-yl)-1-methyl-indole as shown above and in a similar manner as described in Examples 1-2.

Example 167: Preparation of 2-amino-3-(1-methyl-7-nitro-4-(pyridin-4-yl)-1H-indol-3-yl)propanoic Acid (167)

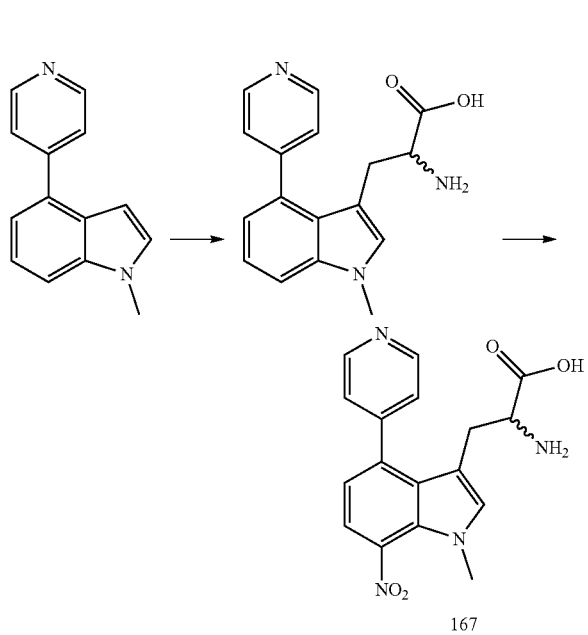

167

Example 167 can be prepared from 4-(pyridin-4-yl)-1-methyl-indole as shown above and in a similar manner as described in Examples 1-2.

Example 168: Preparation of 2-amino-3-(2,5-dimethyl-4-nitro-1H-indol-3-yl)propanoic Acid (168)

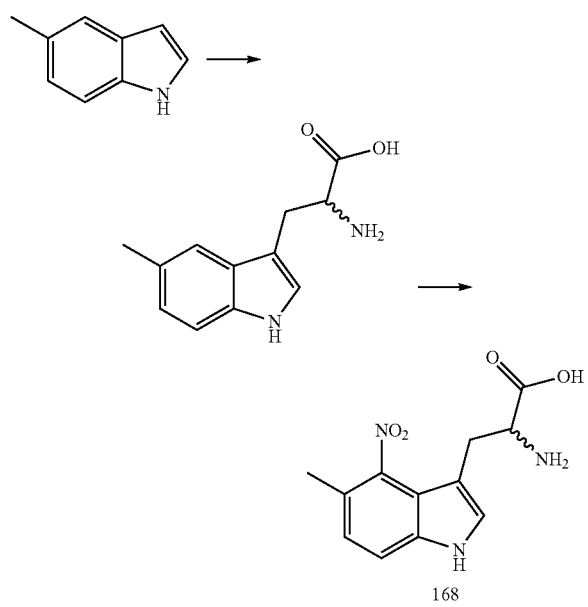

168

Example 168 can be prepared from 2,5-dimethyl-1H-indole as shown above and in a similar manner as described in Examples 1-2.

Example 169: Preparation of 2-amino-3-(2,6-dimethyl-4-nitro-1H-indol-3-yl)propanoic Acid (169)

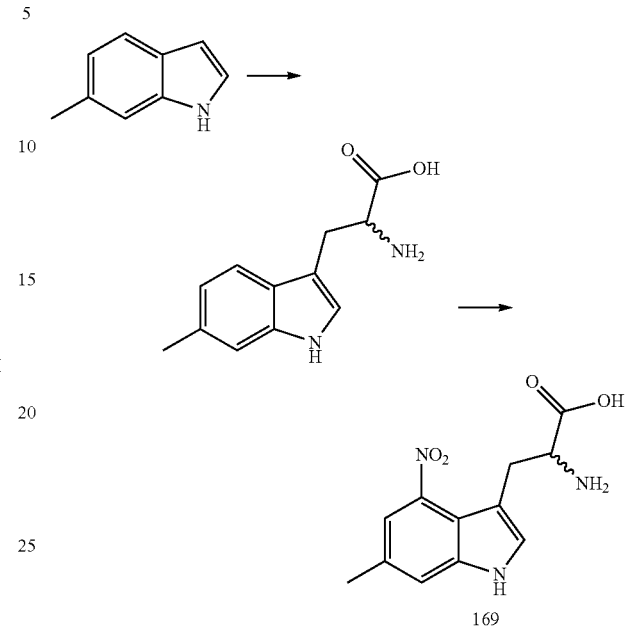

169

Example 169 can be prepared from 2,6-dimethyl-1H-indole as shown above and in a similar manner as described in Examples 1-2.

Example 170: Preparation of 2-amino-3-(2,7-dimethyl-4-nitro-1H-indol-3-yl)propanoic Acid (170)

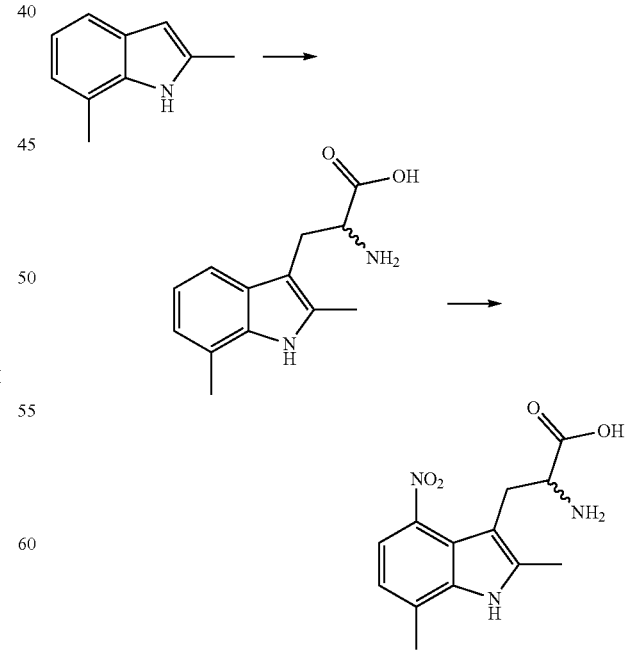

170

Example 170 can be prepared from 2,7-dimethyl-1H-indole as shown above and in a similar manner as described in Examples 1-2.

Example 171: Preparation of 2-amino-3-(2,4-dimethyl-7-nitro-1H-indol-3-yl)propanoic Acid (171)

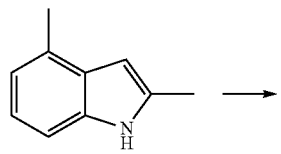

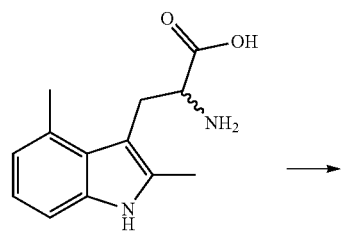

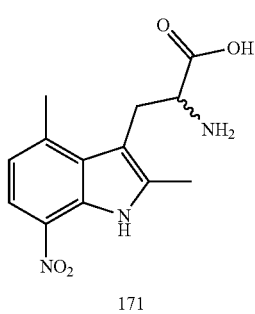

171

Example 171 can be prepared from 2,4-dimethyl-1H-indole as shown above and in a similar manner as described in Examples 1-2.

Example 172: Preparation of 2-amino-3-(6-fluoro-2-methyl-4-nitro-1H-indol-3-yl)propanoic Acid (172)

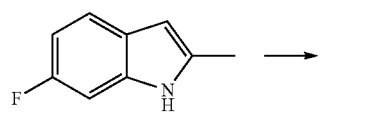

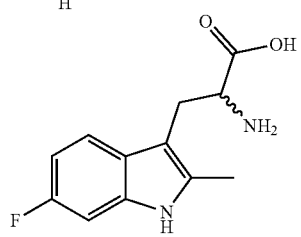

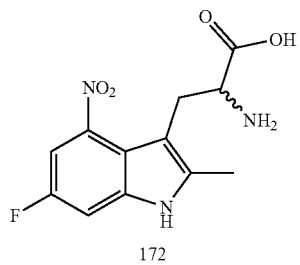

172

Example 172 can be prepared from 6-fluoro-2-methyl-1H-indole as shown above and in a similar manner as described in Examples 1-2.

Example 173: Preparation of 2-amino-3-(7-fluoro-2-methyl-4-nitro-1H-indol-3-yl)propanoic Acid (173)

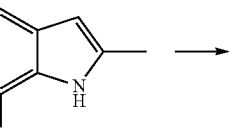

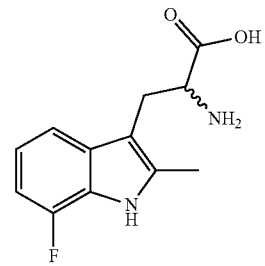

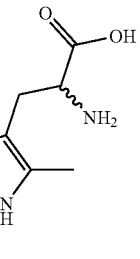

173

Example 173 can be prepared from 7-fluoro-2-methyl-indole as shown above and in a similar manner as described in Examples 1-2.

Example 174: Preparation of 2-amino-3-(4-fluoro-2-methyl-7-nitro-1H-indol-3-yl)propanoic Acid (174)

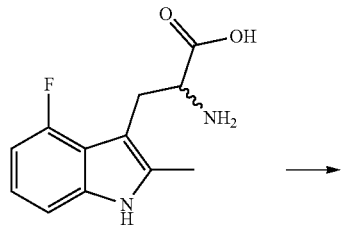

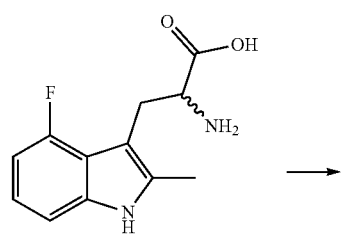

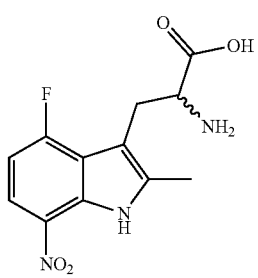

174

Example 174 can be prepared from 4-fluoro-2-methyl-indole as shown above and in a similar manner as described in Examples 1-2.

Example 175: Preparation of 2-amino-3-(5-chloro-2-methyl-4-nitro-1H-indol-3-yl)propanoic Acid (175)

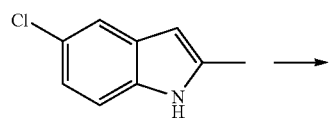

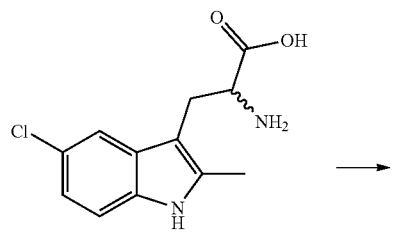

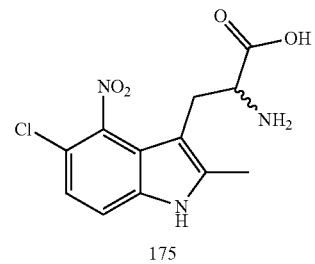

175

Example 175 can be prepared from 5-chloro-2-methyl-indole as shown above and in a similar manner as described in Examples 1-2.

Example 176: Preparation of 2-amino-3-(6-chloro-2-methyl-4-nitro-1H-indol-3-yl)propanoic Acid (176)

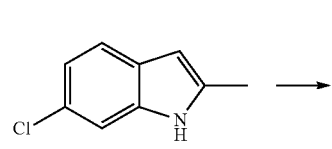

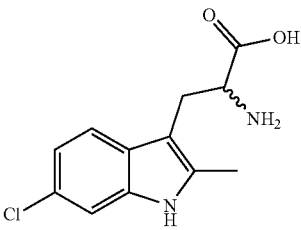

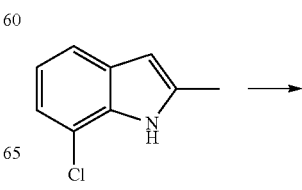

176

Example 176 can be prepared from 6-chloro-2-methyl-indole as shown above and in a similar manner as described in Examples 1-2.

Example 177: Preparation of 2-amino-3-(7-chloro-2-methyl-4-nitro-1H-indol-3-yl)propanoic Acid (177)

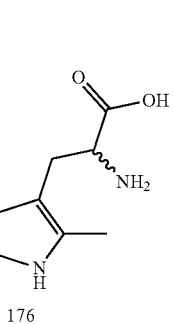

-continued

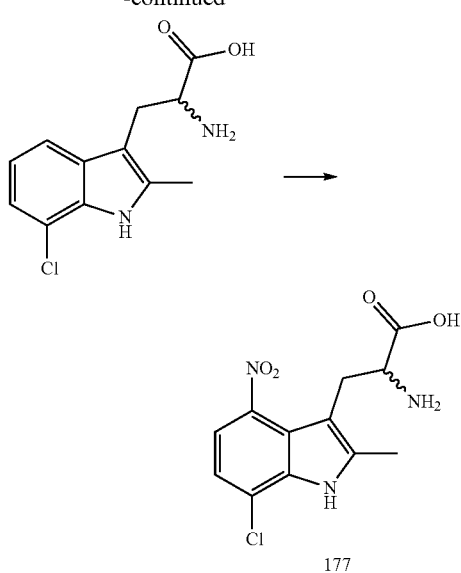

Example 177 can be prepared from 7-chloro-2-methyl-indole as shown above and in a similar manner as described in Examples 1-2.

Example 178: Preparation of 2-amino-3-(4-chloro-2-methyl-7-nitro-1H-indol-3-yl)propanoic Acid (178)

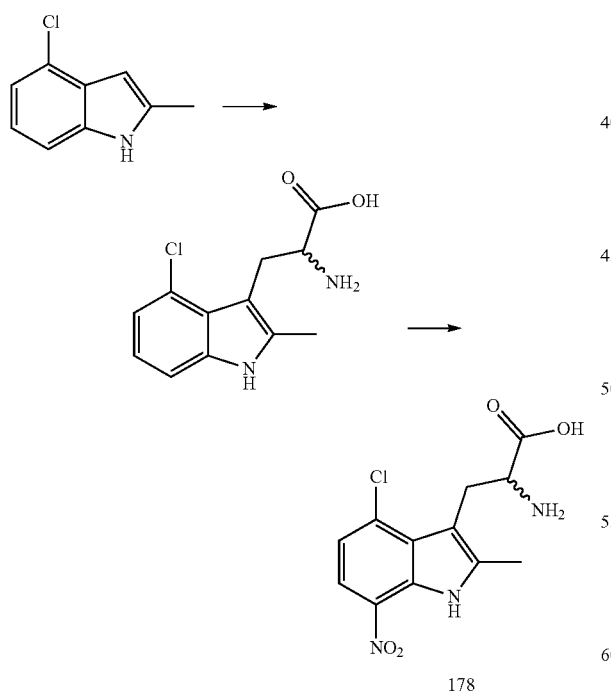

Example 178 can be prepared from 4-chloro-2-methyl-indole as shown above and in a similar manner as described in Examples 1-2.

Example 179: Preparation of 2-amino-3-(5-bromo-2-methyl-4-nitro-1H-indol-3-yl)propanoic Acid (179)

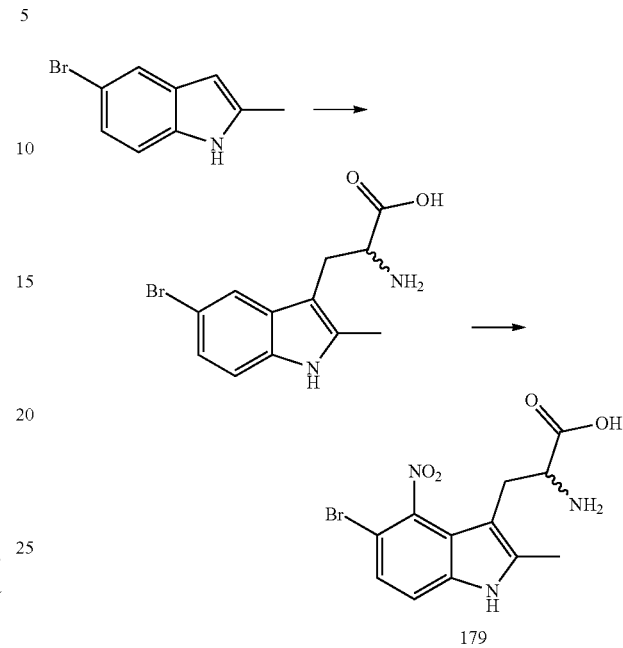

Example 179 can be prepared from 5-bromo-2-methyl-indole as shown above and in a similar manner as described in Examples 1-2.

Example 180: Preparation of 2-amino-3-(6-bromo-2-methyl-4-nitro-1H-indol-3-yl)propanoic Acid (180)

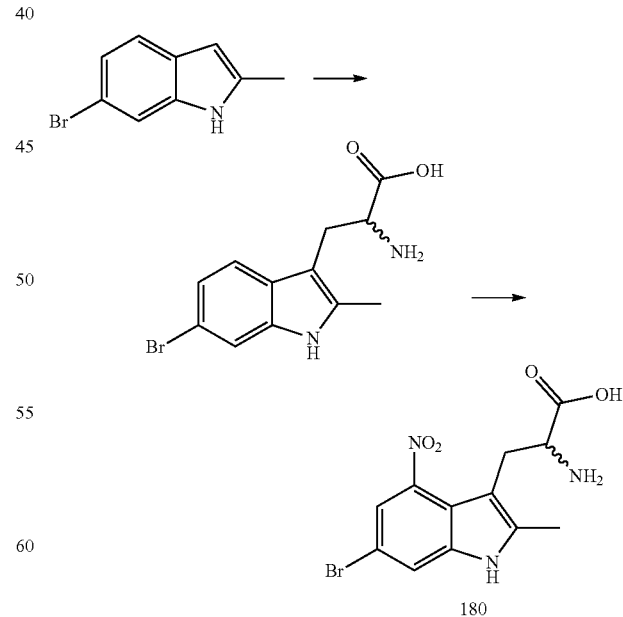

Example 180 can be prepared from 6-bromo-2-methyl-indole as shown above and in a similar manner as described in Examples 1-2.

Example 181: Preparation of 2-amino-3-(7-bromo-2-methyl-4-nitro-1H-indol-3-yl)propanoic Acid (181)

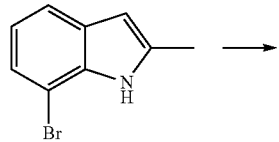

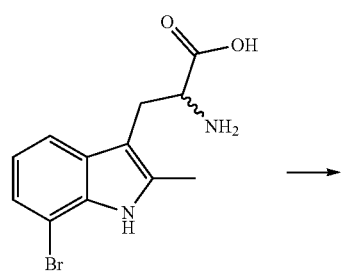

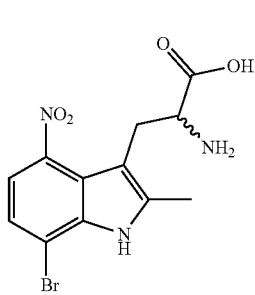

181

Example 181 can be prepared from 7-bromo-2-methyl-indole as shown above and in a similar manner as described in Examples 1-2.

Example 182: Preparation of 2-amino-3-(4-bromo-2-methyl-7-nitro-1H-indol-3-yl)propanoic Acid (182)

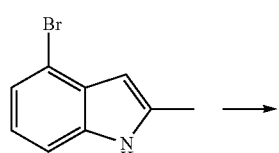

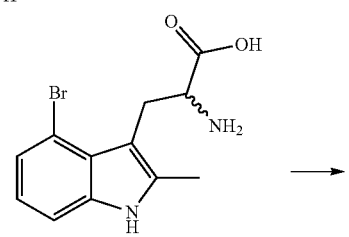

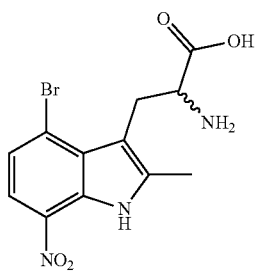

182

Example 182 can be prepared from 4-bromo-2-methyl-indole as shown above and in a similar manner as described in Examples 1-2.

Example 183: Preparation of 2-amino-3-(5-methoxy-2-methyl-4-nitro-1H-indol-3-yl)propanoic Acid (183)

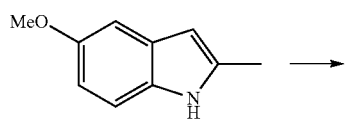

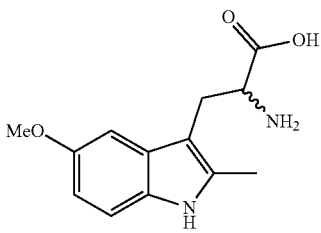

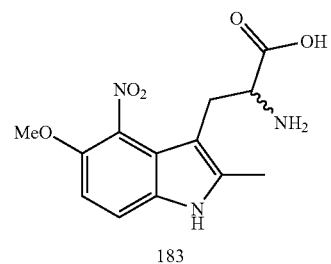

183

Example 183 can be prepared from 5-methoxy-2-methyl-indole as shown above and in a similar manner as described in Examples 1-2.

Example 184: Preparation of 2-amino-3-(6-methoxy-2-methyl-4-nitro-1H-indol-3-yl)propanoic Acid (184)

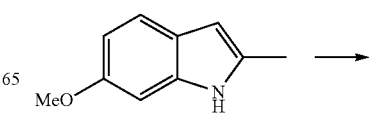

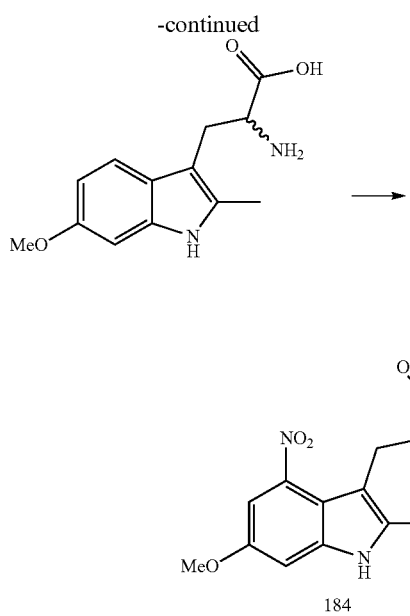

184

Example 184 can be prepared from 6-methoxy-2-methyl-indole as shown above and in a similar manner as described in Examples 1-2.

Example 185: Preparation of 2-amino-3-(7-methoxy-2-methyl-4-nitro-1H-indol-3-yl)propanoic Acid (185)

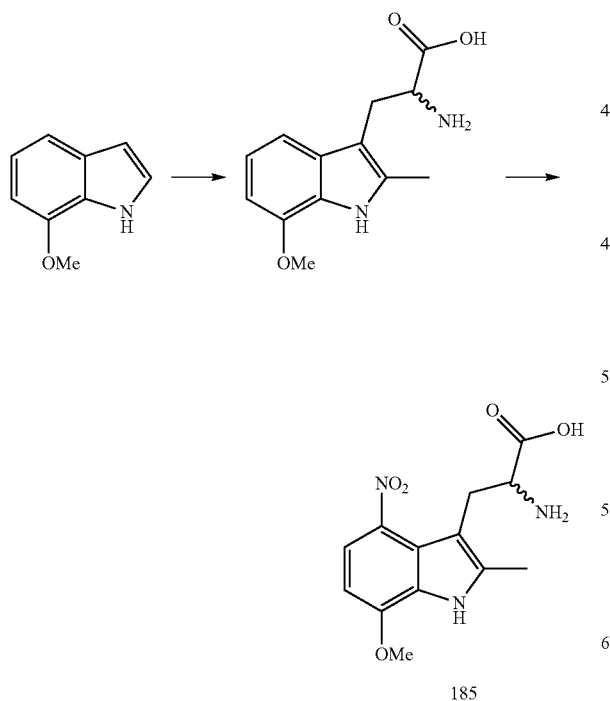

185

Example 185 can be prepared from 7-methoxy-2-methyl-indole as shown above and in a similar manner as described in Examples 1-2.

Example 186: Preparation of 2-amino-3-(4-methoxy-2-methyl-7-nitro-1H-indol-3-yl)propanoic Acid (186)

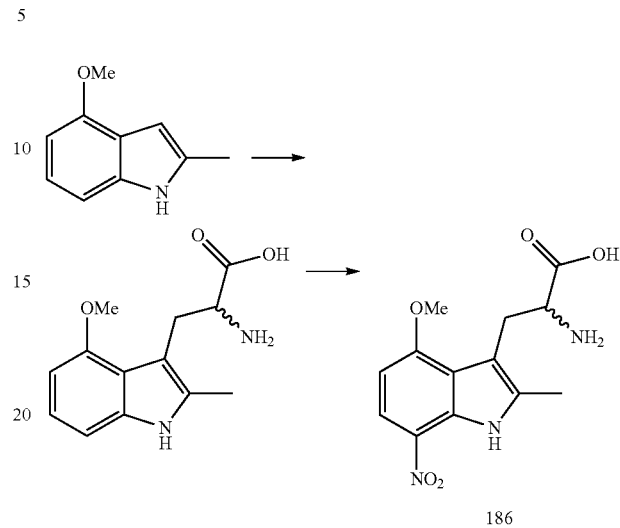

186

Example 186 can be prepared from 4-methoxy-2-methyl-indole as shown above and in a similar manner as described in Examples 1-2.

Example 187: Preparation of 2-amino-3-(5-amino-2-methyl-4-nitro-1H-indol-3-yl)propanoic Acid (187)

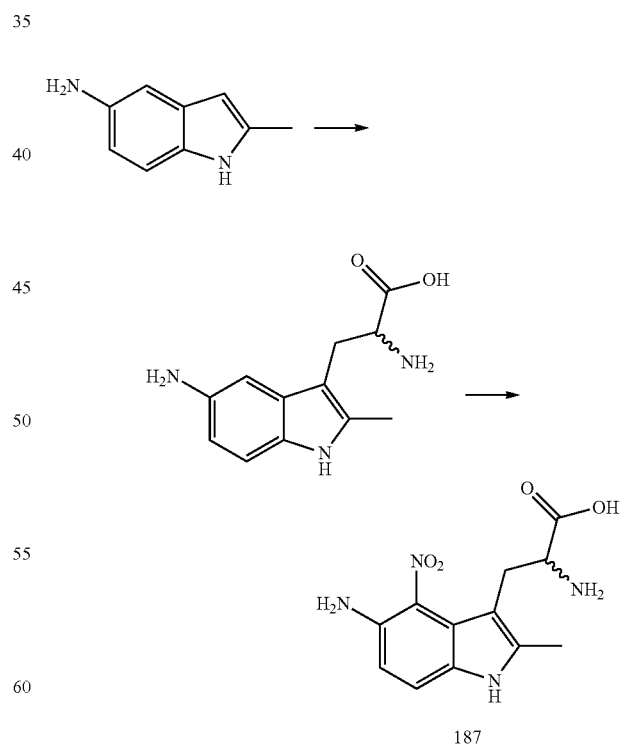

187

Example 187 can be prepared from 5-amino-2-methyl-indole as shown above and in a similar manner as described in Examples 1-2.

Example 188: Preparation of 2-amino-3-(6-amino-2-methyl-4-nitro-1H-indol-3-yl)propanoic Acid (188)

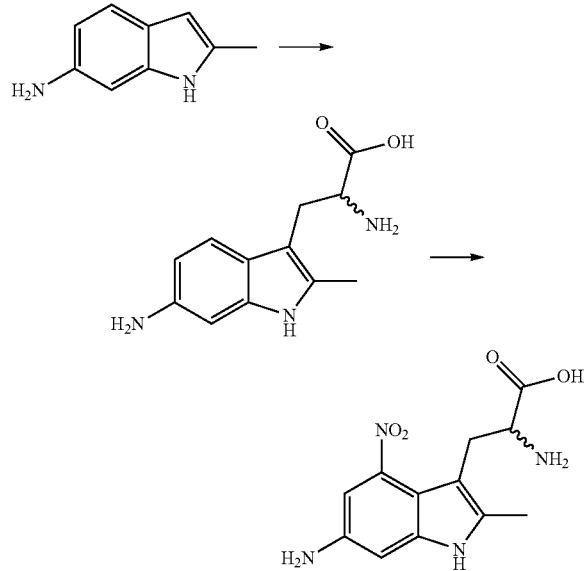

188

Example 188 can be prepared from 6-amino-2-methyl-indole as shown above and in a similar manner as described in Examples 1-2.

Example 189: Preparation of 2-amino-3-(7-amino-2-methyl-4-nitro-1H-indol-3-yl)propanoic Acid (189)

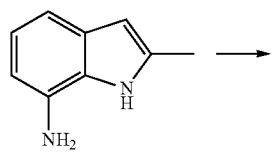

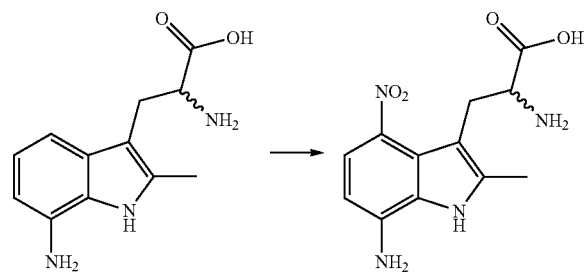

189

Example 189 can be prepared from 7-amino-2-methyl-indole as shown above and in a similar manner as described in Examples 1-2.

Example 190: Preparation of 2-amino-3-(4-amino-2-methyl-7-nitro-1H-indol-3-yl)propanoic Acid (190)

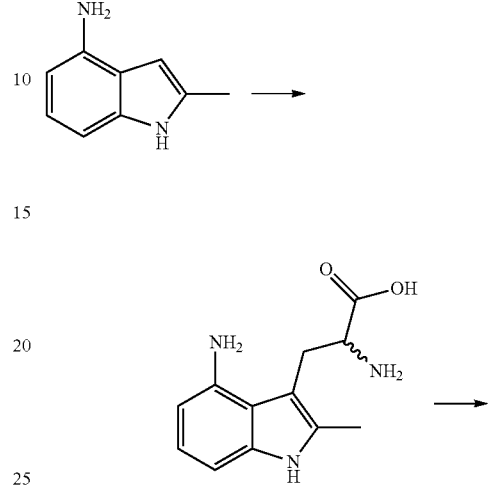

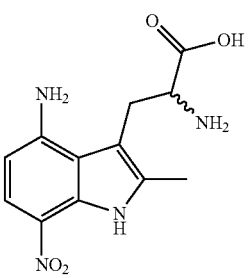

190

Example 190 can be prepared from 4-amino-2-methyl-indole as shown above and in a similar manner as described in Examples 1-2.

Example 191: Preparation of 2-amino-3-(5-hydroxy-2-methyl-4-nitro-1H-indol-3-yl)propanoic Acid (191)

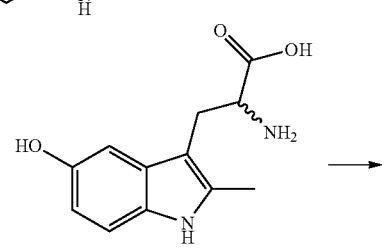

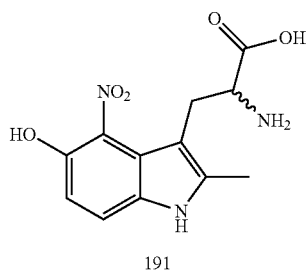

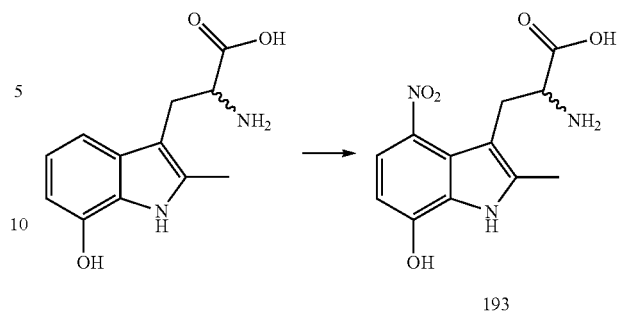

Example 191 can be prepared from 5-hydroxy-2-methyl-indole as shown above and in a similar manner as described in Examples 1-2.

Example 193 can be prepared from 7-hydroxy-2-methyl-indole as shown above and in a similar manner as described in Examples 1-2.

Example 192: Preparation of 2-amino-3-(6-hydroxy-2-methyl-4-nitro-1H-indol-3-yl)propanoic Acid (192)

Example 194: Preparation of 2-amino-3-(4-hydroxy-2-methyl-7-nitro-1H-indol-3-yl)propanoic Acid (194)

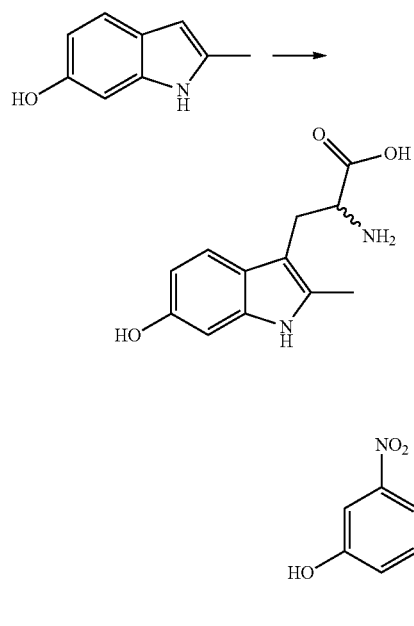

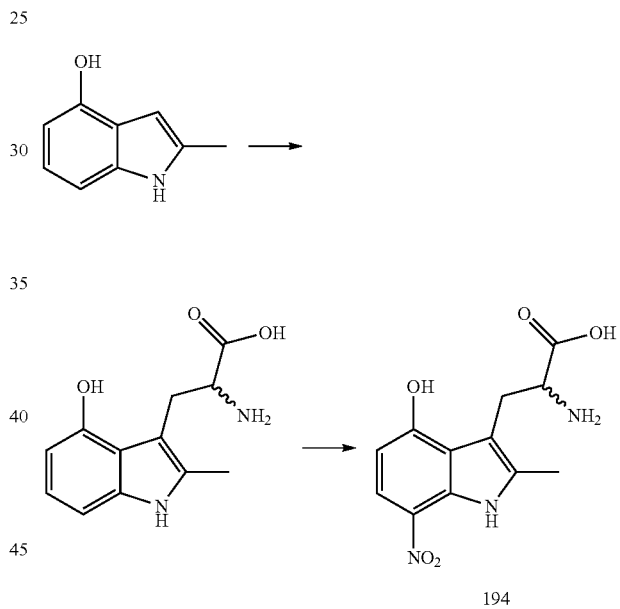

Example 192 can be prepared from 6-hydroxy-2-methyl-indole as shown above and in a similar manner as described in Examples 1-2.

Example 194 can be prepared from 4-hydroxy-2-methyl-indole as shown above and in a similar manner as described in Examples 1-2.

Example 193: Preparation of 2-amino-3-(7-hydroxy-2-methyl-4-nitro-1H-indol-3-yl)propanoic Acid (193)

Example 195: Preparation of 2-amino-3-(2-methyl-4-nitro-5-phenyl-1H-indol-3-yl)propanoic Acid (195)

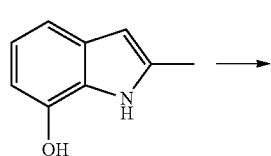

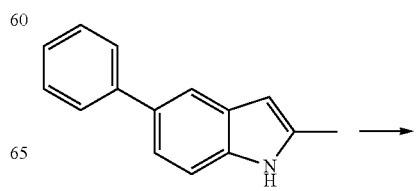

-continued

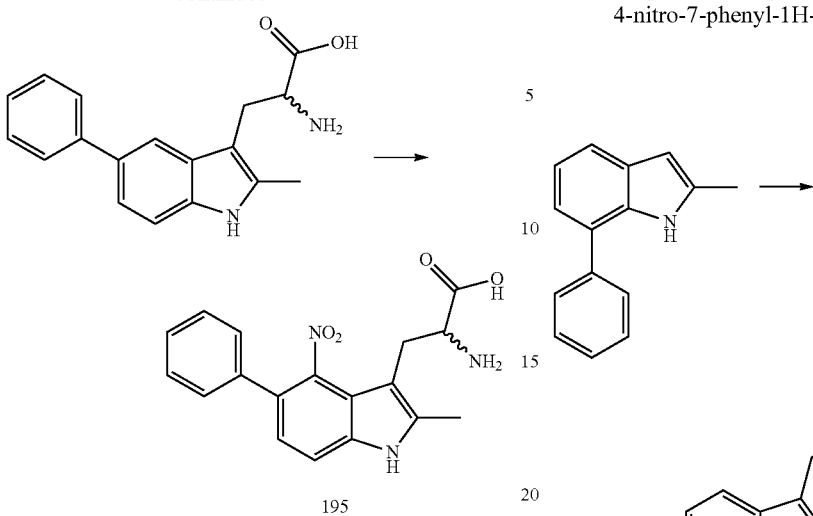

195

Example 195 can be prepared from 5-phenyl-2-methyl-indole as shown above and in a similar manner as described in Examples 1-2.

Example 196: Preparation of 2-amino-3-(2-methyl-4-nitro-6-phenyl-1H-indol-3-yl)propanoic Acid (196)

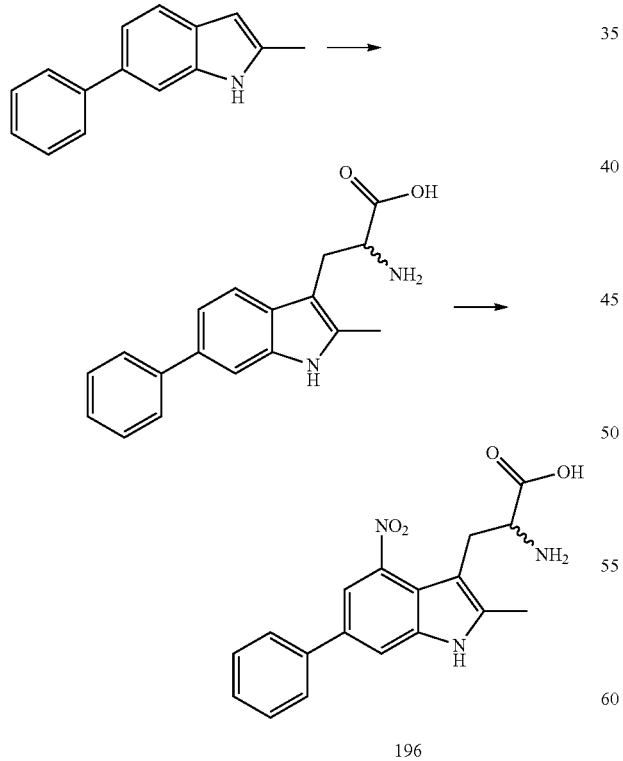

196

Example 196 can be prepared from 6-phenyl-2-methyl-indole as shown above and in a similar manner as described in Examples 1-2.

Example 197: Preparation of 2-amino-3-(2-methyl-4-nitro-7-phenyl-1H-indol-3-yl)propanoic Acid (197)

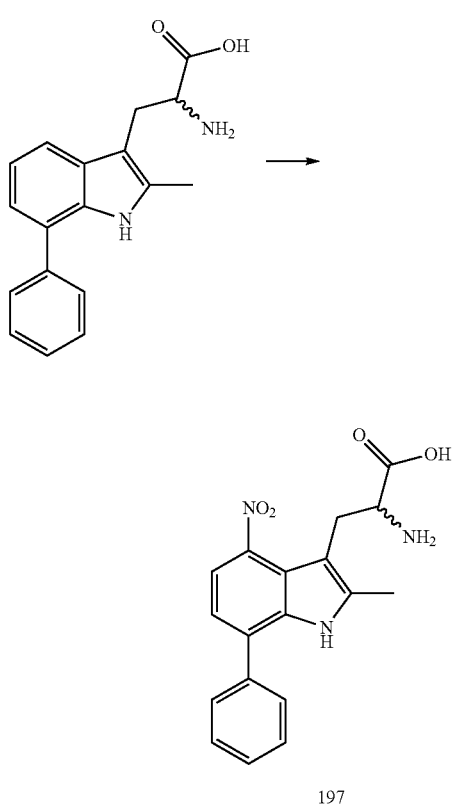

197

Example 197 can be prepared from 7-phenyl-2-methyl-indole as shown above and in a similar manner as described in Examples 1-2.

Example 198: Preparation of 2-amino-3-(2-methyl-7-nitro-4-phenyl-1H-indol-3-yl)propanoic Acid (198)

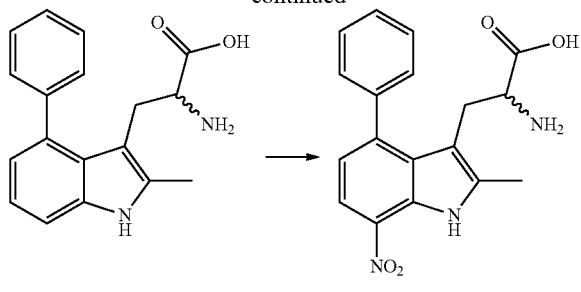

198

Example 198 can be prepared from 4-phenyl-2-methyl-indole as shown above and in a similar manner as described in Examples 1-2.

Example 199: Preparation of 2-amino-3-(5-cyclopropyl-2-methyl-4-nitro-1H-indol-3-yl)propanoic Acid (199)

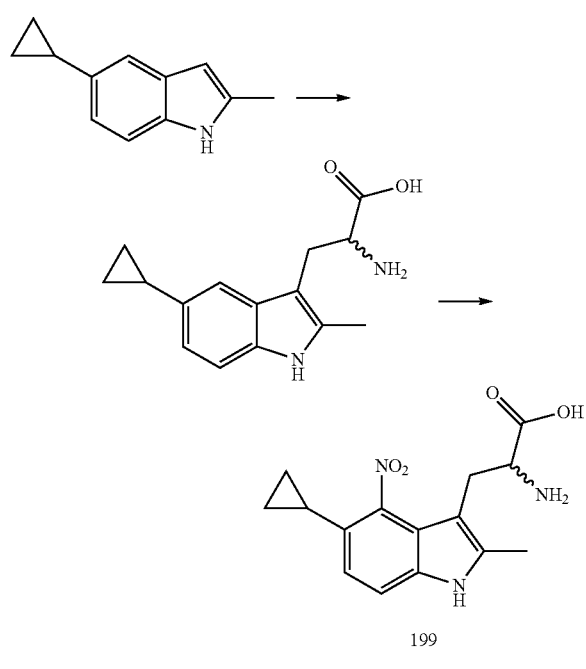

199

Example 199 can be prepared from 5-cyclopropyl-2-methyl-indole as shown above and in a similar manner as described in Examples 1-2.

Example 200: Preparation of 2-amino-3-(6-cyclopropyl-2-methyl-4-nitro-1H-indol-3-yl)propanoic Acid (200)

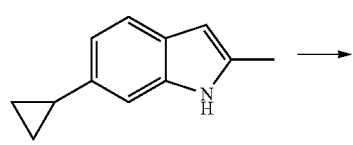

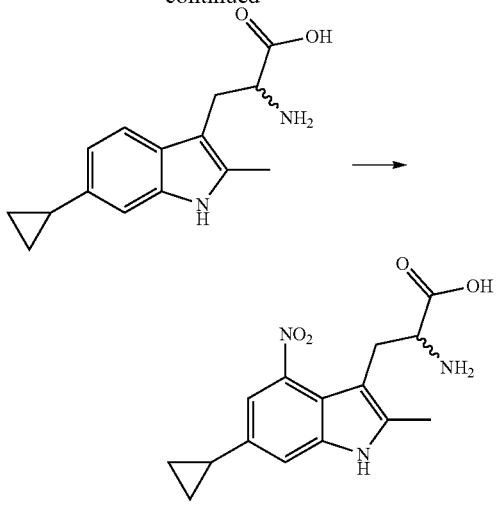

200

Example 200 can be prepared from 6-cyclopropyl-2-methyl-indole as shown above and in a similar manner as described in Examples 1-2.

Example 201: Preparation of 2-amino-3-(7-cyclopropyl-2-methyl-4-nitro-1H-indol-3-yl)propanoic Acid (201)

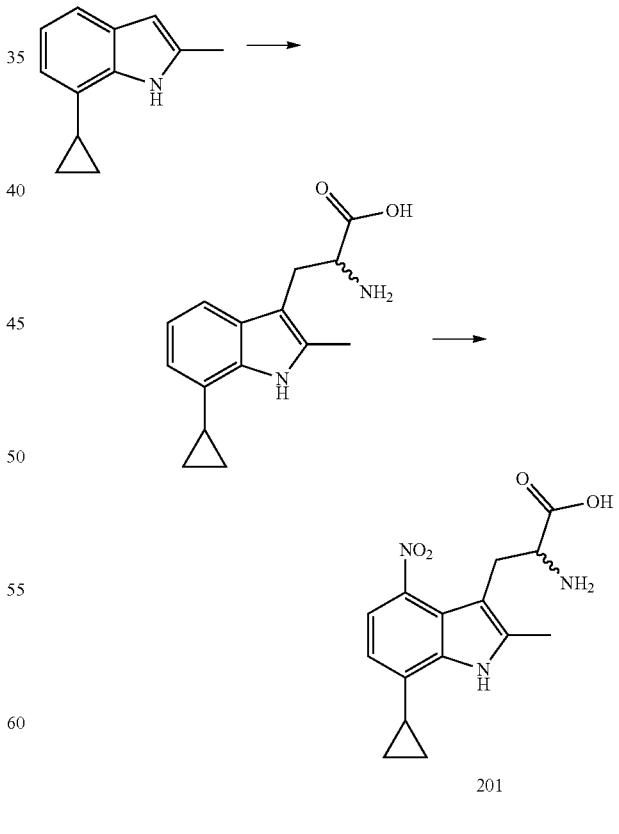

201

Example 201 can be prepared from 7-cyclopropyl-2-methyl-indole as shown above and in a similar manner as described in Examples 1-2.

Example 202: Preparation of 2-amino-3-(4-cyclo-propyl-2-methyl-7-nitro-1H-indol-3-yl)propanoic Acid (202)

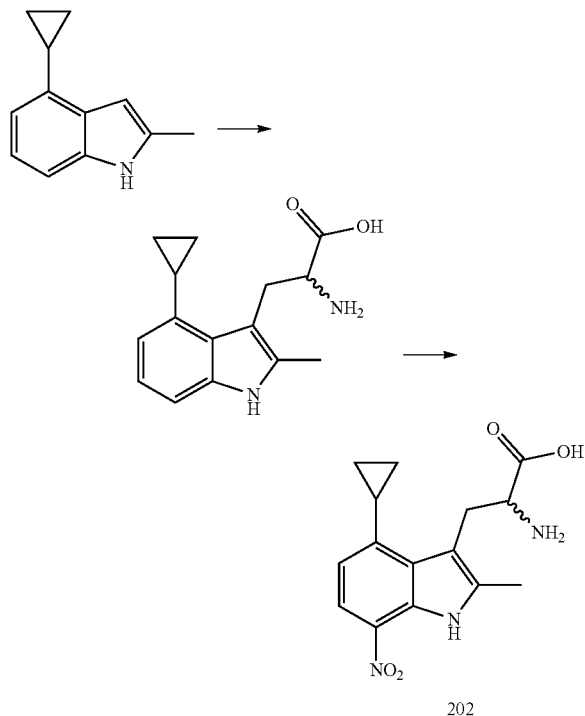

202

Example 202 can be prepared from 4-cyclopropyl-2-methyl-indole as shown above and in a similar manner as described in Examples 1-2.

Example 203: Preparation of 2-amino-3-(2-methyl-4-nitro-5-vinyl-1H-indol-3-yl)propanoic Acid (203)

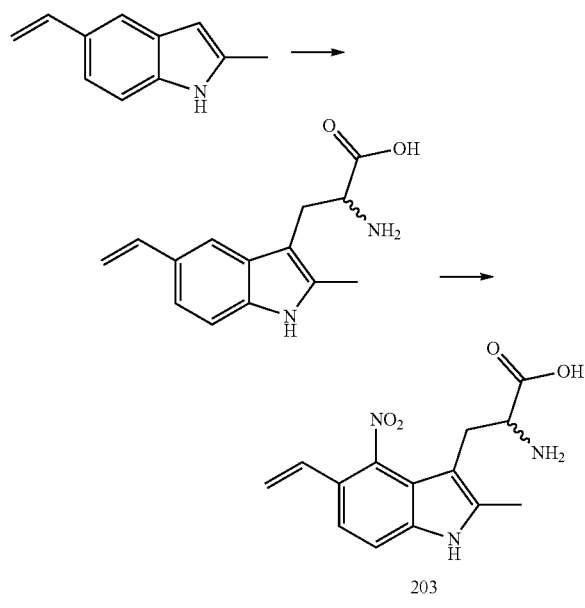

203

Example 203 can be prepared from 5-vinyl-2-methyl-indole as shown above and in a similar manner as described in Examples 1-2.

Example 204: Preparation of 2-amino-3-(2-methyl-4-nitro-6-vinyl-1H-indol-3-yl)propanoic Acid (204)

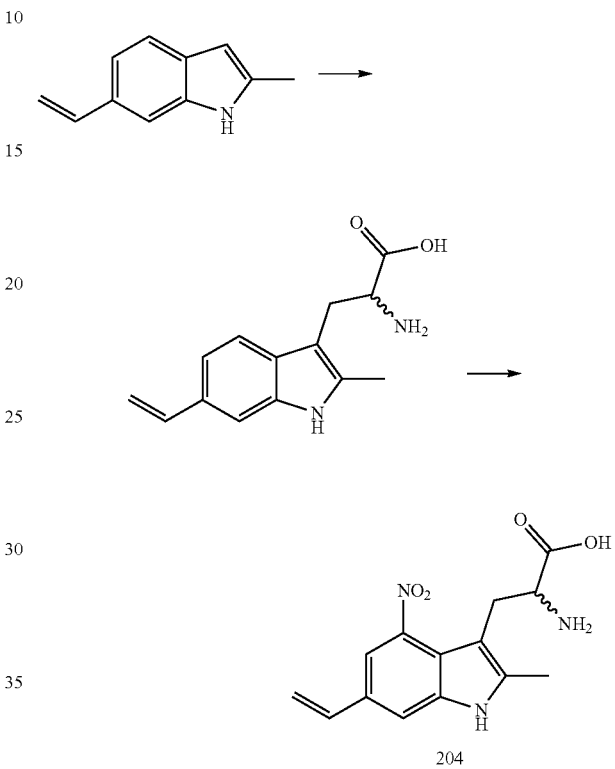

204

Example 204 can be prepared from 6-vinyl-2-methyl-indole as shown above and in a similar manner as described in Examples 1-2.

Example 205: Preparation of 2-amino-3-(2-methyl-4-nitro-7-vinyl-1H-indol-3-yl)propanoic Acid (205)

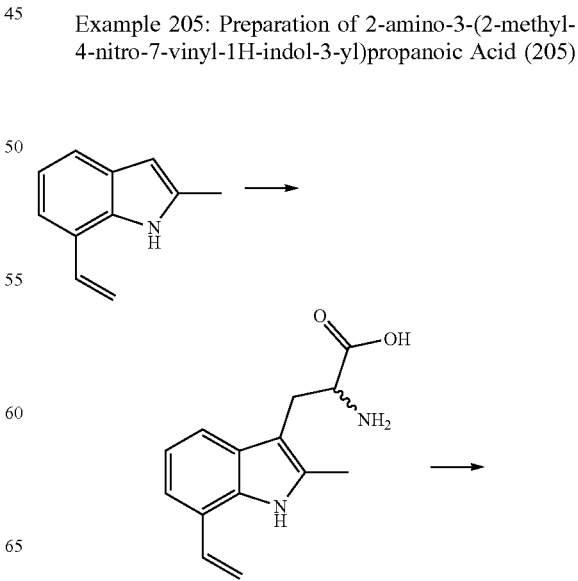

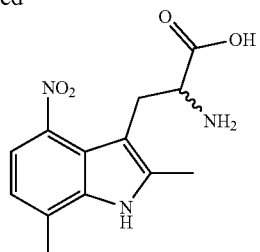

205

Example 205 can be prepared from 7-vinyl-2-methyl-indole as shown above and in a similar manner as described in Examples 1-2.

Example 206: Preparation of 2-amino-3-(2-methyl-7-nitro-4-vinyl-1H-indol-3-yl)propanoic Acid (206)

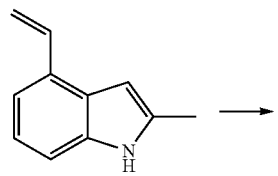

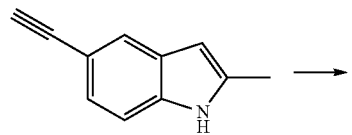

206

Example 206 can be prepared from 4-vinyl-2-methyl-indole as shown above and in a similar manner as described in Examples 1-2.

Example 207: Preparation of 2-amino-3-(5-ethynyl-2-methyl-4-nitro-1H-indol-3-yl)propanoic Acid (207)

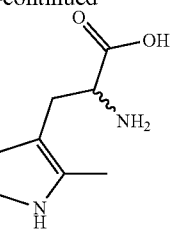 

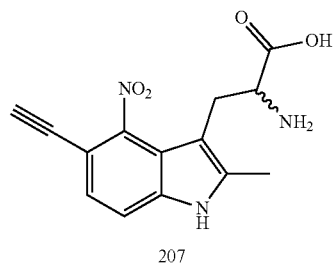

207

Example 207 can be prepared from 5-ethynyl-2-methyl-indole as shown above and in a similar manner as described in Examples 1-2.

Example 208: Preparation of 2-amino-3-(6-ethynyl-2-methyl-4-nitro-1H-indol-3-yl)propanoic Acid (208)

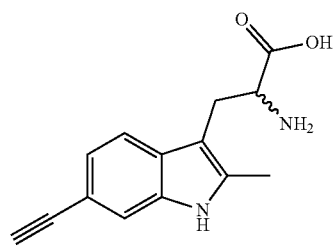 

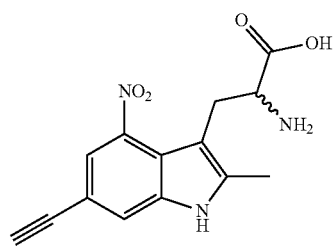

208

Example 208 can be prepared from 6-ethynyl-2-methyl-indole as shown above and in a similar manner as described in Examples 1-2.

Example 209: Preparation of 2-amino-3-(7-ethynyl-2-methyl-4-nitro-1H-indol-3-yl)propanoic Acid (209)

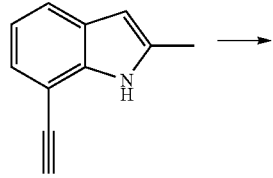

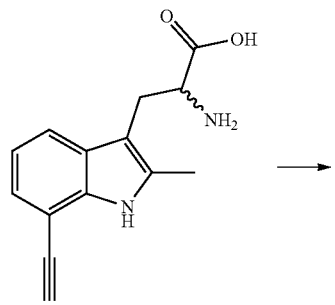

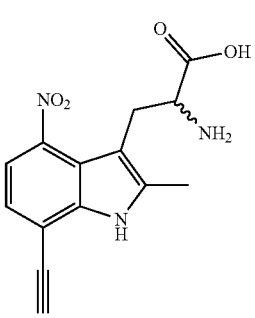

Example 209 can be prepared from 7-ethynyl-2-methyl-indole as shown above and in a similar manner as described in Examples 1-2.

Example 210: Preparation of 2-amino-3-(4-ethynyl-2-methyl-7-nitro-1H-indol-3-yl)propanoic Acid (210)

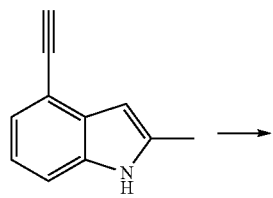

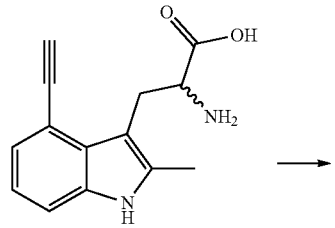

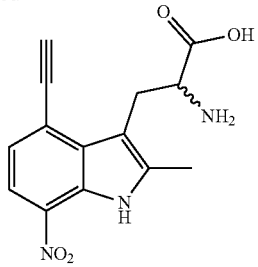

Example 210 can be prepared from 4-ethynyl-2-methyl-indole as shown above and in a similar manner as described in Examples 1-2.

Example 211: Preparation of 2-amino-3-(2-methyl-5-morpholino-4-nitro-1H-indol-3-yl)propanoic Acid (211)

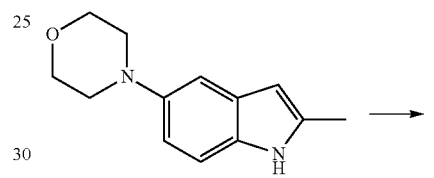

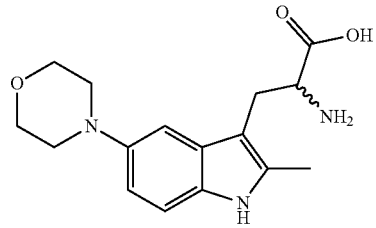

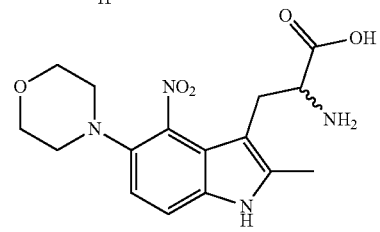

Example 211 can be prepared from 5-morpholino-2-methyl-indole as shown above and in a similar manner as described in Examples 1-2.

Example 212: Preparation of 2-amino-3-(2-methyl-6-morpholino-4-nitro-1H-indol-3-yl)propanoic Acid (212)

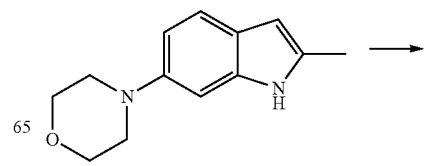

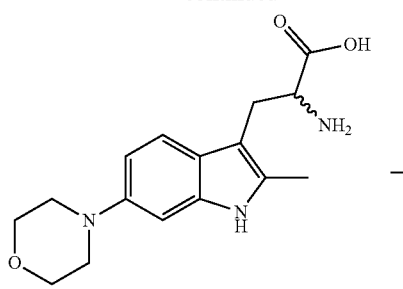

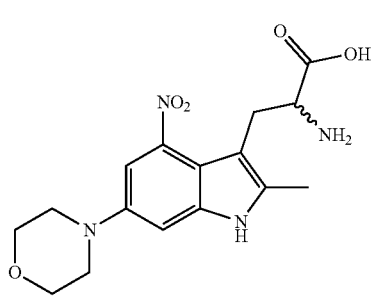

212

Example 212 can be prepared from 6-morpholino-2-methyl-indole as shown above and in a similar manner as described in Examples 1-2.

Example 213: Preparation of 2-amino-3-(2-methyl-7-morpholino-4-nitro-1H-indol-3-yl)propanoic Acid (213)

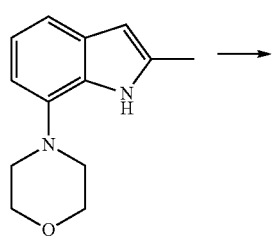

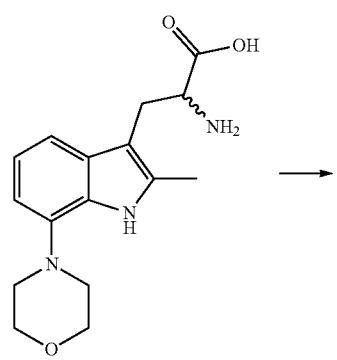

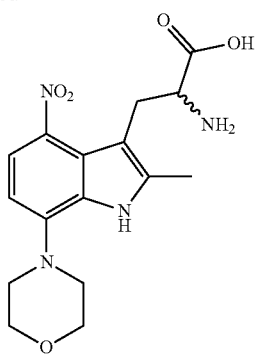

213

Example 213 can be prepared from 7-morpholino-2-methyl-indole as shown above and in a similar manner as described in Examples 1-2.

Example 214: Preparation of 2-amino-3-(2-methyl-4-morpholino-)-47-nitro-1H-indol-3-yl)propanoic Acid (214)

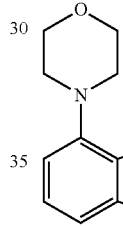

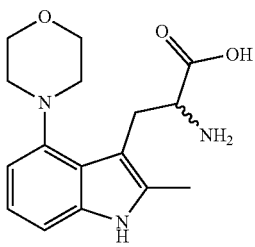

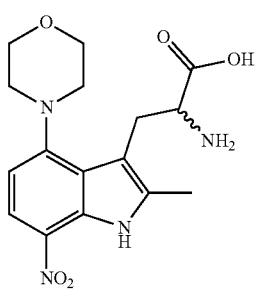

214

Example 214 can be prepared from 4-morpholino-2-methyl-indole as shown above and in a similar manner as described in Examples 1-2.

Example 215: Preparation of 2-amino-3-(2-methyl-5-(methylthio)-4-nitro-1H-indol-3-yl)propanoic Acid (215)

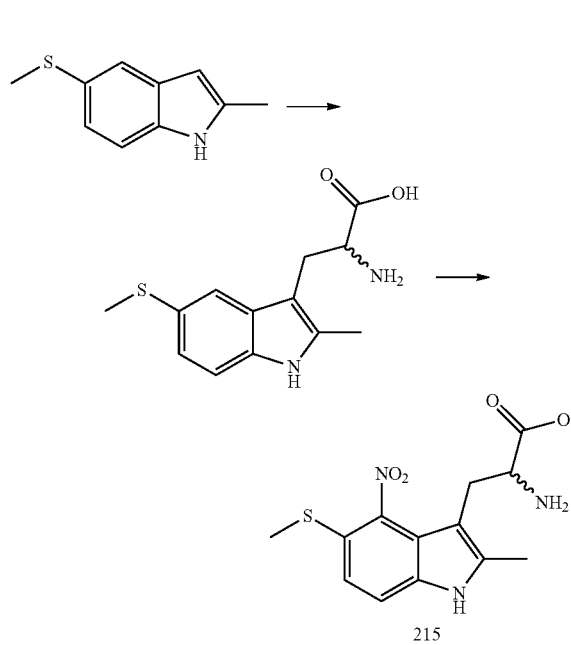

Example 215 can be prepared from 5-(methylthio)-2-methyl-indole as shown above and in a similar manner as described in Examples 1-2.

Example 216: Preparation of 2-amino-3-(2-methyl-6-(methylthio)-4-nitro-1H-indol-3-yl)propanoic Acid (216)

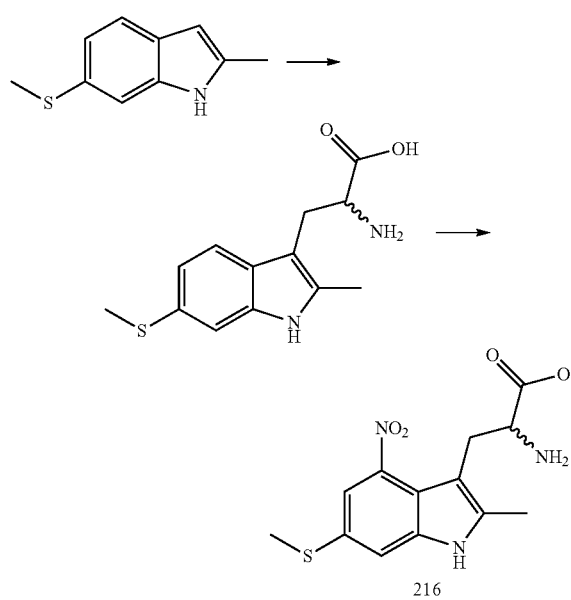

Example 216 can be prepared from 6-(methylthio)-2-methyl-indole as shown above and in a similar manner as described in Examples 1-2.

Example 217: Preparation of 2-amino-3-(2-methyl-7-(methylthio)-4-nitro-1H-indol-3-yl)propanoic Acid (217)

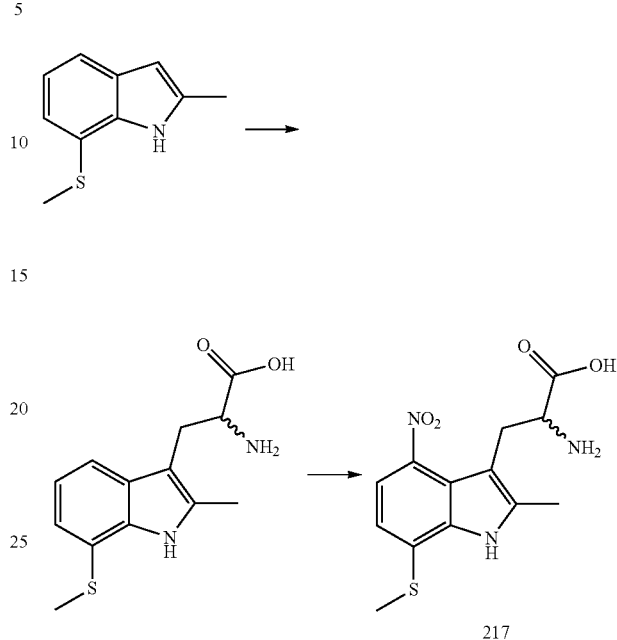

Example 217 can be prepared from 7-(methylthio)-2-methyl-indole as shown above and in a similar manner as described in Examples 1-2.

Example 218: Preparation of 2-amino-3-(2-methyl-4-(methylthio)-7-nitro-1H-indol-3-yl)propanoic Acid (218)

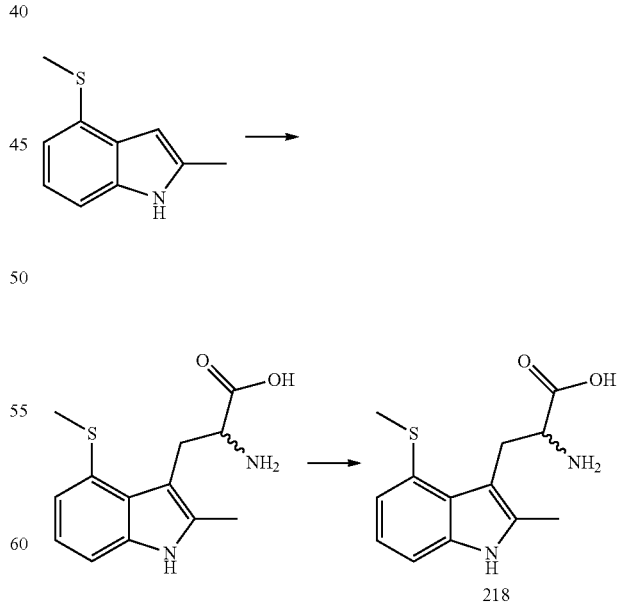

Example 218 can be prepared from 4-(methylthio)-2-methyl-indole as shown above and in a similar manner as described in Examples 1-2.

Example 219: Preparation of 2-amino-3-(2-methyl-4-nitro-5-(pyridin-4-yl)-1H-indol-3-yl)propanoic Acid (219)

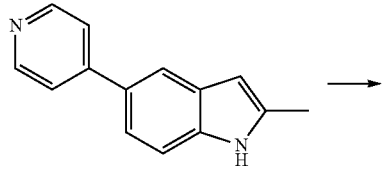

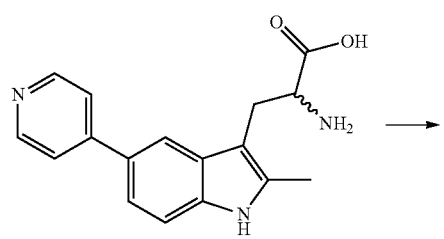

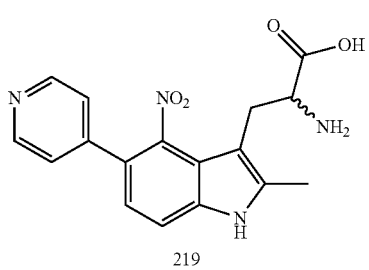

219

Example 219 can be prepared from 5-(pyridin-4-yl)-2-methyl-indole as shown above and in a similar manner as described in Examples 1-2.

Example 220: Preparation of 2-amino-3-(2-methyl-4-nitro-6-(pyridin-4-yl)-1H-indol-3-yl)propanoic Acid (220)

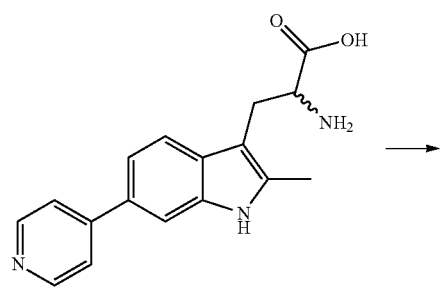

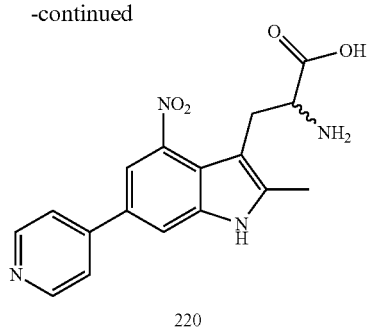

220

Example 220 can be prepared from 6-(pyridin-4-yl)-2-methyl-indole as shown above and in a similar manner as described in Examples 1-2.

Example 221: Preparation of 2-amino-3-(2-methyl-4-nitro-7-(pyridin-4-yl)-1H-indol-3-yl)propanoic Acid (221)

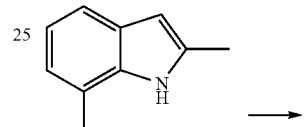

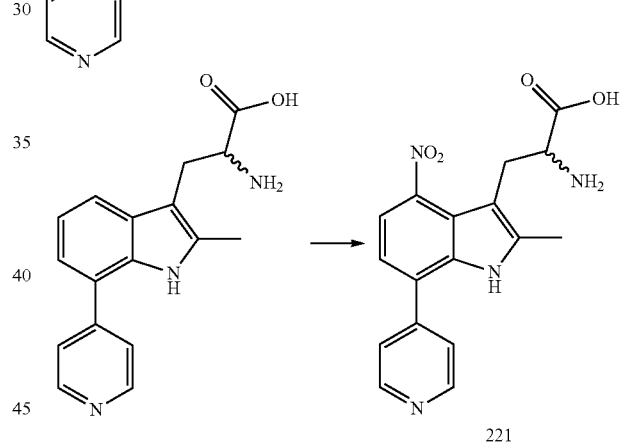

221

Example 221 can be prepared from 7-(pyridin-4-yl)-2-methyl-indole as shown above and in a similar manner as described in Examples 1-2.

Example 222: Preparation of 2-amino-3-(2-methyl-7-nitro-4-(pyridin-4-yl)-1H-indol-3-yl)propanoic Acid (222)

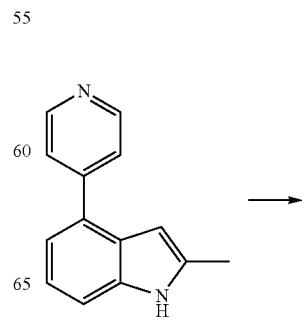

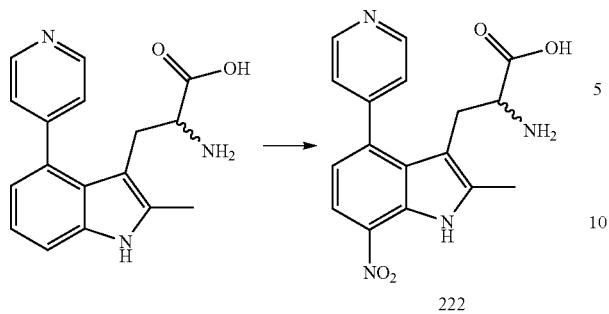

222

Example 222 can be prepared from 4-(pyridin-4-yl)-2-methyl-indole as shown above and in a similar manner as described in Examples 1-2.

Example 223: Preparation of 2-amino-3-(1,2,5-trimethyl-4-nitro-1H-indol-3-yl)propanoic Acid (223)

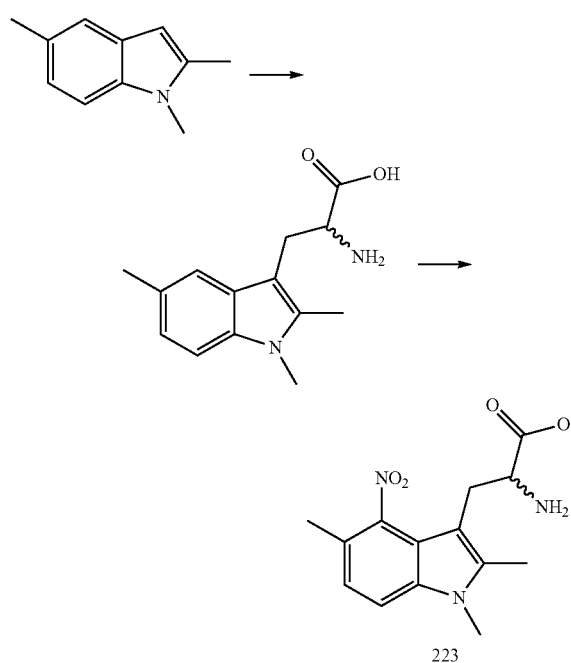

223

Example 223 can be prepared from 1,2,5-trimethyl-1H-indole as shown above and in a similar manner as described in Examples 1-2.

Example 224: Preparation of 2-amino-3-(1,2,6-trimethyl-4-nitro-1H-indol-3-yl)propanoic Acid (224)

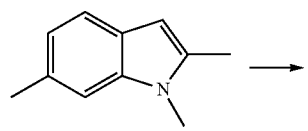

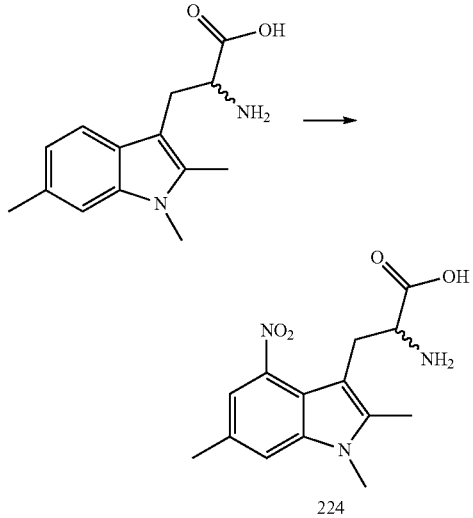

224

Example 224 can be prepared from 1,2,6-trimethyl-1H-indole as shown above and in a similar manner as described in Examples 1-2.

Example 225: Preparation of 2-amino-3-(1,2,7-trimethyl-4-nitro-1H-indol-3-yl)propanoic Acid (225)

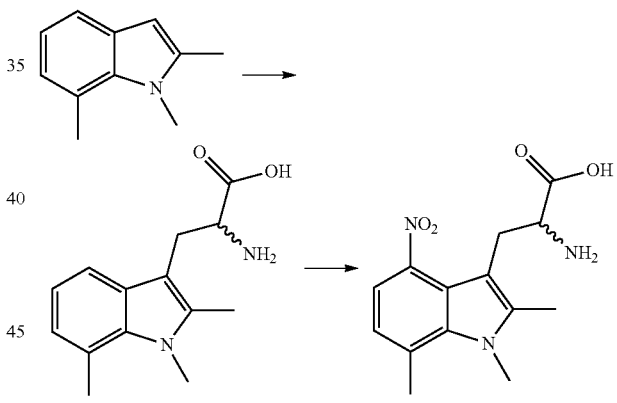

225

Example 225 can be prepared from 1,2,7-trimethyl-1H-indole as shown above and in a similar manner as described in Examples 1-2.

Example 226: Preparation of 2-amino-3-(1,2,4-trimethyl-7-nitro-1H-indol-3-yl)propanoic Acid (226)

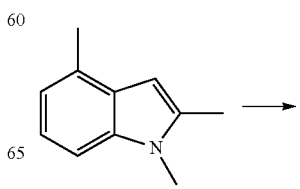

-continued

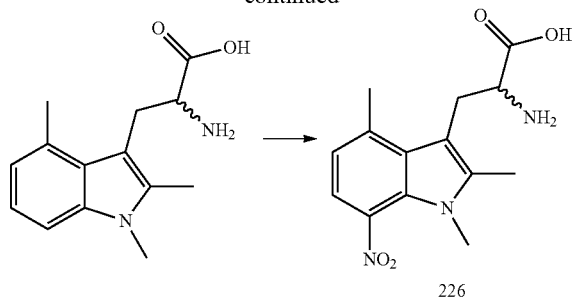
226

Example 226 can be prepared from 1,2,4-trimethyl-1H-indole as shown above and in a similar manner as described in Examples 1-2.

Example 227: Preparation of 2-amino-3-(6-fluoro-1,2-dimethyl-4-nitro-1H-indol-3-yl)propanoic Acid (227)

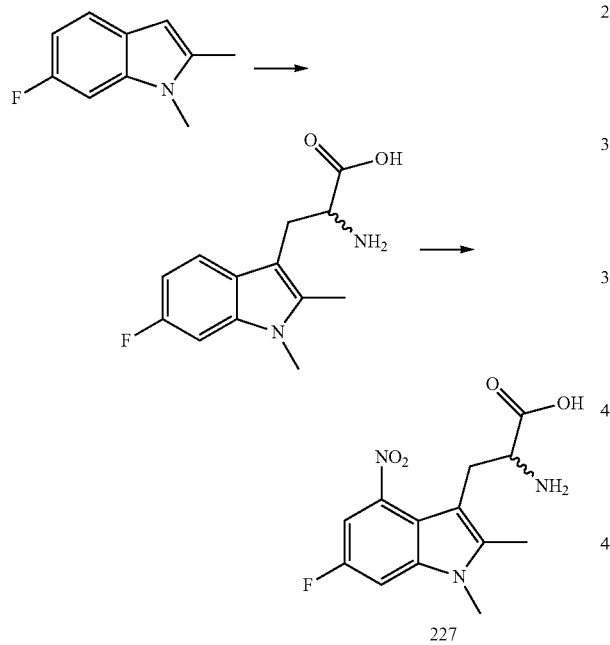
227

Example 227 can be prepared from 6-fluoro-1,2-dimethyl-1H-indole as shown above and in a similar manner as described in Examples 1-2.

Example 228: Preparation of 2-amino-3-(7-fluoro-1,2-dimethyl-4-nitro-1H-indol-3-yl)propanoic Acid (228)

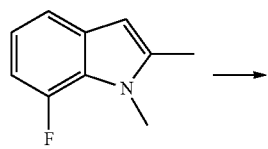

-continued

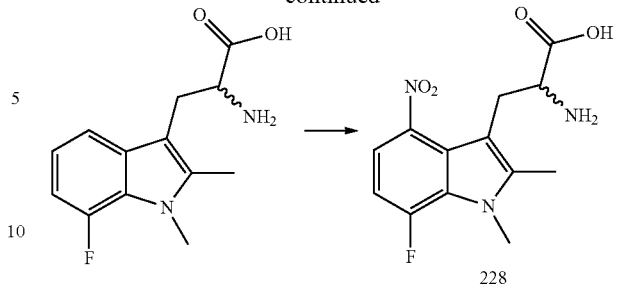
228

Example 228 can be prepared from 7-fluoro-1,2-dimethyl-indole as shown above and in a similar manner as described in Examples 1-2.

Example 229: Preparation of 2-amino-3-(4-fluoro-1,2-dimethyl-7-nitro-1H-indol-3-yl)propanoic Acid (229)

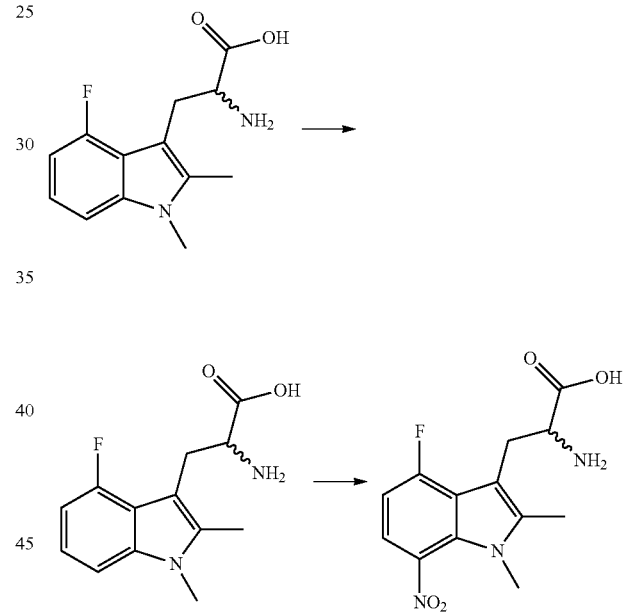
229

Example 229 can be prepared from 4-fluoro-1,2-dimethyl-indole as shown above and in a similar manner as described in Examples 1-2.

Example 230: Preparation of 2-amino-3-(5-chloro-1,2-dimethyl-4-nitro-1H-indol-3-yl)propanoic Acid (230)

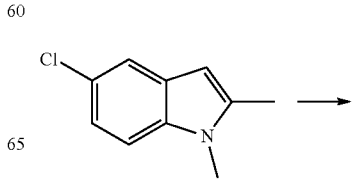

-continued

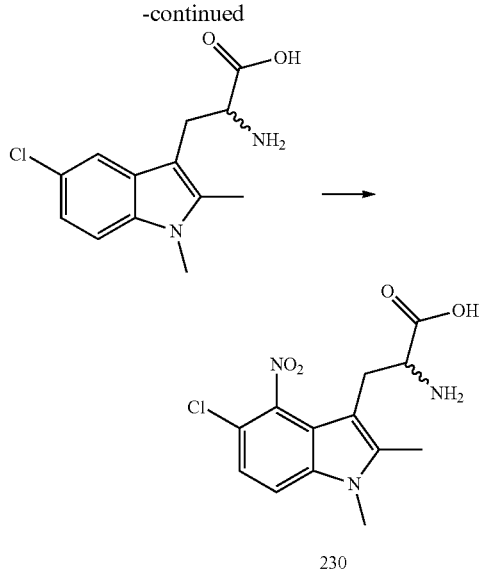

230

Example 230 can be prepared from 5-chloro-1,2-dimethyl-indole as shown above and in a similar manner as described in Examples 1-2.

Example 231: Preparation of 2-amino-3-(6-chloro-1,2-dimethyl-4-nitro-1H-indol-3-yl)propanoic Acid (231)

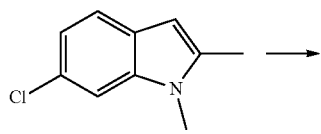

231

Example 231 can be prepared from 6-chloro-1,2-dimethyl-indole as shown above and in a similar manner as described in Examples 1-2.

Example 232: Preparation of 2-amino-3-(7-chloro-1,2-dimethyl-4-nitro-1H-indol-3-yl)propanoic Acid (232)

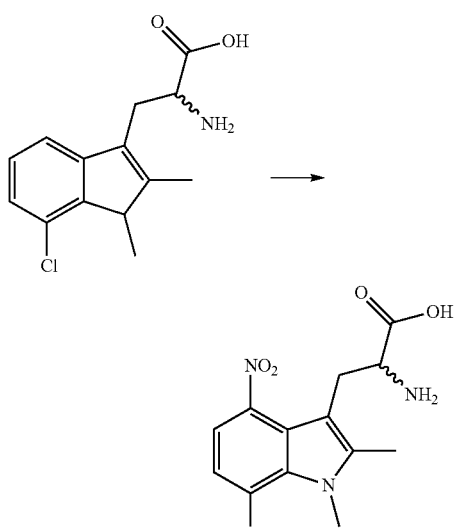

232

Example 232 can be prepared from 7-chloro-1,2-dimethyl-indole as shown above and in a similar manner as described in Examples 1-2.

Example 233: Preparation of 2-amino-3-(4-chloro-1,2-dimethyl-7-nitro-1H-indol-3-yl)propanoic Acid (233)

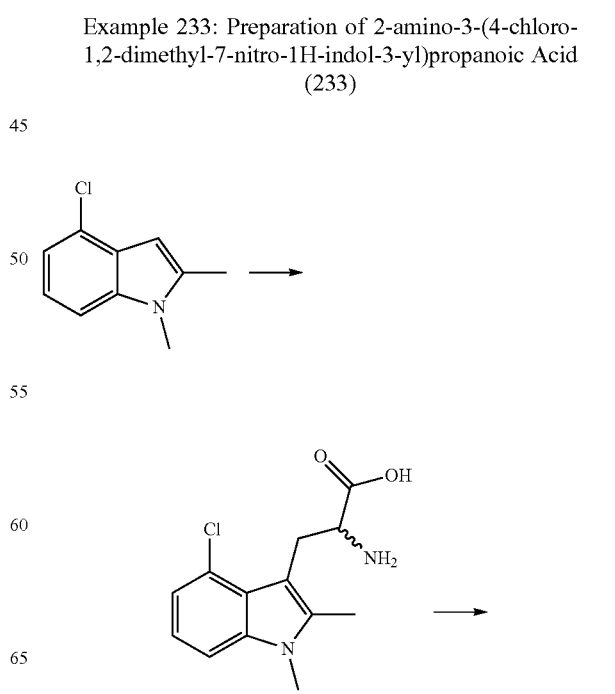

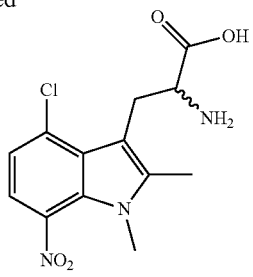

233

Example 233 can be prepared from 4-chloro-1,2-dimethyl-indole as shown above and in a similar manner as described in Examples 1-2.

Example 234: Preparation of 2-amino-3-(5-bromo-1,2-dimethyl-4-nitro-1H-indol-3-yl)propanoic Acid (234)

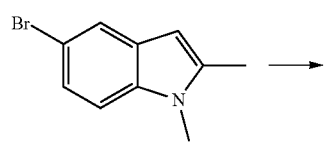

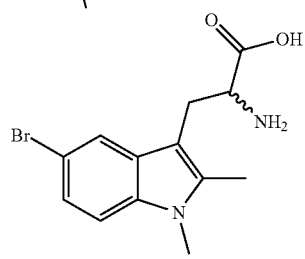

234

Example 234 can be prepared from 5-bromo-1,2-dimethyl-indole as shown above and in a similar manner as described in Examples 1-2.

Example 235: Preparation of 2-amino-3-(6-bromo-1,2-dimethyl-4-nitro-1H-indol-3-yl)propanoic Acid (235)

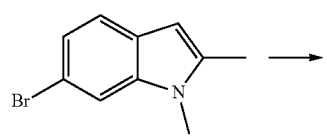

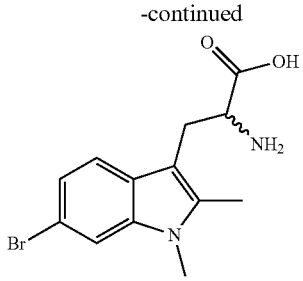

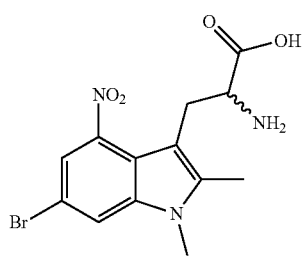

235

Example 235 can be prepared from 6-bromo-1,2-dimethyl-indole as shown above and in a similar manner as described in Examples 1-2.

Example 236: Preparation of 2-amino-3-(7-bromo-1,2-dimethyl-4-nitro-1H-indol-3-yl)propanoic Acid (236)

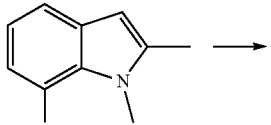

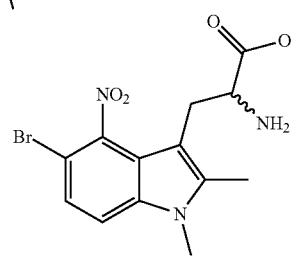

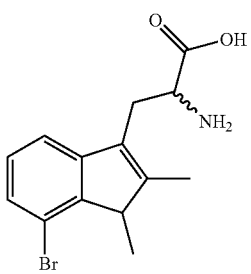

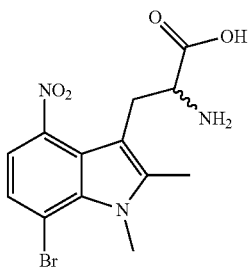

236

Example 236 can be prepared from 7-bromo-1,2-dimethyl-indole as shown above and in a similar manner as described in Examples 1-2.

Example 237: Preparation of 2-amino-3-(4-bromo-1,2-dimethyl-7-nitro-1H-indol-3-yl)propanoic Acid (237)

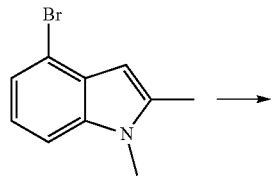

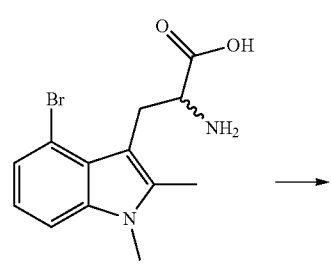

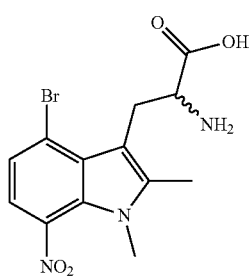

237

Example 237 can be prepared from 4-bromo-1,2-dimethyl-indole as shown above and in a similar manner as described in Examples 1-2.

Example 238: Preparation of 2-amino-3-(5-methoxy-1,2-dimethyl-4-nitro-1H-indol-3-yl)propanoic Acid (238)

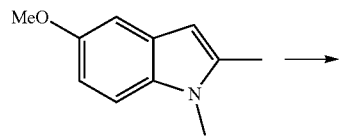

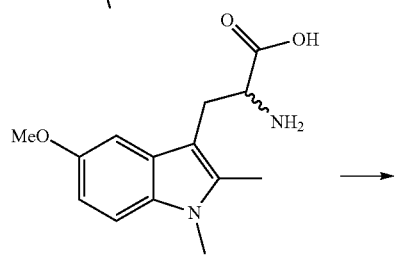

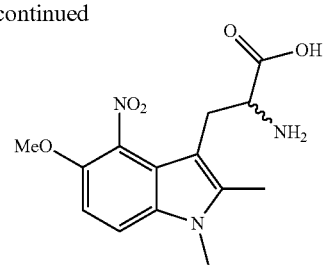

238

Example 238 can be prepared from 5-methoxy-1,2-dimethyl-indole as shown above and in a similar manner as described in Examples 1-2.

Example 239: Preparation of 2-amino-3-(6-methoxy-1,2-dimethyl-4-nitro-1H-indol-3-yl)propanoic Acid (239)

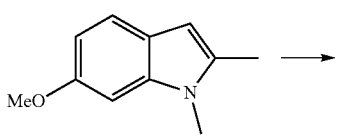

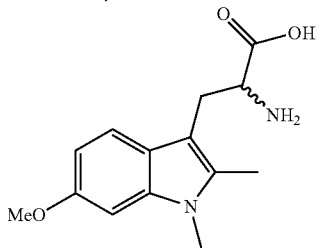

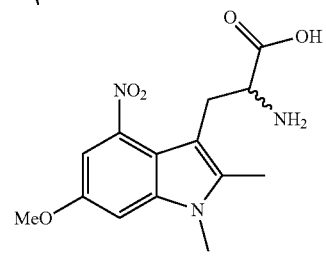

239

Example 239 can be prepared from 6-methoxy-1,2-dimethyl-indole as shown above and in a similar manner as described in Examples 1-2.

Example 240: Preparation of 2-amino-3-(7-methoxy-1,2-dimethyl-4-nitro-1H-indol-3-yl)propanoic Acid (240)

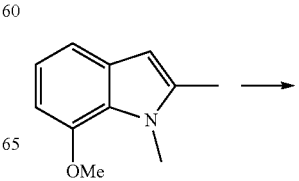

-continued

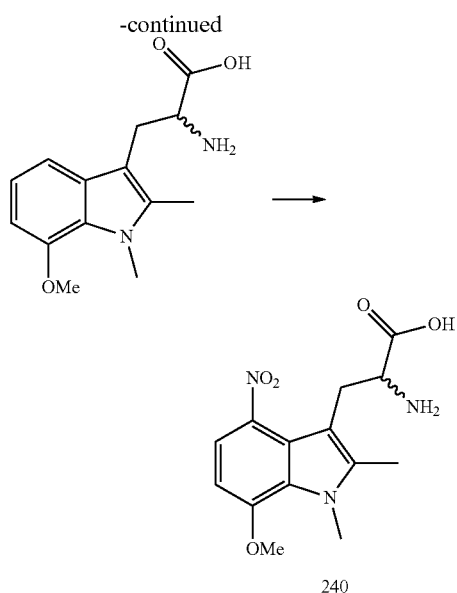

240

Example 240 can be prepared from 7-methoxy-1,2-dimethyl-indole as shown above and in a similar manner as described in Examples 1-2.

Example 241: Preparation of 2-amino-3-(4-methoxy-1,2-dimethyl-7-nitro-1H-indol-3-yl)propanoic Acid (241)

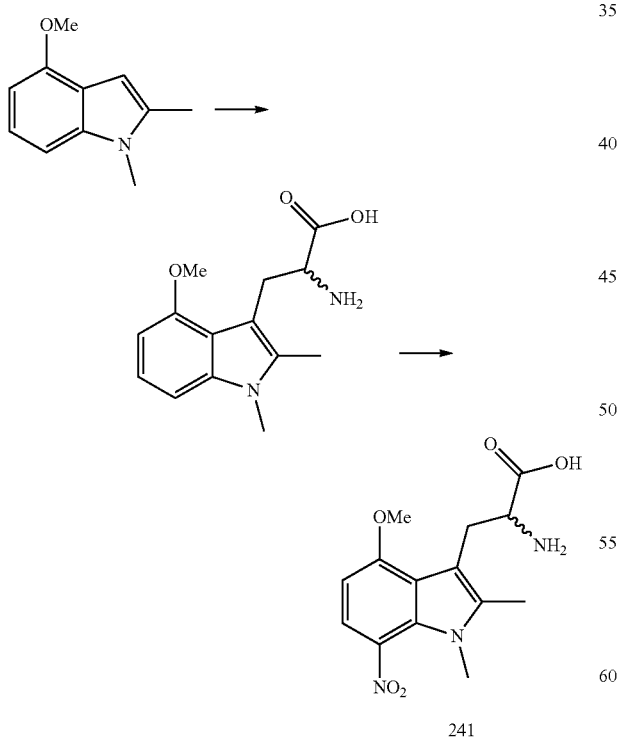

241

Example 241 can be prepared from 4-methoxy-1,2-dimethyl-indole as shown above and in a similar manner as described in Examples 1-2.

Example 242: Preparation of 2-amino-3-(5-amino-1,2-dimethyl-4-nitro-1H-indol-3-yl)propanoic Acid (242)

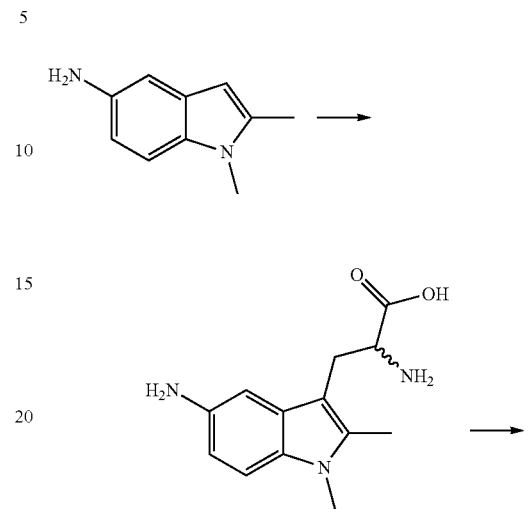

242

Example 242 can be prepared from 5-amino-1,2-dimethyl-indole as shown above and in a similar manner as described in Examples 1-2.

Example 243: Preparation of 2-amino-3-(6-amino-1,2-dimethyl-4-nitro-1H-indol-3-yl)propanoic Acid (243)

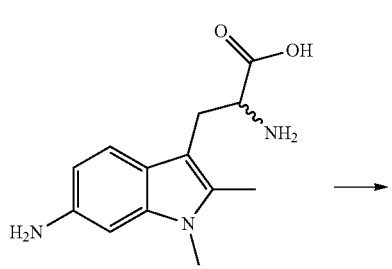

-continued

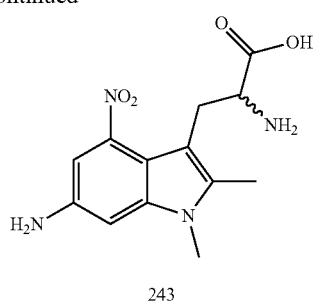

243

Example 243 can be prepared from 6-amino-1,2-dimethyl-indole as shown above and in a similar manner as described in Examples 1-2.

Example 244: Preparation of 2-amino-3-(7-amino-1,2-dimethyl-4-nitro-1H-indol-3-yl)propanoic Acid (244)

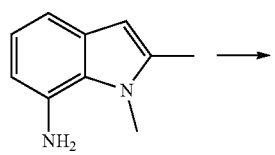

244

Example 244 can be prepared from 7-amino-1,2-dimethyl-indole as shown above and in a similar manner as described in Examples 1-2.

Example 245: Preparation of 2-amino-3-(4-amino-1,2-dimethyl-7-nitro-1H-indol-3-yl)propanoic Acid (245)

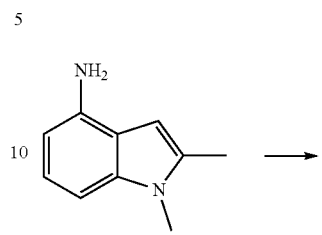

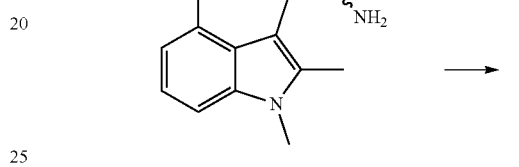

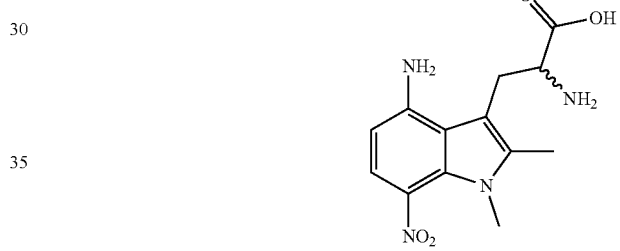

245

Example 245 can be prepared from 4-amino-1,2-dimethyl-indole as shown above and in a similar manner as described in Examples 1-2.

Example 246: Preparation of 2-amino-3-(5-hydroxy-1,2-dimethyl-4-nitro-1H-indol-3-yl)propanoic Acid (246)

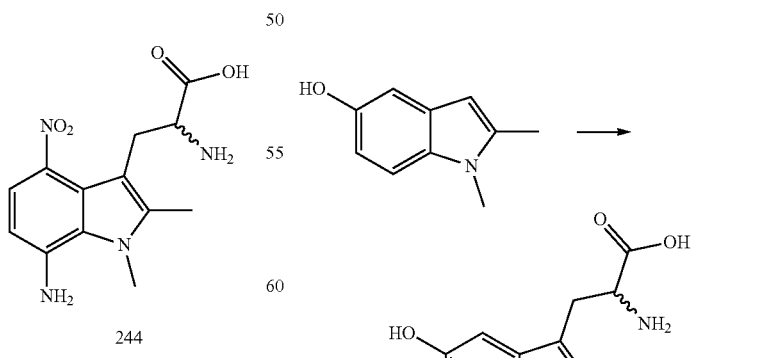

201

-continued

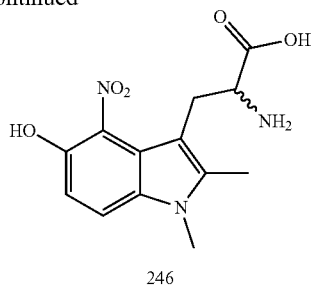

246

Example 246 can be prepared from 5-hydroxy-1,2-dimethyl-indole as shown above and in a similar manner as described in Examples 1-2.

Example 247: Preparation of 2-amino-3-(6-hydroxy-1,2-dimethyl-4-nitro-1H-indol-3-yl)propanoic Acid (247)

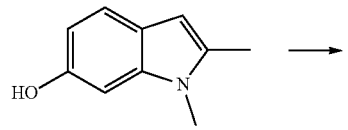

247

Example 247 can be prepared from 6-hydroxy-1,2-dimethyl-indole as shown above and in a similar manner as described in Examples 1-2.

Example 248: Preparation of 2-amino-3-(7-hydroxy-1,2-dimethyl-4-nitro-1H-indol-3-yl)propanoic Acid (248)

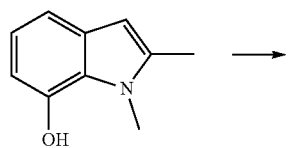

202

-continued

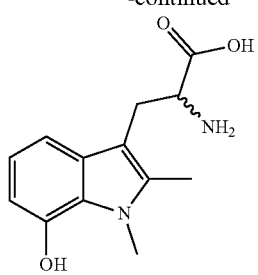

248

Example 248 can be prepared from 7-hydroxy-1,2-dimethyl-indole as shown above and in a similar manner as described in Examples 1-2.

Example 249: Preparation of 2-amino-3-(4-hydroxy-1,2-dimethyl-7-nitro-1H-indol-3-yl)propanoic Acid (249)

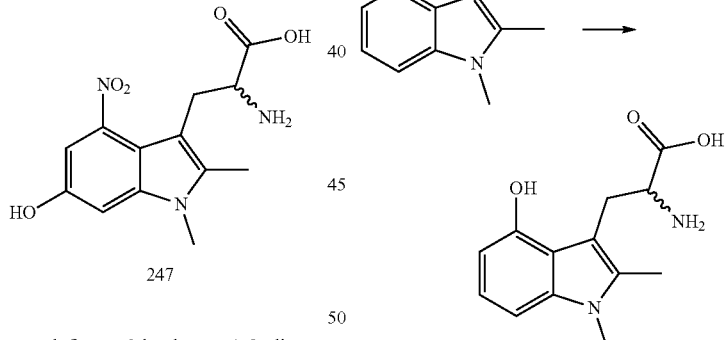

249

Example 249 can be prepared from 4-hydroxy-1,2-dimethyl-indole as shown above and in a similar manner as described in Examples 1-2.

Example 250: Preparation of 2-amino-3-(1,2-dimethyl-4-nitro-5-phenyl-1H-indol-3-yl)propanoic Acid (250)

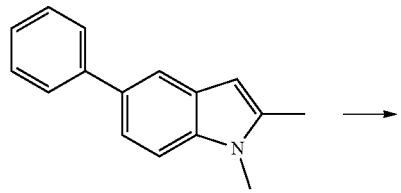

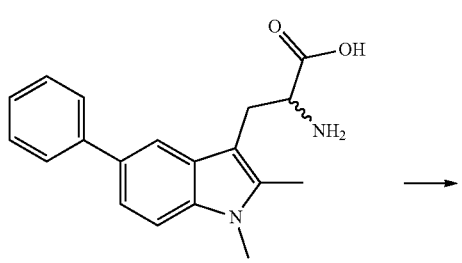

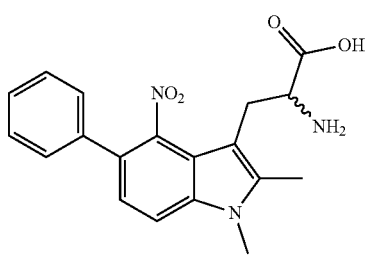

250

Example 250 can be prepared from 5-phenyl-1,2-dimethyl-indole as shown above and in a similar manner as described in Examples 1-2.

Example 251: Preparation of 2-amino-3-(1,2-dimethyl-4-nitro-6-phenyl-1H-indol-3-yl)propanoic Acid (251)

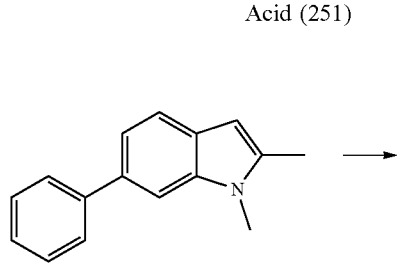

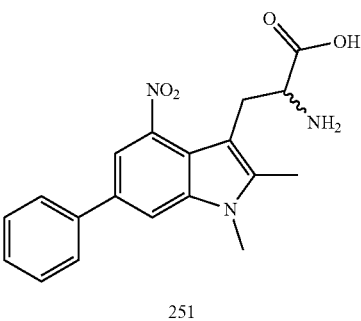

251

Example 251 can be prepared from 6-phenyl-1,2-dimethyl-indole as shown above and in a similar manner as described in Examples 1-2.

Example 252: Preparation of 2-amino-3-(1,2-dimethyl-4-nitro-7-phenyl-1H-indol-3-yl)propanoic Acid (252)

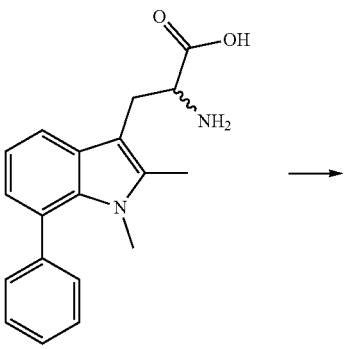

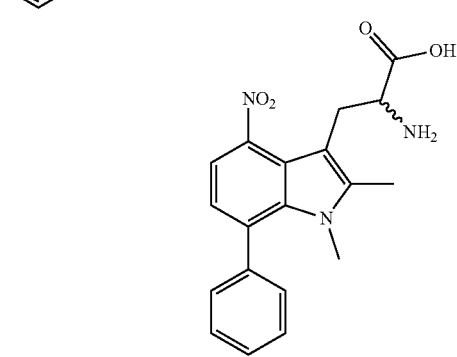

252

Example 252 can be prepared from 7-phenyl-1,2-dimethyl-indole as shown above and in a similar manner as described in Examples 1-2.

Example 253: Preparation of 2-amino-3-(1,2-dimethyl-7-nitro-4-phenyl-1H-indol-3-yl)propanoic Acid (253)

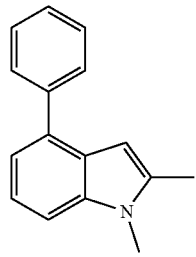

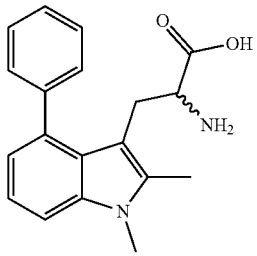

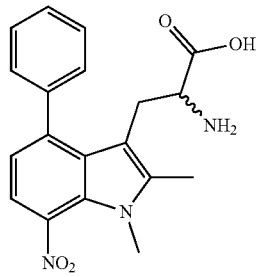

253

Example 253 can be prepared from 4-phenyl-1,2-dimethyl-indole as shown above and in a similar manner as described in Examples 1-2.

Example 254: Preparation of 2-amino-3-(5-cyclopropyl-1,2-dimethyl-4-nitro-1H-indol-3-yl)propanoic Acid (254)

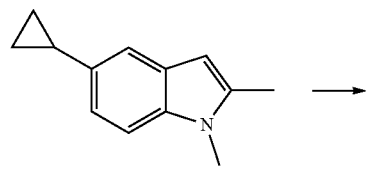

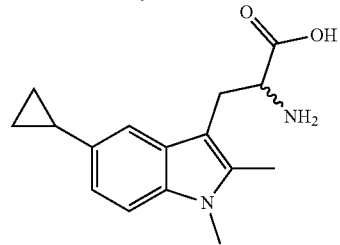

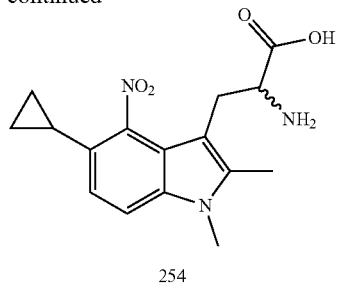

254

Example 254 can be prepared from 5-cyclopropyl-1,2-dimethyl-indole as shown above and in a similar manner as described in Examples 1-2.

Example 255: Preparation of 2-amino-3-(6-cyclopropyl-1,2-dimethyl-4-nitro-1H-indol-3-yl)propanoic Acid (255)

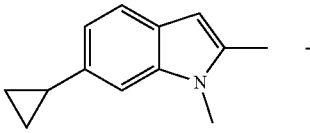

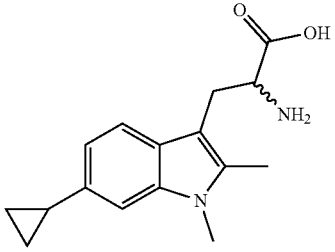

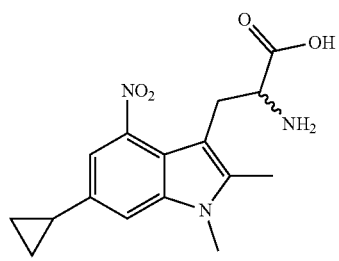

255

Example 255 can be prepared from 6-cyclopropyl-1,2-dimethyl-indole as shown above and in a similar manner as described in Examples 1-2.

Example 256: Preparation of 2-amino-3-(7-cyclopropyl-1,2-dimethyl-4-nitro-1H-indol-3-yl)propanoic Acid (256)

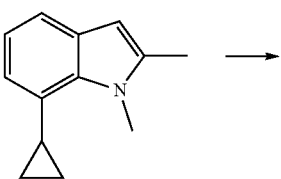

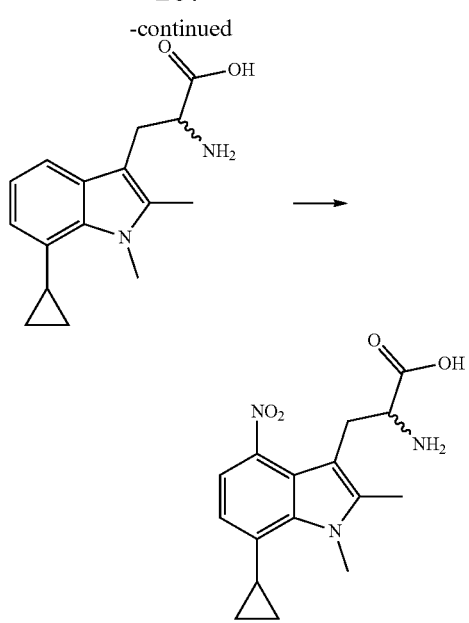

256

Example 256 can be prepared from 7-cyclopropyl-1,2-dimethyl-indole as shown above and in a similar manner as described in Examples 1-2.

Example 257: Preparation of 2-amino-3-(4-cyclopropyl-1,2-dimethyl-7-nitro-1H-indol-3-yl)propanoic Acid (257)

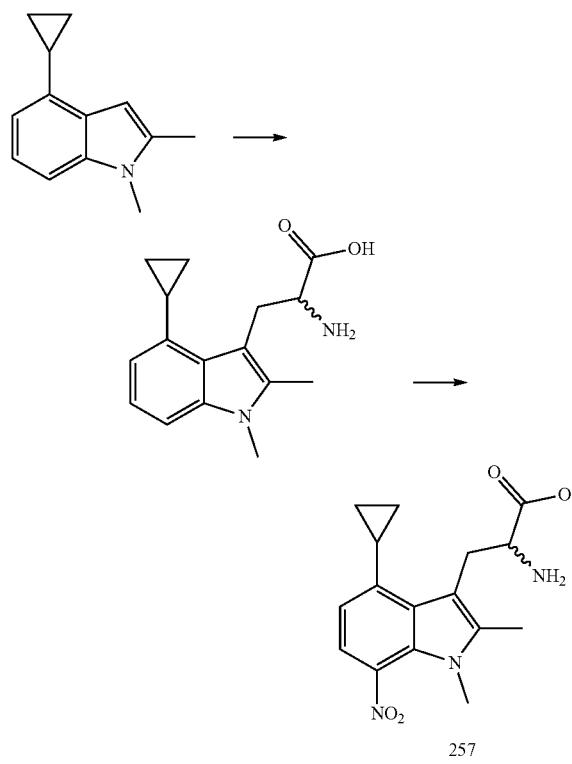

257

Example 257 can be prepared from 4-cyclopropyl-1,2-dimethyl-indole as shown above and in a similar manner as described in Examples 1-2.

Example 258: Preparation of 2-amino-3-(1,2-dimethyl-4-nitro-5-vinyl-1H-indol-3-yl)propanoic Acid (258)

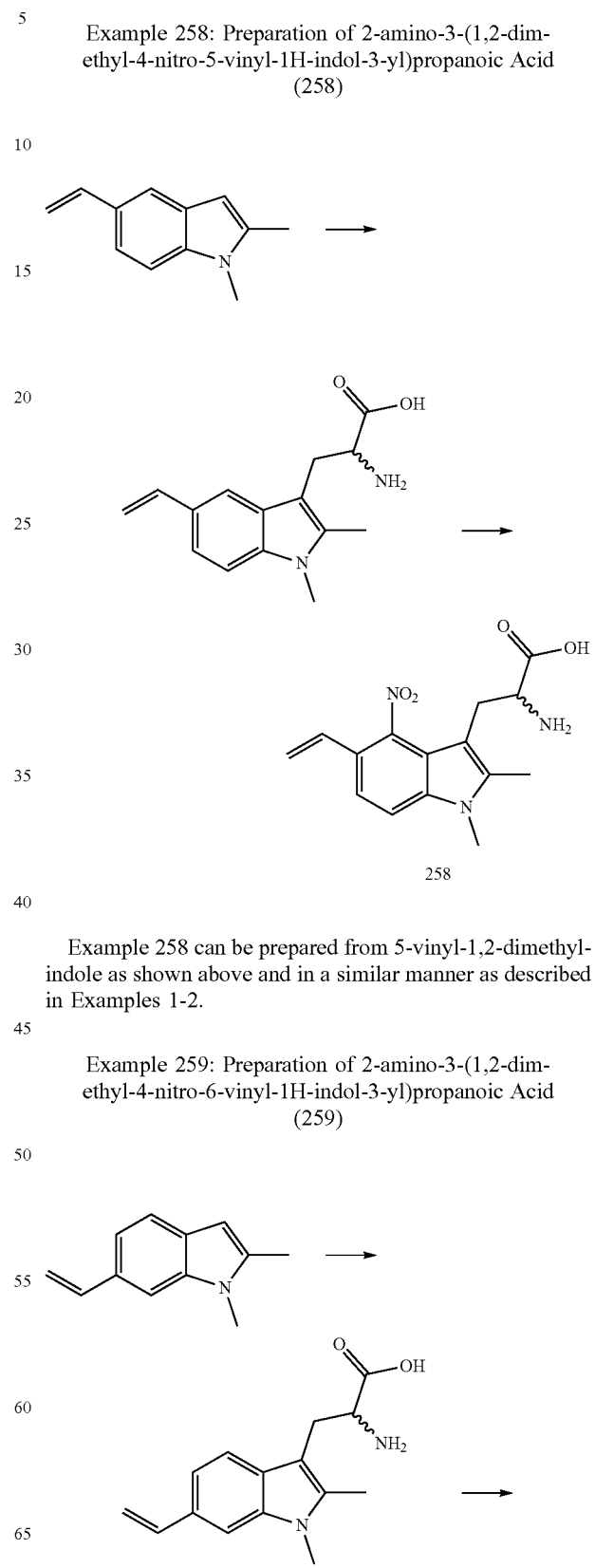

258

Example 258 can be prepared from 5-vinyl-1,2-dimethyl-indole as shown above and in a similar manner as described in Examples 1-2.

Example 259: Preparation of 2-amino-3-(1,2-dimethyl-4-nitro-6-vinyl-1H-indol-3-yl)propanoic Acid (259)

209

-continued

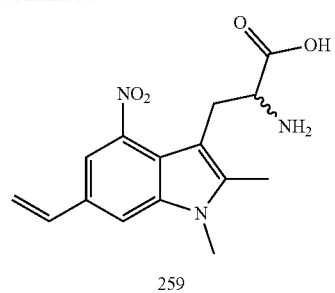

259

Example 259 can be prepared from 6-vinyl-1,2-dimethyl-indole as shown above and in a similar manner as described in Examples 1-2.

Example 260: Preparation of 2-amino-3-(1,2-dimethyl-4-nitro-7-vinyl-1H-indol-3-yl)propanoic Acid (260)

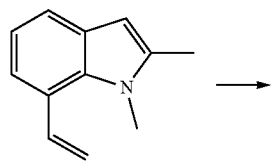

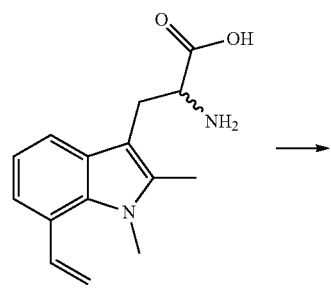

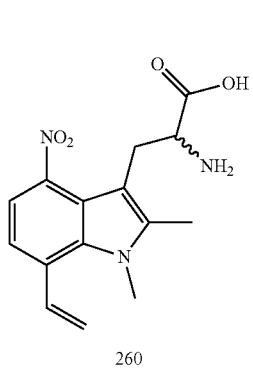

260

Example 260 can be prepared from 7-vinyl-1,2-dimethyl-indole as shown above and in a similar manner as described in Examples 1-2.

210

Example 261: Preparation of 2-amino-3-(1,2-dimethyl-7-nitro-4-vinyl-1H-indol-3-yl)propanoic Acid (261)

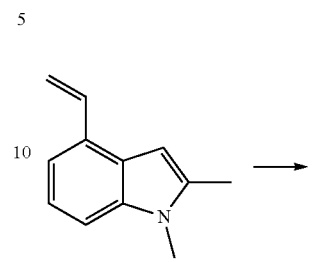

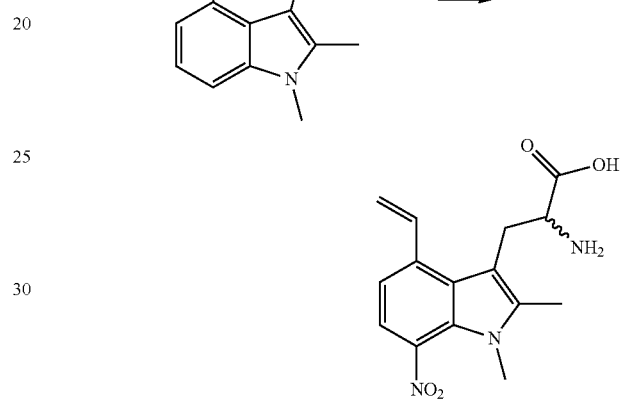

261

Example 261 can be prepared from 4-vinyl-1,2-dimethyl-indole as shown above and in a similar manner as described in Examples 1-2.

Example 262: Preparation of 2-amino-3-(5-ethynyl-1,2-dimethyl-4-nitro-1H-indol-3-yl)propanoic Acid (262)

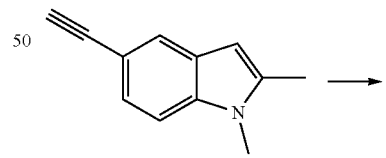

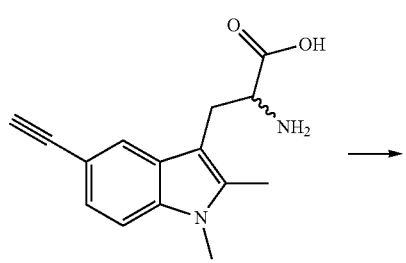

211

-continued

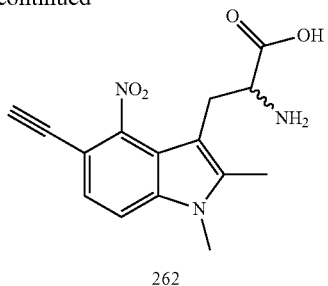

262

Example 262 can be prepared from 5-ethynyl-1,2-dimethyl-indole as shown above and in a similar manner as described in Examples 1-2.

Example 263: Preparation of 2-amino-3-(6-ethynyl-1,2-dimethyl-4-nitro-1H-indol-3-yl)propanoic Acid (263)

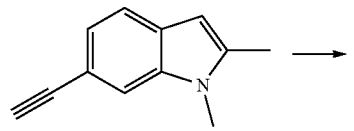

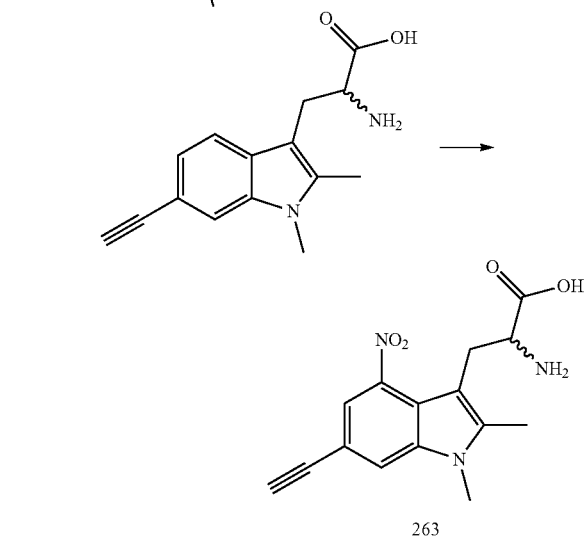

263

Example 263 can be prepared from 6-ethynyl-1,2-dimethyl-indole as shown above and in a similar manner as described in Examples 1-2.

Example 264: Preparation of 2-amino-3-(7-ethynyl-1,2-dimethyl-4-nitro-1H-indol-3-yl)propanoic Acid (264)

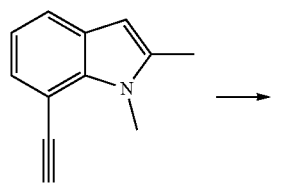

212

-continued

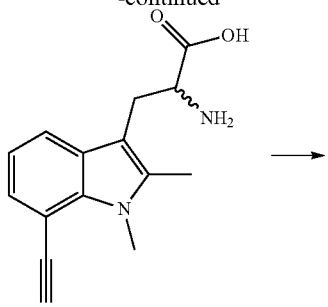

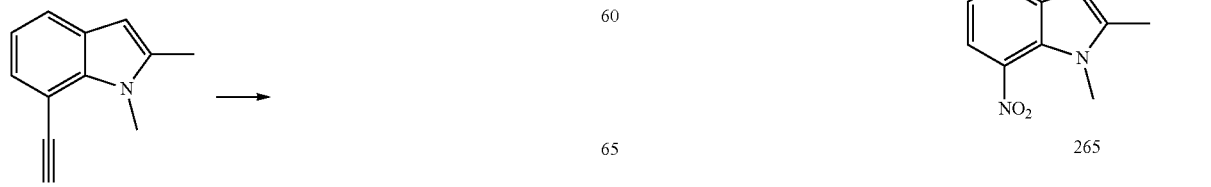

264

Example 264 can be prepared from 7-ethynyl-1,2-dimethyl-indole as shown above and in a similar manner as described in Examples 1-2.

Example 265: Preparation of 2-amino-3-(4-ethynyl-1,2-dimethyl-7-nitro-1H-indol-3-yl)propanoic Acid (265)

265

Example 265 can be prepared from 4-ethynyl-1,2-dimethyl-indole as shown above and in a similar manner as described in Examples 1-2.

Example 266: Preparation of 2-amino-3-(1,2-dimethyl-5-morpholino-4-nitro-1H-indol-3-yl)propanoic Acid (266)

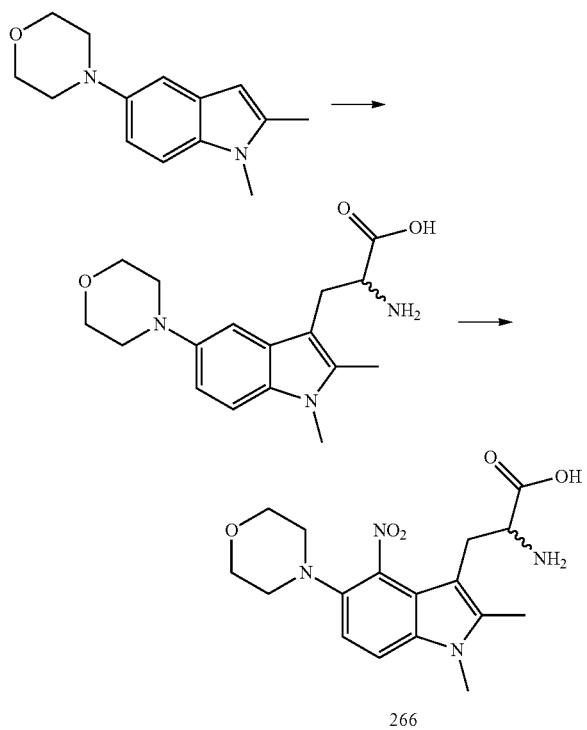

266

Example 266 can be prepared from 5-morpholino-1,2-dimethyl-indole as shown above and in a similar manner as described in Examples 1-2.

Example 267: Preparation of 2-amino-3-(1,2-dimethyl-6-morpholino-4-nitro-1H-indol-3-yl)propanoic Acid (267)

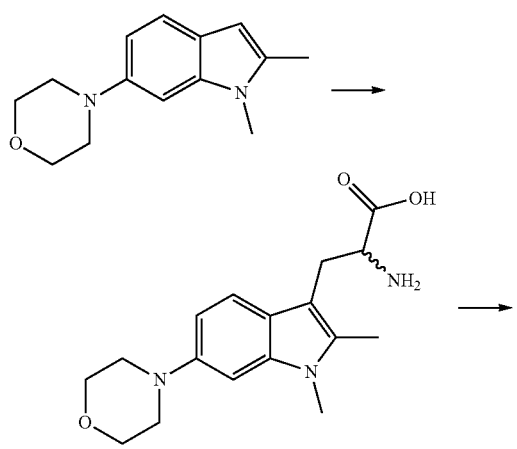

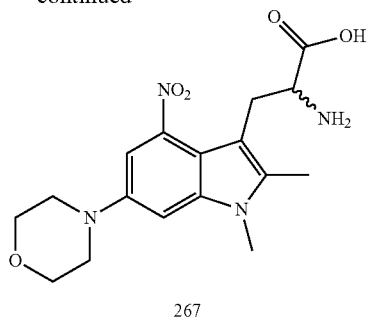

267

Example 267 can be prepared from 6-morpholino-1,2-dimethyl-indole as shown above and in a similar manner as described in Examples 1-2.

Example 268: Preparation of 2-amino-3-(1,2-dimethyl-7-morpholino-4-nitro-1H-indol-3-yl)propanoic Acid (268)

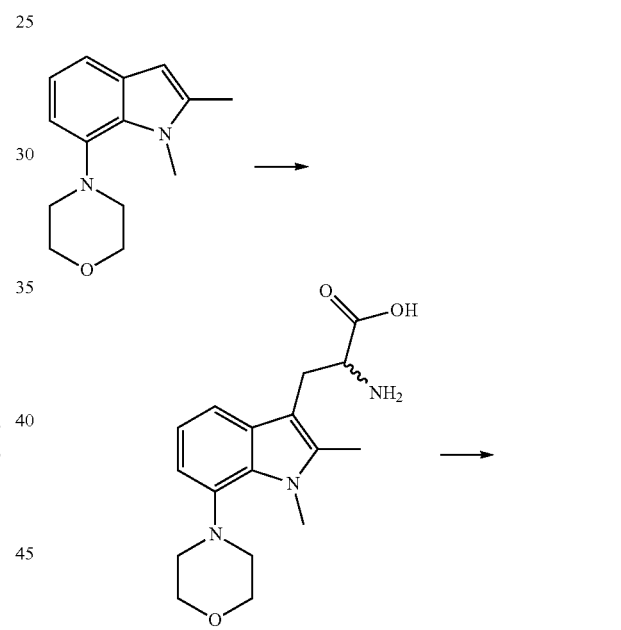

268

Example 268 can be prepared from 7-morpholino-1,2-dimethyl-indole as shown above and in a similar manner as described in Examples 1-2.

Example 269: Preparation of 2-amino-3-(1,2-dimethyl-4-morpholino-7-nitro-1H-indol-3-yl)propanoic Acid (269)

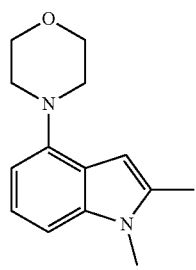

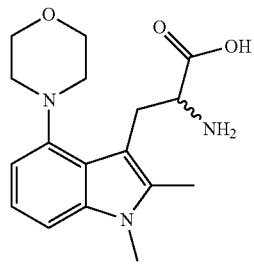

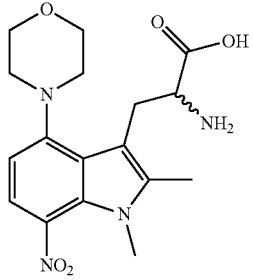

269

Example 269 can be prepared from 4-morpholino-1,2-dimethyl-indole as shown above and in a similar manner as described in Examples 1-2.

Example 270: Preparation of 2-amino-3-(1,2-dimethyl-5-(methylthio)-4-nitro-1H-indol-3-yl)propanoic Acid (270)

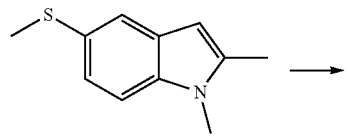

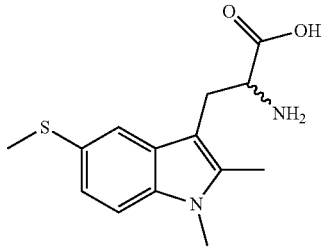

-continued

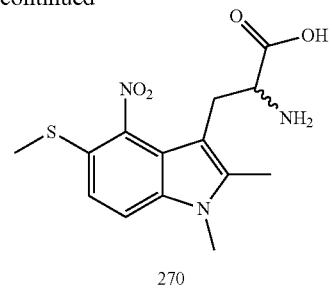

270

Example 270 can be prepared from 5-(methylthio)-1,2-dimethyl-indole as shown above and in a similar manner as described in Examples 1-2.

Example 271: Preparation of 2-amino-3-(1,2-dimethyl-6-(methylthio)-4-nitro-1H-indol-3-yl)propanoic Acid (271)

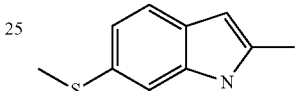

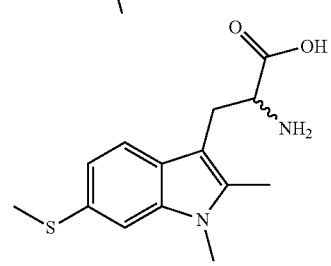

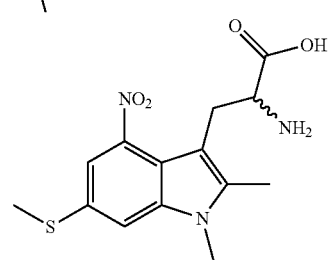

271

Example 271 can be prepared from 6-(methylthio)-1,2-dimethyl-indole as shown above and in a similar manner as described in Examples 1-2.

Example 272: Preparation of 2-amino-3-(1,2-dimethyl-7-(methylthio)-4-nitro-1H-indol-3-yl)propanoic Acid (272)

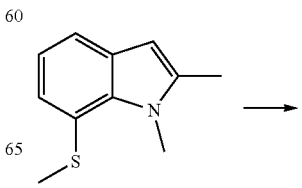

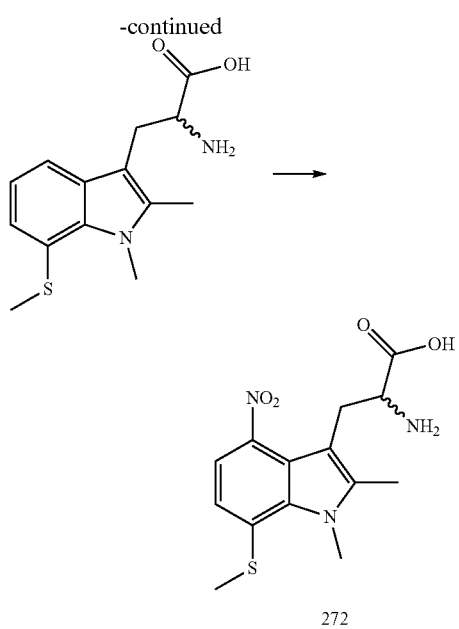

Example 272 can be prepared from 7-(methylthio)-1,2-dimethyl-indole as shown above and in a similar manner as described in Examples 1-2.

Example 273: Preparation of 2-amino-3-(1,2-dimethyl-4-(methylthio)-7-nitro-1H-indol-3-yl)propanoic Acid (273)

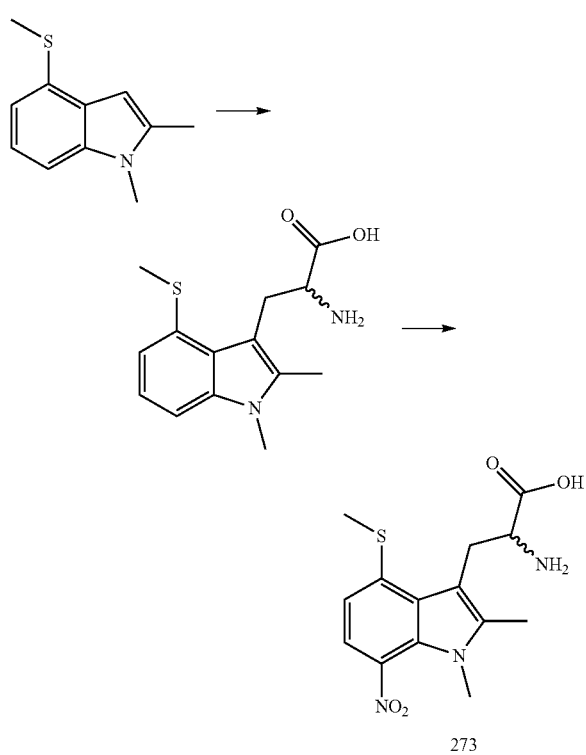

Example 273 can be prepared from 4-(methylthio)-1,2-dimethyl-indole as shown above and in a similar manner as described in Examples 1-2.

Example 274: Preparation of 2-amino-3-(1,2-dimethyl-4-nitro-5-(pyridin-4-yl)-1H-indol-3-yl)propanoic Acid (274)

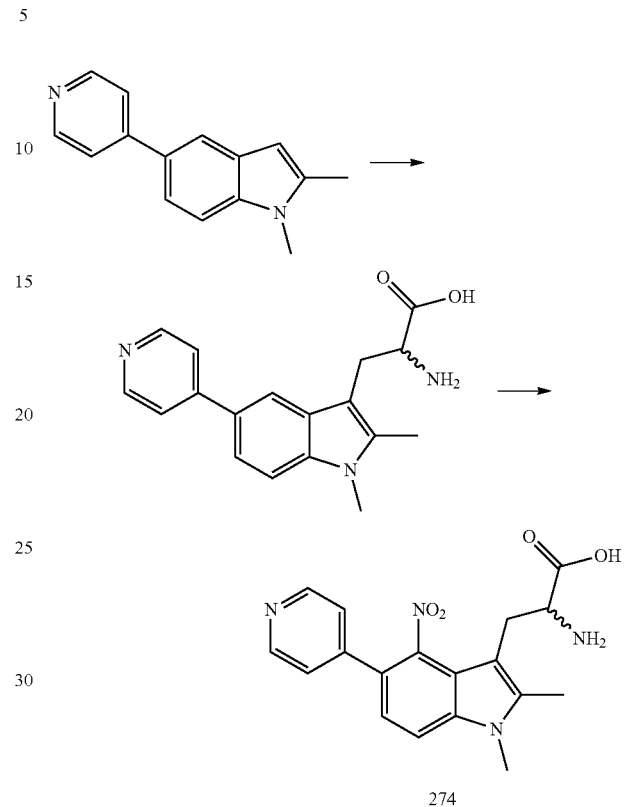

Example 274 can be prepared from 5-(pyridin-4-yl)-1,2-dimethyl-indole as shown above and in a similar manner as described in Examples 1-2.

Example 275: Preparation of 2-amino-3-(1,2-dimethyl-4-nitro-6-(pyridin-4-yl)-1H-indol-3-yl)propanoic Acid (275)

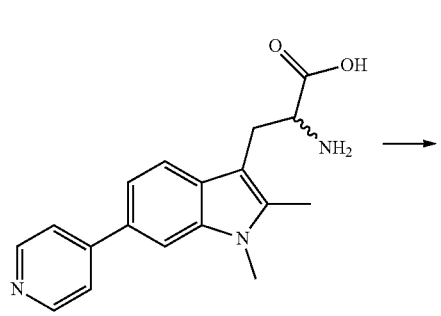

-continued

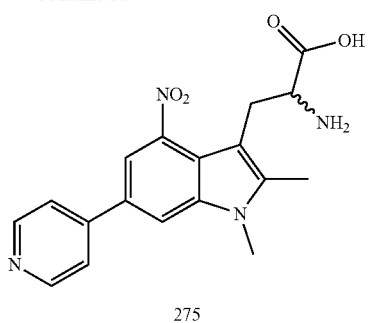

Example 275 can be prepared from 6-(pyridin-4-yl)-1,2-dimethyl-indole as shown above and in a similar manner as described in Examples 1-2.

Example 276: Preparation of 2-amino-3-(1,2-dimethyl-4-nitro-7-(pyridin-4-yl)-1H-indol-3-yl)propanoic Acid (276)

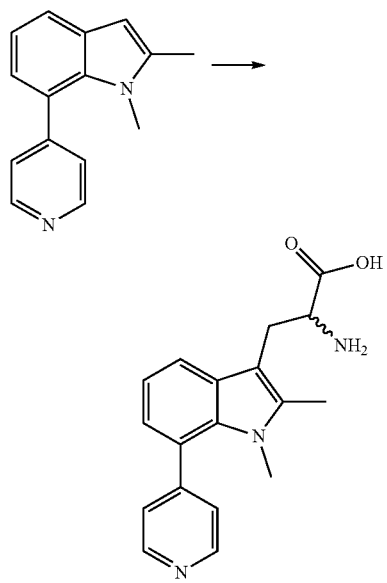

Example 276 can be prepared from 7-(pyridin-4-yl)-1,2-dimethyl-indole as shown above and in a similar manner as described in Examples 1-2.

Example 277: Preparation of 2-amino-3-(1,2-dimethyl-7-nitro-4-(pyridin-4-yl)-1H-indol-3-yl)propanoic Acid (277)

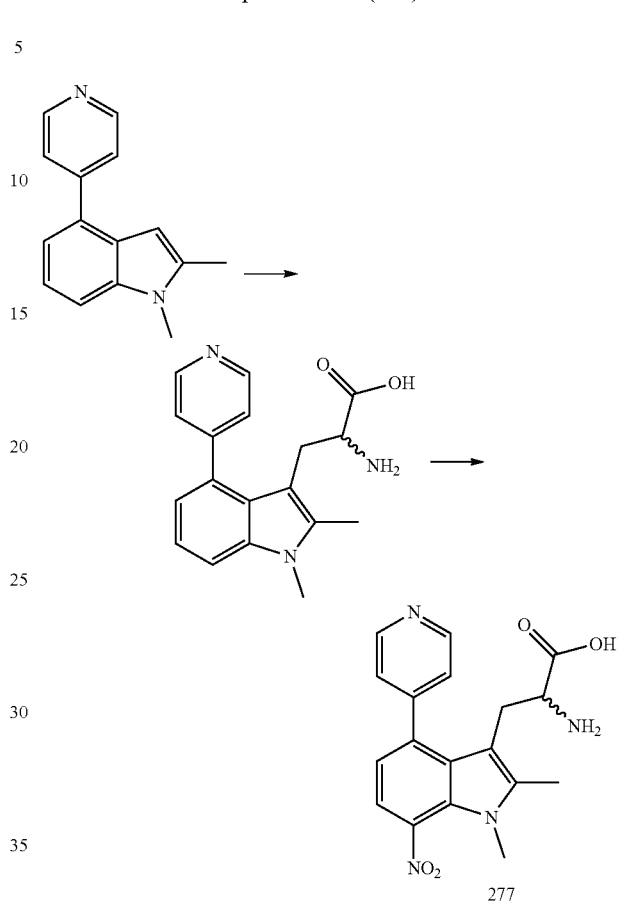

Example 277 can be prepared from 4-(pyridin-4-yl)-1,2-dimethyl-indole as shown above and in a similar manner as described in Examples 1-2.

Example 278: Preparation of 3-(4-nitro-1H-indol-3-yl)-2-oxopropanoic acid (278)

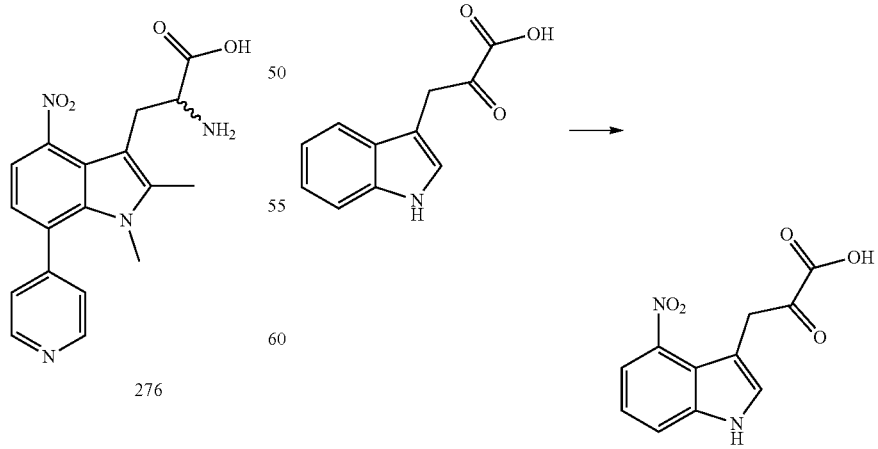

Example 278 can be prepared from 3-(1H-indol-3-yl)-2-oxopropanoic acid as shown above and in a similar manner as described in Examples 1-2.

Example 279: Preparation of 2-hydroxy-3-(4-nitro-1H-indol-3-yl)propanoic Acid (279)

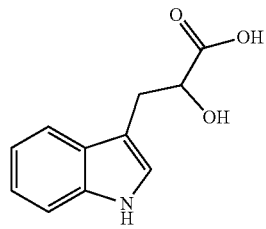

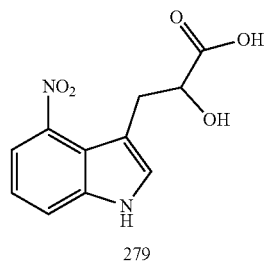

279

Example 279 can be prepared from 2-hydroxy-3-(1H-indol-3-yl)propanoic acid as shown above and in a similar manner as described in Examples 1-2.

Example 280: Preparation of 2-(4-nitro-1H-indol-3-yl)acetic Acid (280)

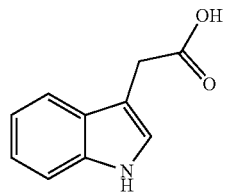

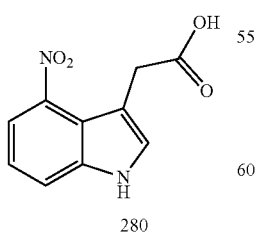

280

Example 280 can be prepared from 2-(1H-indol-3-yl)acetic acid as shown above and in a similar manner as described in Examples 1-2.

Example 281: Preparation of 2-(4-nitro-1H-indol-3-yl)ethan-1-amine (281)

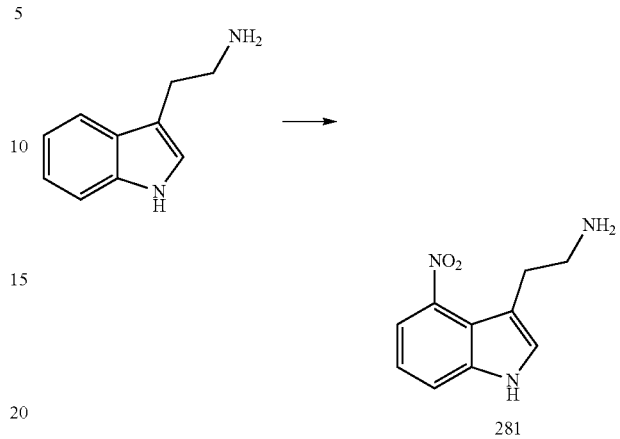

Example 281 can be prepared from 2-(1H-indol-3-yl)ethan-1-amine as shown above and in a similar manner as described in Examples 1-2.

Example 282: Preparation of 3-(2-aminoethyl)-4-nitro-1H-indol-5-ol (282)

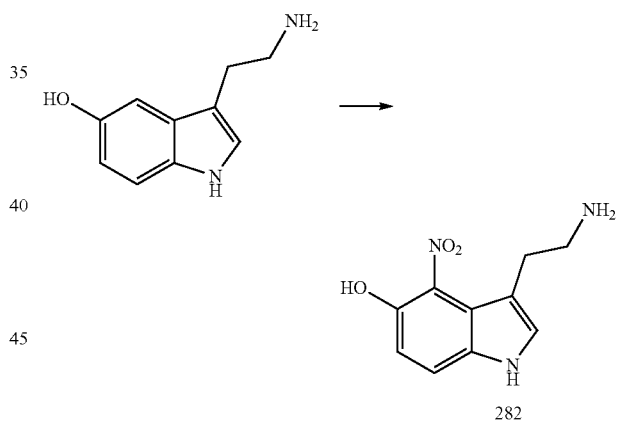

Example 282 can be prepared from 3-(2-aminoethyl)-1H-indol-5-ol as shown above and in a similar manner as described in Examples 1-2.

Example 283: Preparation of 4-nitro-1H-indole-3-carboxylic Acid (283)

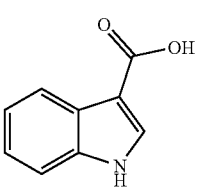

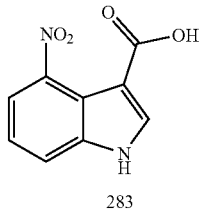
283

Example 283 can be prepared from 1H-indole-3-carboxylic acid as shown above and in a similar manner as described in Examples 1-2.

Example 284: Preparation of (S)-2-amino-3-(4-nitro-1H-indol-3-yl)propan-1-ol (284)

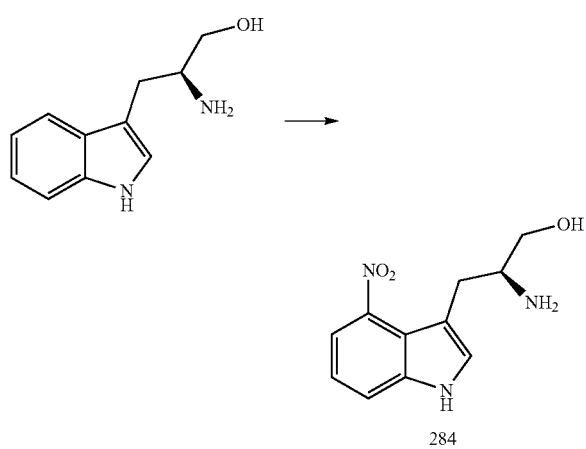
284

Example 284 can be prepared from (S)-2-amino-3-(1H-indol-3-yl)propan-1-ol as shown above and in a similar manner as described in Examples 1-2.

Example 285: Preparation of 2-amino-2-methyl-3-(4-nitro-1H-indol-3-yl)propanoic Acid (285)

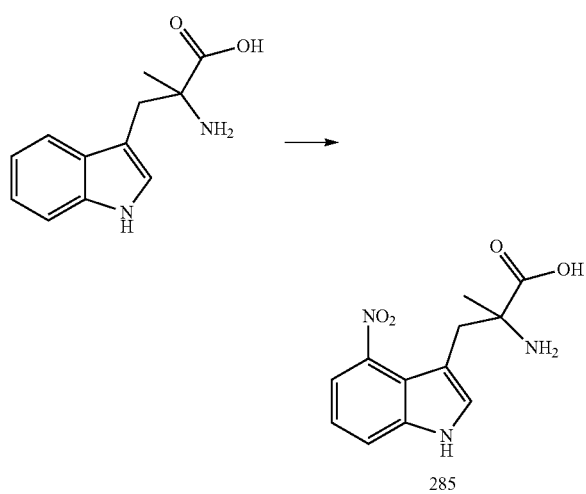
285

Example 285 can be prepared from 2-amino-3-(1H-indol-3-yl)-2-methylpropanoic acid as shown above and in a similar manner as described in Examples 1-2.

Example 286: Preparation of 2-amino-3-(4-nitro-1H-pyrrolo[2,3-b]pyridin-3-yl)propanoic Acid (286)

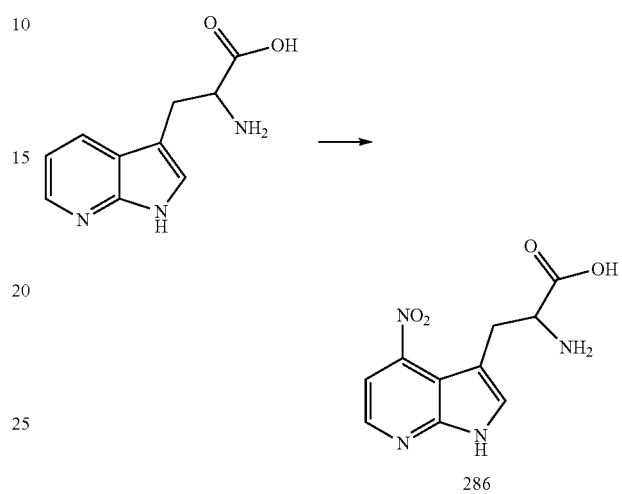
286

Example 286 can be prepared from 2-amino-3-(1H-pyrrolo[2,3-b]pyridin-3-yl)propanoic acid as shown above and in a similar manner as described in Examples 1-2.

| SEQUENCES |
|---|
| >S. scabiei TxtE enzyme; Genebank Accession No. CBG70284.1 (SEQ ID NO: 56)<br>MTVPSPLADPSIVPDPYPVYADLAQRRPVHWVERLNAWAVLTYADCAAGL<br>KDPRLTADRGTEVLAAKFPGQPLPPDNIFHRWTKNVVMYTDPPLHDALRR<br>SVRAGFTRAAHQHYDQVLQKVAHDLVASIPAGATEIDAVPALAAELPVRS<br>AVHAFGVPEEDLGFLIPRVNTIMTYHSGPKDQPVTQEIILEKLTDLHTYA<br>SELLQGMRGKVLPDTVIARLAAAQDGLTETTPEQTVHQLALVFIALFAPT<br>TPGSLSSGTLAFARNPRQVERFLADQACVDNTANEVLRYNASNQFTWRVA<br>AKDVEMGGVRIEAGQTLALFLGSANRDANMFERPNDFDLDRPNSARHLSF<br>GQGVHACLAAQLISLQLKWFYVALLNRFPGIRTAGEPIWNENLEFRSLRS<br>LPLSLR |
| >CYP102A1 (P450BM3) reductase domain (SEQ ID NO: 57)<br>KIPLGGIPSPSTEQSAKKVRKKAENAHNTPLLVLYGSNMGTAEGTARDLA<br>DIAMSKGFAPQVATLDSHAGNLPREGAVLIVTASYNGHPPDNAKQFVDWL<br>DQASADEVKGVRYSVFGCGDKNWATTYQKVPAFIDETLAAKGAENIADRG<br>EADASDDFEGTYEEWREHMWSDVAAYFNLDIENSEDNKSTLSLQFVDSAA<br>DMPLAKMHGAFSTNVVASKELQQPGSARSTRHLEIELPKEASYQEGDHLG<br>VIPRNYEGIVNRVTARFGLDASQQIRLEAEEEKLAHLPLAKTVSVEELLQ<br>YVELQDPVTRTQLRAMAAKTVCPPHKVELEALLEKQAYKEQVLAKRLTML<br>ELLEKYPACEMKFSEFIALLPSIRPRYYSISSSPRVDEKQASITVSVVSG<br>EAWSGYGEYKGIASNYLAELQEGDTITCFISTPQSEFTLPKDPETPLIMV<br>GPGTGVAPFRGFVQARKQLKEQGQSLGEAHLYFGCRSPHEDYLYQEELEN<br>AQSEGIITLHTAFSRMPNQPKTYVQHVMEQDGKKLIELLDQGAHFYICGD<br>GSQMAPAVEATLMKSYADVHQVSEADARLWLQQLEEKGRYAKDVWAG |
| >TxtE w/ CYP102A1 (P450BM3) loop (SEQ ID NO: 58)<br>MTVPSPLADPSIVPDPYPVYADLAQRRPVHWVERLNAWAVLTYADCAAGL<br>KDPRLTADRGTEVLAAKFPGQPLPPDNIFHRWTKNVVMYTDPPLHDALRR<br>SVRAGFTRAAHQHYDQVLQKVAHDLVASIPAGATEIDAVPALAAELPVRS<br>AVHAFGVPEEDLGFLIPRVNTIMTYHSGPKDQPVTQEIILEKLTDLHTYA<br>SELLQGMRGKVLPDTVIARLAAAQDGLTETTPEQTVHQLALVFIALFAPT<br>TPGSLSSGTLAFARNPRQVERFLAAEEAARVLVDPVPSYKQVKQLKYDNT<br>ANEVLRYNASNQFTWRVAAKDVEMGGVRIEAGQTLALFLGSANRDANMFE<br>RPNDFDLDRPNSARHLSFGQGVHACLAAQLISLQLKWFYVALLNRFPGIR<br>TAGEPIWNENLEFRSLRSLPLSLR |

What is claimed is:

1. A fusion protein comprising:
   (i) a TxtE enzyme comprising the amino acid sequence set forth in SEQ ID NO: 56 or 58;
   (ii) an amino acid linker that is between 14 and 16 amino acids in length; and,
   (iii) a catalytic domain of a CYP102A1 (P450BM3) reductase enzyme;
   wherein the linker joins (iii) to a terminus of (i); wherein the fusion protein comprises increased nitration activity compare to cytochrome p450 enzyme.

2. The fusion protein of claim 1, wherein the terminus is a C-terminus.

3. The fusion protein of claim 1, wherein the TxtE enzyme comprises the amino acid sequence set forth in SEQ ID NO: 56.

4. The fusion protein of claim 1, wherein the catalytic domain comprises the amino acid sequence set forth in SEQ ID NO: 57.

5. The fusion protein of claim 1, wherein the amino acid linker is 16 amino acids in length.

6. The fusion protein of claim 1, wherein the amino acid linker is 15 amino acids in length.

7. The fusion protein of claim 1, wherein the amino acid linker is 14 amino acids in length.

8. The fusion protein of claim 1, wherein the fusion protein is not produced by overlap PCR.

9. The fusion protein of claim 1, wherein the amino acid linker comprises or consists of the sequence set forth in any one of SEQ ID NO: 36, 38, or 40.

10. The fusion protein of claim 1, wherein the amino acid linker is selected from the group consisting of flexible amino acid linker, rigid amino acid linker and cleavable amino acid linker.

* * * * *

UNITED STATES PATENT AND TRADEMARK OFFICE
CERTIFICATE OF CORRECTION

| | | |
|---|---|---|
| PATENT NO. | : 11,078,467 B2 | Page 1 of 1 |
| APPLICATION NO. | : 16/345224 | |
| DATED | : August 3, 2021 | |
| INVENTOR(S) | : Yousong Ding et al. | |

It is certified that error appears in the above-identified patent and that said Letters Patent is hereby corrected as shown below:

On the Title Page

(57) ABSTRACT
The disclosure relates to the field of fusion proteins. In some aspects, the disclosure relates to artificial fusion proteins comprising cytochrome P450 enzymes linked to reductase enzymes and uses thereof. In some aspects, the disclosure relates to corn-pounds produced by artificial cytochrome P450 enzymes.
Should be:
(57) ABSTRACT
The disclosure relates to the field of fusion proteins. In some aspects, the disclosure relates to artificial fusion proteins comprising cytochrome P450 enzymes linked to reductase enzymes and uses thereof. In some aspects, the disclosure relates to compounds produced by artificial cytochrome P450 enzymes.

In the Claims

At Column 251, Claim 1, Line 11:
"compare to cytochrome p450 enzyme."
Should read:
--compared to cytochrome p450 enzyme.--.

At Column 252, Claim 10, Line 14:
"acid linker, rigid amino acid linker and cleavable amino acid"
Should read:
--acid linker, rigid amino acid linker, and cleavable amino acid--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 58

<210> SEQ ID NO 1
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1
ataccatggt gaccgtcccc tcgccg                                    26

<210> SEQ ID NO 2
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 2
atagagctcg cggaggctga gcggcag                                   27

<210> SEQ ID NO 3
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 3
ctacatatgt ctgctaaaaa agtacgcaa                                 29

<210> SEQ ID NO 4
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 4
atcctcgagc ccagcccaca cgtcttttg                                 29

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 5
tctgagctca acgctcataa tacgccgctg                                30

<210> SEQ ID NO 6
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 6
tctgagctca aggcagaaaa cgctcataat acg                            33

<210> SEQ ID NO 7
<211> LENGTH: 31
<212> TYPE: DNA
<213> ORGANISM: Artificial Sequence

```
<220> FEATURE:
<223> OTHER INFORMATION: Synthetic Polynucleotide

<400> SEQUENCE: 7
tctgagctcg tacgcaaaaa ggcagaaaac g                                    31

<210> SEQ ID NO 8
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 8
tctgagctca aaaagtacg caaaaaggca g                                     31

<210> SEQ ID NO 9
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 9
tctgagctcg ctaaaaaagt acgcaaaaag gcag                                 34

<210> SEQ ID NO 10
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 10
tctgagctct ctgctaaaaa agtacgcaaa aaggcag                              37

<210> SEQ ID NO 11
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 11
tctgagctcc agtctgctaa aaagtacgc aaaaag                                36

<210> SEQ ID NO 12
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 12
tctgagctcg aacagtctgc taaaaaagta c                                    31

<210> SEQ ID NO 13
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 13
tctgagctca ctgaacagtc tgctaaaaaa g                                    31
```

```
<210> SEQ ID NO 14
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 14
tctgagctca gcactgaaca gtctgctaaa aaag                              34

<210> SEQ ID NO 15
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 15
tctgagctct cacctagcac tgaacagtct gc                                32

<210> SEQ ID NO 16
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 16
tctgagctcg gtattccttc acctagcact gaac                              34

<210> SEQ ID NO 17
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 17
tctgagctcc ttggcggtat tccttcacct ag                                32

<210> SEQ ID NO 18
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 18
tctgagctca aaattccgct tggcggtatt c                                 31

<210> SEQ ID NO 19
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 19
atcctcgagc ccagcccaca cgtcttttgc                                   30

<210> SEQ ID NO 20
<211> LENGTH: 29
<212> TYPE: DNA
<213> ORGANISM: Artificial Sequence
<220> FEATURE:
<223> OTHER INFORMATION: Synthetic Polynucleotide
```

<400> SEQUENCE: 20
cacccatggt gaccgtcccc tcgccgctc					29

<210> SEQ ID NO 21
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 21
cgggttgcgg gcgaacgc					18

<210> SEQ ID NO 22
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 22
gcgttcgccc gcaacccgca tgtattacaa aaagcagcag aagaagc					47

<210> SEQ ID NO 23
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 23
ggccgcgacg cgccaaggag cagttggcca taagcg					36

<210> SEQ ID NO 24
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 24
acctggcgcg tcgcggc					17

<210> SEQ ID NO 25
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 25
gacccagccc acacgtcttt tgc					23

<210> SEQ ID NO 26
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 26

Glu Leu Lys Ile Pro Leu Gly Gly Ile Pro Ser Pro Ser Thr Glu Gln
1               5                   10                  15

Ser Ala Lys Lys Val Arg Lys Lys Ala Glu Asn

```
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 27

Lys Ile Pro Leu Gly Gly Ile Pro Ser Pro Ser Thr Glu Gln Ser Ala
1               5                   10                  15

Lys Lys Val Arg Lys Lys Ala Glu Asn
            20                  25

<210> SEQ ID NO 28
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 28

Glu Leu Leu Gly Gly Ile Pro Ser Pro Ser Thr Glu Gln Ser Ala Lys
1               5                   10                  15

Lys Val Arg Lys Lys Ala Glu Asn
            20

<210> SEQ ID NO 29
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 29

Leu Gly Gly Ile Pro Ser Pro Ser Thr Glu Gln Ser Ala Lys Lys Val
1               5                   10                  15

Arg Lys Lys Ala Glu Asn
            20

<210> SEQ ID NO 30
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 30

Glu Leu Gly Ile Pro Ser Pro Ser Thr Glu Gln Ser Ala Lys Lys Val
1               5                   10                  15

Arg Lys Lys Ala Glu Asn
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 31

Gly Ile Pro Ser Pro Ser Thr Glu Gln Ser Ala Lys Lys Val Arg Lys
1               5                   10                  15
```

Lys Ala Glu Asn
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 32

Glu Leu Ser Pro Ser Thr Glu Gln Ser Ala Lys Lys Val Arg Lys Lys
1               5                   10                  15

Ala Glu Asn

<210> SEQ ID NO 33
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 33

Ser Pro Ser Thr Glu Gln Ser Ala Lys Lys Val Arg Lys Lys Ala Glu
1               5                   10                  15

Asn

<210> SEQ ID NO 34
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 34

Glu Leu Ser Thr Glu Gln Ser Ala Lys Lys Val Arg Lys Lys Ala Glu
1               5                   10                  15

Asn

<210> SEQ ID NO 35
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 35

Ser Thr Glu Gln Ser Ala Lys Lys Val Arg Lys Lys Ala Glu Asn
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 36

Glu Leu Thr Glu Gln Ser Ala Lys Lys Val Arg Lys Lys Ala Glu Asn
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 37

Thr Glu Gln Ser Ala Lys Lys Val Arg Lys Lys Ala Glu Asn
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 38

Glu Leu Ser Gln Ser Ala Lys Lys Val Arg Lys Lys Ala Glu Asn
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 39

Ser Gln Ser Ala Lys Lys Val Arg Lys Lys Ala Glu Asn
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 40

Glu Leu Gln Ser Ala Lys Lys Val Arg Lys Lys Ala Glu Asn
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 41

Gln Ser Ala Lys Lys Val Arg Lys Lys Ala Glu Asn
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 42

Glu Leu Ser Ala Lys Lys Val Arg Lys Lys Ala Glu Asn
1               5                   10

<210> SEQ ID NO 43
<211> LENGTH: 11
<212> TYPE: PRT
<213> ORGANISM: Artificial Sequence
<220> FEATURE:

```
<223> OTHER INFORMATION: Synthetic Polypeptide

<400> SEQUENCE: 43

Ser Ala Lys Lys Val Arg Lys Lys Ala Glu Asn
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 44

Glu Gln Ser Ala Lys Lys Val Arg Lys Lys Ala Glu Asn
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 45

Ser Ala Lys Lys Val Arg Lys Lys Ala Glu Asn
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 46

Glu Leu Ala Lys Lys Val Arg Lys Lys Ala Glu Asn
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 47

Ala Lys Lys Val Arg Lys Lys Ala Glu Asn
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 48

Glu Leu Lys Lys Val Arg Lys Lys Ala Glu Asn
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 49

Lys Lys Val Arg Lys Lys Ala Glu Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 50

Glu Leu Val Arg Lys Lys Ala Glu Asn
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 51

Val Arg Lys Lys Ala Glu Asn
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 52

Glu Leu Lys Ala Glu Asn
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 53

Lys Ala Glu Asn
1

<210> SEQ ID NO 54
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 54

Glu Leu Asn
1

<210> SEQ ID NO 55
<211> LENGTH: 1
<212> TYPE: PRT
<213> ORGANISM: Artificial Sequence
<220> FEATURE:
<223> OTHER INFORMATION: Synthetic Polypeptide

<400> SEQUENCE: 55

Asn
1

<210> SEQ ID NO 56
<211> LENGTH: 406
<212> TYPE: PRT
<213> ORGANISM: Aritifical Sequence
<220> FEATURE:
<223> OTHER INFORMATION: Synthetic Polypeptide

<400> SEQUENCE: 56

```
Met Thr Val Pro Ser Pro Leu Ala Asp Pro Ser Ile Val Pro Asp Pro
1               5                   10                  15

Tyr Pro Val Tyr Ala Asp Leu Ala Gln Arg Arg Pro Val His Trp Val
            20                  25                  30

Glu Arg Leu Asn Ala Trp Ala Val Leu Thr Tyr Ala Asp Cys Ala Ala
        35                  40                  45

Gly Leu Lys Asp Pro Arg Leu Thr Ala Asp Arg Gly Thr Glu Val Leu
    50                  55                  60

Ala Ala Lys Phe Pro Gly Gln Pro Leu Pro Pro Asp Asn Ile Phe His
65                  70                  75                  80

Arg Trp Thr Lys Asn Val Val Met Tyr Thr Asp Pro Pro Leu His Asp
                85                  90                  95

Ala Leu Arg Arg Ser Val Arg Ala Gly Phe Thr Arg Ala Ala His Gln
            100                 105                 110

His Tyr Asp Gln Val Leu Gln Lys Val Ala His Asp Leu Val Ala Ser
        115                 120                 125

Ile Pro Ala Gly Ala Thr Glu Ile Asp Ala Val Pro Ala Leu Ala Ala
    130                 135                 140

Glu Leu Pro Val Arg Ser Ala Val His Ala Phe Gly Val Pro Glu Glu
145                 150                 155                 160

Asp Leu Gly Phe Leu Ile Pro Arg Val Asn Thr Ile Met Thr Tyr His
                165                 170                 175

Ser Gly Pro Lys Asp Gln Pro Val Thr Gln Glu Ile Ile Leu Glu Lys
            180                 185                 190

Leu Thr Asp Leu His Thr Tyr Ala Ser Glu Leu Leu Gln Gly Met Arg
        195                 200                 205

Gly Lys Val Leu Pro Asp Thr Val Ile Ala Arg Leu Ala Ala Ala Gln
    210                 215                 220

Asp Gly Leu Thr Glu Thr Thr Pro Glu Gln Thr Val His Gln Leu Ala
225                 230                 235                 240

Leu Val Phe Ile Ala Leu Phe Ala Pro Thr Thr Pro Gly Ser Leu Ser
                245                 250                 255

Ser Gly Thr Leu Ala Phe Ala Arg Asn Pro Arg Gln Val Glu Arg Phe
            260                 265                 270

Leu Ala Asp Gln Ala Cys Val Asp Asn Thr Ala Asn Glu Val Leu Arg
        275                 280                 285

Tyr Asn Ala Ser Asn Gln Phe Thr Trp Arg Val Ala Ala Lys Asp Val
    290                 295                 300

Glu Met Gly Gly Val Arg Ile Glu Ala Gly Gln Thr Leu Ala Leu Phe
305                 310                 315                 320

Leu Gly Ser Ala Asn Arg Asp Ala Asn Met Phe Glu Arg Pro Asn Asp
                325                 330                 335

Phe Asp Leu Asp Arg Pro Asn Ser Ala Arg His Leu Ser Phe Gly Gln
```

```
            340                 345                 350
Gly Val His Ala Cys Leu Ala Ala Gln Leu Ile Ser Leu Gln Leu Lys
            355                 360                 365

Trp Phe Tyr Val Ala Leu Leu Asn Arg Phe Pro Gly Ile Arg Thr Ala
370                 375                 380

Gly Glu Pro Ile Trp Asn Glu Asn Leu Glu Phe Arg Ser Leu Arg Ser
385                 390                 395                 400

Leu Pro Leu Ser Leu Arg
                405

<210> SEQ ID NO 57
<211> LENGTH: 597
<212> TYPE: PRT
<213> ORGANISM: Artificial Sequence
<220> FEATURE:
<223> OTHER INFORMATION: Synthetic Polypeptide

<400> SEQUENCE: 57

Lys Ile Pro Leu Gly Gly Ile Pro Ser Pro Ser Thr Glu Gln Ser Ala
1               5                   10                  15

Lys Lys Val Arg Lys Lys Ala Glu Asn Ala His Asn Thr Pro Leu Leu
            20                  25                  30

Val Leu Tyr Gly Ser Asn Met Gly Thr Ala Glu Gly Thr Ala Arg Asp
        35                  40                  45

Leu Ala Asp Ile Ala Met Ser Lys Gly Phe Ala Pro Gln Val Ala Thr
    50                  55                  60

Leu Asp Ser His Ala Gly Asn Leu Pro Arg Glu Gly Ala Val Leu Ile
65                  70                  75                  80

Val Thr Ala Ser Tyr Asn Gly His Pro Pro Asp Asn Ala Lys Gln Phe
                85                  90                  95

Val Asp Trp Leu Asp Gln Ala Ser Ala Asp Glu Val Lys Gly Val Arg
            100                 105                 110

Tyr Ser Val Phe Gly Cys Gly Asp Lys Asn Trp Ala Thr Thr Tyr Gln
        115                 120                 125

Lys Val Pro Ala Phe Ile Asp Glu Thr Leu Ala Ala Lys Gly Ala Glu
    130                 135                 140

Asn Ile Ala Asp Arg Gly Glu Ala Asp Ala Ser Asp Asp Phe Glu Gly
145                 150                 155                 160

Thr Tyr Glu Glu Trp Arg Glu His Met Trp Ser Asp Val Ala Ala Tyr
                165                 170                 175

Phe Asn Leu Asp Ile Glu Asn Ser Glu Asp Asn Lys Ser Thr Leu Ser
            180                 185                 190

Leu Gln Phe Val Asp Ser Ala Ala Asp Met Pro Leu Ala Lys Met His
        195                 200                 205

Gly Ala Phe Ser Thr Asn Val Val Ala Ser Lys Glu Leu Gln Gln Pro
    210                 215                 220

Gly Ser Ala Arg Ser Thr Arg His Leu Glu Ile Glu Leu Pro Lys Glu
225                 230                 235                 240

Ala Ser Tyr Gln Glu Gly Asp His Leu Gly Val Ile Pro Arg Asn Tyr
                245                 250                 255

Glu Gly Ile Val Asn Arg Val Thr Ala Arg Phe Gly Leu Asp Ala Ser
            260                 265                 270

Gln Gln Ile Arg Leu Glu Ala Glu Glu Lys Leu Ala His Leu Pro
        275                 280                 285

Leu Ala Lys Thr Val Ser Val Glu Glu Leu Leu Gln Tyr Val Glu Leu
```

```
                290                 295                 300

Gln Asp Pro Val Thr Arg Thr Gln Leu Arg Ala Met Ala Ala Lys Thr
305                 310                 315                 320

Val Cys Pro His Lys Val Glu Leu Glu Ala Leu Leu Glu Lys Gln
            325                 330                 335

Ala Tyr Lys Glu Gln Val Leu Ala Lys Arg Leu Thr Met Leu Glu Leu
            340                 345                 350

Leu Glu Lys Tyr Pro Ala Cys Glu Met Lys Phe Ser Glu Phe Ile Ala
            355                 360                 365

Leu Leu Pro Ser Ile Arg Pro Arg Tyr Tyr Ser Ile Ser Ser Ser Pro
            370                 375                 380

Arg Val Asp Glu Lys Gln Ala Ser Ile Thr Val Ser Val Val Ser Gly
385                 390                 395                 400

Glu Ala Trp Ser Gly Tyr Gly Glu Tyr Lys Gly Ile Ala Ser Asn Tyr
            405                 410                 415

Leu Ala Glu Leu Gln Glu Gly Asp Thr Ile Thr Cys Phe Ile Ser Thr
            420                 425                 430

Pro Gln Ser Glu Phe Thr Leu Pro Lys Asp Pro Glu Thr Pro Leu Ile
            435                 440                 445

Met Val Gly Pro Gly Thr Gly Val Ala Pro Phe Arg Gly Phe Val Gln
            450                 455                 460

Ala Arg Lys Gln Leu Lys Glu Gln Gly Gln Ser Leu Gly Glu Ala His
465                 470                 475                 480

Leu Tyr Phe Gly Cys Arg Ser Pro His Glu Asp Tyr Leu Tyr Gln Glu
            485                 490                 495

Glu Leu Glu Asn Ala Gln Ser Glu Gly Ile Ile Thr Leu His Thr Ala
            500                 505                 510

Phe Ser Arg Met Pro Asn Gln Pro Lys Thr Tyr Val Gln His Val Met
            515                 520                 525

Glu Gln Asp Gly Lys Lys Leu Ile Glu Leu Leu Asp Gln Gly Ala His
            530                 535                 540

Phe Tyr Ile Cys Gly Asp Gly Ser Gln Met Ala Pro Ala Val Glu Ala
545                 550                 555                 560

Thr Leu Met Lys Ser Tyr Ala Asp Val His Gln Val Ser Glu Ala Asp
            565                 570                 575

Ala Arg Leu Trp Leu Gln Gln Leu Glu Glu Lys Gly Arg Tyr Ala Lys
            580                 585                 590

Asp Val Trp Ala Gly
            595

<210> SEQ ID NO 58
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 58

Met Thr Val Pro Ser Pro Leu Ala Asp Pro Ser Ile Val Pro Asp Pro
1               5                   10                  15

Tyr Pro Val Tyr Ala Asp Leu Ala Gln Arg Arg Pro Val His Trp Val
            20                  25                  30

Glu Arg Leu Asn Ala Trp Ala Val Leu Thr Tyr Ala Asp Cys Ala Ala
            35                  40                  45

Gly Leu Lys Asp Pro Arg Leu Thr Ala Asp Arg Gly Thr Glu Val Leu
```

```
                50                  55                  60
Ala Ala Lys Phe Pro Gly Gln Pro Leu Pro Pro Asp Asn Ile Phe His
 65                  70                  75                  80

Arg Trp Thr Lys Asn Val Val Met Tyr Thr Asp Pro Pro Leu His Asp
                 85                  90                  95

Ala Leu Arg Arg Ser Val Arg Ala Gly Phe Thr Arg Ala Ala His Gln
                100                 105                 110

His Tyr Asp Gln Val Leu Gln Lys Val Ala His Asp Leu Val Ala Ser
                115                 120                 125

Ile Pro Ala Gly Ala Thr Glu Ile Asp Ala Val Pro Ala Leu Ala Ala
130                 135                 140

Glu Leu Pro Val Arg Ser Ala Val His Ala Phe Gly Val Pro Glu Glu
145                 150                 155                 160

Asp Leu Gly Phe Leu Ile Pro Arg Val Asn Thr Ile Met Thr Tyr His
                165                 170                 175

Ser Gly Pro Lys Asp Gln Pro Val Thr Gln Glu Ile Ile Leu Glu Lys
                180                 185                 190

Leu Thr Asp Leu His Thr Tyr Ala Ser Glu Leu Leu Gln Gly Met Arg
                195                 200                 205

Gly Lys Val Leu Pro Asp Thr Val Ile Ala Arg Leu Ala Ala Ala Gln
210                 215                 220

Asp Gly Leu Thr Glu Thr Thr Pro Glu Gln Thr Val His Gln Leu Ala
225                 230                 235                 240

Leu Val Phe Ile Ala Leu Phe Ala Pro Thr Thr Pro Gly Ser Leu Ser
                245                 250                 255

Ser Gly Thr Leu Ala Phe Ala Arg Asn Pro Arg Gln Val Glu Arg Phe
                260                 265                 270

Leu Ala Ala Glu Glu Ala Ala Arg Val Leu Val Asp Pro Val Pro Ser
                275                 280                 285

Tyr Lys Gln Val Lys Gln Leu Lys Tyr Asp Asn Thr Ala Asn Glu Val
                290                 295                 300

Leu Arg Tyr Asn Ala Ser Asn Gln Phe Thr Trp Arg Val Ala Ala Lys
305                 310                 315                 320

Asp Val Glu Met Gly Gly Val Arg Ile Glu Ala Gly Gln Thr Leu Ala
                325                 330                 335

Leu Phe Leu Gly Ser Ala Asn Arg Asp Ala Asn Met Phe Glu Arg Pro
                340                 345                 350

Asn Asp Phe Asp Leu Asp Arg Pro Asn Ser Ala Arg His Leu Ser Phe
                355                 360                 365

Gly Gln Gly Val His Ala Cys Leu Ala Ala Gln Leu Ile Ser Leu Gln
                370                 375                 380

Leu Lys Trp Phe Tyr Val Ala Leu Leu Asn Arg Phe Pro Gly Ile Arg
385                 390                 395                 400

Thr Ala Gly Glu Pro Ile Trp Asn Glu Asn Leu Glu Phe Arg Ser Leu
                405                 410                 415

Arg Ser Leu Pro Leu Ser Leu Arg
                420
```